(12) United States Patent
Yates et al.

(10) Patent No.: US 10,238,387 B2
(45) Date of Patent: *Mar. 26, 2019

(54) SURGICAL INSTRUMENT COMPRISING A CONTROL SYSTEM

(71) Applicant: Ethicon LLC, Guaynabo, PR (US)

(72) Inventors: David C. Yates, West Chester, OH (US); Thomas W. Huitema, Cincinnati, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 505 days.

This patent is subject to a terminal disclaimer.

(21) Appl. No.: 14/862,478

(22) Filed: Sep. 23, 2015

(65) Prior Publication Data
US 2016/0008023 A1    Jan. 14, 2016

Related U.S. Application Data

(63) Continuation of application No. 14/668,406, filed on Mar. 25, 2015, which is a continuation of application
(Continued)

(51) Int. Cl.
*A61B 17/072* (2006.01)
*A61B 17/068* (2006.01)
(Continued)

(52) U.S. Cl.
CPC .......... *A61B 17/068* (2013.01); *A61B 17/072* (2013.01); *A61B 17/07207* (2013.01);
(Continued)

(58) Field of Classification Search
CPC ................ A61B 17/068; A61B 17/072; A61B 17/07207; A61B 17/105; A61B 17/00234;
(Continued)

(56) References Cited

U.S. PATENT DOCUMENTS 66,052 A    6/1867  Smith
662,587 A   11/1900  Blake
(Continued)

FOREIGN PATENT DOCUMENTS

AU    2008207624 A1    3/2009
AU    2010214687 A1    9/2010
(Continued)

OTHER PUBLICATIONS

"Biomedical Coatings," Fort Wayne Metals, Research Products Corporation, obtained online at www.fwmetals.com on Jun. 21,2010 (1 page).
(Continued)

*Primary Examiner* — Scott A. Smith

(57) ABSTRACT

A surgical instrument is disclosed. The surgical instrument comprises a first jaw, a second jaw, a staple cartridge, a firing system, an electric motor, a power source, and a control system. The first jaw is movable relative to the second jaw to capture tissue between the first jaw and the second jaw. The staple cartridge is supported by the second jaw and comprises staples removably stored therein. The firing system is configured to drive the staples toward the first jaw. The electric motor is mechanically coupled to the firing system. The power source is electrically couplable to the electric motor. The control system is electrically connected to the power source. The control system is configured to determine a first level of power supplied by the power source and apply a second level of power to the electric motor if the first level of power exceeds a predetermined threshold. The second level of power is lower than the first level of power.

16 Claims, 39 Drawing Sheets

Related U.S. Application Data

No. 12/031,573, filed on Feb. 14, 2008, now abandoned.

(51) Int. Cl.

| | | |
|---|---|---|
| *A61B 17/10* | (2006.01) | |
| *A61B 18/14* | (2006.01) | |
| *A61B 17/32* | (2006.01) | |
| *A61B 17/3205* | (2006.01) | |
| *A61B 90/98* | (2016.01) | |
| *A61B 17/115* | (2006.01) | |
| *A61B 17/00* | (2006.01) | |
| *A61B 18/00* | (2006.01) | |
| *A61B 18/12* | (2006.01) | |
| *A61B 90/00* | (2016.01) | |

(52) U.S. Cl.
CPC ........ *A61B 17/105* (2013.01); *A61B 17/3205* (2013.01); *A61B 17/320016* (2013.01); *A61B 18/14* (2013.01); *A61B 18/1445* (2013.01); *A61B 90/98* (2016.02); *A61B 17/0686* (2013.01); *A61B 17/115* (2013.01); *A61B 2017/00017* (2013.01); *A61B 2017/00022* (2013.01); *A61B 2017/00398* (2013.01); *A61B 2017/00734* (2013.01); *A61B 2017/07214* (2013.01); *A61B 2018/0063* (2013.01); *A61B 2018/00875* (2013.01); *A61B 2018/124* (2013.01); *A61B 2018/1455* (2013.01); *A61B 2090/0807* (2016.02)

(58) Field of Classification Search
CPC ........... A61B 2017/00398; A61B 2017/00734; A61B 2017/07214; A61B 17/115; A61B 17/1155; A61B 2017/00022
USPC .. 227/19, 175.1, 175.2, 176.1, 178.1, 180.1; 606/32, 34, 139, 153, 219; 318/244, 318/400.11, 599; 323/212
See application file for complete search history.

(56) References Cited

U.S. PATENT DOCUMENTS

| | | |
|---|---|---|
| 670,748 A | 3/1901 | Weddeler |
| 719,487 A | 2/1903 | Minor |
| 804,229 A | 11/1905 | Hutchinson |
| 951,393 A | 3/1910 | Hahn |
| 1,306,107 A | 6/1919 | Elliott |
| 1,314,601 A | 9/1919 | McCaskey |
| 1,677,337 A | 7/1928 | Grove |
| 1,794,907 A | 3/1931 | Kelly |
| 1,849,427 A | 3/1932 | Hook |
| 1,944,116 A | 1/1934 | Stratman |
| 1,954,048 A | 4/1934 | Jeffrey et al. |
| 2,037,727 A | 4/1936 | La Chapelle |
| 2,132,295 A | 10/1938 | Hawkins |
| 2,161,632 A | 6/1939 | Nattenheimer |
| 2,211,117 A | 8/1940 | Hess |
| 2,214,870 A | 9/1940 | West |
| 2,224,882 A | 12/1940 | Peck |
| 2,318,379 A | 5/1943 | Davis et al. |
| 2,329,440 A | 9/1943 | La Place |
| 2,441,096 A | 5/1948 | Happe |
| 2,448,741 A | 9/1948 | Scott et al. |
| 2,450,527 A | 10/1948 | Smith |
| 2,526,902 A | 10/1950 | Rublee |
| 2,527,256 A | 10/1950 | Jackson |
| 2,578,686 A | 12/1951 | Fish |
| 2,638,901 A | 5/1953 | Sugarbaker |
| 2,674,149 A | 4/1954 | Benson |
| 2,711,461 A | 6/1955 | Happe |
| 2,742,955 A | 4/1956 | Dominguez |
| 2,804,848 A | 9/1957 | O'Farrell et al. |
| 2,808,482 A | 10/1957 | Zanichkowsky et al. |
| 2,853,074 A | 9/1958 | Olson |
| 2,887,004 A | 5/1959 | Stewart |
| 2,957,353 A | 10/1960 | Lewis |
| 2,959,974 A | 11/1960 | Emrick |
| 3,032,769 A | 5/1962 | Palmer |
| 3,060,972 A | 10/1962 | Sheldon |
| 3,075,062 A | 1/1963 | Iaccarino |
| 3,078,465 A | 2/1963 | Bobrov |
| 3,079,606 A | 3/1963 | Bobrov et al. |
| 3,080,564 A | 3/1963 | Strekopitov et al. |
| 3,166,072 A | 1/1965 | Sullivan, Jr. |
| 3,180,236 A | 4/1965 | Beckett |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,269,631 A | 8/1966 | Takaro |
| 3,275,211 A | 9/1966 | Hirsch et al. |
| 3,317,103 A | 5/1967 | Cullen et al. |
| 3,317,105 A | 5/1967 | Astafjev et al. |
| 3,357,296 A | 12/1967 | Lefever |
| 3,359,978 A | 12/1967 | Smith, Jr. |
| 3,480,193 A | 11/1969 | Ralston |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,509,629 A | 5/1970 | Kidokoro |
| 3,551,987 A | 1/1971 | Wilkinson |
| 3,568,675 A | 3/1971 | Harvey |
| 3,572,159 A | 3/1971 | Tschanz |
| 3,583,393 A | 6/1971 | Takahashi |
| 3,589,589 A | 6/1971 | Akopov |
| 3,598,943 A | 8/1971 | Barrett |
| 3,608,549 A | 9/1971 | Merrill |
| 3,618,842 A | 11/1971 | Bryan |
| 3,638,652 A | 2/1972 | Kelley |
| 3,640,317 A | 2/1972 | Panfili |
| 3,643,851 A | 2/1972 | Green et al. |
| 3,650,453 A | 3/1972 | Smith, Jr. |
| 3,661,666 A | 5/1972 | Foster et al. |
| 3,662,939 A | 5/1972 | Bryan |
| 3,688,966 A | 9/1972 | Perkins et al. |
| 3,695,646 A | 10/1972 | Mommsen |
| 3,709,221 A | 1/1973 | Riely |
| 3,717,294 A | 2/1973 | Green |
| 3,734,207 A | 5/1973 | Fishbein |
| 3,740,994 A | 6/1973 | De Carlo, Jr. |
| 3,744,495 A | 7/1973 | Johnson |
| 3,746,002 A | 7/1973 | Haller |
| 3,747,603 A | 7/1973 | Adler |
| 3,751,902 A | 8/1973 | Kingsbury et al. |
| 3,752,161 A | 8/1973 | Bent |
| 3,799,151 A | 3/1974 | Fukaumi et al. |
| 3,808,452 A | 4/1974 | Hutchinson |
| 3,815,476 A | 6/1974 | Green et al. |
| 3,819,100 A | 6/1974 | Noiles et al. |
| 3,821,919 A | 7/1974 | Knohl |
| 3,836,171 A | 9/1974 | Hayashi et al. |
| 3,837,555 A | 9/1974 | Green |
| 3,841,474 A | 10/1974 | Maier |
| 3,851,196 A | 11/1974 | Hinds |
| 3,863,639 A | 2/1975 | Kleaveland |
| 3,883,624 A | 5/1975 | McKenzie et al. |
| 3,885,491 A | 5/1975 | Curtis |
| 3,892,228 A | 7/1975 | Mitsui |
| 3,894,174 A | 7/1975 | Cartun |
| 3,902,247 A | 9/1975 | Fleer et al. |
| 3,940,844 A | 3/1976 | Colby et al. |
| 3,944,163 A | 3/1976 | Hayashi et al. |
| 3,950,686 A | 4/1976 | Randall |
| 3,952,747 A | 4/1976 | Kimmell, Jr. |
| 3,955,581 A | 5/1976 | Spasiano et al. |
| 3,959,879 A | 6/1976 | Sellers |
| RE28,932 E | 8/1976 | Noiles et al. |
| 3,972,734 A | 8/1976 | King |
| 3,981,051 A | 9/1976 | Brumlik |

(56) References Cited

U.S. PATENT DOCUMENTS

| | | |
|---|---|---|
| 4,025,216 A | 5/1977 | Hives |
| 4,027,746 A | 6/1977 | Kine |
| 4,034,143 A | 7/1977 | Sweet |
| 4,054,108 A | 10/1977 | Gill |
| 4,060,089 A | 11/1977 | Noiles |
| 4,066,133 A | 1/1978 | Voss |
| 4,100,820 A | 7/1978 | Evett |
| 4,106,446 A | 8/1978 | Yamada et al. |
| 4,108,211 A | 8/1978 | Tanaka |
| 4,111,206 A | 9/1978 | Vishnevsky et al. |
| 4,127,227 A | 11/1978 | Green |
| 4,129,059 A | 12/1978 | Van Eck |
| 4,135,517 A | 1/1979 | Reale |
| 4,154,122 A | 5/1979 | Severin |
| 4,169,990 A | 10/1979 | Lerdman |
| 4,180,285 A | 12/1979 | Reneau |
| 4,185,701 A | 1/1980 | Boys |
| 4,190,042 A | 2/1980 | Sinnreich |
| 4,198,734 A | 4/1980 | Brumlik |
| 4,198,982 A | 4/1980 | Fortner et al. |
| 4,207,898 A | 6/1980 | Becht |
| 4,213,562 A | 7/1980 | Garrett et al. |
| 4,226,242 A | 10/1980 | Jarvik |
| 4,239,431 A | 12/1980 | Davini |
| 4,241,861 A | 12/1980 | Fleischer |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,274,398 A | 6/1981 | Scott, Jr. |
| 4,275,813 A | 6/1981 | Noiles |
| 4,278,091 A | 7/1981 | Borzone |
| 4,289,131 A | 9/1981 | Mueller |
| 4,289,133 A | 9/1981 | Rothfuss |
| 4,290,542 A | 9/1981 | Fedotov et al. |
| D261,356 S | 10/1981 | Robinson |
| 4,296,654 A | 10/1981 | Mercer |
| 4,296,881 A | 10/1981 | Lee |
| 4,304,236 A | 12/1981 | Conta et al. |
| 4,305,539 A | 12/1981 | Korolkov et al. |
| 4,312,363 A | 1/1982 | Rothfuss et al. |
| 4,312,685 A | 1/1982 | Riedl |
| 4,317,451 A | 3/1982 | Cerwin et al. |
| 4,319,576 A | 3/1982 | Rothfuss |
| 4,321,002 A | 3/1982 | Froehlich |
| 4,321,746 A | 3/1982 | Grinage |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,350,151 A | 9/1982 | Scott |
| 4,353,371 A | 10/1982 | Cosman |
| 4,357,940 A | 11/1982 | Muller |
| 4,361,057 A | 11/1982 | Kochera |
| 4,366,544 A | 12/1982 | Shima et al. |
| 4,373,147 A | 2/1983 | Carlson, Jr. |
| 4,376,380 A | 3/1983 | Burgess |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,393,728 A | 7/1983 | Larson et al. |
| 4,396,139 A | 8/1983 | Hall et al. |
| 4,397,311 A | 8/1983 | Kanshin et al. |
| 4,402,445 A | 9/1983 | Green |
| 4,406,621 A | 9/1983 | Bailey |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,417,890 A | 11/1983 | Dennehey et al. |
| 4,423,456 A | 12/1983 | Zaidenweber |
| 4,428,376 A | 1/1984 | Mericle |
| 4,429,695 A | 2/1984 | Green |
| 4,430,997 A | 2/1984 | DiGiovanni et al. |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,452,376 A | 6/1984 | Klieman et al. |
| 4,454,887 A | 6/1984 | Kruger |
| 4,461,305 A | 7/1984 | Cibley |
| 4,467,805 A | 8/1984 | Fukuda |
| 4,469,481 A | 9/1984 | Kobayashi |
| 4,470,414 A | 9/1984 | Imagawa et al. |
| 4,471,780 A | 9/1984 | Menges et al. |
| 4,471,781 A | 9/1984 | Di Giovanni et al. |
| 4,473,077 A | 9/1984 | Noiles et al. |
| 4,475,679 A | 10/1984 | Fleury, Jr. |
| 4,478,220 A | 10/1984 | Di Giovanni et al. |
| 4,480,641 A | 11/1984 | Failla et al. |
| 4,485,816 A | 12/1984 | Krumme |
| 4,485,817 A | 12/1984 | Swiggett |
| 4,486,928 A | 12/1984 | Tucker et al. |
| 4,488,523 A | 12/1984 | Shichman |
| 4,489,875 A | 12/1984 | Crawford et al. |
| 4,493,983 A | 1/1985 | Taggert |
| 4,499,895 A | 2/1985 | Takayama |
| 4,500,024 A | 2/1985 | DiGiovanni et al. |
| 4,503,842 A | 3/1985 | Takayama |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,512,038 A | 4/1985 | Alexander et al. |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,357 A | 7/1985 | Pawloski et al. |
| 4,530,453 A | 7/1985 | Green |
| 4,531,522 A | 7/1985 | Bedi et al. |
| 4,532,927 A | 8/1985 | Miksza, Jr. |
| 4,540,202 A | 9/1985 | Amphoux et al. |
| 4,548,202 A | 10/1985 | Duncan |
| 4,556,058 A | 12/1985 | Green |
| 4,560,915 A | 12/1985 | Soultanian |
| 4,565,109 A | 1/1986 | Tsay |
| 4,565,189 A | 1/1986 | Mabuchi |
| 4,566,620 A | 1/1986 | Green et al. |
| 4,569,346 A | 2/1986 | Poirier |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,165 A | 3/1986 | Green et al. |
| 4,576,167 A | 3/1986 | Noiles |
| 4,580,712 A | 4/1986 | Green |
| 4,585,153 A | 4/1986 | Failla et al. |
| 4,586,501 A | 5/1986 | Claracq |
| 4,586,502 A | 5/1986 | Bedi et al. |
| 4,589,416 A | 5/1986 | Green |
| 4,589,870 A | 5/1986 | Citrin et al. |
| 4,591,085 A | 5/1986 | Di Giovanni |
| RE32,214 E | 7/1986 | Schramm |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,612,933 A | 9/1986 | Brinkerhoff et al. |
| D286,180 S | 10/1986 | Korthoff |
| D286,442 S | 10/1986 | Korthoff et al. |
| 4,617,914 A | 10/1986 | Ueda |

(56) References Cited

U.S. PATENT DOCUMENTS

| | | |
|---|---|---|
| 4,619,262 A | 10/1986 | Taylor |
| 4,619,391 A | 10/1986 | Sharkany et al. |
| D287,278 S | 12/1986 | Spreckelmeier |
| 4,628,459 A | 12/1986 | Shinohara et al. |
| 4,629,107 A | 12/1986 | Fedotov et al. |
| 4,632,290 A | 12/1986 | Green et al. |
| 4,633,861 A | 1/1987 | Chow et al. |
| 4,633,874 A | 1/1987 | Chow et al. |
| 4,634,419 A | 1/1987 | Kreizman et al. |
| 4,635,638 A | 1/1987 | Weintraub et al. |
| 4,641,076 A | 2/1987 | Linden |
| 4,642,618 A | 2/1987 | Johnson et al. |
| 4,643,173 A | 2/1987 | Bell et al. |
| 4,643,731 A | 2/1987 | Eckenhoff |
| 4,646,722 A | 3/1987 | Silverstein et al. |
| 4,646,745 A | 3/1987 | Noiles |
| 4,652,820 A | 3/1987 | Maresca |
| 4,654,028 A | 3/1987 | Suma |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,278 A | 6/1987 | Chin |
| 4,671,280 A | 6/1987 | Dorband et al. |
| 4,671,445 A | 6/1987 | Barker et al. |
| 4,672,964 A | 6/1987 | Dee et al. |
| 4,675,944 A | 6/1987 | Wells |
| 4,676,245 A | 6/1987 | Fukuda |
| 4,679,460 A | 7/1987 | Yoshigai |
| 4,679,719 A | 7/1987 | Kramer |
| 4,684,051 A | 8/1987 | Akopov et al. |
| 4,688,555 A | 8/1987 | Wardle |
| 4,691,703 A | 9/1987 | Auth et al. |
| 4,693,248 A | 9/1987 | Failla |
| 4,698,579 A | 10/1987 | Richter et al. |
| 4,700,703 A | 10/1987 | Resnick et al. |
| 4,705,038 A | 11/1987 | Sjostrom et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,721,099 A | 1/1988 | Chikama |
| 4,724,840 A | 2/1988 | McVay et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,744,363 A | 5/1988 | Hasson |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,763,669 A | 8/1988 | Jaeger |
| 4,767,044 A | 8/1988 | Green |
| 4,773,420 A | 9/1988 | Green |
| 4,777,780 A | 10/1988 | Holzwarth |
| 4,781,186 A | 11/1988 | Simpson et al. |
| 4,784,137 A | 11/1988 | Kulik et al. |
| 4,787,387 A | 11/1988 | Burbank, III et al. |
| 4,790,225 A | 12/1988 | Moody et al. |
| 4,790,314 A | 12/1988 | Weaver |
| 4,805,617 A | 2/1989 | Bedi et al. |
| 4,805,823 A | 2/1989 | Rothfuss |
| 4,807,628 A | 2/1989 | Peters et al. |
| 4,809,695 A | 3/1989 | Gwathmey et al. |
| 4,815,460 A | 3/1989 | Porat et al. |
| 4,817,643 A | 4/1989 | Olson |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,828,542 A | 5/1989 | Hermann |
| 4,828,944 A | 5/1989 | Yabe et al. |
| 4,830,855 A | 5/1989 | Stewart |
| 4,833,937 A | 5/1989 | Nagano |
| 4,834,720 A | 5/1989 | Blinkhorn |
| 4,838,859 A | 6/1989 | Strassmann |
| 4,844,068 A | 7/1989 | Arata et al. |
| 4,848,637 A | 7/1989 | Pruitt |
| 4,856,078 A | 8/1989 | Konopka |
| 4,860,644 A | 8/1989 | Kohl et al. |
| 4,862,891 A | 9/1989 | Smith |
| 4,863,423 A | 9/1989 | Wallace |
| 4,865,030 A | 9/1989 | Polyak |
| 4,868,530 A | 9/1989 | Ahs |
| 4,869,414 A | 9/1989 | Green et al. |
| 4,869,415 A | 9/1989 | Fox |
| 4,873,977 A | 10/1989 | Avant et al. |
| 4,875,486 A | 10/1989 | Rapoport et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,894,051 A | 1/1990 | Shiber |
| 4,896,584 A | 1/1990 | Stoll et al. |
| 4,896,678 A | 1/1990 | Ogawa |
| 4,900,303 A | 2/1990 | Lemelson |
| 4,903,697 A | 2/1990 | Resnick et al. |
| 4,909,789 A | 3/1990 | Taguchi et al. |
| 4,915,100 A | 4/1990 | Green |
| 4,919,679 A | 4/1990 | Averill et al. |
| 4,921,479 A | 5/1990 | Grayzel |
| 4,925,082 A | 5/1990 | Kim |
| 4,928,699 A | 5/1990 | Sasai |
| 4,930,503 A | 6/1990 | Pruitt |
| 4,930,674 A | 6/1990 | Barak |
| 4,931,047 A | 6/1990 | Broadwin et al. |
| 4,931,737 A | 6/1990 | Hishiki |
| 4,932,960 A | 6/1990 | Green et al. |
| 4,933,843 A | 6/1990 | Scheller et al. |
| D309,350 S | 7/1990 | Sutherland et al. |
| 4,938,408 A | 7/1990 | Bedi et al. |
| 4,941,623 A | 7/1990 | Pruitt |
| 4,943,182 A | 7/1990 | Hoblingre |
| 4,944,443 A | 7/1990 | Oddsen et al. |
| 4,946,067 A | 8/1990 | Kelsall |
| 4,948,327 A | 8/1990 | Crupi, Jr. |
| 4,949,707 A | 8/1990 | LeVahn et al. |
| 4,951,860 A | 8/1990 | Peters et al. |
| 4,951,861 A | 8/1990 | Schulze et al. |
| 4,955,959 A | 9/1990 | Tompkins et al. |
| 4,957,212 A | 9/1990 | Duck et al. |
| 4,962,877 A | 10/1990 | Hervas |
| 4,964,559 A | 10/1990 | Deniega et al. |
| 4,964,863 A | 10/1990 | Kanshin et al. |
| 4,965,709 A | 10/1990 | Ngo |
| 4,973,274 A | 11/1990 | Hirukawa |
| 4,973,302 A | 11/1990 | Armour et al. |
| 4,978,049 A | 12/1990 | Green |
| 4,978,333 A | 12/1990 | Broadwin et al. |
| 4,979,952 A | 12/1990 | Kubota et al. |
| 4,984,564 A | 1/1991 | Yuen |
| 4,986,808 A | 1/1991 | Broadwin et al. |
| 4,987,049 A | 1/1991 | Komamura et al. |
| 4,988,334 A | 1/1991 | Hornlein et al. |
| 4,995,877 A | 2/1991 | Ams et al. |
| 4,995,959 A | 2/1991 | Metzner |
| 4,996,975 A | 3/1991 | Nakamura |
| 5,002,543 A | 3/1991 | Bradshaw et al. |
| 5,002,553 A | 3/1991 | Shiber |
| 5,005,754 A | 4/1991 | Van Overloop |
| 5,009,661 A | 4/1991 | Michelson |
| 5,012,411 A | 4/1991 | Policastro et al. |
| 5,014,898 A | 5/1991 | Heidrich |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |

(56) References Cited

U.S. PATENT DOCUMENTS

| | | |
|---|---|---|
| 5,024,652 A | 6/1991 | Dumenek et al. |
| 5,024,671 A | 6/1991 | Tu et al. |
| 5,027,834 A | 7/1991 | Pruitt |
| 5,030,226 A | 7/1991 | Green et al. |
| 5,031,814 A | 7/1991 | Tompkins et al. |
| 5,035,040 A | 7/1991 | Kerrigan et al. |
| 5,038,109 A | 8/1991 | Goble et al. |
| 5,038,247 A | 8/1991 | Kelley et al. |
| 5,040,715 A | 8/1991 | Green et al. |
| 5,042,707 A | 8/1991 | Taheri |
| 5,061,269 A | 10/1991 | Muller |
| 5,062,491 A | 11/1991 | Takeshima et al. |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,077,506 A | 12/1991 | Krause |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,089,606 A | 2/1992 | Cole et al. |
| 5,094,247 A | 3/1992 | Hernandez et al. |
| 5,098,004 A | 3/1992 | Kerrigan |
| 5,098,360 A | 3/1992 | Hirota |
| 5,100,042 A | 3/1992 | Gravener et al. |
| 5,100,420 A | 3/1992 | Green et al. |
| 5,104,025 A | 4/1992 | Main et al. |
| 5,104,397 A | 4/1992 | Vasconcelos et al. |
| 5,104,400 A | 4/1992 | Berguer et al. |
| 5,106,008 A | 4/1992 | Tompkins et al. |
| 5,108,368 A | 4/1992 | Hammerslag et al. |
| 5,109,722 A | 5/1992 | Hufnagle et al. |
| 5,111,987 A | 5/1992 | Moeinzadeh et al. |
| 5,116,349 A | 5/1992 | Aranyi |
| D327,323 S | 6/1992 | Hunt |
| 5,119,009 A | 6/1992 | McCaleb et al. |
| 5,122,156 A | 6/1992 | Granger et al. |
| 5,124,990 A | 6/1992 | Williamson |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,168,605 A | 12/1992 | Bartlett |
| 5,170,925 A | 12/1992 | Madden et al. |
| 5,171,247 A | 12/1992 | Hughett et al. |
| 5,171,249 A | 12/1992 | Stefanchik et al. |
| 5,171,253 A | 12/1992 | Klieman |
| 5,173,133 A | 12/1992 | Morin et al. |
| 5,176,677 A | 1/1993 | Wuchinich |
| 5,176,688 A | 1/1993 | Narayan et al. |
| 5,187,422 A | 2/1993 | Izenbaard et al. |
| 5,188,102 A | 2/1993 | Idemoto et al. |
| 5,188,111 A | 2/1993 | Yates et al. |
| 5,190,517 A | 3/1993 | Zieve et al. |
| 5,190,544 A | 3/1993 | Chapman et al. |
| 5,190,560 A | 3/1993 | Woods et al. |
| 5,192,288 A | 3/1993 | Thompson et al. |
| 5,195,505 A | 3/1993 | Josefsen |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,197,970 A | 3/1993 | Green et al. |
| 5,200,280 A | 4/1993 | Karasa |
| 5,201,750 A | 4/1993 | Hocherl et al. |
| 5,205,459 A | 4/1993 | Brinkerhoff et al. |
| 5,207,697 A | 5/1993 | Carusillo et al. |
| 5,209,747 A | 5/1993 | Knoepfler |
| 5,209,756 A | 5/1993 | Seedhom et al. |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,220,269 A | 6/1993 | Chen et al. |
| 5,221,036 A | 6/1993 | Takase |
| 5,221,281 A | 6/1993 | Klicek |
| 5,222,945 A | 6/1993 | Basnight |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| D338,729 S | 8/1993 | Sprecklemeier et al. |
| 5,234,447 A | 8/1993 | Kaster et al. |
| 5,236,424 A | 8/1993 | Imran |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,007 A | 11/1993 | Spetzler et al. |
| 5,258,008 A | 11/1993 | Wilk |
| 5,258,009 A | 11/1993 | Conners |
| 5,258,010 A | 11/1993 | Green et al. |
| 5,258,012 A | 11/1993 | Luscombe et al. |
| 5,259,366 A | 11/1993 | Reydel et al. |
| 5,259,835 A | 11/1993 | Clark et al. |
| 5,260,637 A | 11/1993 | Pizzi |
| 5,261,877 A | 11/1993 | Fine et al. |
| 5,261,922 A | 11/1993 | Hood |
| 5,263,629 A | 11/1993 | Trumbull et al. |
| 5,263,937 A | 11/1993 | Shipp |
| 5,263,973 A | 11/1993 | Cook |
| 5,264,218 A | 11/1993 | Rogozinski |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,322 A | 1/1994 | Brinkerhoff et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,282,806 A | 2/1994 | Haber et al. |
| 5,282,829 A | 2/1994 | Hermes |
| 5,284,128 A | 2/1994 | Hart |
| 5,285,381 A | 2/1994 | Iskarous et al. |
| 5,285,945 A | 2/1994 | Brinkerhoff et al. |
| 5,286,253 A | 2/1994 | Fucci |
| 5,289,963 A | 3/1994 | McGarry et al. |
| 5,290,271 A | 3/1994 | Jernberg |
| 5,290,310 A | 3/1994 | Makower et al. |
| 5,292,053 A | 3/1994 | Bilotti et al. |
| 5,297,714 A | 3/1994 | Kramer |
| 5,304,204 A | 4/1994 | Bregen |
| D347,474 S | 5/1994 | Olson |
| 5,307,976 A | 5/1994 | Olson et al. |
| 5,308,576 A | 5/1994 | Green et al. |
| 5,309,387 A | 5/1994 | Mori et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,313,935 A | 5/1994 | Kortenbach et al. |
| 5,313,967 A | 5/1994 | Lieber et al. |
| 5,314,424 A | 5/1994 | Nicholas |
| 5,314,445 A | 5/1994 | Heidmueller nee Degwitz et al. |
| 5,314,466 A | 5/1994 | Stern et al. |
| 5,318,221 A | 6/1994 | Green et al. |

(56) References Cited

U.S. PATENT DOCUMENTS

| | | |
|---|---|---|
| 5,320,627 A | 6/1994 | Sorensen et al. |
| D348,930 S | 7/1994 | Olson |
| 5,326,013 A | 7/1994 | Green et al. |
| 5,329,923 A | 7/1994 | Lundquist |
| 5,330,487 A | 7/1994 | Thornton et al. |
| 5,330,502 A | 7/1994 | Hassler et al. |
| 5,331,971 A | 7/1994 | Bales et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,130 A | 8/1994 | Ray |
| 5,336,229 A | 8/1994 | Noda |
| 5,336,232 A | 8/1994 | Green et al. |
| 5,339,799 A | 8/1994 | Kami et al. |
| 5,341,724 A | 8/1994 | Vatel |
| 5,341,807 A | 8/1994 | Nardella |
| 5,341,810 A | 8/1994 | Dardel |
| 5,342,380 A | 8/1994 | Hood |
| 5,342,381 A | 8/1994 | Tidemand |
| 5,342,385 A | 8/1994 | Norelli et al. |
| 5,342,395 A | 8/1994 | Jarrett et al. |
| 5,342,396 A | 8/1994 | Cook |
| 5,343,382 A | 8/1994 | Hale et al. |
| 5,343,391 A | 8/1994 | Mushabac |
| 5,344,059 A | 9/1994 | Green et al. |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,355 A | 9/1994 | Sklar |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,250 A | 10/1994 | Christensen |
| 5,354,303 A | 10/1994 | Spaeth et al. |
| 5,356,006 A | 10/1994 | Alpern et al. |
| 5,356,064 A | 10/1994 | Green et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,359,993 A | 11/1994 | Slater et al. |
| 5,360,305 A | 11/1994 | Kerrigan |
| 5,360,428 A | 11/1994 | Hutchinson, Jr. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,369,565 A | 11/1994 | Chen et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,375,588 A | 12/1994 | Yoon |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,381,943 A | 1/1995 | Allen et al. |
| 5,382,247 A | 1/1995 | Cimino et al. |
| 5,383,880 A * | 1/1995 | Hooven ............... A61B 17/072 227/175.1 |
| 5,383,881 A | 1/1995 | Green et al. |
| 5,383,882 A | 1/1995 | Buess et al. |
| 5,383,888 A | 1/1995 | Zvenyatsky et al. |
| 5,383,895 A | 1/1995 | Holmes et al. |
| 5,388,568 A | 2/1995 | van der Heide |
| 5,389,098 A | 2/1995 | Tsuruta et al. |
| 5,389,102 A | 2/1995 | Green et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit et al. |
| 5,397,046 A | 3/1995 | Savage et al. |
| 5,397,324 A | 3/1995 | Carroll et al. |
| 5,400,267 A | 3/1995 | Denen et al. |
| 5,403,276 A | 4/1995 | Schechter et al. |
| 5,403,312 A * | 4/1995 | Yates ............... A61B 17/07207 606/142 |
| 5,404,106 A | 4/1995 | Matsuda |
| 5,404,870 A | 4/1995 | Brinkerhoff et al. |
| 5,404,960 A | 4/1995 | Wada et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,408,409 A | 4/1995 | Glassman et al. |
| 5,409,498 A | 4/1995 | Braddock et al. |
| 5,409,703 A | 4/1995 | McAnalley et al. |
| D357,981 S | 5/1995 | Green et al. |
| 5,411,481 A | 5/1995 | Allen et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson et al. |
| 5,415,335 A | 5/1995 | Knodell, Jr. |
| 5,417,203 A | 5/1995 | Tovey et al. |
| 5,417,361 A | 5/1995 | Williamson, IV |
| 5,419,766 A | 5/1995 | Chang et al. |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,423,835 A | 6/1995 | Green et al. |
| 5,425,745 A | 6/1995 | Green et al. |
| 5,427,298 A | 6/1995 | Tegtmeier |
| 5,431,322 A | 7/1995 | Green et al. |
| 5,431,323 A | 7/1995 | Smith et al. |
| 5,431,654 A | 7/1995 | Nic |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,439,155 A | 8/1995 | Viola |
| 5,439,156 A | 8/1995 | Grant et al. |
| 5,439,479 A | 8/1995 | Shichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,443,197 A | 8/1995 | Malis et al. |
| 5,443,463 A | 8/1995 | Stern et al. |
| 5,444,113 A | 8/1995 | Sinclair et al. |
| 5,445,155 A | 8/1995 | Sieben |
| 5,445,304 A | 8/1995 | Plyley et al. |
| 5,445,604 A | 8/1995 | Lang |
| 5,445,644 A | 8/1995 | Pietrafitta et al. |
| 5,447,265 A | 9/1995 | Vidal et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |

(56) References Cited

U.S. PATENT DOCUMENTS

| | | |
|---|---|---|
| 5,454,822 A | 10/1995 | Schob et al. |
| 5,454,827 A | 10/1995 | Aust et al. |
| 5,456,401 A | 10/1995 | Green et al. |
| 5,456,917 A | 10/1995 | Wise et al. |
| 5,458,279 A | 10/1995 | Plyley |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,819 A | 11/1995 | Weilant et al. |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,470,010 A | 11/1995 | Rothfuss et al. |
| 5,471,129 A | 11/1995 | Mann |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,476,206 A | 12/1995 | Green et al. |
| 5,476,479 A | 12/1995 | Green et al. |
| 5,476,481 A | 12/1995 | Schondorf |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,483,952 A | 1/1996 | Aranyi |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,489,290 A | 2/1996 | Furnish |
| 5,490,819 A | 2/1996 | Nicholas et al. |
| 5,492,671 A | 2/1996 | Krafft |
| 5,496,312 A | 3/1996 | Klicek |
| 5,496,317 A | 3/1996 | Goble et al. |
| 5,497,933 A | 3/1996 | DeFonzo et al. |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,149 A | 5/1996 | Green et al. |
| 5,514,157 A | 5/1996 | Nicholas et al. |
| 5,518,163 A | 5/1996 | Hooven |
| 5,518,164 A | 5/1996 | Hooven |
| 5,520,609 A | 5/1996 | Moll et al. |
| 5,520,634 A | 5/1996 | Fox et al. |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,264 A | 6/1996 | Moll et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,531,856 A | 7/1996 | Moll et al. |
| 5,533,521 A | 7/1996 | Granger |
| 5,533,581 A | 7/1996 | Barth et al. |
| 5,533,661 A | 7/1996 | Main et al. |
| 5,535,934 A * | 7/1996 | Boiarski .......... A61B 17/07207 227/175.1 |
| 5,535,935 A | 7/1996 | Vidal et al. |
| 5,535,937 A | 7/1996 | Boiarski et al. |
| 5,540,375 A | 7/1996 | Bolanos et al. |
| 5,540,705 A | 7/1996 | Meade et al. |
| 5,541,376 A | 7/1996 | Ladtkow et al. |
| 5,541,489 A | 7/1996 | Dunstan |
| 5,542,594 A | 8/1996 | McKean et al. |
| 5,542,949 A | 8/1996 | Yoon |
| 5,543,119 A | 8/1996 | Sutter et al. |
| 5,543,695 A | 8/1996 | Culp et al. |
| 5,544,802 A | 8/1996 | Crainich |
| 5,547,117 A | 8/1996 | Hamblin et al. |
| 5,549,583 A | 8/1996 | Sanford et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,624 A | 9/1996 | Francese et al. |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,020 A | 9/1996 | Hou |
| 5,556,416 A | 9/1996 | Clark et al. |
| 5,558,533 A | 9/1996 | Hashizawa et al. |
| 5,558,665 A | 9/1996 | Kieturakis |
| 5,558,671 A * | 9/1996 | Yates .............. A61B 17/07207 606/34 |
| 5,560,530 A | 10/1996 | Bolanos et al. |
| 5,560,532 A | 10/1996 | DeFonzo et al. |
| 5,561,881 A | 10/1996 | Klinger et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,563,481 A | 10/1996 | Krause |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,571,488 A | 11/1996 | Beerstecher et al. |
| 5,573,169 A | 11/1996 | Green et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,578,052 A | 11/1996 | Koros et al. |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,583,114 A | 12/1996 | Barrows et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |

(56) References Cited

U.S. PATENT DOCUMENTS

| | | |
|---|---|---|
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,601,573 A | 2/1997 | Fogelberg et al. |
| 5,601,604 A | 2/1997 | Vincent |
| 5,602,449 A | 2/1997 | Krause et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,450 A | 3/1997 | Zvenyatsky et al. |
| 5,607,474 A | 3/1997 | Athanasiou et al. |
| 5,609,285 A | 3/1997 | Grant et al. |
| 5,609,601 A | 3/1997 | Kolesa et al. |
| 5,611,709 A | 3/1997 | McAnulty |
| 5,613,499 A | 3/1997 | Palmer et al. |
| 5,613,937 A | 3/1997 | Garrison et al. |
| 5,613,966 A | 3/1997 | Makower et al. |
| 5,614,887 A | 3/1997 | Buchbinder |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,326 A | 4/1997 | Younker |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,632,432 A | 5/1997 | Schulze et al. |
| 5,632,433 A | 5/1997 | Grant et al. |
| 5,633,374 A | 5/1997 | Humphrey et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| D381,077 S | 7/1997 | Hunt |
| 5,643,291 A | 7/1997 | Pier et al. |
| 5,643,294 A | 7/1997 | Tovey et al. |
| 5,643,319 A | 7/1997 | Green et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,651,762 A | 7/1997 | Bridges |
| 5,651,821 A | 7/1997 | Uchida |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,417 A | 8/1997 | Di Troia |
| 5,657,429 A | 8/1997 | Wang et al. |
| 5,657,921 A | 8/1997 | Young et al. |
| 5,658,238 A | 8/1997 | Suzuki et al. |
| 5,658,281 A | 8/1997 | Heard |
| 5,658,298 A | 8/1997 | Vincent et al. |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,662,667 A | 9/1997 | Knodel |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,681,341 A | 10/1997 | Lunsford et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A * | 12/1997 | Schulze ............ A61B 17/07207 606/41 |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,700,276 A | 12/1997 | Benecke |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,335 A | 1/1998 | Heck |
| 5,709,680 A * | 1/1998 | Yates ............... A61B 17/07207 606/41 |
| 5,709,706 A | 1/1998 | Kienzle et al. |
| 5,711,472 A | 1/1998 | Bryan |
| 5,712,460 A | 1/1998 | Carr et al. |
| 5,713,128 A | 2/1998 | Schrenk et al. |
| 5,713,505 A | 2/1998 | Huitema |
| 5,713,895 A | 2/1998 | Lontine et al. |
| 5,713,896 A * | 2/1998 | Nardella .......... A61B 17/07207 606/41 |
| 5,713,920 A | 2/1998 | Bezwada et al. |
| 5,715,604 A | 2/1998 | Lanzoni |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,718,714 A | 2/1998 | Livneh |
| 5,720,744 A | 2/1998 | Eggleston et al. |
| D393,067 S | 3/1998 | Geary et al. |
| 5,724,025 A | 3/1998 | Tavori |
| 5,725,536 A | 3/1998 | Oberlin et al. |
| 5,725,554 A | 3/1998 | Simon et al. |
| 5,728,110 A | 3/1998 | Vidal et al. |
| 5,728,113 A | 3/1998 | Sherts |

(56) References Cited

U.S. PATENT DOCUMENTS

| | | |
|---|---|---|
| 5,728,121 A | 3/1998 | Bimbo et al. |
| 5,730,758 A | 3/1998 | Allgeyer |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,629 A | 4/1998 | Moll et al. |
| 5,738,648 A | 4/1998 | Lands et al. |
| 5,741,271 A | 4/1998 | Nakao et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,749,968 A | 5/1998 | Melanson et al. |
| 5,752,644 A | 5/1998 | Bolanos et al. |
| 5,752,965 A | 5/1998 | Francis et al. |
| 5,752,970 A | 5/1998 | Yoon |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,303 A | 6/1998 | Knodel et al. |
| 5,769,748 A | 6/1998 | Eyerly et al. |
| 5,769,791 A | 6/1998 | Benaron et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,748 A | 7/1998 | Palmer et al. |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,791,231 A | 8/1998 | Cohn et al. |
| 5,792,135 A | 8/1998 | Madhani et al. |
| 5,792,162 A | 8/1998 | Jolly et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,637 A | 8/1998 | Ervin |
| 5,797,906 A | 8/1998 | Rhum et al. |
| 5,797,927 A | 8/1998 | Yoon |
| 5,797,941 A | 8/1998 | Schulze et al. |
| 5,797,959 A | 8/1998 | Castro et al. |
| 5,799,857 A | 9/1998 | Robertson et al. |
| 5,800,379 A | 9/1998 | Edwards |
| 5,800,423 A | 9/1998 | Jensen |
| 5,804,726 A | 9/1998 | Geib et al. |
| 5,804,936 A | 9/1998 | Brodsky et al. |
| 5,806,676 A | 9/1998 | Wasgien |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A * | 9/1998 | Yates ............... A61B 17/07207 227/180.1 |
| 5,810,846 A | 9/1998 | Virnich et al. |
| 5,810,855 A | 9/1998 | Rayburn et al. |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A * | 10/1998 | Williamson, IV ............... A61B 17/07207 606/42 |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,824,333 A | 10/1998 | Scopelianos et al. |
| 5,826,776 A | 10/1998 | Schulze et al. |
| 5,827,271 A | 10/1998 | Buysse et al. |
| 5,827,298 A | 10/1998 | Hart et al. |
| 5,829,662 A | 11/1998 | Allen et al. |
| 5,830,598 A | 11/1998 | Patterson |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,369 A | 11/1998 | Chatterjee et al. |
| 5,839,639 A | 11/1998 | Sauer et al. |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,847,566 A | 12/1998 | Marritt et al. |
| 5,849,011 A | 12/1998 | Jones et al. |
| 5,849,020 A | 12/1998 | Long et al. |
| 5,849,023 A | 12/1998 | Mericle |
| 5,851,179 A | 12/1998 | Ritson et al. |
| 5,853,366 A | 12/1998 | Dowlatshahi |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,865,638 A | 2/1999 | Trafton |
| 5,868,361 A | 2/1999 | Rinderer |
| 5,868,760 A | 2/1999 | McGuckin, Jr. |
| 5,868,790 A | 2/1999 | Vincent et al. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,607 A | 3/1999 | Nunes et al. |
| 5,878,937 A | 3/1999 | Green et al. |
| 5,878,938 A | 3/1999 | Bittner et al. |
| 5,881,777 A | 3/1999 | Bassi et al. |
| 5,891,094 A | 4/1999 | Masterson et al. |
| 5,891,160 A | 4/1999 | Williamson, IV et al. |
| 5,891,558 A | 4/1999 | Bell et al. |
| 5,893,506 A | 4/1999 | Powell |
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,824 A | 5/1999 | Kurtz et al. |
| 5,899,914 A | 5/1999 | Zirps et al. |
| 5,901,895 A | 5/1999 | Heaton et al. |
| 5,902,312 A | 5/1999 | Frater et al. |
| 5,903,117 A | 5/1999 | Gregory |
| 5,904,647 A | 5/1999 | Ouchi |
| 5,904,693 A | 5/1999 | Dicesare et al. |
| 5,904,702 A | 5/1999 | Ek et al. |
| 5,906,577 A | 5/1999 | Beane et al. |
| 5,906,625 A | 5/1999 | Bito et al. |
| 5,907,211 A | 5/1999 | Hall et al. |
| 5,908,402 A | 6/1999 | Blythe |

(56) References Cited

U.S. PATENT DOCUMENTS

| | | |
|---|---|---|
| 5,908,427 A | 6/1999 | McKean et al. |
| 5,909,062 A | 6/1999 | Krietzman |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,924,864 A | 7/1999 | Loge et al. |
| 5,928,137 A | 7/1999 | Green |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,941,890 A | 8/1999 | Voegele et al. |
| 5,944,172 A | 8/1999 | Hannula |
| 5,944,715 A | 8/1999 | Goble et al. |
| 5,946,978 A | 9/1999 | Yamashita |
| 5,947,984 A | 9/1999 | Whipple |
| 5,947,996 A | 9/1999 | Logeman |
| 5,948,030 A | 9/1999 | Miller et al. |
| 5,948,429 A | 9/1999 | Bell et al. |
| 5,951,301 A | 9/1999 | Younker |
| 5,951,516 A | 9/1999 | Bunyan |
| 5,951,552 A | 9/1999 | Long et al. |
| 5,951,574 A | 9/1999 | Stefanchik et al. |
| 5,951,581 A | 9/1999 | Saadat et al. |
| 5,954,259 A | 9/1999 | Viola et al. |
| 5,964,394 A | 10/1999 | Robertson |
| 5,964,774 A | 10/1999 | McKean et al. |
| 5,971,916 A | 10/1999 | Koren |
| 5,973,221 A | 10/1999 | Collyer et al. |
| D416,089 S | 11/1999 | Barton et al. |
| 5,976,122 A | 11/1999 | Madhani et al. |
| 5,977,746 A | 11/1999 | Hershberger et al. |
| 5,984,949 A | 11/1999 | Levin |
| 5,988,479 A | 11/1999 | Palmer |
| 5,990,379 A | 11/1999 | Gregory |
| 5,993,466 A | 11/1999 | Yoon |
| 5,997,528 A | 12/1999 | Bisch et al. |
| 5,997,552 A | 12/1999 | Person et al. |
| 6,001,108 A | 12/1999 | Wang et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,007,521 A | 12/1999 | Bidwell et al. |
| 6,010,054 A | 1/2000 | Johnson et al. |
| 6,010,513 A | 1/2000 | Tormala et al. |
| 6,010,520 A | 1/2000 | Pattison |
| 6,012,494 A | 1/2000 | Balazs |
| 6,013,076 A | 1/2000 | Goble et al. |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,018,227 A | 1/2000 | Kumar et al. |
| 6,019,745 A | 2/2000 | Gray |
| 6,022,352 A | 2/2000 | Vandewalle |
| 6,023,641 A | 2/2000 | Thompson |
| 6,024,708 A | 2/2000 | Bales et al. |
| 6,024,741 A | 2/2000 | Williamson, IV et al. |
| 6,024,748 A | 2/2000 | Manzo et al. |
| 6,024,750 A | 2/2000 | Mastri et al. |
| 6,024,764 A | 2/2000 | Schroeppel |
| 6,027,501 A | 2/2000 | Goble et al. |
| 6,030,384 A | 2/2000 | Nezhat |
| 6,032,849 A | 3/2000 | Mastri et al. |
| 6,033,105 A | 3/2000 | Barker et al. |
| 6,033,378 A | 3/2000 | Lundquist et al. |
| 6,033,399 A | 3/2000 | Gines |
| 6,033,427 A | 3/2000 | Lee |
| 6,036,667 A | 3/2000 | Manna et al. |
| 6,037,724 A | 3/2000 | Buss et al. |
| 6,037,927 A | 3/2000 | Rosenberg |
| 6,039,733 A | 3/2000 | Buysse et al. |
| 6,039,734 A | 3/2000 | Goble |
| 6,042,601 A | 3/2000 | Smith |
| 6,042,607 A | 3/2000 | Williamson, IV et al. |
| 6,043,626 A | 3/2000 | Snyder et al. |
| 6,045,560 A | 4/2000 | McKean et al. |
| 6,047,861 A | 4/2000 | Vidal et al. |
| 6,049,145 A | 4/2000 | Austin et al. |
| 6,050,172 A | 4/2000 | Corves et al. |
| 6,050,472 A | 4/2000 | Shibata |
| 6,050,989 A | 4/2000 | Fox et al. |
| 6,050,990 A | 4/2000 | Tankovich et al. |
| 6,050,996 A | 4/2000 | Schmaltz et al. |
| 6,053,390 A | 4/2000 | Green et al. |
| 6,053,899 A | 4/2000 | Slanda et al. |
| 6,053,922 A | 4/2000 | Krause et al. |
| RE36,720 E | 5/2000 | Green et al. |
| 6,056,735 A | 5/2000 | Okada et al. |
| 6,056,746 A | 5/2000 | Goble et al. |
| 6,059,806 A | 5/2000 | Hoegerle |
| 6,062,360 A | 5/2000 | Shields |
| 6,063,025 A | 5/2000 | Bridges et al. |
| 6,063,050 A | 5/2000 | Manna et al. |
| 6,063,095 A | 5/2000 | Wang et al. |
| 6,063,097 A | 5/2000 | Oi et al. |
| 6,063,098 A | 5/2000 | Houser et al. |
| 6,065,679 A | 5/2000 | Levie et al. |
| 6,065,919 A | 5/2000 | Peck |
| 6,066,132 A | 5/2000 | Chen et al. |
| 6,066,151 A | 5/2000 | Miyawaki et al. |
| 6,068,627 A | 5/2000 | Orszulak et al. |
| 6,071,233 A | 6/2000 | Ishikawa et al. |
| 6,074,386 A | 6/2000 | Goble et al. |
| 6,074,401 A | 6/2000 | Gardiner et al. |
| 6,077,280 A | 6/2000 | Fossum |
| 6,077,286 A | 6/2000 | Cuschieri et al. |
| 6,077,290 A | 6/2000 | Marini |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,223 A * | 7/2000 | Baker ............... A61B 18/1445 606/49 |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,104,162 A | 8/2000 | Sainsbury et al. |
| 6,104,304 A | 8/2000 | Clark et al. |
| 6,106,511 A | 8/2000 | Jensen |
| 6,109,500 A | 8/2000 | Alli et al. |
| 6,110,187 A | 8/2000 | Donlon |
| 6,113,618 A | 9/2000 | Nic |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,120,462 A | 9/2000 | Hibner et al. |
| 6,123,241 A | 9/2000 | Walter et al. |
| 6,123,701 A | 9/2000 | Nezhat |
| H001904 H | 10/2000 | Yates et al. |
| 6,126,058 A | 10/2000 | Adams et al. |
| 6,126,359 A | 10/2000 | Dittrich et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,139,546 A | 10/2000 | Koenig et al. |
| 6,142,149 A | 11/2000 | Steen |
| 6,142,933 A | 11/2000 | Longo et al. |
| 6,147,135 A | 11/2000 | Yuan et al. |
| 6,149,660 A | 11/2000 | Laufer et al. |

(56) References Cited

U.S. PATENT DOCUMENTS

| | | |
|---|---|---|
| 6,151,323 A | 11/2000 | O'Connell et al. |
| 6,152,935 A | 11/2000 | Kammerer et al. |
| 6,155,473 A | 12/2000 | Tompkins et al. |
| 6,156,056 A | 12/2000 | Kearns et al. |
| 6,157,169 A | 12/2000 | Lee |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,162,220 A | 12/2000 | Nezhat |
| 6,162,537 A | 12/2000 | Martin et al. |
| 6,165,175 A | 12/2000 | Wampler et al. |
| 6,165,184 A | 12/2000 | Verdura et al. |
| 6,165,188 A | 12/2000 | Saadat et al. |
| 6,167,185 A | 12/2000 | Smiley et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,173,074 B1 | 1/2001 | Russo |
| 6,174,308 B1 | 1/2001 | Goble et al. |
| 6,174,309 B1 | 1/2001 | Wrublewski et al. |
| 6,174,318 B1 | 1/2001 | Bates et al. |
| 6,175,290 B1 | 1/2001 | Forsythe et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,185,356 B1 | 2/2001 | Parker et al. |
| 6,186,142 B1 | 2/2001 | Schmidt et al. |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,330 B1 | 3/2001 | Benderev et al. |
| 6,202,914 B1 | 3/2001 | Geiste et al. |
| 6,206,894 B1 | 3/2001 | Thompson et al. |
| 6,206,897 B1 | 3/2001 | Jamiolkowski et al. |
| 6,206,904 B1 | 3/2001 | Ouchi |
| 6,209,414 B1 | 4/2001 | Uneme |
| 6,210,403 B1 | 4/2001 | Klicek |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,221,007 B1 | 4/2001 | Green |
| 6,221,023 B1 * | 4/2001 | Matsuba .............. A61B 5/0215 600/486 |
| 6,223,100 B1 | 4/2001 | Green |
| 6,223,835 B1 | 5/2001 | Habedank et al. |
| 6,224,617 B1 | 5/2001 | Saadat et al. |
| 6,228,080 B1 | 5/2001 | Gines |
| 6,228,081 B1 | 5/2001 | Goble |
| 6,228,083 B1 | 5/2001 | Lands et al. |
| 6,228,084 B1 | 5/2001 | Kirwan, Jr. |
| 6,228,089 B1 | 5/2001 | Wahrburg |
| 6,228,098 B1 | 5/2001 | Kayan et al. |
| 6,231,565 B1 | 5/2001 | Tovey et al. |
| 6,234,178 B1 | 5/2001 | Goble et al. |
| 6,237,604 B1 | 5/2001 | Burnside et al. |
| 6,238,384 B1 | 5/2001 | Peer |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,116 B1 | 6/2001 | Chevillon et al. |
| 6,248,117 B1 | 6/2001 | Blatter |
| 6,249,076 B1 | 6/2001 | Madden et al. |
| 6,249,105 B1 | 6/2001 | Andrews et al. |
| 6,250,532 B1 | 6/2001 | Green et al. |
| 6,251,485 B1 | 6/2001 | Harris et al. |
| 6,254,534 B1 | 7/2001 | Butler et al. |
| 6,254,619 B1 | 7/2001 | Garabet et al. |
| 6,254,642 B1 | 7/2001 | Taylor |
| 6,258,107 B1 | 7/2001 | Balazs et al. |
| 6,261,286 B1 | 7/2001 | Goble et al. |
| 6,261,679 B1 | 7/2001 | Chen et al. |
| 6,264,086 B1 | 7/2001 | McGuckin, Jr. |
| 6,264,087 B1 | 7/2001 | Whitman |
| 6,264,617 B1 | 7/2001 | Bales et al. |
| 6,270,508 B1 | 8/2001 | Klieman et al. |
| 6,270,916 B1 | 8/2001 | Sink et al. |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,280,407 B1 | 8/2001 | Manna et al. |
| 6,293,927 B1 | 9/2001 | McGuckin, Jr. |
| 6,293,942 B1 | 9/2001 | Goble et al. |
| 6,296,640 B1 | 10/2001 | Wampler et al. |
| 6,302,311 B1 | 10/2001 | Adams et al. |
| 6,302,743 B1 | 10/2001 | Chiu et al. |
| 6,305,891 B1 | 10/2001 | Burlingame |
| 6,306,134 B1 | 10/2001 | Goble et al. |
| 6,306,149 B1 | 10/2001 | Meade |
| 6,306,424 B1 | 10/2001 | Vyakarnam et al. |
| 6,309,397 B1 | 10/2001 | Julian et al. |
| 6,309,403 B1 | 10/2001 | Minor et al. |
| 6,312,435 B1 | 11/2001 | Wallace et al. |
| 6,315,184 B1 | 11/2001 | Whitman |
| 6,319,510 B1 | 11/2001 | Yates |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,805 B1 | 12/2001 | Ogilvie et al. |
| 6,325,810 B1 | 12/2001 | Hamilton et al. |
| 6,328,498 B1 | 12/2001 | Mersch |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,348,061 B1 | 2/2002 | Whitman |
| D454,951 S | 3/2002 | Bon |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,358,263 B2 | 3/2002 | Mark et al. |
| 6,364,877 B1 | 4/2002 | Goble et al. |
| 6,364,888 B1 | 4/2002 | Niemeyer et al. |
| 6,370,981 B2 | 4/2002 | Watarai |
| 6,371,114 B1 | 4/2002 | Schmidt et al. |
| 6,373,152 B1 | 4/2002 | Wang et al. |
| 6,377,011 B1 | 4/2002 | Ben-Ur |
| 6,383,201 B1 | 5/2002 | Dong |
| 6,387,092 B1 | 5/2002 | Burnside et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,392,854 B1 | 5/2002 | O'Gorman |
| 6,398,779 B1 | 6/2002 | Buysse et al. |
| 6,398,781 B1 | 6/2002 | Goble et al. |
| 6,398,797 B2 | 6/2002 | Bombard et al. |
| 6,402,766 B2 | 6/2002 | Bowman et al. |
| 6,406,440 B1 | 6/2002 | Stefanchik |
| 6,406,472 B1 | 6/2002 | Jensen |
| 6,409,724 B1 | 6/2002 | Penny et al. |
| H002037 H | 7/2002 | Yates et al. |
| 6,412,639 B1 | 7/2002 | Hickey |
| 6,413,274 B1 | 7/2002 | Pedros |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| RE37,814 E | 8/2002 | Allgeyer |
| 6,428,070 B1 | 8/2002 | Takanashi et al. |
| 6,428,487 B1 | 8/2002 | Burdorff et al. |
| 6,429,611 B1 | 8/2002 | Li |

(56) References Cited

U.S. PATENT DOCUMENTS

| | | |
|---|---|---|
| 6,430,298 B1 | 8/2002 | Kettl et al. |
| 6,432,065 B1 | 8/2002 | Burdorff et al. |
| 6,436,097 B1 | 8/2002 | Nardella |
| 6,436,107 B1 | 8/2002 | Wang et al. |
| 6,436,110 B2 | 8/2002 | Bowman et al. |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,441,577 B2 | 8/2002 | Blumenkranz et al. |
| D462,758 S | 9/2002 | Epstein et al. |
| 6,443,973 B1 | 9/2002 | Whitman |
| 6,445,530 B1 | 9/2002 | Baker |
| 6,447,518 B1 | 9/2002 | Krause et al. |
| 6,447,523 B1 | 9/2002 | Middleman et al. |
| 6,447,799 B1 | 9/2002 | Ullman |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,458,077 B1 | 10/2002 | Boebel et al. |
| 6,458,147 B1 | 10/2002 | Cruise et al. |
| 6,460,627 B1 | 10/2002 | Below et al. |
| 6,468,275 B1 | 10/2002 | Wampler et al. |
| 6,468,286 B2 | 10/2002 | Mastri et al. |
| 6,471,106 B1 | 10/2002 | Reining |
| 6,471,659 B2 | 10/2002 | Eggers et al. |
| 6,478,210 B2 | 11/2002 | Adams et al. |
| 6,482,200 B2 | 11/2002 | Shippert |
| 6,482,217 B1 | 11/2002 | Pintor et al. |
| 6,485,490 B2 | 11/2002 | Wampler et al. |
| 6,485,503 B2 | 11/2002 | Jacobs et al. |
| 6,485,667 B1 | 11/2002 | Tan |
| 6,486,286 B1 | 11/2002 | McGall et al. |
| 6,488,196 B1 | 12/2002 | Fenton, Jr. |
| 6,488,197 B1 | 12/2002 | Whitman |
| 6,488,659 B1 | 12/2002 | Rosenman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,885 B1 | 12/2002 | Dhindsa |
| 6,494,896 B1 | 12/2002 | D'Alessio et al. |
| 6,498,480 B1 | 12/2002 | Manara |
| 6,500,176 B1 | 12/2002 | Truckai et al. |
| 6,500,194 B2 | 12/2002 | Benderev et al. |
| 6,503,139 B2 | 1/2003 | Coral |
| 6,503,257 B2 | 1/2003 | Grant et al. |
| 6,503,259 B2 | 1/2003 | Huxel et al. |
| 6,505,768 B2 | 1/2003 | Whitman |
| 6,506,197 B1 | 1/2003 | Rollero et al. |
| 6,510,854 B2 | 1/2003 | Goble |
| 6,511,468 B1 | 1/2003 | Cragg et al. |
| 6,512,360 B1 | 1/2003 | Goto et al. |
| 6,514,252 B2 | 2/2003 | Nezhat et al. |
| 6,516,073 B1 | 2/2003 | Schulz et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,520,971 B1 | 2/2003 | Perry et al. |
| 6,520,972 B2 | 2/2003 | Peters |
| 6,522,101 B2 | 2/2003 | Malackowski |
| 6,524,180 B1 | 2/2003 | Simms et al. |
| 6,527,782 B2 | 3/2003 | Hogg et al. |
| 6,527,785 B2 | 3/2003 | Sancoff et al. |
| 6,532,958 B1 | 3/2003 | Buan et al. |
| 6,533,157 B1 | 3/2003 | Whitman |
| 6,533,723 B1 | 3/2003 | Lockery et al. |
| 6,533,784 B2 | 3/2003 | Truckai et al. |
| 6,535,764 B2 | 3/2003 | Imran et al. |
| 6,539,816 B2 | 4/2003 | Kogiso et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,558,429 B2 | 5/2003 | Taylor |
| 6,561,187 B2 | 5/2003 | Schmidt et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,364 B2 | 6/2003 | Butler et al. |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,585,664 B2 | 7/2003 | Burdorff et al. |
| 6,587,750 B2 | 7/2003 | Gerbi et al. |
| 6,588,643 B2 | 7/2003 | Bolduc et al. |
| 6,588,931 B2 | 7/2003 | Betzner et al. |
| 6,589,118 B1 | 7/2003 | Soma et al. |
| 6,589,164 B1 | 7/2003 | Flaherty |
| 6,592,538 B1 | 7/2003 | Hotchkiss et al. |
| 6,592,597 B2 | 7/2003 | Grant et al. |
| 6,594,552 B1 | 7/2003 | Nowlin et al. |
| 6,596,296 B1 | 7/2003 | Nelson et al. |
| 6,596,304 B1 | 7/2003 | Bayon et al. |
| 6,596,432 B2 | 7/2003 | Kawakami et al. |
| 6,599,323 B2 | 7/2003 | Melican et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,603,050 B2 | 8/2003 | Heaton |
| 6,605,078 B2 | 8/2003 | Adams |
| 6,605,669 B2 | 8/2003 | Awokola et al. |
| 6,605,911 B1 | 8/2003 | Klesing |
| 6,607,475 B2 | 8/2003 | Doyle et al. |
| 6,611,793 B1 | 8/2003 | Burnside et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,111 B2 | 9/2003 | Stephens et al. |
| 6,620,166 B1 | 9/2003 | Wenstrom, Jr. et al. |
| 6,625,517 B1 | 9/2003 | Bogdanov et al. |
| 6,626,834 B2 | 9/2003 | Dunne et al. |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,648,901 B2 | 11/2003 | Fleischman et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,659,940 B2 | 12/2003 | Adler |
| 6,663,623 B1 | 12/2003 | Oyama et al. |
| 6,663,641 B1 | 12/2003 | Kovac et al. |
| 6,666,854 B1 | 12/2003 | Lange |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,670,806 B2 | 12/2003 | Wendt et al. |
| 6,671,185 B2 | 12/2003 | Duval |

(56) References Cited

U.S. PATENT DOCUMENTS

| | | | |
|---|---|---|---|
| D484,977 S | 1/2004 | Ryan et al. |
| 6,676,660 B2 | 1/2004 | Wampler et al. |
| 6,677,687 B2 | 1/2004 | Ho et al. |
| 6,679,269 B2 | 1/2004 | Swanson |
| 6,679,410 B2 | 1/2004 | Wursch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,682,544 B2 | 1/2004 | Mastri et al. |
| 6,685,698 B2 | 2/2004 | Morley et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,692,692 B2 | 2/2004 | Stetzel |
| 6,695,198 B2 | 2/2004 | Adams et al. |
| 6,695,199 B2 | 2/2004 | Whitman |
| 6,695,774 B2 | 2/2004 | Hale et al. |
| 6,696,814 B2 | 2/2004 | Henderson et al. |
| 6,697,048 B2 | 2/2004 | Rosenberg et al. |
| 6,698,643 B2 | 3/2004 | Whitman |
| 6,699,177 B1 | 3/2004 | Wang et al. |
| 6,699,214 B2 | 3/2004 | Gellman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 * | 4/2004 | Whitman ......... A61B 17/07207 606/219 |
| 6,720,734 B2 | 4/2004 | Norris |
| 6,722,550 B1 | 4/2004 | Ricordi et al. |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,723,109 B2 | 4/2004 | Solingen |
| 6,726,697 B2 | 4/2004 | Nicholas et al. |
| 6,726,706 B2 | 4/2004 | Dominguez |
| 6,729,119 B2 | 5/2004 | Schnipke et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,743,230 B2 | 6/2004 | Lutze et al. |
| 6,744,385 B2 | 6/2004 | Kazuya et al. |
| 6,747,121 B2 | 6/2004 | Gogolewski |
| 6,747,300 B2 | 6/2004 | Nadd et al. |
| 6,749,560 B1 | 6/2004 | Konstorum et al. |
| 6,749,600 B1 | 6/2004 | Levy |
| 6,752,768 B2 | 6/2004 | Burdorff et al. |
| 6,752,816 B2 | 6/2004 | Culp et al. |
| 6,754,959 B1 | 6/2004 | Guiette, III et al. |
| 6,755,195 B1 | 6/2004 | Lemke et al. |
| 6,755,338 B2 | 6/2004 | Hahnen et al. |
| 6,755,843 B2 | 6/2004 | Chung et al. |
| 6,756,705 B2 | 6/2004 | Pulford, Jr. |
| 6,758,846 B2 | 7/2004 | Goble et al. |
| 6,761,685 B2 | 7/2004 | Adams et al. |
| 6,762,339 B1 | 7/2004 | Klun et al. |
| 6,764,445 B2 | 7/2004 | Ramans et al. |
| 6,766,957 B2 | 7/2004 | Matsuura et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,070 B1 | 8/2004 | Balbierz |
| 6,770,072 B2 | 8/2004 | Truckai et al. |
| 6,773,409 B2 | 8/2004 | Truckai et al. |
| 6,773,438 B1 | 8/2004 | Knodel et al. |
| 6,775,575 B2 | 8/2004 | Bommannan et al. |
| 6,777,838 B2 | 8/2004 | Miekka et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,788,018 B1 | 9/2004 | Blumenkranz |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,793,669 B2 | 9/2004 | Nakamura et al. |
| 6,796,921 B1 | 9/2004 | Buck et al. |
| 6,802,822 B1 | 10/2004 | Dodge |
| 6,802,843 B2 | 10/2004 | Truckai et al. |
| 6,802,844 B2 | 10/2004 | Ferree |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,810,359 B2 | 10/2004 | Sakaguchi |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,836,611 B2 | 12/2004 | Popovic et al. |
| 6,837,846 B2 | 1/2005 | Jaffe et al. |
| 6,837,883 B2 | 1/2005 | Moll et al. |
| 6,838,493 B2 | 1/2005 | Williams et al. |
| 6,840,423 B2 | 1/2005 | Adams et al. |
| 6,841,967 B2 | 1/2005 | Kim et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,847,190 B2 | 1/2005 | Schaefer et al. |
| 6,849,071 B2 | 2/2005 | Whitman et al. |
| 6,850,817 B1 | 2/2005 | Green |
| 6,852,122 B2 | 2/2005 | Rush |
| 6,852,330 B2 | 2/2005 | Bowman et al. |
| 6,853,879 B2 | 2/2005 | Sunaoshi |
| 6,858,005 B2 | 2/2005 | Ohline et al. |
| 6,859,882 B2 | 2/2005 | Fung |
| RE38,708 E | 3/2005 | Bolanos et al. |
| D502,994 S | 3/2005 | Blake, III |
| 6,861,142 B1 | 3/2005 | Wilkie et al. |
| 6,861,954 B2 | 3/2005 | Levin |
| 6,863,668 B2 | 3/2005 | Gillespie et al. |
| 6,863,694 B1 | 3/2005 | Boyce et al. |
| 6,866,178 B2 | 3/2005 | Adams et al. |
| 6,866,671 B2 | 3/2005 | Tierney et al. |
| 6,867,248 B1 | 3/2005 | Martin et al. |
| 6,869,430 B2 | 3/2005 | Balbierz et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,884,392 B2 | 4/2005 | Malkin et al. |
| 6,884,428 B2 | 4/2005 | Binette et al. |
| 6,887,710 B2 | 5/2005 | Call et al. |
| 6,889,116 B2 | 5/2005 | Jinno |
| 6,893,435 B2 | 5/2005 | Goble |
| 6,894,140 B2 | 5/2005 | Roby |

(56) References Cited

U.S. PATENT DOCUMENTS

| | | | |
|---|---|---|---|
| 6,899,538 B2 | 5/2005 | Matoba | |
| 6,899,593 B1 | 5/2005 | Moeller et al. | |
| 6,905,057 B2 | 6/2005 | Swayze et al. | |
| 6,905,497 B2 * | 6/2005 | Truckai | A61B 18/1442 606/49 |
| 6,905,498 B2 | 6/2005 | Hooven | |
| 6,908,472 B2 | 6/2005 | Wiener et al. | |
| 6,911,033 B2 | 6/2005 | de Guillebon et al. | |
| 6,911,916 B1 | 6/2005 | Wang et al. | |
| 6,913,579 B2 | 7/2005 | Truckai et al. | |
| 6,913,608 B2 | 7/2005 | Liddicoat et al. | |
| 6,913,613 B2 | 7/2005 | Schwarz et al. | |
| 6,921,397 B2 | 7/2005 | Corcoran et al. | |
| 6,921,412 B1 | 7/2005 | Black et al. | |
| 6,923,093 B2 | 8/2005 | Ullah | |
| 6,923,803 B2 | 8/2005 | Goble | |
| 6,923,819 B2 | 8/2005 | Meade et al. | |
| 6,926,716 B2 | 8/2005 | Baker et al. | |
| 6,928,902 B1 | 8/2005 | Eyssallenne | |
| 6,929,641 B2 | 8/2005 | Goble et al. | |
| 6,929,644 B2 | 8/2005 | Truckai et al. | |
| 6,931,830 B2 | 8/2005 | Liao | |
| 6,932,218 B2 | 8/2005 | Kosann et al. | |
| 6,932,810 B2 | 8/2005 | Ryan | |
| 6,936,042 B2 | 8/2005 | Wallace et al. | |
| 6,936,948 B2 | 8/2005 | Bell et al. | |
| D509,297 S | 9/2005 | Wells | |
| D509,589 S | 9/2005 | Wells | |
| 6,939,358 B2 | 9/2005 | Palacios et al. | |
| 6,942,662 B2 | 9/2005 | Goble et al. | |
| 6,942,674 B2 | 9/2005 | Belef et al. | |
| 6,945,444 B2 | 9/2005 | Gresham et al. | |
| 6,945,981 B2 | 9/2005 | Donofrio et al. | |
| 6,951,562 B2 | 10/2005 | Zwirnmann | |
| 6,953,138 B1 | 10/2005 | Dworak et al. | |
| 6,953,139 B2 | 10/2005 | Milliman et al. | |
| 6,953,461 B2 * | 10/2005 | McClurken | A61B 18/14 606/206 |
| 6,958,035 B2 | 10/2005 | Friedman et al. | |
| 6,959,851 B2 | 11/2005 | Heinrich | |
| 6,959,852 B2 | 11/2005 | Shelton, IV et al. | |
| 6,960,107 B1 | 11/2005 | Schaub et al. | |
| 6,960,163 B2 | 11/2005 | Ewers et al. | |
| 6,960,220 B2 | 11/2005 | Marino et al. | |
| 6,962,587 B2 | 11/2005 | Johnson et al. | |
| 6,963,792 B1 | 11/2005 | Green | |
| 6,964,363 B2 | 11/2005 | Wales et al. | |
| 6,966,907 B2 | 11/2005 | Goble | |
| 6,966,909 B2 | 11/2005 | Marshall et al. | |
| 6,968,908 B2 | 11/2005 | Tokunaga et al. | |
| 6,969,385 B2 | 11/2005 | Moreyra | |
| 6,969,395 B2 | 11/2005 | Eskuri | |
| 6,971,988 B2 | 12/2005 | Orban, III | |
| 6,972,199 B2 | 12/2005 | Lebouitz et al. | |
| 6,974,435 B2 | 12/2005 | Daw et al. | |
| 6,974,462 B2 | 12/2005 | Sater | |
| 6,978,921 B2 | 12/2005 | Shelton, IV et al. | |
| 6,978,922 B2 | 12/2005 | Bilotti et al. | |
| 6,981,628 B2 | 1/2006 | Wales | |
| 6,981,941 B2 | 1/2006 | Whitman et al. | |
| 6,981,978 B2 | 1/2006 | Gannoe | |
| 6,984,203 B2 | 1/2006 | Tartaglia et al. | |
| 6,984,231 B2 | 1/2006 | Goble et al. | |
| 6,986,451 B1 | 1/2006 | Mastri et al. | |
| 6,988,649 B2 | 1/2006 | Shelton, IV et al. | |
| 6,988,650 B2 | 1/2006 | Schwemberger et al. | |
| 6,989,034 B2 | 1/2006 | Hammer et al. | |
| 6,990,731 B2 | 1/2006 | Haytayan | |
| 6,990,796 B2 | 1/2006 | Schnipke et al. | |
| 6,993,200 B2 | 1/2006 | Tastl et al. | |
| 6,993,413 B2 | 1/2006 | Sunaoshi | |
| 6,994,708 B2 | 2/2006 | Manzo | |
| 6,995,729 B2 | 2/2006 | Govari et al. | |
| 6,996,433 B2 | 2/2006 | Burbank et al. | |
| 6,997,931 B2 | 2/2006 | Sauer et al. | |
| 6,997,935 B2 | 2/2006 | Anderson et al. | |
| 6,998,736 B2 | 2/2006 | Lee et al. | |
| 6,998,816 B2 | 2/2006 | Wieck et al. | |
| 7,000,818 B2 | 2/2006 | Shelton, IV et al. | |
| 7,000,819 B2 | 2/2006 | Swayze et al. | |
| 7,000,911 B2 | 2/2006 | McCormick et al. | |
| 7,001,380 B2 | 2/2006 | Goble | |
| 7,001,408 B2 | 2/2006 | Knodel et al. | |
| 7,004,174 B2 | 2/2006 | Eggers et al. | |
| 7,007,176 B2 | 2/2006 | Goodfellow et al. | |
| 7,008,433 B2 | 3/2006 | Voellmicke et al. | |
| 7,008,435 B2 | 3/2006 | Cummins | |
| 7,009,039 B2 | 3/2006 | Yayon et al. | |
| 7,011,657 B2 | 3/2006 | Truckai et al. | |
| 7,014,640 B2 | 3/2006 | Kemppainen et al. | |
| 7,018,357 B2 | 3/2006 | Emmons | |
| 7,018,390 B2 | 3/2006 | Turovskiy et al. | |
| 7,021,669 B1 | 4/2006 | Lindermeir et al. | |
| 7,023,159 B2 | 4/2006 | Gorti et al. | |
| 7,025,064 B2 | 4/2006 | Wang et al. | |
| 7,025,732 B2 | 4/2006 | Thompson et al. | |
| 7,025,743 B2 | 4/2006 | Mann et al. | |
| 7,025,775 B2 | 4/2006 | Gadberry et al. | |
| 7,028,570 B2 | 4/2006 | Ohta et al. | |
| 7,029,435 B2 | 4/2006 | Nakao | |
| 7,029,439 B2 | 4/2006 | Roberts et al. | |
| 7,030,904 B2 | 4/2006 | Adair et al. | |
| 7,032,798 B2 | 4/2006 | Whitman et al. | |
| 7,032,799 B2 | 4/2006 | Viola et al. | |
| 7,033,356 B2 | 4/2006 | Latterell et al. | |
| 7,035,716 B2 | 4/2006 | Harris et al. | |
| 7,035,762 B2 | 4/2006 | Menard et al. | |
| 7,036,680 B1 | 5/2006 | Flannery | |
| 7,037,314 B2 | 5/2006 | Armstrong | |
| 7,037,344 B2 | 5/2006 | Kagan et al. | |
| 7,041,088 B2 | 5/2006 | Nawrocki et al. | |
| 7,041,102 B2 | 5/2006 | Truckai et al. | |
| 7,041,868 B2 | 5/2006 | Greene et al. | |
| 7,043,852 B2 | 5/2006 | Hayashida et al. | |
| 7,044,350 B2 | 5/2006 | Kameyama et al. | |
| 7,044,352 B2 | 5/2006 | Shelton, IV et al. | |
| 7,044,353 B2 | 5/2006 | Mastri et al. | |
| 7,046,082 B2 | 5/2006 | Komiya et al. | |
| 7,048,687 B1 | 5/2006 | Reuss et al. | |
| 7,048,745 B2 | 5/2006 | Tierney et al. | |
| 7,052,454 B2 | 5/2006 | Taylor | |
| 7,052,494 B2 | 5/2006 | Goble et al. | |
| 7,052,499 B2 | 5/2006 | Steger et al. | |
| 7,055,730 B2 | 6/2006 | Ehrenfels et al. | |
| 7,055,731 B2 | 6/2006 | Shelton, IV et al. | |
| 7,056,284 B2 | 6/2006 | Martone et al. | |
| 7,056,330 B2 | 6/2006 | Gayton | |
| 7,059,331 B2 | 6/2006 | Adams et al. | |
| 7,059,508 B2 | 6/2006 | Shelton, IV et al. | |
| 7,063,671 B2 | 6/2006 | Couvillon, Jr. | |
| 7,063,712 B2 | 6/2006 | Vargas et al. | |
| 7,064,509 B1 | 6/2006 | Fu et al. | |
| 7,066,879 B2 | 6/2006 | Fowler et al. | |
| 7,066,944 B2 | 6/2006 | Laufer et al. | |
| 7,067,038 B2 | 6/2006 | Trokhan et al. | |
| 7,070,083 B2 | 7/2006 | Jankowski | |
| 7,070,559 B2 | 7/2006 | Adams et al. | |
| 7,070,597 B2 | 7/2006 | Truckai et al. | |
| 7,071,287 B2 | 7/2006 | Rhine et al. | |
| 7,075,770 B1 | 7/2006 | Smith | |
| 7,077,856 B2 | 7/2006 | Whitman | |
| 7,080,769 B2 | 7/2006 | Vresh et al. | |
| 7,081,114 B2 | 7/2006 | Rashidi | |
| 7,083,073 B2 | 8/2006 | Yoshie et al. | |
| 7,083,075 B2 | 8/2006 | Swayze et al. | |
| 7,083,571 B2 | 8/2006 | Wang et al. | |
| 7,083,615 B2 | 8/2006 | Peterson et al. | |
| 7,083,619 B2 | 8/2006 | Truckai et al. | |
| 7,083,620 B2 | 8/2006 | Jahns et al. | |
| 7,083,626 B2 | 8/2006 | Hart et al. | |
| 7,087,049 B2 | 8/2006 | Nowlin et al. | |
| 7,087,054 B2 | 8/2006 | Truckai et al. | |
| 7,087,071 B2 | 8/2006 | Nicholas et al. | |
| 7,090,637 B2 | 8/2006 | Danitz et al. | |

(56) References Cited

U.S. PATENT DOCUMENTS

| | | |
|---|---|---|
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,091,412 B2 | 8/2006 | Wang et al. |
| 7,094,202 B2 | 8/2006 | Nobis et al. |
| 7,094,247 B2 | 8/2006 | Monassevitch et al. |
| 7,094,916 B2 | 8/2006 | DeLuca et al. |
| 7,096,972 B2 | 8/2006 | Orozco, Jr. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,101,187 B1 | 9/2006 | Deconinck et al. |
| 7,101,394 B2 | 9/2006 | Hamm et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,768 B2 | 9/2006 | Cummins et al. |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,116,100 B1 | 10/2006 | Mock et al. |
| 7,118,020 B2 | 10/2006 | Lee et al. |
| 7,118,528 B1 | 10/2006 | Piskun |
| 7,118,563 B2 | 10/2006 | Weckwerth et al. |
| 7,118,582 B1 | 10/2006 | Wang et al. |
| 7,119,534 B2 | 10/2006 | Butzmann |
| 7,121,446 B2 | 10/2006 | Arad et al. |
| 7,122,028 B2 | 10/2006 | Looper et al. |
| 7,125,403 B2 | 10/2006 | Julian et al. |
| 7,125,409 B2 | 10/2006 | Truckai et al. |
| 7,126,303 B2 | 10/2006 | Farritor et al. |
| 7,126,879 B2 | 10/2006 | Snyder |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,587 B2 | 11/2006 | Schwemberger et al. |
| 7,135,027 B2 | 11/2006 | Delmotte |
| 7,137,980 B2 | 11/2006 | Buysse et al. |
| 7,137,981 B2 | 11/2006 | Long |
| 7,139,016 B2 | 11/2006 | Squilla et al. |
| 7,140,527 B2 | 11/2006 | Ehrenfels et al. |
| 7,140,528 B2 | 11/2006 | Shelton, IV |
| 7,141,055 B2 | 11/2006 | Abrams et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,146,191 B2 | 12/2006 | Kerner et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,648 B2 | 12/2006 | Lin |
| 7,147,650 B2 | 12/2006 | Lee |
| 7,150,748 B2 | 12/2006 | Ebbutt et al. |
| 7,153,300 B2 | 12/2006 | Goble |
| 7,155,316 B2 | 12/2006 | Sutherland et al. |
| 7,156,863 B2 | 1/2007 | Sonnenschein et al. |
| 7,159,750 B2 | 1/2007 | Racenet et al. |
| 7,160,296 B2 | 1/2007 | Pearson et al. |
| 7,160,299 B2 | 1/2007 | Baily |
| 7,161,036 B2 | 1/2007 | Oikawa et al. |
| 7,161,580 B2 | 1/2007 | Bailey et al. |
| 7,163,563 B2 | 1/2007 | Schwartz et al. |
| 7,166,133 B2 | 1/2007 | Evans et al. |
| 7,168,604 B2 | 1/2007 | Milliman et al. |
| 7,170,910 B2 | 1/2007 | Chen et al. |
| 7,171,279 B2 | 1/2007 | Buckingham et al. |
| 7,172,104 B2 | 2/2007 | Scirica et al. |
| 7,172,593 B2 | 2/2007 | Trieu et al. |
| 7,172,615 B2 | 2/2007 | Morriss et al. |
| 7,174,636 B2 | 2/2007 | Lowe |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,187,960 B2 | 3/2007 | Abreu |
| 7,188,758 B2 | 3/2007 | Viola et al. |
| 7,189,207 B2 | 3/2007 | Viola |
| 7,190,147 B2 | 3/2007 | Gileff et al. |
| 7,195,627 B2 | 3/2007 | Amoah et al. |
| 7,196,911 B2 | 3/2007 | Takano et al. |
| D541,418 S | 4/2007 | Schechter et al. |
| 7,199,537 B2 | 4/2007 | Okamura et al. |
| 7,202,576 B1 | 4/2007 | Dechene et al. |
| 7,202,653 B2 | 4/2007 | Pai |
| 7,204,404 B2 | 4/2007 | Nguyen et al. |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,211,979 B2 | 5/2007 | Khatib et al. |
| 7,213,736 B2 | 5/2007 | Wales et al. |
| 7,214,224 B2 | 5/2007 | Goble |
| 7,215,517 B2 | 5/2007 | Takamatsu |
| 7,217,285 B2 | 5/2007 | Vargas et al. |
| 7,220,260 B2 | 5/2007 | Fleming et al. |
| 7,220,272 B2 | 5/2007 | Weadock |
| 7,225,959 B2 | 6/2007 | Patton et al. |
| 7,225,963 B2 | 6/2007 | Scirica |
| 7,225,964 B2 | 6/2007 | Mastri et al. |
| 7,226,450 B2 | 6/2007 | Athanasiou et al. |
| 7,229,408 B2 | 6/2007 | Douglas et al. |
| 7,234,624 B2 | 6/2007 | Gresham et al. |
| 7,235,072 B2 | 6/2007 | Sartor et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,238,901 B2 | 7/2007 | Kim et al. |
| 7,239,657 B1 | 7/2007 | Gunnarsson |
| 7,241,288 B2 | 7/2007 | Braun |
| 7,241,289 B2 | 7/2007 | Braun |
| 7,246,734 B2 | 7/2007 | Shelton, IV |
| 7,247,161 B2 | 7/2007 | Johnston et al. |
| 7,249,267 B2 | 7/2007 | Chapuis |
| 7,252,641 B2 | 8/2007 | Thompson et al. |
| 7,252,660 B2 | 8/2007 | Kunz |
| 7,255,012 B2 | 8/2007 | Hedtke |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,677 B2 | 9/2007 | Johnson et al. |
| 7,267,679 B2 | 9/2007 | McGuckin, Jr. et al. |
| 7,272,002 B2 | 9/2007 | Drapeau |
| 7,273,483 B2 | 9/2007 | Wiener et al. |
| 7,275,674 B2 | 10/2007 | Racenet et al. |
| 7,276,044 B2 | 10/2007 | Ferry et al. |
| 7,276,068 B2 | 10/2007 | Johnson et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,286,850 B2 | 10/2007 | Frielink et al. |
| 7,287,682 B1 | 10/2007 | Ezzat et al. |
| 7,289,139 B2 | 10/2007 | Amling et al. |
| 7,293,685 B2 | 11/2007 | Ehrenfels et al. |

(56) References Cited

U.S. PATENT DOCUMENTS

| | | |
|---|---|---|
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,311,238 B2 | 12/2007 | Liu |
| 7,313,430 B2 | 12/2007 | Urquhart et al. |
| 7,314,473 B2 | 1/2008 | Jinno et al. |
| 7,322,859 B2 | 1/2008 | Evans |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,331,343 B2 | 2/2008 | Schmidt et al. |
| 7,331,403 B2 | 2/2008 | Berry et al. |
| 7,331,969 B1 | 2/2008 | Inganas et al. |
| 7,334,717 B2 | 2/2008 | Rethy et al. |
| 7,334,718 B2 | 2/2008 | McAlister et al. |
| 7,335,199 B2 | 2/2008 | Goble et al. |
| 7,336,045 B2 | 2/2008 | Clermonts |
| 7,336,048 B2 | 2/2008 | Lohr |
| 7,336,184 B2 | 2/2008 | Smith et al. |
| 7,337,774 B2 | 3/2008 | Webb |
| 7,338,505 B2 | 3/2008 | Belson |
| 7,338,513 B2 | 3/2008 | Lee et al. |
| 7,341,591 B2 | 3/2008 | Grinberg |
| 7,343,920 B2 | 3/2008 | Toby et al. |
| 7,344,532 B2 | 3/2008 | Goble et al. |
| 7,344,533 B2 | 3/2008 | Pearson et al. |
| 7,346,344 B2 | 3/2008 | Fontaine |
| 7,346,406 B2 | 3/2008 | Brotto et al. |
| 7,348,763 B1 | 3/2008 | Reinhart et al. |
| 7,348,875 B2 | 3/2008 | Hughes et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,168 B2 | 4/2008 | Makower et al. |
| 7,361,195 B2 | 4/2008 | Schwartz et al. |
| 7,364,060 B2 | 4/2008 | Milliman |
| 7,364,061 B2 | 4/2008 | Swayze et al. |
| 7,368,124 B2 | 5/2008 | Chun et al. |
| 7,371,210 B2 | 5/2008 | Brock et al. |
| 7,371,403 B2 | 5/2008 | McCarthy et al. |
| 7,377,918 B2 | 5/2008 | Amoah |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,384,403 B2 | 6/2008 | Sherman |
| 7,384,417 B2 | 6/2008 | Cucin |
| 7,386,365 B2 | 6/2008 | Nixon |
| 7,386,730 B2 | 6/2008 | Uchikubo |
| 7,388,217 B2 | 6/2008 | Buschbeck et al. |
| 7,388,484 B2 | 6/2008 | Hsu |
| 7,391,173 B2 | 6/2008 | Schena |
| 7,394,190 B2 | 7/2008 | Huang |
| 7,396,356 B2 | 7/2008 | Mollenauer |
| 7,397,364 B2 | 7/2008 | Govari |
| 7,398,707 B2 | 7/2008 | Morley et al. |
| 7,398,907 B2 | 7/2008 | Racenet et al. |
| 7,398,908 B2 | 7/2008 | Holsten et al. |
| 7,400,107 B2 | 7/2008 | Schneider et al. |
| 7,400,752 B2 | 7/2008 | Zacharias |
| 7,401,000 B2 | 7/2008 | Nakamura |
| 7,401,721 B2 | 7/2008 | Holsten et al. |
| 7,404,449 B2 | 7/2008 | Bermingham et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,408,310 B2 | 8/2008 | Hong et al. |
| 7,410,085 B2 | 8/2008 | Wolf et al. |
| 7,410,086 B2 | 8/2008 | Ortiz et al. |
| 7,410,483 B2 | 8/2008 | Danitz et al. |
| 7,413,563 B2 | 8/2008 | Corcoran et al. |
| 7,416,101 B2 * | 8/2008 | Shelton, IV ..... A61B 17/07207 227/175.1 |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,321 B2 | 9/2008 | Tereschouk |
| 7,419,495 B2 | 9/2008 | Menn et al. |
| 7,422,136 B1 | 9/2008 | Marczyk |
| 7,422,138 B2 | 9/2008 | Bilotti et al. |
| 7,424,965 B2 | 9/2008 | Racenet et al. |
| 7,427,607 B2 | 9/2008 | Suzuki |
| D578,644 S | 10/2008 | Shumer et al. |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,435,249 B2 | 10/2008 | Buysse et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,443,547 B2 | 10/2008 | Moreno et al. |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,461,767 B2 | 12/2008 | Viola et al. |
| 7,462,187 B2 | 12/2008 | Johnston et al. |
| 7,464,845 B2 | 12/2008 | Chou |
| 7,464,846 B2 * | 12/2008 | Shelton, IV ..... A61B 17/07207 227/175.1 |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,221 B2 | 1/2009 | Ewers et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,124 B2 | 2/2009 | Kuhns et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,489,055 B2 | 2/2009 | Jeong et al. |
| 7,490,749 B2 | 2/2009 | Schall et al. |

(56) References Cited

U.S. PATENT DOCUMENTS

| | | |
|---|---|---|
| 7,491,232 B2 | 2/2009 | Bolduc et al. |
| 7,494,039 B2 | 2/2009 | Racenet et al. |
| 7,494,499 B2 | 2/2009 | Nagase et al. |
| 7,494,501 B2 | 2/2009 | Ahlberg et al. |
| 7,500,979 B2 | 3/2009 | Hueil et al. |
| 7,501,198 B2 | 3/2009 | Barley et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,534 B2 | 3/2009 | Burdorff et al. |
| 7,510,566 B2 | 3/2009 | Jacobs et al. |
| 7,513,407 B1 | 4/2009 | Chang |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,527,632 B2 | 5/2009 | Houghton et al. |
| 7,530,984 B2 | 5/2009 | Sonnenschein et al. |
| 7,530,985 B2 | 5/2009 | Takemoto et al. |
| 7,533,906 B2 | 5/2009 | Luettgen et al. |
| 7,534,259 B2 | 5/2009 | Lashinski et al. |
| 7,540,867 B2 | 6/2009 | Jinno et al. |
| 7,542,807 B2 | 6/2009 | Bertolero et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,553,173 B2 | 6/2009 | Kowalick |
| 7,553,275 B2 | 6/2009 | Padget et al. |
| 7,554,343 B2 | 6/2009 | Bromfield |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,561,637 B2 | 7/2009 | Jonsson et al. |
| 7,562,910 B2 | 7/2009 | Kertesz et al. |
| 7,563,269 B2 | 7/2009 | Hashiguchi |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,578,825 B2 | 8/2009 | Huebner |
| 7,583,063 B2 | 9/2009 | Dooley |
| 7,586,289 B2 | 9/2009 | Andruk et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,591,818 B2 | 9/2009 | Bertolero et al. |
| 7,597,229 B2 | 10/2009 | Boudreaux et al. |
| 7,597,230 B2 | 10/2009 | Racenet et al. |
| 7,597,693 B2 | 10/2009 | Garrison |
| 7,597,699 B2 | 10/2009 | Rogers |
| 7,598,972 B2 | 10/2009 | Tomita |
| 7,600,663 B2 | 10/2009 | Green |
| 7,604,150 B2 | 10/2009 | Boudreaux |
| 7,604,151 B2 | 10/2009 | Hess et al. |
| 7,604,668 B2 | 10/2009 | Farnsworth et al. |
| 7,607,557 B2 | 10/2009 | Shelton, IV et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,067 B2 | 11/2009 | Lee et al. |
| 7,617,961 B2 | 11/2009 | Viola |
| 7,624,902 B2 | 12/2009 | Marczyk et al. |
| 7,624,903 B2 | 12/2009 | Green et al. |
| 7,625,370 B2 | 12/2009 | Hart et al. |
| 7,630,841 B2 | 12/2009 | Comisky et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,457 B2 | 1/2010 | Stefanchik et al. |
| 7,648,519 B2 | 1/2010 | Lee et al. |
| 7,650,185 B2 | 1/2010 | Maile et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,004 B2 | 2/2010 | Long |
| 7,655,288 B2 | 2/2010 | Bauman et al. |
| 7,655,584 B2 | 2/2010 | Biran et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,658,705 B2 | 2/2010 | Melvin et al. |
| 7,659,219 B2 | 2/2010 | Biran et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,682,307 B2 | 3/2010 | Danitz et al. |
| 7,682,367 B2 | 3/2010 | Shah et al. |
| 7,682,686 B2 | 3/2010 | Curro et al. |
| 7,686,201 B2 | 3/2010 | Csiky |
| 7,686,804 B2 | 3/2010 | Johnson et al. |
| 7,686,826 B2 | 3/2010 | Lee et al. |
| 7,688,028 B2 | 3/2010 | Phillips et al. |
| 7,691,098 B2 | 4/2010 | Wallace et al. |
| 7,691,103 B2 | 4/2010 | Fernandez et al. |
| 7,691,106 B2 | 4/2010 | Schenberger et al. |
| 7,694,864 B2 | 4/2010 | Okada et al. |
| 7,694,865 B2 | 4/2010 | Scirica |
| 7,695,485 B2 | 4/2010 | Whitman et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,703,653 B2 | 4/2010 | Shah et al. |
| 7,708,180 B2 | 5/2010 | Murray et al. |
| 7,708,181 B2 | 5/2010 | Cole et al. |
| 7,708,182 B2 | 5/2010 | Viola |
| 7,708,758 B2 | 5/2010 | Lee et al. |
| 7,712,182 B2 | 5/2010 | Zeiler et al. |
| 7,713,190 B2 | 5/2010 | Brock et al. |
| 7,714,239 B2 | 5/2010 | Smith |
| 7,714,334 B2 | 5/2010 | Lin |
| 7,717,312 B2 * | 5/2010 | Beetel ............... A61B 17/068 227/175.1 |
| 7,717,313 B2 | 5/2010 | Criscuolo et al. |
| 7,717,846 B2 | 5/2010 | Zirps et al. |

(56) References Cited

U.S. PATENT DOCUMENTS

| | | | |
|---|---|---|---|
| 7,717,873 B2 | 5/2010 | Swick |
| 7,717,915 B2 | 5/2010 | Miyazawa |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,725,214 B2 | 5/2010 | Diolaiti |
| 7,726,171 B2 | 6/2010 | Langlotz et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,728,553 B2 | 6/2010 | Carrier et al. |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,736,254 B2 | 6/2010 | Schena |
| 7,736,306 B2 | 6/2010 | Brustad et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,742,036 B2 | 6/2010 | Grant et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,747,146 B2 | 6/2010 | Milano et al. |
| 7,748,587 B2 | 7/2010 | Haramiishi et al. |
| 7,748,632 B2 | 7/2010 | Coleman et al. |
| 7,749,204 B2 | 7/2010 | Dhanaraj et al. |
| 7,751,870 B2 | 7/2010 | Whitman |
| 7,753,245 B2 | 7/2010 | Boudreaux et al. |
| 7,753,246 B2 | 7/2010 | Scirica |
| 7,753,904 B2 | 7/2010 | Shelton, IV et al. |
| 7,757,924 B2 | 7/2010 | Gerbi et al. |
| 7,758,612 B2 | 7/2010 | Shipp |
| 7,762,462 B2 | 7/2010 | Gelbman |
| 7,762,998 B2 | 7/2010 | Birk et al. |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,658 B2 | 8/2010 | Ito et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,772,725 B2 | 8/2010 | Siman-Tov |
| 7,775,972 B2 | 8/2010 | Brock et al. |
| 7,776,037 B2 | 8/2010 | Odom |
| 7,776,060 B2 | 8/2010 | Mooradian et al. |
| 7,776,065 B2 | 8/2010 | Griffiths et al. |
| 7,778,004 B2 | 8/2010 | Nerheim et al. |
| 7,780,054 B2 | 8/2010 | Wales |
| 7,780,055 B2 | 8/2010 | Scirica et al. |
| 7,780,309 B2 | 8/2010 | McMillan et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,787,256 B2 | 8/2010 | Chan et al. |
| 7,789,283 B2 | 9/2010 | Shah |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,871 B2 | 10/2010 | Li et al. |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,811,275 B2 | 10/2010 | Birk et al. |
| 7,814,816 B2 | 10/2010 | Alberti et al. |
| 7,815,092 B2 | 10/2010 | Whitman et al. |
| 7,815,565 B2 | 10/2010 | Stefanchik et al. |
| 7,815,662 B2 | 10/2010 | Spivey et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,799 B2 | 10/2010 | Merril et al. |
| 7,819,884 B2 | 10/2010 | Lee et al. |
| 7,819,886 B2 | 10/2010 | Whitfield et al. |
| 7,823,592 B2 | 11/2010 | Bettuchi et al. |
| 7,823,760 B2 * | 11/2010 | Zemlok ............ A61B 17/07207 227/175.1 |
| 7,824,401 B2 | 11/2010 | Manzo et al. |
| 7,824,422 B2 | 11/2010 | Benchetrit |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,831,292 B2 | 11/2010 | Quaid et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,835,823 B2 | 11/2010 | Sillman et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,425 B2 | 11/2010 | Saeki et al. |
| 7,837,685 B2 | 11/2010 | Weinberg et al. |
| 7,837,694 B2 | 11/2010 | Tethrake et al. |
| 7,838,789 B2 | 11/2010 | Stoffers et al. |
| 7,839,109 B2 | 11/2010 | Carmen, Jr. et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,843,158 B2 | 11/2010 | Prisco |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,846,085 B2 | 12/2010 | Silverman et al. |
| 7,846,149 B2 | 12/2010 | Jankowski |
| 7,848,066 B2 | 12/2010 | Yanagishima |
| 7,850,623 B2 | 12/2010 | Griffin et al. |
| 7,850,642 B2 | 12/2010 | Moll et al. |
| 7,850,982 B2 | 12/2010 | Stopek et al. |
| 7,854,735 B2 | 12/2010 | Houser et al. |
| 7,854,736 B2 | 12/2010 | Ryan |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,502 B2 | 1/2011 | Pool et al. |
| 7,862,546 B2 | 1/2011 | Conlon et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |

(56) References Cited

U.S. PATENT DOCUMENTS

| | | | |
|---|---|---|---|
| 7,870,989 B2 | 1/2011 | Viola et al. |
| 7,871,418 B2 | 1/2011 | Thompson et al. |
| 7,871,440 B2 | 1/2011 | Schwartz et al. |
| 7,875,055 B2 | 1/2011 | Cichocki, Jr. |
| 7,879,063 B2 | 2/2011 | Khosravi |
| 7,879,070 B2 | 2/2011 | Ortiz et al. |
| 7,883,461 B2 | 2/2011 | Albrecht et al. |
| 7,883,465 B2 | 2/2011 | Donofrio et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,887,536 B2 | 2/2011 | Johnson et al. |
| 7,887,563 B2 | 2/2011 | Cummins |
| 7,891,531 B1 | 2/2011 | Ward |
| 7,891,532 B2 | 2/2011 | Mastri et al. |
| 7,892,200 B2 | 2/2011 | Birk et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,869 B2 | 3/2011 | DiSilvestro et al. |
| 7,896,877 B2 | 3/2011 | Hall et al. |
| 7,896,895 B2 | 3/2011 | Boudreaux et al. |
| 7,896,897 B2 | 3/2011 | Gresham et al. |
| 7,898,198 B2 | 3/2011 | Murphree |
| 7,900,805 B2 | 3/2011 | Shelton, IV et al. |
| 7,900,806 B2 | 3/2011 | Chen et al. |
| 7,901,381 B2 | 3/2011 | Birk et al. |
| 7,905,380 B2 | 3/2011 | Shelton, IV et al. |
| 7,905,381 B2 | 3/2011 | Baxter, III et al. |
| 7,905,881 B2 | 3/2011 | Masuda et al. |
| 7,905,889 B2 | 3/2011 | Catanese, III et al. |
| 7,905,902 B2 | 3/2011 | Huitema et al. |
| 7,909,039 B2 | 3/2011 | Hur |
| 7,909,191 B2 | 3/2011 | Baker et al. |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,918,848 B2 | 4/2011 | Lau et al. |
| 7,918,861 B2 | 4/2011 | Brock et al. |
| 7,918,867 B2 | 4/2011 | Dana et al. |
| 7,922,061 B2 | 4/2011 | Shelton, IV et al. |
| 7,922,063 B2 * | 4/2011 | Zemlok ............ A61B 17/07207 227/175.1 |
| 7,922,743 B2 | 4/2011 | Heinrich et al. |
| 7,923,144 B2 | 4/2011 | Kohn et al. |
| 7,926,691 B2 | 4/2011 | Viola et al. |
| 7,927,328 B2 | 4/2011 | Orszulak et al. |
| 7,928,281 B2 | 4/2011 | Augustine |
| 7,930,040 B1 | 4/2011 | Kelsch et al. |
| 7,930,065 B2 | 4/2011 | Larkin et al. |
| 7,931,660 B2 | 4/2011 | Aranyi et al. |
| 7,931,695 B2 | 4/2011 | Ringeisen |
| 7,931,877 B2 | 4/2011 | Steffens et al. |
| 7,934,630 B2 | 5/2011 | Shelton, IV et al. |
| 7,934,631 B2 | 5/2011 | Balbierz et al. |
| 7,935,773 B2 | 5/2011 | Hadba et al. |
| 7,938,307 B2 | 5/2011 | Bettuchi |
| 7,941,865 B2 | 5/2011 | Seman, Jr. et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,945,792 B2 | 5/2011 | Cherpantier |
| 7,945,798 B2 | 5/2011 | Carlson et al. |
| 7,946,453 B2 | 5/2011 | Voegele et al. |
| 7,947,011 B2 | 5/2011 | Birk et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,951,166 B2 | 5/2011 | Orban, III et al. |
| 7,954,682 B2 | 6/2011 | Giordano et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,955,253 B2 | 6/2011 | Ewers et al. |
| 7,955,257 B2 | 6/2011 | Frasier et al. |
| 7,955,322 B2 | 6/2011 | Devengenzo et al. |
| 7,955,327 B2 | 6/2011 | Sartor et al. |
| 7,955,380 B2 | 6/2011 | Chu et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,913 B2 | 6/2011 | Devengenzo et al. |
| 7,963,963 B2 | 6/2011 | Francischelli et al. |
| 7,963,964 B2 | 6/2011 | Santilli et al. |
| 7,964,206 B2 | 6/2011 | Suokas et al. |
| 7,966,236 B2 | 6/2011 | Noriega et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,791 B2 | 6/2011 | Franer et al. |
| 7,967,839 B2 | 6/2011 | Flock et al. |
| 7,972,298 B2 | 7/2011 | Wallace et al. |
| 7,972,315 B2 | 7/2011 | Birk et al. |
| 7,976,213 B2 | 7/2011 | Bertolotti et al. |
| 7,976,563 B2 | 7/2011 | Summerer |
| 7,979,137 B2 | 7/2011 | Tracey et al. |
| 7,980,443 B2 | 7/2011 | Scheib et al. |
| 7,981,132 B2 | 7/2011 | Dubrul et al. |
| 7,987,405 B2 | 7/2011 | Turner et al. |
| 7,988,015 B2 | 8/2011 | Mason, II et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,988,779 B2 | 8/2011 | Disalvo et al. |
| 7,992,757 B2 | 8/2011 | Wheeler et al. |
| 7,993,360 B2 | 8/2011 | Hacker et al. |
| 7,994,670 B2 | 8/2011 | Ji |
| 7,997,054 B2 | 8/2011 | Bertsch et al. |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,370 B2 | 8/2011 | Hirsch et al. |
| 8,007,465 B2 | 8/2011 | Birk et al. |
| 8,007,479 B2 | 8/2011 | Birk et al. |
| 8,007,511 B2 | 8/2011 | Brock et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,028,882 B2 | 10/2011 | Viola |

(56) References Cited

U.S. PATENT DOCUMENTS

| | | |
|---|---|---|
| 8,028,883 B2 | 10/2011 | Stopek |
| 8,028,884 B2 | 10/2011 | Sniffin et al. |
| 8,028,885 B2 | 10/2011 | Smith et al. |
| 8,029,510 B2 | 10/2011 | Hoegerle |
| 8,031,069 B2 | 10/2011 | Cohn et al. |
| 8,033,438 B2 | 10/2011 | Scirica |
| 8,033,439 B2 | 10/2011 | Racenet et al. |
| 8,033,440 B2 | 10/2011 | Wenchell et al. |
| 8,034,077 B2 | 10/2011 | Smith et al. |
| 8,034,337 B2 | 10/2011 | Simard |
| 8,034,363 B2 | 10/2011 | Li et al. |
| 8,035,487 B2 | 10/2011 | Malackowski |
| 8,037,591 B2 | 10/2011 | Spivey et al. |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,044,536 B2 | 10/2011 | Nguyen et al. |
| 8,044,604 B2 | 10/2011 | Hagino et al. |
| 8,047,236 B2 | 11/2011 | Perry |
| 8,048,503 B2 | 11/2011 | Farnsworth et al. |
| 8,052,636 B2 | 11/2011 | Moll et al. |
| 8,056,787 B2 | 11/2011 | Boudreaux et al. |
| 8,056,788 B2 | 11/2011 | Mastri et al. |
| 8,056,789 B1 | 11/2011 | White et al. |
| 8,057,508 B2 | 11/2011 | Shelton, IV |
| 8,058,771 B2 | 11/2011 | Giordano et al. |
| 8,060,250 B2 | 11/2011 | Reiland et al. |
| 8,061,014 B2 | 11/2011 | Smith et al. |
| 8,061,576 B2 | 11/2011 | Cappola |
| 8,062,236 B2 | 11/2011 | Soltz |
| 8,062,330 B2 | 11/2011 | Prommersberger et al. |
| 8,063,619 B2 | 11/2011 | Zhu et al. |
| 8,066,158 B2 | 11/2011 | Vogel et al. |
| 8,066,166 B2 | 11/2011 | Demmy et al. |
| 8,066,167 B2 | 11/2011 | Measamer et al. |
| 8,066,168 B2 | 11/2011 | Vidal et al. |
| 8,066,720 B2 | 11/2011 | Knodel et al. |
| D650,074 S | 12/2011 | Hunt et al. |
| 8,070,033 B2 | 12/2011 | Milliman et al. |
| 8,070,035 B2 | 12/2011 | Holsten et al. |
| 8,070,743 B2 | 12/2011 | Kagan et al. |
| 8,074,858 B2 | 12/2011 | Marczyk |
| 8,074,861 B2 | 12/2011 | Ehrenfels et al. |
| 8,075,476 B2 | 12/2011 | Vargas |
| 8,075,571 B2 | 12/2011 | Vitali et al. |
| 8,079,950 B2 | 12/2011 | Stern et al. |
| 8,079,989 B2 | 12/2011 | Birk et al. |
| 8,080,004 B2 | 12/2011 | Downey et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,084,969 B2 | 12/2011 | David et al. |
| 8,085,013 B2 | 12/2011 | Wei et al. |
| 8,087,563 B2 | 1/2012 | Milliman et al. |
| 8,089,509 B2 | 1/2012 | Chatenever et al. |
| 8,091,753 B2 | 1/2012 | Viola |
| 8,091,756 B2 | 1/2012 | Viola |
| 8,092,443 B2 | 1/2012 | Bischoff |
| 8,092,932 B2 | 1/2012 | Phillips et al. |
| 8,093,572 B2 | 1/2012 | Kuduvalli |
| 8,096,458 B2 | 1/2012 | Hessler |
| 8,097,017 B2 | 1/2012 | Viola |
| 8,100,310 B2 | 1/2012 | Zemlok |
| 8,100,824 B2 | 1/2012 | Hegeman et al. |
| 8,100,872 B2 | 1/2012 | Patel |
| 8,102,278 B2 | 1/2012 | Deck et al. |
| 8,105,350 B2 | 1/2012 | Lee et al. |
| 8,107,925 B2 | 1/2012 | Natsuno et al. |
| 8,108,033 B2 | 1/2012 | Drew et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,408 B2 | 2/2012 | Wenchell et al. |
| 8,113,410 B2 | 2/2012 | Hall et al. |
| 8,114,100 B2 | 2/2012 | Smith et al. |
| 8,118,206 B2 | 2/2012 | Zand et al. |
| 8,118,207 B2 | 2/2012 | Racenet et al. |
| 8,120,301 B2 | 2/2012 | Goldberg et al. |
| 8,122,128 B2 | 2/2012 | Burke, II et al. |
| 8,123,103 B2 | 2/2012 | Milliman |
| 8,123,523 B2 | 2/2012 | Carron et al. |
| 8,123,766 B2 | 2/2012 | Bauman et al. |
| 8,123,767 B2 | 2/2012 | Bauman et al. |
| 8,125,168 B2 | 2/2012 | Johnson et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,128,662 B2 | 3/2012 | Altarac et al. |
| 8,132,703 B2 | 3/2012 | Milliman et al. |
| 8,132,706 B2 | 3/2012 | Marczyk et al. |
| 8,134,306 B2 | 3/2012 | Drader et al. |
| 8,136,711 B2 | 3/2012 | Beardsley et al. |
| 8,136,712 B2 | 3/2012 | Zingman |
| 8,136,713 B2 | 3/2012 | Hathaway et al. |
| 8,137,339 B2 | 3/2012 | Jinno et al. |
| 8,140,417 B2 | 3/2012 | Shibata |
| 8,141,762 B2 | 3/2012 | Bedi et al. |
| 8,141,763 B2 | 3/2012 | Milliman |
| 8,142,200 B2 | 3/2012 | Crunkilton et al. |
| 8,142,425 B2 | 3/2012 | Eggers |
| 8,142,461 B2 | 3/2012 | Houser et al. |
| 8,142,515 B2 | 3/2012 | Therin et al. |
| 8,143,520 B2 | 3/2012 | Cutler |
| 8,146,790 B2 | 4/2012 | Milliman |
| 8,147,421 B2 | 4/2012 | Farquhar et al. |
| 8,147,456 B2 | 4/2012 | Fisher et al. |
| 8,147,485 B2 | 4/2012 | Wham et al. |
| 8,152,041 B2 | 4/2012 | Kostrzewski |
| 8,152,756 B2 | 4/2012 | Webster et al. |
| 8,154,239 B2 | 4/2012 | Katsuki et al. |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,162,668 B2 | 4/2012 | Toly |
| 8,162,933 B2 | 4/2012 | Francischelli et al. |
| 8,162,965 B2 | 4/2012 | Reschke et al. |
| 8,167,185 B2 | 5/2012 | Shelton, IV et al. |
| 8,167,622 B2 | 5/2012 | Zhou |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,004 B2 | 5/2012 | Ho |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,776 B2 | 5/2012 | Humayun et al. |
| 8,177,797 B2 | 5/2012 | Shimoji et al. |
| 8,179,705 B2 | 5/2012 | Chapuis |
| 8,180,458 B2 | 5/2012 | Kane et al. |
| 8,181,839 B2 | 5/2012 | Beetel |
| 8,181,840 B2 | 5/2012 | Milliman |
| 8,182,422 B2 | 5/2012 | Bayer et al. |
| 8,183,807 B2 | 5/2012 | Tsai et al. |
| 8,186,555 B2 | 5/2012 | Shelton, IV et al. |
| 8,186,556 B2 | 5/2012 | Viola |
| 8,186,558 B2 | 5/2012 | Sapienza |
| 8,186,560 B2 | 5/2012 | Hess et al. |
| 8,191,752 B2 | 6/2012 | Scirica |
| 8,192,460 B2 | 6/2012 | Orban, III et al. |
| 8,192,651 B2 | 6/2012 | Young et al. |
| 8,196,795 B2 | 6/2012 | Moore et al. |
| 8,196,796 B2 | 6/2012 | Shelton, IV et al. |

(56) References Cited

U.S. PATENT DOCUMENTS

| | | |
|---|---|---|
| 8,197,501 B2 | 6/2012 | Shadeck et al. |
| 8,197,502 B2 | 6/2012 | Smith et al. |
| 8,197,837 B2 | 6/2012 | Jamiolkowski et al. |
| 8,201,720 B2 | 6/2012 | Hessler |
| 8,201,721 B2 | 6/2012 | Zemlok et al. |
| 8,202,549 B2 | 6/2012 | Stucky et al. |
| 8,205,779 B2 | 6/2012 | Ma et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,210,721 B2 | 7/2012 | Chen et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,532 B2 | 7/2012 | Marczyk |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,424 B2 | 7/2012 | Cha |
| 8,225,799 B2 | 7/2012 | Bettuchi |
| 8,225,979 B2 | 7/2012 | Farascioni et al. |
| 8,226,553 B2 | 7/2012 | Shelton, IV et al. |
| 8,226,635 B2 | 7/2012 | Petrie et al. |
| 8,226,675 B2 | 7/2012 | Houser et al. |
| 8,226,715 B2 | 7/2012 | Hwang et al. |
| 8,227,946 B2 | 7/2012 | Kim |
| 8,228,048 B2 | 7/2012 | Spencer |
| 8,229,549 B2 | 7/2012 | Whitman et al. |
| 8,231,040 B2 | 7/2012 | Zemlok et al. |
| 8,231,041 B2 | 7/2012 | Marczyk et al. |
| 8,231,042 B2 | 7/2012 | Hessler et al. |
| 8,231,043 B2 | 7/2012 | Tarinelli et al. |
| 8,235,272 B2 | 8/2012 | Nicholas et al. |
| 8,236,010 B2 | 8/2012 | Ortiz et al. |
| 8,236,020 B2 | 8/2012 | Smith et al. |
| 8,237,388 B2 | 8/2012 | Jinno et al. |
| 8,240,537 B2 | 8/2012 | Marczyk |
| 8,241,271 B2 | 8/2012 | Millman et al. |
| 8,241,284 B2 | 8/2012 | Dycus et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,608 B2 | 8/2012 | Omori et al. |
| 8,246,637 B2 | 8/2012 | Viola et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,386 B2 | 9/2012 | Lee et al. |
| 8,257,391 B2 | 9/2012 | Orban, III et al. |
| 8,257,634 B2 | 9/2012 | Scirica |
| 8,258,745 B2 | 9/2012 | Smith et al. |
| 8,262,655 B2 | 9/2012 | Ghabrial et al. |
| 8,267,300 B2 | 9/2012 | Boudreaux |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,269,121 B2 | 9/2012 | Smith |
| 8,272,553 B2 | 9/2012 | Mastri et al. |
| 8,272,554 B2 | 9/2012 | Whitman et al. |
| 8,272,918 B2 | 9/2012 | Lam |
| 8,273,404 B2 | 9/2012 | Dave et al. |
| 8,276,801 B2 | 10/2012 | Zemlok et al. |
| 8,276,802 B2 | 10/2012 | Kostrzewski |
| 8,277,473 B2 | 10/2012 | Sunaoshi et al. |
| 8,281,446 B2 | 10/2012 | Moskovich |
| 8,281,973 B2 | 10/2012 | Wenchell et al. |
| 8,281,974 B2 | 10/2012 | Hessler et al. |
| 8,282,654 B2 | 10/2012 | Ferrari et al. |
| 8,285,367 B2 | 10/2012 | Hyde et al. |
| 8,286,723 B2 | 10/2012 | Puzio et al. |
| 8,286,845 B2 | 10/2012 | Perry et al. |
| 8,286,846 B2 | 10/2012 | Smith et al. |
| 8,287,522 B2 | 10/2012 | Moses et al. |
| 8,287,561 B2 | 10/2012 | Nunez et al. |
| 8,292,147 B2 | 10/2012 | Viola |
| 8,292,150 B2 | 10/2012 | Bryant |
| 8,292,151 B2 | 10/2012 | Viola |
| 8,292,152 B2 | 10/2012 | Milliman et al. |
| 8,292,155 B2 | 10/2012 | Shelton, IV et al. |
| 8,292,157 B2 | 10/2012 | Smith et al. |
| 8,292,888 B2 | 10/2012 | Whitman |
| 8,298,161 B2 | 10/2012 | Vargas |
| 8,298,189 B2 | 10/2012 | Fisher et al. |
| 8,298,233 B2 | 10/2012 | Mueller |
| 8,298,677 B2 | 10/2012 | Wiesner et al. |
| 8,302,323 B2 | 11/2012 | Fortier et al. |
| 8,308,040 B2 | 11/2012 | Huang et al. |
| 8,308,042 B2 | 11/2012 | Aranyi |
| 8,308,043 B2 | 11/2012 | Bindra et al. |
| 8,308,046 B2 | 11/2012 | Prommersberger |
| 8,308,659 B2 | 11/2012 | Scheibe et al. |
| 8,308,725 B2 | 11/2012 | Bell et al. |
| 8,310,188 B2 | 11/2012 | Nakai |
| 8,313,496 B2 | 11/2012 | Sauer et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,744 B2 | 11/2012 | Kirschenman |
| 8,317,790 B2 | 11/2012 | Bell et al. |
| 8,319,002 B2 | 11/2012 | Daniels et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,322,901 B2 | 12/2012 | Michelotti |
| 8,323,789 B2 | 12/2012 | Rozhin et al. |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,691 B2 | 12/2012 | Schaaf |
| 8,333,764 B2 | 12/2012 | Francischelli et al. |
| 8,333,779 B2 | 12/2012 | Smith et al. |
| 8,334,468 B2 | 12/2012 | Palmer et al. |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,343,150 B2 | 1/2013 | Artale |
| 8,347,978 B2 | 1/2013 | Forster et al. |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,837 B2 | 1/2013 | Wenchell |
| 8,348,959 B2 | 1/2013 | Wolford et al. |
| 8,348,972 B2 | 1/2013 | Soltz et al. |
| 8,349,987 B2 | 1/2013 | Kapiamba et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |
| 8,357,161 B2 | 1/2013 | Mueller |
| 8,360,296 B2 | 1/2013 | Zingman |
| 8,360,297 B2 | 1/2013 | Shelton, IV et al. |

(56) References Cited

U.S. PATENT DOCUMENTS

| | | |
|---|---|---|
| 8,360,298 B2 | 1/2013 | Farascioni et al. |
| 8,360,299 B2 | 1/2013 | Zemlok et al. |
| 8,361,501 B2 | 1/2013 | DiTizio et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,366,787 B2 | 2/2013 | Brown et al. |
| 8,371,393 B2 | 2/2013 | Higuchi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,371,494 B2 | 2/2013 | Racenet et al. |
| 8,372,094 B2 | 2/2013 | Bettuchi et al. |
| 8,376,865 B2 | 2/2013 | Forster et al. |
| 8,377,029 B2 | 2/2013 | Nagao et al. |
| 8,377,044 B2 | 2/2013 | Coe et al. |
| 8,382,773 B2 | 2/2013 | Whitfield et al. |
| 8,382,790 B2 | 2/2013 | Uenohara et al. |
| 8,387,848 B2 | 3/2013 | Johnson et al. |
| 8,388,633 B2 | 3/2013 | Rousseau et al. |
| 8,389,588 B2 | 3/2013 | Ringeisen et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,973 B1 | 3/2013 | Hausen |
| 8,398,633 B2 | 3/2013 | Mueller |
| 8,398,669 B2 | 3/2013 | Kim |
| 8,398,673 B2 | 3/2013 | Hinchliffe et al. |
| 8,400,851 B2 | 3/2013 | Byun |
| 8,403,138 B2 | 3/2013 | Weisshaupt et al. |
| 8,403,198 B2 | 3/2013 | Sorrentino et al. |
| 8,403,832 B2 | 3/2013 | Cunningham et al. |
| 8,403,945 B2 | 3/2013 | Whitfield et al. |
| 8,403,946 B2 | 3/2013 | Whitfield et al. |
| 8,403,950 B2 | 3/2013 | Palmer et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,409,174 B2 | 4/2013 | Omori |
| 8,409,175 B2 | 4/2013 | Lee et al. |
| 8,409,222 B2 | 4/2013 | Whitfield et al. |
| 8,409,223 B2 | 4/2013 | Sorrentino et al. |
| 8,411,500 B2 | 4/2013 | Gapihan et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,418,073 B2 | 4/2013 | Mohr et al. |
| 8,418,906 B2 | 4/2013 | Farascioni et al. |
| 8,418,908 B1 | 4/2013 | Beardsley |
| 8,418,909 B2 | 4/2013 | Kostrzewski |
| 8,419,717 B2 | 4/2013 | Diolaiti et al. |
| 8,419,747 B2 | 4/2013 | Hinman et al. |
| 8,419,754 B2 | 4/2013 | Laby et al. |
| 8,423,182 B2 | 4/2013 | Robinson et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,427,430 B2 | 4/2013 | Lee et al. |
| 8,430,292 B2 | 4/2013 | Patel et al. |
| 8,430,892 B2 | 4/2013 | Bindra et al. |
| 8,430,898 B2 | 4/2013 | Wiener et al. |
| 8,435,257 B2 | 5/2013 | Smith et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,549 B2 | 5/2013 | Viola et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,495 B2 | 6/2013 | Kawano et al. |
| 8,454,628 B2 | 6/2013 | Smith et al. |
| 8,454,640 B2 | 6/2013 | Johnston et al. |
| 8,457,757 B2 | 6/2013 | Cauller et al. |
| 8,459,520 B2 | 6/2013 | Giordano et al. |
| 8,459,521 B2 | 6/2013 | Zemlok et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,475 B2 | 6/2013 | Isbell, Jr. |
| 8,465,502 B2 | 6/2013 | Zergiebel |
| 8,465,515 B2 | 6/2013 | Drew et al. |
| 8,469,946 B2 | 6/2013 | Sugita |
| 8,469,973 B2 | 6/2013 | Meade et al. |
| 8,470,355 B2 | 6/2013 | Skalla et al. |
| 8,474,677 B2 | 7/2013 | Woodard, Jr. et al. |
| 8,475,453 B2 | 7/2013 | Marczyk et al. |
| 8,475,454 B1 | 7/2013 | Alshemari |
| 8,475,474 B2 | 7/2013 | Bombard et al. |
| 8,479,968 B2 | 7/2013 | Hodgkinson et al. |
| 8,479,969 B2 | 7/2013 | Shelton, IV |
| 8,480,703 B2 | 7/2013 | Nicholas et al. |
| 8,485,412 B2 | 7/2013 | Shelton, IV et al. |
| 8,485,413 B2 | 7/2013 | Scheib et al. |
| 8,485,970 B2 | 7/2013 | Widenhouse et al. |
| 8,487,199 B2 | 7/2013 | Palmer et al. |
| 8,490,853 B2 | 7/2013 | Criscuolo et al. |
| 8,491,581 B2 | 7/2013 | Deville et al. |
| 8,491,603 B2 | 7/2013 | Yeung et al. |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,992 B2 | 8/2013 | Whitman et al. |
| 8,499,993 B2 | 8/2013 | Shelton, IV et al. |
| 8,500,721 B2 | 8/2013 | Jinno |
| 8,500,762 B2 | 8/2013 | Sholev et al. |
| 8,502,091 B2 | 8/2013 | Palmer et al. |
| 8,505,799 B2 | 8/2013 | Viola et al. |
| 8,505,801 B2 | 8/2013 | Ehrenfels et al. |
| 8,506,555 B2 | 8/2013 | Ruiz Morales |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,511,308 B2 | 8/2013 | Hecox et al. |
| 8,512,359 B2 | 8/2013 | Whitman et al. |
| 8,512,402 B2 | 8/2013 | Marczyk et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,521,273 B2 | 8/2013 | Kliman |
| 8,523,043 B2 | 9/2013 | Ullrich et al. |
| 8,523,881 B2 | 9/2013 | Cabiri et al. |
| 8,523,900 B2 | 9/2013 | Jinno et al. |
| 8,529,588 B2 | 9/2013 | Ahlberg et al. |
| 8,529,600 B2 | 9/2013 | Woodard, Jr. et al. |
| 8,529,819 B2 | 9/2013 | Ostapoff et al. |
| 8,532,747 B2 | 9/2013 | Nock et al. |
| 8,534,528 B2 | 9/2013 | Shelton, IV |
| 8,535,304 B2 | 9/2013 | Sklar et al. |
| 8,535,340 B2 | 9/2013 | Allen |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,540,735 B2 | 9/2013 | Mitelberg et al. |
| 8,550,984 B2 | 10/2013 | Takemoto |
| 8,551,076 B2 | 10/2013 | Duval et al. |
| 8,555,660 B2 | 10/2013 | Takenaka et al. |
| 8,556,151 B2 | 10/2013 | Viola |
| 8,556,918 B2 | 10/2013 | Bauman et al. |
| 8,556,935 B1 | 10/2013 | Knodel et al. |
| 8,560,147 B2 | 10/2013 | Taylor et al. |

(56) References Cited

U.S. PATENT DOCUMENTS

| | | |
|---|---|---|
| 8,561,617 B2 | 10/2013 | Lindh et al. |
| 8,561,870 B2 | 10/2013 | Baxter, III et al. |
| 8,561,871 B2 | 10/2013 | Rajappa et al. |
| 8,561,873 B2 | 10/2013 | Ingmanson et al. |
| 8,562,598 B2 | 10/2013 | Falkenstein et al. |
| 8,567,656 B2 | 10/2013 | Shelton, IV et al. |
| 8,568,416 B2 | 10/2013 | Schmitz et al. |
| 8,568,425 B2 | 10/2013 | Ross et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,465 B2 | 11/2013 | Shelton, IV |
| 8,574,199 B2 | 11/2013 | von Bulow et al. |
| 8,574,263 B2 | 11/2013 | Mueller |
| 8,575,880 B2 | 11/2013 | Grantz |
| 8,579,176 B2 | 11/2013 | Smith et al. |
| 8,579,178 B2 | 11/2013 | Holsten et al. |
| 8,579,897 B2 | 11/2013 | Vakharia et al. |
| 8,579,937 B2 | 11/2013 | Gresham |
| 8,584,919 B2 | 11/2013 | Hueil et al. |
| 8,584,920 B2 | 11/2013 | Hodgkinson |
| 8,584,921 B2 | 11/2013 | Scirica |
| 8,585,583 B2 | 11/2013 | Sakaguchi et al. |
| 8,585,721 B2 | 11/2013 | Kirsch |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,596,515 B2 | 12/2013 | Okoniewski |
| 8,597,745 B2 | 12/2013 | Farnsworth et al. |
| 8,599,450 B2 | 12/2013 | Kubo et al. |
| 8,602,287 B2 | 12/2013 | Yates et al. |
| 8,602,288 B2 | 12/2013 | Shelton, IV et al. |
| 8,603,077 B2 | 12/2013 | Cooper et al. |
| 8,603,089 B2 | 12/2013 | Viola |
| 8,603,110 B2 | 12/2013 | Maruyama et al. |
| 8,603,135 B2 | 12/2013 | Mueller |
| 8,608,043 B2 | 12/2013 | Scirica |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,616,427 B2 | 12/2013 | Viola |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,631,992 B1 | 1/2014 | Hausen et al. |
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,191 B2 | 1/2014 | Meagher |
| 8,636,193 B2 | 1/2014 | Whitman et al. |
| 8,636,736 B2 | 1/2014 | Yates et al. |
| 8,636,766 B2 | 1/2014 | Milliman et al. |
| 8,639,936 B2 | 1/2014 | Hu et al. |
| 8,640,788 B2 | 2/2014 | Dachs, II et al. |
| 8,646,674 B2 | 2/2014 | Schulte et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,657,174 B2 | 2/2014 | Yates et al. |
| 8,657,175 B2 | 2/2014 | Sonnenschein et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,657,482 B2 | 2/2014 | Malackowski et al. |
| 8,657,808 B2 | 2/2014 | McPherson et al. |
| 8,657,814 B2 | 2/2014 | Werneth et al. |
| 8,657,821 B2 | 2/2014 | Palermo |
| 8,662,370 B2 | 3/2014 | Takei |
| 8,663,106 B2 | 3/2014 | Stivoric et al. |
| 8,663,192 B2 | 3/2014 | Hester et al. |
| 8,663,245 B2 | 3/2014 | Francischelli et al. |
| 8,663,262 B2 | 3/2014 | Smith et al. |
| 8,663,270 B2 | 3/2014 | Donnigan et al. |
| 8,664,792 B2 | 3/2014 | Rebsdorf |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,672,922 B2 | 3/2014 | Loh et al. |
| 8,672,935 B2 | 3/2014 | Okada et al. |
| 8,672,951 B2 | 3/2014 | Smith et al. |
| 8,673,210 B2 | 3/2014 | Deshays |
| 8,675,820 B2 | 3/2014 | Baic et al. |
| 8,678,263 B2 | 3/2014 | Viola |
| 8,679,093 B2 | 3/2014 | Farra |
| 8,679,098 B2 | 3/2014 | Hart |
| 8,679,137 B2 | 3/2014 | Bauman et al. |
| 8,679,154 B2 | 3/2014 | Smith et al. |
| 8,679,156 B2 | 3/2014 | Smith et al. |
| 8,679,454 B2 | 3/2014 | Guire et al. |
| 8,684,248 B2 | 4/2014 | Milliman |
| 8,684,249 B2 | 4/2014 | Racenet et al. |
| 8,684,250 B2 | 4/2014 | Bettuchi et al. |
| 8,684,253 B2 | 4/2014 | Giordano et al. |
| 8,684,962 B2 | 4/2014 | Kirschenman et al. |
| 8,685,004 B2 | 4/2014 | Zemlock et al. |
| 8,685,020 B2 | 4/2014 | Weizman et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,708,210 B2 | 4/2014 | Zemlok et al. |
| 8,708,211 B2 | 4/2014 | Zemlok et al. |
| 8,708,213 B2 | 4/2014 | Shelton, IV et al. |
| 8,714,352 B2 | 5/2014 | Farascioni et al. |
| 8,714,429 B2 | 5/2014 | Demmy |
| 8,714,430 B2 | 5/2014 | Natarajan et al. |
| 8,715,256 B2 | 5/2014 | Greener |
| 8,715,302 B2 | 5/2014 | Ibrahim et al. |
| 8,720,766 B2 | 5/2014 | Hess et al. |
| 8,721,630 B2 | 5/2014 | Ortiz et al. |
| 8,721,666 B2 | 5/2014 | Schroeder et al. |
| 8,727,197 B2 | 5/2014 | Hess et al. |
| 8,727,199 B2 | 5/2014 | Wenchell |
| 8,727,200 B2 | 5/2014 | Roy |
| 8,727,961 B2 | 5/2014 | Ziv |
| 8,728,099 B2 | 5/2014 | Cohn et al. |
| 8,728,119 B2 | 5/2014 | Cummins |
| 8,733,470 B2 | 5/2014 | Matthias et al. |
| 8,733,612 B2 | 5/2014 | Ma |
| 8,733,613 B2 | 5/2014 | Huitema et al. |
| 8,733,614 B2 | 5/2014 | Ross et al. |
| 8,734,336 B2 | 5/2014 | Bonadio et al. |
| 8,734,359 B2 | 5/2014 | Ibanez et al. |
| 8,734,478 B2 | 5/2014 | Widenhouse et al. |
| 8,739,033 B2 | 5/2014 | Rosenberg |
| 8,739,417 B2 | 6/2014 | Tokunaga et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,740,987 B2 | 6/2014 | Geremakis et al. |
| 8,746,529 B2 | 6/2014 | Shelton, IV et al. |
| 8,746,530 B2 | 6/2014 | Giordano et al. |
| 8,746,533 B2 | 6/2014 | Whitman et al. |
| 8,746,535 B2 | 6/2014 | Shelton, IV et al. |
| 8,747,238 B2 | 6/2014 | Shelton, IV et al. |
| 8,747,441 B2 | 6/2014 | Konieczynski et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,748 B2 | 6/2014 | Whitman et al. |
| 8,752,749 B2 | 6/2014 | Moore et al. |
| 8,757,287 B2 | 6/2014 | Mak et al. |

(56) References Cited

U.S. PATENT DOCUMENTS

| | | |
|---|---|---|
| 8,757,465 B2 | 6/2014 | Woodard, Jr. et al. |
| 8,758,235 B2 | 6/2014 | Jaworek |
| 8,758,366 B2 | 6/2014 | McLean et al. |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,764,732 B2 | 7/2014 | Hartwell |
| 8,770,458 B2 | 7/2014 | Scirica |
| 8,770,459 B2 | 7/2014 | Racenet et al. |
| 8,770,460 B2 | 7/2014 | Belzer |
| 8,771,169 B2 | 7/2014 | Whitman et al. |
| 8,777,004 B2 | 7/2014 | Shelton, IV et al. |
| 8,777,082 B2 | 7/2014 | Scirica |
| 8,777,083 B2 | 7/2014 | Racenet et al. |
| 8,777,898 B2 | 7/2014 | Suon et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,304 B2 | 7/2014 | Mikkaichi et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,658 B2 | 7/2014 | Cigarini et al. |
| 8,790,684 B2 | 7/2014 | Dave et al. |
| 8,794,496 B2 | 8/2014 | Scirica |
| 8,794,497 B2 | 8/2014 | Zingman |
| 8,795,276 B2 | 8/2014 | Dietz et al. |
| 8,795,308 B2 | 8/2014 | Valin |
| 8,795,324 B2 | 8/2014 | Kawai et al. |
| 8,800,681 B2 | 8/2014 | Rousson et al. |
| 8,800,837 B2 | 8/2014 | Zemlok |
| 8,800,838 B2 | 8/2014 | Shelton, IV |
| 8,800,839 B2 | 8/2014 | Beetel |
| 8,800,840 B2 | 8/2014 | Jankowski |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,806,973 B2 | 8/2014 | Ross et al. |
| 8,807,414 B2 | 8/2014 | Ross et al. |
| 8,808,161 B2 | 8/2014 | Gregg et al. |
| 8,808,274 B2 | 8/2014 | Hartwell |
| 8,808,294 B2 | 8/2014 | Fox et al. |
| 8,808,308 B2 | 8/2014 | Boukhny et al. |
| 8,808,311 B2 | 8/2014 | Heinrich et al. |
| 8,808,325 B2 | 8/2014 | Hess et al. |
| 8,810,197 B2 | 8/2014 | Juergens |
| 8,811,017 B2 | 8/2014 | Fujii et al. |
| 8,813,866 B2 | 8/2014 | Suzuki |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,822,934 B2 | 9/2014 | Sayeh et al. |
| 8,825,164 B2 | 9/2014 | Tweden et al. |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,833,219 B2 | 9/2014 | Pierce |
| 8,833,630 B2 | 9/2014 | Milliman |
| 8,833,632 B2 | 9/2014 | Swensgard |
| 8,834,498 B2 | 9/2014 | Byrum et al. |
| 8,840,003 B2 | 9/2014 | Morgan et al. |
| 8,840,603 B2 | 9/2014 | Shelton, IV et al. |
| 8,840,609 B2 | 9/2014 | Stuebe |
| 8,844,789 B2 | 9/2014 | Shelton, IV et al. |
| 8,851,215 B2 | 10/2014 | Goto |
| 8,851,354 B2 | 10/2014 | Swensgard et al. |
| 8,852,185 B2 | 10/2014 | Twomey |
| 8,852,199 B2 | 10/2014 | Deslauriers et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,864,010 B2 | 10/2014 | Williams |
| 8,870,050 B2 | 10/2014 | Hodgkinson |
| 8,870,912 B2 | 10/2014 | Brisson et al. |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,876,858 B2 | 11/2014 | Braun |
| 8,887,979 B2 | 11/2014 | Mastri et al. |
| 8,888,688 B2 | 11/2014 | Julian et al. |
| 8,888,695 B2 | 11/2014 | Piskun et al. |
| 8,888,792 B2 | 11/2014 | Harris et al. |
| 8,888,809 B2 | 11/2014 | Davison et al. |
| 8,893,946 B2 | 11/2014 | Boudreaux et al. |
| 8,893,949 B2 | 11/2014 | Shelton, IV et al. |
| 8,894,647 B2 | 11/2014 | Beardsley et al. |
| 8,894,654 B2 | 11/2014 | Anderson |
| 8,899,460 B2 | 12/2014 | Wojcicki |
| 8,899,461 B2 | 12/2014 | Farascioni |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,905,287 B2 | 12/2014 | Racenet et al. |
| 8,905,977 B2 | 12/2014 | Shelton et al. |
| 8,910,846 B2 | 12/2014 | Viola |
| 8,911,426 B2 | 12/2014 | Coppeta et al. |
| 8,911,448 B2 | 12/2014 | Stein |
| 8,911,460 B2 | 12/2014 | Neurohr et al. |
| 8,911,471 B2 | 12/2014 | Spivey et al. |
| 8,920,433 B2 | 12/2014 | Barrier et al. |
| 8,920,435 B2 | 12/2014 | Smith et al. |
| 8,920,438 B2 | 12/2014 | Aranyi et al. |
| 8,920,443 B2 | 12/2014 | Hiles et al. |
| 8,920,444 B2 | 12/2014 | Hiles et al. |
| 8,922,163 B2 | 12/2014 | Macdonald |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,506 B2 | 1/2015 | Widenhouse et al. |
| 8,926,598 B2 | 1/2015 | Mollere et al. |
| 8,931,576 B2 | 1/2015 | Iwata |
| 8,931,679 B2 | 1/2015 | Kostrzewski |
| 8,931,680 B2 | 1/2015 | Milliman |
| 8,931,682 B2 | 1/2015 | Timm et al. |
| 8,936,614 B2 | 1/2015 | Allen, IV |
| 8,939,343 B2 | 1/2015 | Milliman et al. |
| 8,939,344 B2 | 1/2015 | Olson et al. |
| 8,945,163 B2 | 2/2015 | Voegele et al. |
| 8,955,732 B2 | 2/2015 | Zemlok et al. |
| 8,956,342 B1 | 2/2015 | Russo et al. |
| 8,956,390 B2 | 2/2015 | Shah et al. |
| 8,958,860 B2 | 2/2015 | Banerjee et al. |
| 8,960,519 B2 | 2/2015 | Whitman et al. |
| 8,960,520 B2 | 2/2015 | McCuen |
| 8,960,521 B2 | 2/2015 | Kostrzewski |
| 8,961,504 B2 | 2/2015 | Hoarau et al. |
| 8,963,714 B2 | 2/2015 | Medhal et al. |
| 8,967,443 B2 | 3/2015 | McCuen |
| 8,967,444 B2 | 3/2015 | Beetel |
| 8,967,446 B2 | 3/2015 | Beardsley et al. |
| 8,967,448 B2 | 3/2015 | Carter et al. |
| 8,968,276 B2 | 3/2015 | Zemlok et al. |
| 8,968,312 B2 | 3/2015 | Marczyk et al. |
| 8,968,337 B2 | 3/2015 | Whitfield et al. |
| 8,968,340 B2 | 3/2015 | Chowaniec et al. |
| 8,968,355 B2 | 3/2015 | Malkowski et al. |
| 8,968,358 B2 | 3/2015 | Reschke |
| 8,970,507 B2 | 3/2015 | Holbein et al. |
| 8,973,803 B2 | 3/2015 | Hall et al. |
| 8,973,804 B2 | 3/2015 | Hess et al. |

(56) References Cited

U.S. PATENT DOCUMENTS

| | | |
|---|---|---|
| 8,974,440 B2 | 3/2015 | Farritor et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,843 B2 | 3/2015 | Timm et al. |
| 8,979,890 B2 | 3/2015 | Boudreaux |
| 8,982,195 B2 | 3/2015 | Claus et al. |
| 8,991,676 B2 | 3/2015 | Hess et al. |
| 8,991,677 B2 | 3/2015 | Moore et al. |
| 8,991,678 B2 | 3/2015 | Wellman et al. |
| 8,992,042 B2 | 3/2015 | Eichenholz |
| 8,992,422 B2 | 3/2015 | Spivey et al. |
| 8,992,565 B2 | 3/2015 | Brisson et al. |
| 8,996,165 B2 | 3/2015 | Wang et al. |
| 8,998,058 B2 | 4/2015 | Moore et al. |
| 8,998,059 B2 | 4/2015 | Smith et al. |
| 8,998,061 B2 | 4/2015 | Williams et al. |
| 9,002,518 B2 | 4/2015 | Manzo et al. |
| 9,004,339 B1 | 4/2015 | Park |
| 9,005,230 B2 | 4/2015 | Yates et al. |
| 9,005,238 B2 | 4/2015 | DeSantis et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,011,439 B2 | 4/2015 | Shalaby et al. |
| 9,011,471 B2 | 4/2015 | Timm et al. |
| 9,016,539 B2 | 4/2015 | Kostrzewski et al. |
| 9,016,540 B2 | 4/2015 | Whitman et al. |
| 9,016,541 B2 | 4/2015 | Viola et al. |
| 9,016,542 B2 | 4/2015 | Shelton, IV et al. |
| 9,016,545 B2 | 4/2015 | Aranyi et al. |
| 9,017,331 B2 | 4/2015 | Fox |
| 9,017,355 B2 | 4/2015 | Smith et al. |
| 9,017,369 B2 | 4/2015 | Renger et al. |
| 9,017,371 B2 | 4/2015 | Whitman et al. |
| 9,021,684 B2 | 5/2015 | Lenker et al. |
| 9,023,014 B2 | 5/2015 | Chowaniec et al. |
| 9,023,071 B2 | 5/2015 | Miller et al. |
| 9,027,817 B2 | 5/2015 | Milliman et al. |
| 9,028,494 B2 | 5/2015 | Shelton, IV et al. |
| 9,028,495 B2 | 5/2015 | Mueller et al. |
| 9,028,519 B2 | 5/2015 | Yates et al. |
| 9,030,169 B2 | 5/2015 | Christensen et al. |
| 9,033,203 B2 | 5/2015 | Woodard, Jr. et al. |
| 9,033,204 B2 | 5/2015 | Shelton, IV et al. |
| 9,034,505 B2 | 5/2015 | Detry et al. |
| 9,038,881 B1 | 5/2015 | Schaller et al. |
| 9,039,690 B2 | 5/2015 | Kersten et al. |
| 9,039,694 B2 | 5/2015 | Ross et al. |
| 9,039,720 B2 | 5/2015 | Madan |
| 9,043,027 B2 | 5/2015 | Durant et al. |
| 9,044,227 B2 | 6/2015 | Shelton, IV et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,050,083 B2 | 6/2015 | Yates et al. |
| 9,050,084 B2 | 6/2015 | Schmid et al. |
| 9,050,100 B2 | 6/2015 | Yates et al. |
| 9,050,120 B2 | 6/2015 | Swarup et al. |
| 9,050,123 B2 | 6/2015 | Krause et al. |
| 9,055,941 B2 | 6/2015 | Schmid et al. |
| 9,055,942 B2 | 6/2015 | Balbierz et al. |
| 9,055,943 B2 | 6/2015 | Zemlok et al. |
| 9,055,944 B2 | 6/2015 | Hodgkinson et al. |
| 9,055,961 B2 | 6/2015 | Manzo et al. |
| 9,060,770 B2 | 6/2015 | Shelton, IV et al. |
| 9,060,776 B2 | 6/2015 | Yates et al. |
| 9,060,794 B2 | 6/2015 | Kang et al. |
| 9,060,894 B2 | 6/2015 | Wubbeling |
| 9,061,392 B2 | 6/2015 | Forgues et al. |
| 9,072,515 B2 | 7/2015 | Hall et al. |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Gleiman |
| 9,086,875 B2 | 7/2015 | Harrat et al. |
| 9,089,326 B2 | 7/2015 | Krumanaker et al. |
| 9,089,330 B2 | 7/2015 | Widenhouse et al. |
| 9,089,352 B2 | 7/2015 | Jeong |
| 9,091,588 B2 | 7/2015 | Lefler |
| 9,095,339 B2 | 8/2015 | Moore et al. |
| 9,095,346 B2 | 8/2015 | Houser et al. |
| 9,095,362 B2 | 8/2015 | Dachs, II et al. |
| 9,096,033 B2 | 8/2015 | Holop et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,101,475 B2 | 8/2015 | Wei et al. |
| 9,107,663 B2 | 8/2015 | Swensgard |
| 9,107,690 B2 | 8/2015 | Bales, Jr. et al. |
| 9,110,587 B2 | 8/2015 | Kim et al. |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,873 B2 | 8/2015 | Marczyk et al. |
| 9,113,874 B2 | 8/2015 | Shelton, IV et al. |
| 9,113,876 B2 | 8/2015 | Zemlok et al. |
| 9,113,880 B2 | 8/2015 | Zemlok et al. |
| 9,113,881 B2 | 8/2015 | Scirica |
| 9,113,883 B2 | 8/2015 | Aronhalt et al. |
| 9,113,884 B2 | 8/2015 | Shelton, IV et al. |
| 9,113,887 B2 | 8/2015 | Behnke, II et al. |
| 9,119,657 B2 | 9/2015 | Shelton, IV et al. |
| 9,119,898 B2 | 9/2015 | Bayon et al. |
| 9,119,957 B2 | 9/2015 | Gantz et al. |
| 9,123,286 B2 | 9/2015 | Park |
| 9,124,097 B2 | 9/2015 | Cruz |
| 9,125,654 B2 | 9/2015 | Aronhalt et al. |
| 9,125,662 B2 | 9/2015 | Shelton, IV |
| 9,126,317 B2 | 9/2015 | Lawton et al. |
| 9,131,835 B2 | 9/2015 | Widenhouse et al. |
| 9,131,940 B2 | 9/2015 | Huitema et al. |
| 9,131,950 B2 | 9/2015 | Matthew |
| 9,131,957 B2 | 9/2015 | Skarbnik et al. |
| 9,138,225 B2 | 9/2015 | Huang et al. |
| 9,138,226 B2 | 9/2015 | Racenet et al. |
| 9,144,455 B2 | 9/2015 | Kennedy et al. |
| 9,149,274 B2 | 10/2015 | Spivey et al. |
| 9,149,324 B2 | 10/2015 | Huang et al. |
| 9,149,325 B2 | 10/2015 | Worrell et al. |
| 9,153,994 B2 | 10/2015 | Wood et al. |
| 9,161,753 B2 | 10/2015 | Prior |
| 9,161,803 B2 | 10/2015 | Yates et al. |
| 9,168,038 B2 | 10/2015 | Shelton, IV et al. |
| 9,168,039 B1 | 10/2015 | Knodel |
| 9,168,054 B2 | 10/2015 | Turner et al. |
| 9,168,144 B2 | 10/2015 | Rivin et al. |
| 9,179,911 B2 | 11/2015 | Morgan et al. |
| 9,179,912 B2 | 11/2015 | Yates et al. |
| 9,182,244 B2 | 11/2015 | Luke et al. |
| 9,186,046 B2 | 11/2015 | Ramamurthy et al. |
| 9,186,137 B2 | 11/2015 | Farascioni et al. |
| 9,186,140 B2 | 11/2015 | Hiles et al. |
| 9,186,142 B2 | 11/2015 | Fanelli et al. |
| 9,186,143 B2 | 11/2015 | Timm et al. |
| 9,186,148 B2 | 11/2015 | Felder et al. |
| 9,186,221 B2 | 11/2015 | Burbank |
| 9,192,380 B2 | 11/2015 | (Tarinelli) Racenet et al. |
| 9,192,384 B2 | 11/2015 | Bettuchi |
| 9,192,430 B2 | 11/2015 | Rachlin et al. |
| 9,192,434 B2 | 11/2015 | Twomey et al. |
| 9,193,045 B2 | 11/2015 | Saur et al. |
| 9,198,642 B2 | 12/2015 | Storz |
| 9,198,644 B2 | 12/2015 | Balek et al. |
| 9,198,661 B2 | 12/2015 | Swensgard |
| 9,198,662 B2 | 12/2015 | Barton et al. |
| 9,198,683 B2 | 12/2015 | Friedman et al. |
| 9,204,830 B2 | 12/2015 | Zand et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |

(56) References Cited

U.S. PATENT DOCUMENTS

| | | |
|---|---|---|
| 9,204,923 B2 | 12/2015 | Manzo et al. |
| 9,204,924 B2 | 12/2015 | Marczyk et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,013 B2 | 12/2015 | Scirica et al. |
| 9,216,019 B2 | 12/2015 | Schmid et al. |
| 9,216,020 B2 | 12/2015 | Zhang et al. |
| 9,216,030 B2 | 12/2015 | Fan et al. |
| 9,216,062 B2 | 12/2015 | Duque et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,220,508 B2 | 12/2015 | Dannaher |
| 9,220,559 B2 | 12/2015 | Worrell et al. |
| 9,220,570 B2 | 12/2015 | Kim et al. |
| 9,226,750 B2 | 1/2016 | Weir et al. |
| 9,226,751 B2 | 1/2016 | Shelton, IV et al. |
| 9,226,767 B2 | 1/2016 | Stulen et al. |
| 9,232,941 B2 | 1/2016 | Mandakolathur Vasudevan et al. |
| 9,232,945 B2 | 1/2016 | Zingman |
| 9,232,979 B2 | 1/2016 | Parihar et al. |
| 9,233,610 B2 | 1/2016 | Kim et al. |
| 9,237,891 B2 | 1/2016 | Shelton, IV |
| 9,237,892 B2 | 1/2016 | Hodgkinson |
| 9,237,895 B2 | 1/2016 | McCarthy et al. |
| 9,237,921 B2 | 1/2016 | Messerly et al. |
| 9,240,740 B2 | 1/2016 | Zeng et al. |
| 9,241,714 B2 | 1/2016 | Timm et al. |
| 9,241,716 B2 | 1/2016 | Whitman |
| 9,241,731 B2 | 1/2016 | Boudreaux et al. |
| 9,259,274 B2 | 2/2016 | Prisco |
| 9,261,172 B2 | 2/2016 | Solomon et al. |
| 9,265,500 B2 | 2/2016 | Sorrentino et al. |
| 9,265,516 B2 | 2/2016 | Casey et al. |
| 9,265,585 B2 | 2/2016 | Wingardner et al. |
| 9,271,718 B2 | 3/2016 | Milad et al. |
| 9,271,727 B2 | 3/2016 | McGuckin, Jr. et al. |
| 9,271,753 B2 | 3/2016 | Butler et al. |
| 9,271,799 B2 | 3/2016 | Shelton, IV et al. |
| 9,272,406 B2 | 3/2016 | Aronhalt et al. |
| 9,277,919 B2 | 3/2016 | Timmer et al. |
| 9,277,922 B2 | 3/2016 | Carter et al. |
| 9,282,962 B2 | 3/2016 | Schmid et al. |
| 9,282,963 B2 | 3/2016 | Bryant |
| 9,282,966 B2 | 3/2016 | Shelton, IV et al. |
| 9,282,974 B2 | 3/2016 | Shelton, IV |
| 9,283,028 B2 | 3/2016 | Johnson |
| 9,283,045 B2 | 3/2016 | Rhee et al. |
| 9,283,054 B2 | 3/2016 | Morgan et al. |
| 9,289,206 B2 | 3/2016 | Hess et al. |
| 9,289,207 B2 | 3/2016 | Shelton, IV |
| 9,289,210 B2 | 3/2016 | Baxter, III et al. |
| 9,289,211 B2 | 3/2016 | Williams et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,293,757 B2 | 3/2016 | Toussaint et al. |
| 9,295,464 B2 | 3/2016 | Shelton, IV et al. |
| 9,295,465 B2 | 3/2016 | Farascioni |
| 9,295,466 B2 | 3/2016 | Hodgkinson et al. |
| 9,295,468 B2 | 3/2016 | Heinrich et al. |
| 9,295,514 B2 | 3/2016 | Shelton, IV et al. |
| 9,295,522 B2 | 3/2016 | Kostrzewski |
| 9,295,784 B2 | 3/2016 | Eggert et al. |
| 9,301,691 B2 | 4/2016 | Hufnagel et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,307,965 B2 | 4/2016 | Ming et al. |
| 9,307,986 B2 | 4/2016 | Hall et al. |
| 9,307,987 B2 | 4/2016 | Swensgard et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,308,009 B2 | 4/2016 | Madan et al. |
| 9,308,011 B2 | 4/2016 | Chao et al. |
| 9,314,246 B2 | 4/2016 | Shelton, IV et al. |
| 9,314,247 B2 | 4/2016 | Shelton, IV et al. |
| 9,314,261 B2 | 4/2016 | Bales, Jr. et al. |
| 9,314,908 B2 | 4/2016 | Tanimoto et al. |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,326,767 B2 | 5/2016 | Koch, Jr. et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,326,788 B2 | 5/2016 | Batross et al. |
| 9,326,812 B2 | 5/2016 | Waaler et al. |
| 9,332,890 B2 | 5/2016 | Ozawa |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,333,040 B2 | 5/2016 | Shellenberger et al. |
| 9,333,082 B2 | 5/2016 | Wei et al. |
| 9,339,226 B2 | 5/2016 | van der Walt et al. |
| 9,345,477 B2 | 5/2016 | Anim et al. |
| 9,345,480 B2 | 5/2016 | Hessler et al. |
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,351,728 B2 | 5/2016 | Sniffin et al. |
| 9,351,730 B2 | 5/2016 | Schmid et al. |
| 9,351,731 B2 | 5/2016 | Carter et al. |
| 9,351,732 B2 | 5/2016 | Hodgkinson |
| 9,358,003 B2 | 6/2016 | Hall et al. |
| 9,358,005 B2 | 6/2016 | Shelton, IV et al. |
| 9,358,015 B2 | 6/2016 | Sorrentino et al. |
| 9,358,031 B2 | 6/2016 | Manzo |
| 9,364,217 B2 | 6/2016 | Kostrzewski et al. |
| 9,364,219 B2 | 6/2016 | Olson et al. |
| 9,364,220 B2 | 6/2016 | Williams |
| 9,364,226 B2 | 6/2016 | Zemlok et al. |
| 9,364,229 B2 | 6/2016 | D'Agostino et al. |
| 9,364,230 B2 | 6/2016 | Shelton, IV et al. |
| 9,364,231 B2 | 6/2016 | Wenchell |
| 9,364,233 B2 | 6/2016 | Alexander, III et al. |
| 9,364,279 B2 | 6/2016 | Houser et al. |
| 9,368,991 B2 | 6/2016 | Qahouq |
| 9,370,341 B2 | 6/2016 | Ceniccola et al. |
| 9,370,358 B2 | 6/2016 | Shelton, IV et al. |
| 9,370,364 B2 | 6/2016 | Smith et al. |
| 9,375,206 B2 | 6/2016 | Vidal et al. |
| 9,375,255 B2 | 6/2016 | Houser et al. |
| 9,381,058 B2 | 7/2016 | Houser et al. |
| 9,386,983 B2 | 7/2016 | Swensgard et al. |
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,387,003 B2 | 7/2016 | Kaercher et al. |
| 9,393,015 B2 | 7/2016 | Laurent et al. |
| 9,393,017 B2 | 7/2016 | Flanagan et al. |
| 9,393,018 B2 | 7/2016 | Wang et al. |
| 9,398,911 B2 | 7/2016 | Auld |
| 9,402,604 B2 | 8/2016 | Williams et al. |
| 9,402,626 B2 | 8/2016 | Ortiz et al. |
| 9,402,627 B2 | 8/2016 | Stevenson et al. |
| 9,408,604 B2 | 8/2016 | Shelton, IV et al. |
| 9,408,606 B2 | 8/2016 | Shelton, IV |
| 9,408,622 B2 | 8/2016 | Stulen et al. |
| 9,411,370 B2 | 8/2016 | Benni et al. |
| 9,414,838 B2 | 8/2016 | Shelton, IV et al. |
| 9,414,849 B2 | 8/2016 | Nagashimada |
| 9,414,880 B2 | 8/2016 | Monson et al. |
| 9,420,967 B2 | 8/2016 | Zand et al. |
| 9,421,003 B2 | 8/2016 | Williams et al. |
| 9,421,014 B2 | 8/2016 | Ingmanson et al. |
| 9,421,030 B2 | 8/2016 | Cole et al. |
| 9,421,060 B2 | 8/2016 | Monson et al. |
| 9,427,223 B2 | 8/2016 | Park et al. |

(56) References Cited

U.S. PATENT DOCUMENTS

| | | |
|---|---|---|
| 9,427,231 B2 | 8/2016 | Racenet et al. |
| 9,433,411 B2 | 9/2016 | Racenet et al. |
| 9,433,419 B2 | 9/2016 | Gonzalez et al. |
| 9,433,420 B2 | 9/2016 | Hodgkinson |
| 9,439,649 B2 | 9/2016 | Shelton, IV et al. |
| 9,439,650 B2 | 9/2016 | McGuckin, Jr. et al. |
| 9,439,651 B2 | 9/2016 | Smith et al. |
| 9,445,808 B2 | 9/2016 | Woodard, Jr. et al. |
| 9,445,813 B2 | 9/2016 | Shelton, IV et al. |
| 9,451,958 B2 | 9/2016 | Shelton, IV et al. |
| 9,461,340 B2 | 10/2016 | Li et al. |
| 9,463,040 B2 | 10/2016 | Jeong et al. |
| 9,463,260 B2 | 10/2016 | Stopek |
| 9,468,438 B2 | 10/2016 | Baber et al. |
| 9,468,447 B2 | 10/2016 | Aman et al. |
| 9,470,297 B2 | 10/2016 | Aranyi et al. |
| 9,471,969 B2 | 10/2016 | Zeng et al. |
| 9,474,506 B2 | 10/2016 | Magnin et al. |
| 9,474,523 B2 | 10/2016 | Meade et al. |
| 9,474,540 B2 | 10/2016 | Stokes et al. |
| 9,475,180 B2 | 10/2016 | Eshleman et al. |
| 9,480,476 B2 | 11/2016 | Aldridge et al. |
| 9,480,492 B2 | 11/2016 | Aranyi et al. |
| 9,483,095 B2 | 11/2016 | Tran et al. |
| 9,486,186 B2 | 11/2016 | Fiebig et al. |
| 9,486,213 B2 | 11/2016 | Altman et al. |
| 9,486,214 B2 | 11/2016 | Shelton, IV |
| 9,486,302 B2 | 11/2016 | Boey et al. |
| 9,488,197 B2 | 11/2016 | Wi |
| 9,492,146 B2 | 11/2016 | Kostrzewski et al. |
| 9,492,167 B2 | 11/2016 | Shelton, IV et al. |
| 9,492,170 B2 | 11/2016 | Bear et al. |
| 9,492,189 B2 | 11/2016 | Williams et al. |
| 9,492,192 B2 | 11/2016 | To et al. |
| 9,498,213 B2 | 11/2016 | Marczyk et al. |
| 9,498,219 B2 | 11/2016 | Moore et al. |
| 9,504,521 B2 | 11/2016 | Deutmeyer et al. |
| D775,336 S | 12/2016 | Shelton, IV et al. |
| 9,510,828 B2 | 12/2016 | Yates et al. |
| 9,510,830 B2 | 12/2016 | Shelton, IV et al. |
| 9,510,846 B2 | 12/2016 | Sholev et al. |
| 9,510,895 B2 | 12/2016 | Houser et al. |
| 9,510,925 B2 | 12/2016 | Hotter et al. |
| 9,517,063 B2 | 12/2016 | Swayze et al. |
| 9,517,068 B2 | 12/2016 | Shelton, IV et al. |
| 9,521,996 B2 | 12/2016 | Armstrong |
| 9,522,029 B2 | 12/2016 | Yates et al. |
| 9,526,481 B2 | 12/2016 | Storz et al. |
| 9,526,499 B2 | 12/2016 | Kostrzewski et al. |
| 9,526,564 B2 | 12/2016 | Rusin |
| 9,532,783 B2 | 1/2017 | Swayze et al. |
| 9,545,258 B2 | 1/2017 | Smith et al. |
| 9,549,732 B2 | 1/2017 | Yates et al. |
| 9,549,735 B2 | 1/2017 | Shelton, IV et al. |
| 9,554,794 B2 | 1/2017 | Baber et al. |
| 9,554,796 B2 | 1/2017 | Kostrzewski |
| 9,554,812 B2 | 1/2017 | Lnkpen et al. |
| 9,559,624 B2 | 1/2017 | Philipp |
| 9,561,031 B2 | 2/2017 | Heinrich et al. |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,566,061 B2 | 2/2017 | Aronhalt et al. |
| 9,566,067 B2 | 2/2017 | Milliman et al. |
| 9,572,574 B2 | 2/2017 | Shelton, IV et al. |
| 9,572,577 B2 | 2/2017 | Lloyd et al. |
| 9,572,592 B2 | 2/2017 | Price et al. |
| 9,574,644 B2 | 2/2017 | Parihar |
| 9,585,550 B2 | 3/2017 | Abel et al. |
| 9,585,657 B2 | 3/2017 | Shelton, IV et al. |
| 9,585,658 B2 | 3/2017 | Shelton, IV |
| 9,585,659 B2 | 3/2017 | Viola et al. |
| 9,585,660 B2 | 3/2017 | Laurent et al. |
| 9,585,662 B2 | 3/2017 | Shelton, IV et al. |
| 9,585,663 B2 | 3/2017 | Shelton, IV et al. |
| 9,585,672 B2 | 3/2017 | Bastia |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,592,054 B2 | 3/2017 | Schmid et al. |
| 9,597,073 B2 | 3/2017 | Sorrentino et al. |
| 9,597,075 B2 | 3/2017 | Shelton, IV et al. |
| 9,597,080 B2 | 3/2017 | Milliman et al. |
| 9,597,104 B2 | 3/2017 | Nicholas et al. |
| 9,597,143 B2 | 3/2017 | Madan et al. |
| 9,603,595 B2 | 3/2017 | Shelton, IV et al. |
| 9,603,598 B2 | 3/2017 | Shelton, IV et al. |
| 9,603,991 B2 | 3/2017 | Shelton, IV et al. |
| 9,610,080 B2 | 4/2017 | Whitfield et al. |
| 9,614,258 B2 | 4/2017 | Takahashi et al. |
| 9,615,826 B2 | 4/2017 | Shelton, IV et al. |
| 9,629,623 B2 | 4/2017 | Lytle, IV et al. |
| 9,629,626 B2 | 4/2017 | Soltz et al. |
| 9,629,629 B2 | 4/2017 | Leimbach et al. |
| 9,629,652 B2 | 4/2017 | Mumaw et al. |
| 9,629,814 B2 | 4/2017 | Widenhouse et al. |
| 9,636,850 B2 | 5/2017 | Stopek (Nee Prommersberger) et al. |
| 9,642,620 B2 | 5/2017 | Baxter, III et al. |
| 9,649,096 B2 | 5/2017 | Sholev |
| 9,649,110 B2 | 5/2017 | Parihar et al. |
| 9,649,111 B2 | 5/2017 | Shelton, IV et al. |
| 9,655,613 B2 | 5/2017 | Schaller |
| 9,655,614 B2 | 5/2017 | Swensgard et al. |
| 9,655,615 B2 | 5/2017 | Knodel et al. |
| 9,655,624 B2 | 5/2017 | Shelton, IV et al. |
| 9,662,108 B2 | 5/2017 | Williams |
| 9,662,110 B2 | 5/2017 | Huang et al. |
| 9,662,116 B2 | 5/2017 | Smith et al. |
| 9,662,131 B2 | 5/2017 | Omori et al. |
| 9,668,729 B2 | 6/2017 | Williams et al. |
| 9,668,732 B2 | 6/2017 | Patel et al. |
| 9,675,344 B2 | 6/2017 | Combrowski et al. |
| 9,675,351 B2 | 6/2017 | Hodgkinson et al. |
| 9,675,355 B2 | 6/2017 | Shelton, IV et al. |
| 9,675,372 B2 | 6/2017 | Laurent et al. |
| 9,675,375 B2 | 6/2017 | Houser et al. |
| 9,675,405 B2 | 6/2017 | Trees et al. |
| 9,681,870 B2 | 6/2017 | Baxter, III et al. |
| 9,681,873 B2 | 6/2017 | Smith et al. |
| 9,681,884 B2 | 6/2017 | Clem et al. |
| 9,687,230 B2 | 6/2017 | Leimbach et al. |
| 9,687,231 B2 | 6/2017 | Baxter, III et al. |
| 9,687,232 B2 | 6/2017 | Shelton, IV et al. |
| 9,687,233 B2 | 6/2017 | Fernandez et al. |
| 9,687,236 B2 | 6/2017 | Leimbach et al. |
| 9,687,237 B2 | 6/2017 | Schmid et al. |
| 9,687,253 B2 | 6/2017 | Detry et al. |
| 9,689,466 B2 | 6/2017 | Kanai et al. |
| 9,690,362 B2 | 6/2017 | Leimbach et al. |
| 9,693,772 B2 | 7/2017 | Ingmanson et al. |
| 9,693,774 B2 | 7/2017 | Gettinger et al. |
| 9,693,777 B2 | 7/2017 | Schellin et al. |
| 9,700,309 B2 | 7/2017 | Jaworek et al. |
| 9,700,310 B2 | 7/2017 | Morgan et al. |
| 9,700,312 B2 | 7/2017 | Kostrzewski et al. |
| 9,700,317 B2 | 7/2017 | Aronhalt et al. |
| 9,700,318 B2 | 7/2017 | Scirica et al. |
| 9,700,319 B2 | 7/2017 | Motooka et al. |
| 9,700,321 B2 | 7/2017 | Shelton, IV et al. |
| 9,706,981 B2 | 7/2017 | Nicholas et al. |
| 9,706,991 B2 | 7/2017 | Hess et al. |
| 9,706,993 B2 | 7/2017 | Hessler et al. |
| 9,707,026 B2 | 7/2017 | Malackowski et al. |
| 9,707,043 B2 | 7/2017 | Bozung |
| 9,707,684 B2 | 7/2017 | Ruiz Morales et al. |
| 9,713,468 B2 | 7/2017 | Harris et al. |
| 9,713,470 B2 | 7/2017 | Scirica et al. |
| 9,724,091 B2 | 8/2017 | Shelton, IV et al. |
| 9,724,092 B2 | 8/2017 | Baxter, III et al. |
| 9,724,094 B2 | 8/2017 | Baber et al. |
| 9,724,096 B2 | 8/2017 | Thompson et al. |
| 9,724,098 B2 | 8/2017 | Baxter, III et al. |
| 9,724,163 B2 | 8/2017 | Orban |

(56) References Cited

U.S. PATENT DOCUMENTS

| | | |
|---|---|---|
| 9,730,692 B2 | 8/2017 | Shelton, IV et al. |
| 9,730,695 B2 | 8/2017 | Leimbach et al. |
| 9,730,697 B2 | 8/2017 | Morgan et al. |
| 9,730,717 B2 | 8/2017 | Katsuki et al. |
| 9,731,410 B2 | 8/2017 | Hirabayashi et al. |
| 9,733,663 B2 | 8/2017 | Leimbach et al. |
| 9,737,297 B2 | 8/2017 | Racenet et al. |
| 9,737,301 B2 | 8/2017 | Baber et al. |
| 9,737,302 B2 | 8/2017 | Shelton, IV et al. |
| 9,737,303 B2 | 8/2017 | Shelton, IV et al. |
| 9,737,365 B2 | 8/2017 | Hegeman et al. |
| 9,743,927 B2 | 8/2017 | Whitman |
| 9,743,928 B2 | 8/2017 | Shelton, IV et al. |
| 9,743,929 B2 | 8/2017 | Leimbach et al. |
| 9,750,498 B2 | 9/2017 | Timm et al. |
| 9,750,499 B2 | 9/2017 | Leimbach et al. |
| 9,750,501 B2 | 9/2017 | Shelton, IV et al. |
| 9,750,639 B2 | 9/2017 | Barnes et al. |
| 9,757,123 B2 | 9/2017 | Giordano et al. |
| 9,757,124 B2 | 9/2017 | Schellin et al. |
| 9,757,126 B2 | 9/2017 | Cappola |
| 9,757,128 B2 | 9/2017 | Baber et al. |
| 9,757,129 B2 | 9/2017 | Williams |
| 9,757,130 B2 | 9/2017 | Shelton, IV |
| 9,763,662 B2 | 9/2017 | Shelton, IV et al. |
| 9,770,245 B2 | 9/2017 | Swayze et al. |
| D800,904 S | 10/2017 | Leimbach et al. |
| 9,775,608 B2 | 10/2017 | Aronhalt et al. |
| 9,775,609 B2 | 10/2017 | Shelton, IV et al. |
| 9,775,610 B2 | 10/2017 | Nicholas et al. |
| 9,775,611 B2 | 10/2017 | Kostrzewski |
| 9,775,613 B2 | 10/2017 | Shelton, IV et al. |
| 9,775,614 B2 | 10/2017 | Shelton, IV et al. |
| 9,782,169 B2 | 10/2017 | Kimsey et al. |
| 9,782,170 B2 | 10/2017 | Zemlok et al. |
| 9,782,214 B2 | 10/2017 | Houser et al. |
| 9,788,834 B2 | 10/2017 | Schmid et al. |
| 9,788,836 B2 | 10/2017 | Overmyer et al. |
| 9,788,847 B2 | 10/2017 | Jinno |
| 9,788,851 B2 | 10/2017 | Dannaher et al. |
| 9,795,379 B2 | 10/2017 | Leimbach et al. |
| 9,795,381 B2 | 10/2017 | Shelton, IV |
| 9,795,382 B2 | 10/2017 | Shelton, IV |
| 9,795,383 B2 | 10/2017 | Aldridge et al. |
| 9,795,384 B2 | 10/2017 | Weaner et al. |
| 9,797,486 B2 | 10/2017 | Zergiebel et al. |
| 9,801,626 B2 | 10/2017 | Parihar et al. |
| 9,801,627 B2 | 10/2017 | Harris et al. |
| 9,801,628 B2 | 10/2017 | Harris et al. |
| 9,801,634 B2 | 10/2017 | Shelton, IV et al. |
| 9,802,033 B2 | 10/2017 | Hibner et al. |
| 9,804,618 B2 | 10/2017 | Leimbach et al. |
| 9,808,244 B2 | 11/2017 | Leimbach et al. |
| 9,808,246 B2 | 11/2017 | Shelton, IV et al. |
| 9,808,247 B2 | 11/2017 | Shelton, IV et al. |
| 9,808,249 B2 | 11/2017 | Shelton, IV |
| 9,814,460 B2 | 11/2017 | Kimsey et al. |
| 9,814,462 B2 | 11/2017 | Woodard, Jr. et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,825,455 B2 | 11/2017 | Sandhu et al. |
| 9,826,976 B2 | 11/2017 | Parihar et al. |
| 9,826,977 B2 | 11/2017 | Leimbach et al. |
| 9,826,978 B2 | 11/2017 | Shelton, IV et al. |
| 9,829,698 B2 | 11/2017 | Haraguchi et al. |
| 9,833,236 B2 | 12/2017 | Shelton, IV et al. |
| 9,833,238 B2 | 12/2017 | Baxter, III et al. |
| 9,833,239 B2 | 12/2017 | Yates et al. |
| 9,833,241 B2 | 12/2017 | Huitema et al. |
| 9,833,242 B2 | 12/2017 | Baxter, III et al. |
| 9,839,420 B2 | 12/2017 | Shelton, IV et al. |
| 9,839,421 B2 | 12/2017 | Zerkle et al. |
| 9,839,422 B2 | 12/2017 | Schellin et al. |
| 9,839,423 B2 | 12/2017 | Vendely et al. |
| 9,839,427 B2 | 12/2017 | Swayze et al. |
| 9,839,428 B2 | 12/2017 | Baxter, III et al. |
| 9,839,429 B2 | 12/2017 | Weisenburgh, II et al. |
| 9,839,480 B2 | 12/2017 | Pribanic et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,873 B2 | 12/2017 | Shelton, IV |
| 9,848,875 B2 | 12/2017 | Aronhalt et al. |
| 9,855,662 B2 | 1/2018 | Ruiz Morales et al. |
| 9,861,261 B2 | 1/2018 | Shahinian |
| 9,861,359 B2 | 1/2018 | Shelton, IV et al. |
| 9,861,361 B2 | 1/2018 | Aronhalt et al. |
| 9,861,382 B2 | 1/2018 | Smith et al. |
| 9,867,612 B2 | 1/2018 | Parihar et al. |
| 9,867,618 B2 | 1/2018 | Hall et al. |
| 9,868,198 B2 | 1/2018 | Nicholas et al. |
| 9,872,682 B2 | 1/2018 | Hess et al. |
| 9,872,683 B2 | 1/2018 | Hopkins et al. |
| 9,872,684 B2 | 1/2018 | Hall et al. |
| 9,877,721 B2 | 1/2018 | Schellin et al. |
| 9,877,723 B2 | 1/2018 | Hall et al. |
| 9,883,860 B2 | 2/2018 | Leimbach et al. |
| 9,883,861 B2 | 2/2018 | Shelton, IV et al. |
| 9,884,456 B2 | 2/2018 | Schellin et al. |
| 9,888,919 B2 | 2/2018 | Leimbach et al. |
| 9,888,924 B2 | 2/2018 | Ebersole et al. |
| 9,889,230 B2 | 2/2018 | Bennett et al. |
| 9,895,147 B2 | 2/2018 | Shelton, IV |
| 9,895,148 B2 | 2/2018 | Shelton, IV et al. |
| 9,895,813 B2 | 2/2018 | Blumenkranz et al. |
| 9,901,341 B2 | 2/2018 | Kostrzewski |
| 9,901,342 B2 | 2/2018 | Shelton, IV et al. |
| 9,901,344 B2 | 2/2018 | Moore et al. |
| 9,901,345 B2 | 2/2018 | Moore et al. |
| 9,901,346 B2 | 2/2018 | Moore et al. |
| 9,907,456 B2 | 3/2018 | Miyoshi |
| 9,907,553 B2 | 3/2018 | Cole et al. |
| 9,907,620 B2 | 3/2018 | Shelton, IV et al. |
| 9,913,642 B2 | 3/2018 | Leimbach et al. |
| 9,913,644 B2 | 3/2018 | McCuen |
| 9,913,646 B2 | 3/2018 | Shelton, IV |
| 9,913,647 B2 | 3/2018 | Weisenburgh, II et al. |
| 9,913,648 B2 | 3/2018 | Shelton, IV et al. |
| 9,913,694 B2 | 3/2018 | Brisson |
| 9,918,704 B2 | 3/2018 | Shelton, IV et al. |
| 9,918,715 B2 | 3/2018 | Menn |
| 9,918,716 B2 | 3/2018 | Baxter, III et al. |
| 9,924,942 B2 | 3/2018 | Swayze et al. |
| 9,924,944 B2 | 3/2018 | Shelton, IV et al. |
| 9,924,945 B2 | 3/2018 | Zheng et al. |
| 9,924,946 B2 | 3/2018 | Vendely et al. |
| 9,924,947 B2 | 3/2018 | Shelton, IV et al. |
| 9,924,961 B2 | 3/2018 | Shelton, IV et al. |
| 9,931,116 B2 | 4/2018 | Racenet et al. |
| 9,931,118 B2 | 4/2018 | Shelton, IV et al. |
| 9,936,949 B2 | 4/2018 | Measamer et al. |
| 9,936,950 B2 | 4/2018 | Shelton, IV et al. |
| 9,936,951 B2 | 4/2018 | Hufnagel et al. |
| 9,936,954 B2 | 4/2018 | Shelton, IV et al. |
| 9,943,309 B2 | 4/2018 | Shelton, IV et al. |
| 9,943,310 B2 | 4/2018 | Harris et al. |
| 9,943,312 B2 | 4/2018 | Posada et al. |
| 9,955,965 B2 | 5/2018 | Chen et al. |
| 9,955,966 B2 | 5/2018 | Zergiebel |
| 9,962,158 B2 | 5/2018 | Hall et al. |
| 9,962,159 B2 | 5/2018 | Heinrich et al. |
| 9,962,161 B2 | 5/2018 | Scheib et al. |
| 9,968,354 B2 | 5/2018 | Shelton, IV et al. |
| 9,968,355 B2 | 5/2018 | Shelton, IV et al. |
| 9,968,356 B2 | 5/2018 | Shelton, IV et al. |
| 9,968,397 B2 | 5/2018 | Taylor et al. |
| 9,974,529 B2 | 5/2018 | Shelton, IV et al. |
| 9,974,538 B2 | 5/2018 | Baxter, III et al. |

(56) References Cited

U.S. PATENT DOCUMENTS

| | | |
|---|---|---|
| 9,974,539 B2 | 5/2018 | Yates et al. |
| 9,980,713 B2 | 5/2018 | Aronhalt et al. |
| 9,980,729 B2 | 5/2018 | Moore et al. |
| 9,987,000 B2 | 6/2018 | Shelton, IV et al. |
| 9,987,003 B2 | 6/2018 | Timm et al. |
| 9,987,006 B2 | 6/2018 | Morgan et al. |
| 9,993,248 B2 | 6/2018 | Shelton, IV et al. |
| 9,993,258 B2 | 6/2018 | Shelton, IV et al. |
| 9,999,408 B2 | 6/2018 | Boudreaux et al. |
| 9,999,426 B2 | 6/2018 | Moore et al. |
| 9,999,431 B2 | 6/2018 | Shelton, IV et al. |
| 10,004,497 B2 | 6/2018 | Overmyer et al. |
| 10,004,498 B2 | 6/2018 | Morgan et al. |
| 10,004,500 B2 | 6/2018 | Shelton, IV et al. |
| 10,004,501 B2 | 6/2018 | Shelton, IV et al. |
| 10,004,505 B2 | 6/2018 | Moore et al. |
| 10,004,506 B2 | 6/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,022,125 B2 | 7/2018 | (Prommersberger) Stopek et al. |
| 10,024,407 B2 | 7/2018 | Aranyi et al. |
| 10,028,742 B2 | 7/2018 | Shelton, IV et al. |
| 10,028,743 B2 | 7/2018 | Shelton, IV et al. |
| 10,028,744 B2 | 7/2018 | Shelton, IV et al. |
| 10,028,761 B2 | 7/2018 | Leimbach et al. |
| 10,029,125 B2 | 7/2018 | Shapiro et al. |
| 10,034,668 B2 | 7/2018 | Ebner |
| 10,039,440 B2 | 8/2018 | Fenech et al. |
| 10,039,529 B2 | 8/2018 | Kerr et al. |
| 10,039,545 B2 | 8/2018 | Sadowski et al. |
| 10,041,822 B2 | 8/2018 | Zemlok |
| 10,045,769 B2 | 8/2018 | Aronhalt et al. |
| 10,045,776 B2 | 8/2018 | Shelton, IV et al. |
| 10,045,778 B2 | 8/2018 | Yates et al. |
| 10,045,779 B2 | 8/2018 | Savage et al. |
| 10,045,781 B2 | 8/2018 | Cropper et al. |
| 10,052,044 B2 | 8/2018 | Shelton, IV et al. |
| 10,052,099 B2 | 8/2018 | Morgan et al. |
| 10,052,100 B2 | 8/2018 | Morgan et al. |
| 10,052,102 B2 | 8/2018 | Baxter, III et al. |
| 10,052,104 B2 | 8/2018 | Shelton, IV et al. |
| 10,052,164 B2 | 8/2018 | Overmyer |
| 10,058,317 B2 | 8/2018 | Fan et al. |
| 10,058,327 B2 | 8/2018 | Weisenburgh, II et al. |
| 10,058,963 B2 | 8/2018 | Shelton, IV et al. |
| 10,064,620 B2 | 9/2018 | Gettinger et al. |
| 10,064,621 B2 | 9/2018 | Kerr et al. |
| 10,064,624 B2 | 9/2018 | Shelton, IV et al. |
| 10,064,639 B2 | 9/2018 | Ishida et al. |
| 10,064,649 B2 | 9/2018 | Golebieski et al. |
| 10,064,688 B2 | 9/2018 | Shelton, IV et al. |
| 10,070,861 B2 | 9/2018 | Spivey et al. |
| 10,070,863 B2 | 9/2018 | Swayze et al. |
| 10,071,452 B2 | 9/2018 | Shelton, IV et al. |
| 10,076,325 B2 | 9/2018 | Huang et al. |
| 10,076,326 B2 | 9/2018 | Yates et al. |
| 10,085,624 B2 | 10/2018 | Isoda et al. |
| 10,085,748 B2 | 10/2018 | Morgan et al. |
| 10,085,751 B2 | 10/2018 | Overmyer et al. |
| 10,085,806 B2 | 10/2018 | Hagn et al. |
| 10,092,292 B2 | 10/2018 | Boudreaux et al. |
| 2001/0000531 A1 | 4/2001 | Casscells et al. |
| 2001/0025183 A1 | 9/2001 | Shahidi |
| 2002/0014510 A1 | 2/2002 | Richter et al. |
| 2002/0022810 A1 | 2/2002 | Urich |
| 2002/0022836 A1 | 2/2002 | Goble et al. |
| 2002/0022861 A1 | 2/2002 | Jacobs et al. |
| 2002/0029032 A1 | 3/2002 | Arkin |
| 2002/0029036 A1 | 3/2002 | Goble et al. |
| 2002/0042620 A1 | 4/2002 | Julian et al. |
| 2002/0091374 A1 | 7/2002 | Cooper |
| 2002/0095175 A1 | 7/2002 | Brock et al. |
| 2002/0103494 A1 | 8/2002 | Pacey |
| 2002/0117534 A1 | 8/2002 | Green et al. |
| 2002/0127265 A1 | 9/2002 | Bowman et al. |
| 2002/0128633 A1 | 9/2002 | Brock et al. |
| 2002/0134811 A1 | 9/2002 | Napier et al. |
| 2002/0135474 A1 | 9/2002 | Sylliassen |
| 2002/0143340 A1 | 10/2002 | Kaneko |
| 2002/0158593 A1 | 10/2002 | Henderson et al. |
| 2002/0185514 A1 | 12/2002 | Adams et al. |
| 2002/0188170 A1 | 12/2002 | Santamore et al. |
| 2002/0188287 A1 | 12/2002 | Zvuloni et al. |
| 2003/0009193 A1 | 1/2003 | Corsaro |
| 2003/0011245 A1 | 1/2003 | Fiebig |
| 2003/0066858 A1 | 4/2003 | Holgersson |
| 2003/0078647 A1 | 4/2003 | Vallana et al. |
| 2003/0083648 A1 | 5/2003 | Wang et al. |
| 2003/0084983 A1 | 5/2003 | Rangachari et al. |
| 2003/0093103 A1 | 5/2003 | Malackowski et al. |
| 2003/0094356 A1 | 5/2003 | Waldron |
| 2003/0096158 A1 | 5/2003 | Takano et al. |
| 2003/0114851 A1 | 6/2003 | Truckai et al. |
| 2003/0139741 A1 | 7/2003 | Goble et al. |
| 2003/0153908 A1 | 8/2003 | Goble et al. |
| 2003/0153968 A1 | 8/2003 | Geis et al. |
| 2003/0163085 A1 | 8/2003 | Tanner et al. |
| 2003/0181900 A1 | 9/2003 | Long |
| 2003/0190584 A1 | 10/2003 | Heasley |
| 2003/0195387 A1 | 10/2003 | Kortenbach et al. |
| 2003/0205029 A1 | 11/2003 | Chapolini et al. |
| 2003/0212005 A1 | 11/2003 | Petito et al. |
| 2003/0216732 A1 | 11/2003 | Truckai et al. |
| 2003/0236505 A1 | 12/2003 | Bonadio et al. |
| 2004/0006335 A1 | 1/2004 | Garrison |
| 2004/0006340 A1 | 1/2004 | Latterell et al. |
| 2004/0007608 A1 | 1/2004 | Ehrenfels et al. |
| 2004/0024457 A1 | 2/2004 | Boyce et al. |
| 2004/0028502 A1 | 2/2004 | Cummins |
| 2004/0030333 A1 | 2/2004 | Goble |
| 2004/0034357 A1 | 2/2004 | Beane et al. |
| 2004/0044364 A1 | 3/2004 | DeVries et al. |
| 2004/0049121 A1 | 3/2004 | Yaron |
| 2004/0049172 A1 | 3/2004 | Root et al. |
| 2004/0059362 A1 | 3/2004 | Knodel et al. |
| 2004/0068161 A1 | 4/2004 | Couvillon |
| 2004/0068224 A1 | 4/2004 | Couvillon et al. |
| 2004/0068307 A1 | 4/2004 | Goble |
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0085180 A1 | 5/2004 | Juang |
| 2004/0093024 A1 | 5/2004 | Lousararian et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin et al. |
| 2004/0108357 A1 | 6/2004 | Milliman et al. |
| 2004/0110439 A1 | 6/2004 | Chaikof et al. |
| 2004/0115022 A1 | 6/2004 | Albertson et al. |
| 2004/0116952 A1 | 6/2004 | Sakurai et al. |
| 2004/0122423 A1 | 6/2004 | Dycus et al. |
| 2004/0133095 A1 | 7/2004 | Dunki-Jacobs et al. |
| 2004/0143297 A1 | 7/2004 | Ramsey |
| 2004/0147909 A1 | 7/2004 | Johnston et al. |
| 2004/0153100 A1 | 8/2004 | Ahlberg et al. |
| 2004/0158261 A1 | 8/2004 | Vu |
| 2004/0164123 A1 | 8/2004 | Racenet et al. |
| 2004/0167572 A1 | 8/2004 | Roth et al. |
| 2004/0181219 A1 | 9/2004 | Goble et al. |
| 2004/0193189 A1 | 9/2004 | Kortenbach et al. |
| 2004/0197367 A1 | 10/2004 | Rezania et al. |
| 2004/0199181 A1 | 10/2004 | Knodel et al. |
| 2004/0204735 A1 | 10/2004 | Shiroff et al. |
| 2004/0222268 A1 | 11/2004 | Bilotti et al. |
| 2004/0225186 A1 | 11/2004 | Horne et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0247415 A1 | 12/2004 | Mangone |
| 2004/0249366 A1 | 12/2004 | Kunz |

(56) References Cited

U.S. PATENT DOCUMENTS

| | | |
|---|---|---|
| 2004/0254455 A1 | 12/2004 | Iddan |
| 2004/0254566 A1 | 12/2004 | Plicchi et al. |
| 2004/0254590 A1 | 12/2004 | Hoffman et al. |
| 2004/0260315 A1 | 12/2004 | Deli et al. |
| 2004/0267310 A1 | 12/2004 | Racenet et al. |
| 2005/0010158 A1 | 1/2005 | Brugger et al. |
| 2005/0010213 A1 | 1/2005 | Stad et al. |
| 2005/0021078 A1 | 1/2005 | Vleugels et al. |
| 2005/0032511 A1 | 2/2005 | Malone et al. |
| 2005/0033352 A1 | 2/2005 | Zepf et al. |
| 2005/0051163 A1 | 3/2005 | Deem et al. |
| 2005/0054946 A1 | 3/2005 | Krzyzanowski |
| 2005/0057225 A1 | 3/2005 | Marquet |
| 2005/0058890 A1 | 3/2005 | Brazell et al. |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080342 A1 | 4/2005 | Gilreath et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0116673 A1 | 6/2005 | Carl et al. |
| 2005/0124855 A1 | 6/2005 | Jaffe et al. |
| 2005/0125897 A1 | 6/2005 | Wyslucha et al. |
| 2005/0130682 A1 | 6/2005 | Takara et al. |
| 2005/0131173 A1 | 6/2005 | McDaniel et al. |
| 2005/0131211 A1 | 6/2005 | Bayley et al. |
| 2005/0131390 A1* | 6/2005 | Heinrich ............ A61B 17/0469 606/1 |
| 2005/0131436 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0139636 A1 | 6/2005 | Schwemberger et al. |
| 2005/0143759 A1 | 6/2005 | Kelly |
| 2005/0143769 A1 | 6/2005 | White et al. |
| 2005/0145671 A1 | 7/2005 | Viola |
| 2005/0150928 A1 | 7/2005 | Kameyama et al. |
| 2005/0154258 A1 | 7/2005 | Tartaglia et al. |
| 2005/0154406 A1 | 7/2005 | Bombard et al. |
| 2005/0159778 A1 | 7/2005 | Heinrich et al. |
| 2005/0165419 A1 | 7/2005 | Sauer et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0177249 A1 | 8/2005 | Kladakis et al. |
| 2005/0182298 A1 | 8/2005 | Ikeda et al. |
| 2005/0184121 A1 | 8/2005 | Heinrich |
| 2005/0186240 A1 | 8/2005 | Ringeisen et al. |
| 2005/0187545 A1 | 8/2005 | Hooven et al. |
| 2005/0203550 A1 | 9/2005 | Laufer et al. |
| 2005/0209614 A1 | 9/2005 | Fenter et al. |
| 2005/0216055 A1 | 9/2005 | Scirica et al. |
| 2005/0222587 A1 | 10/2005 | Jinno et al. |
| 2005/0222611 A1 | 10/2005 | Weitkamp |
| 2005/0222616 A1 | 10/2005 | Rethy et al. |
| 2005/0222665 A1 | 10/2005 | Aranyi |
| 2005/0228224 A1 | 10/2005 | Okada et al. |
| 2005/0228446 A1 | 10/2005 | Mooradian et al. |
| 2005/0230453 A1 | 10/2005 | Viola |
| 2005/0240178 A1 | 10/2005 | Morley et al. |
| 2005/0245965 A1 | 11/2005 | Orban, III et al. |
| 2005/0251063 A1 | 11/2005 | Basude |
| 2005/0256452 A1 | 11/2005 | DeMarchi et al. |
| 2005/0261676 A1 | 11/2005 | Hall et al. |
| 2005/0263563 A1 | 12/2005 | Racenet et al. |
| 2005/0267455 A1 | 12/2005 | Eggers et al. |
| 2005/0274034 A1 | 12/2005 | Hayashida et al. |
| 2005/0283188 A1 | 12/2005 | Loshakove et al. |
| 2006/0008787 A1 | 1/2006 | Hayman et al. |
| 2006/0015009 A1 | 1/2006 | Jaffe et al. |
| 2006/0020258 A1 | 1/2006 | Strauss et al. |
| 2006/0020336 A1 | 1/2006 | Liddicoat |
| 2006/0025812 A1 | 2/2006 | Shelton |
| 2006/0041188 A1 | 2/2006 | Dirusso et al. |
| 2006/0047275 A1 | 3/2006 | Goble |
| 2006/0049229 A1 | 3/2006 | Milliman et al. |
| 2006/0052824 A1 | 3/2006 | Ransick et al. |
| 2006/0052825 A1 | 3/2006 | Ransick et al. |
| 2006/0064086 A1 | 3/2006 | Odom |
| 2006/0079735 A1 | 4/2006 | Martone et al. |
| 2006/0079879 A1 | 4/2006 | Faller et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0100643 A1 | 5/2006 | Laufer et al. |
| 2006/0100649 A1 | 5/2006 | Hart |
| 2006/0111711 A1 | 5/2006 | Goble |
| 2006/0111723 A1 | 5/2006 | Chapolini et al. |
| 2006/0116634 A1 | 6/2006 | Shachar |
| 2006/0142772 A1 | 6/2006 | Ralph et al. |
| 2006/0161050 A1 | 7/2006 | Butler et al. |
| 2006/0161185 A1 | 7/2006 | Saadat et al. |
| 2006/0167471 A1 | 7/2006 | Phillips |
| 2006/0173470 A1 | 8/2006 | Oray et al. |
| 2006/0176031 A1 | 8/2006 | Forman et al. |
| 2006/0178556 A1 | 8/2006 | Nasser et al. |
| 2006/0180633 A1 | 8/2006 | Emmons |
| 2006/0180634 A1 | 8/2006 | Shelton et al. |
| 2006/0185682 A1 | 8/2006 | Marczyk |
| 2006/0199999 A1 | 9/2006 | Ikeda et al. |
| 2006/0201989 A1 | 9/2006 | Ojeda |
| 2006/0206100 A1 | 9/2006 | Eskridge et al. |
| 2006/0217729 A1 | 9/2006 | Eskridge et al. |
| 2006/0235368 A1 | 10/2006 | Oz |
| 2006/0244460 A1 | 11/2006 | Weaver |
| 2006/0252990 A1 | 11/2006 | Kubach |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0261763 A1 | 11/2006 | Iott et al. |
| 2006/0264831 A1 | 11/2006 | Skwarek et al. |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0273135 A1* | 12/2006 | Beetel .................. A61B 17/068 227/175.1 |
| 2006/0282064 A1 | 12/2006 | Shimizu et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0010702 A1 | 1/2007 | Wang et al. |
| 2007/0010838 A1 | 1/2007 | Shelton et al. |
| 2007/0016235 A1 | 1/2007 | Tanaka et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027551 A1 | 2/2007 | Farnsworth et al. |
| 2007/0043387 A1 | 2/2007 | Vargas et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0055228 A1 | 3/2007 | Berg et al. |
| 2007/0073341 A1 | 3/2007 | Smith et al. |
| 2007/0073389 A1 | 3/2007 | Bolduc et al. |
| 2007/0078328 A1 | 4/2007 | Ozaki et al. |
| 2007/0078484 A1 | 4/2007 | Talarico et al. |
| 2007/0084897 A1 | 4/2007 | Shelton et al. |
| 2007/0090788 A1 | 4/2007 | Hansford et al. |
| 2007/0093869 A1 | 4/2007 | Bloom et al. |
| 2007/0102472 A1 | 5/2007 | Shelton |
| 2007/0106113 A1 | 5/2007 | Ravo |
| 2007/0106317 A1 | 5/2007 | Shelton et al. |
| 2007/0134251 A1 | 6/2007 | Ashkenazi et al. |
| 2007/0135686 A1 | 6/2007 | Pruitt et al. |
| 2007/0135803 A1 | 6/2007 | Belson |
| 2007/0155010 A1 | 7/2007 | Farnsworth et al. |
| 2007/0170225 A1 | 7/2007 | Shelton et al. |
| 2007/0173687 A1 | 7/2007 | Shima et al. |
| 2007/0173813 A1 | 7/2007 | Odom |
| 2007/0175950 A1 | 8/2007 | Shelton et al. |
| 2007/0175951 A1 | 8/2007 | Shelton et al. |
| 2007/0175955 A1 | 8/2007 | Shelton et al. |

(56) References Cited

U.S. PATENT DOCUMENTS

| | | |
|---|---|---|
| 2007/0175962 A1* | 8/2007 | Shelton, IV ..... A61B 17/07207 227/178.1 |
| 2007/0179477 A1 | 8/2007 | Danger |
| 2007/0185545 A1 | 8/2007 | Duke |
| 2007/0190110 A1 | 8/2007 | Pameijer et al. |
| 2007/0191868 A1 | 8/2007 | Theroux et al. |
| 2007/0194079 A1 | 8/2007 | Hueil et al. |
| 2007/0194082 A1 | 8/2007 | Morgan et al. |
| 2007/0197954 A1 | 8/2007 | Keenan |
| 2007/0198039 A1 | 8/2007 | Jones et al. |
| 2007/0203510 A1 | 8/2007 | Bettuchi |
| 2007/0208375 A1 | 9/2007 | Nishizawa et al. |
| 2007/0213750 A1 | 9/2007 | Weadock |
| 2007/0225562 A1 | 9/2007 | Spivey et al. |
| 2007/0233163 A1 | 10/2007 | Bombard et al. |
| 2007/0243227 A1 | 10/2007 | Gertner |
| 2007/0244471 A1 | 10/2007 | Malackowski |
| 2007/0246505 A1 | 10/2007 | Pace-Floridia et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0296286 A1 | 12/2007 | Avenell |
| 2008/0003196 A1 | 1/2008 | Jonn et al. |
| 2008/0015598 A1 | 1/2008 | Prommersberger |
| 2008/0021486 A1 | 1/2008 | Oyola et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0042861 A1 | 2/2008 | Dacquay et al. |
| 2008/0051833 A1 | 2/2008 | Gramuglia et al. |
| 2008/0064921 A1 | 3/2008 | Larkin et al. |
| 2008/0065153 A1 | 3/2008 | Allard et al. |
| 2008/0071328 A1 | 3/2008 | Haubrich et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083807 A1 | 4/2008 | Beardsley et al. |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0108443 A1 | 5/2008 | Jinno et al. |
| 2008/0114250 A1 | 5/2008 | Urbano et al. |
| 2008/0125749 A1 | 5/2008 | Olson |
| 2008/0128469 A1 | 6/2008 | Dalessandro et al. |
| 2008/0129253 A1 | 6/2008 | Shiue et al. |
| 2008/0135600 A1 | 6/2008 | Hiranuma et al. |
| 2008/0140115 A1 | 6/2008 | Stopek |
| 2008/0140159 A1 | 6/2008 | Bornhoft et al. |
| 2008/0154299 A1 | 6/2008 | Livneh |
| 2008/0154335 A1 | 6/2008 | Thrope et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0183193 A1 | 7/2008 | Omori et al. |
| 2008/0190989 A1 | 8/2008 | Crews et al. |
| 2008/0196419 A1 | 8/2008 | Dube |
| 2008/0197167 A1 | 8/2008 | Viola et al. |
| 2008/0200755 A1 | 8/2008 | Bakos |
| 2008/0200762 A1 | 8/2008 | Stokes et al. |
| 2008/0200835 A1 | 8/2008 | Monson et al. |
| 2008/0200911 A1 | 8/2008 | Long |
| 2008/0200933 A1 | 8/2008 | Bakos et al. |
| 2008/0200934 A1 | 8/2008 | Fox |
| 2008/0234709 A1 | 9/2008 | Houser |
| 2008/0242939 A1 | 10/2008 | Johnston |
| 2008/0249536 A1 | 10/2008 | Stahler et al. |
| 2008/0249608 A1 | 10/2008 | Dave |
| 2008/0255413 A1 | 10/2008 | Zemlok et al. |
| 2008/0262654 A1 | 10/2008 | Omori et al. |
| 2008/0269596 A1 | 10/2008 | Revie et al. |
| 2008/0281171 A1 | 11/2008 | Fennell et al. |
| 2008/0287944 A1 | 11/2008 | Pearson et al. |
| 2008/0293910 A1 | 11/2008 | Kapiamba et al. |
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0308602 A1 | 12/2008 | Timm et al. |
| 2008/0308603 A1 | 12/2008 | Shelton et al. |
| 2008/0312687 A1 | 12/2008 | Blier |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0012534 A1 | 1/2009 | Madhani et al. |
| 2009/0015195 A1 | 1/2009 | Loth-Krausser |
| 2009/0020958 A1 | 1/2009 | Soul |
| 2009/0048583 A1 | 2/2009 | Williams et al. |
| 2009/0048589 A1 | 2/2009 | Takashino et al. |
| 2009/0076506 A1 | 3/2009 | Baker |
| 2009/0078736 A1 | 3/2009 | Van Lue |
| 2009/0081313 A1 | 3/2009 | Aghion et al. |
| 2009/0088659 A1 | 4/2009 | Graham et al. |
| 2009/0090763 A1 | 4/2009 | Zemlok et al. |
| 2009/0092651 A1 | 4/2009 | Shah et al. |
| 2009/0099579 A1 | 4/2009 | Nentwick et al. |
| 2009/0099876 A1 | 4/2009 | Whitman |
| 2009/0119011 A1 | 5/2009 | Kondo et al. |
| 2009/0143855 A1 | 6/2009 | Weber et al. |
| 2009/0149871 A9 | 6/2009 | Kagan et al. |
| 2009/0171147 A1 | 7/2009 | Lee et al. |
| 2009/0177226 A1 | 7/2009 | Reinprecht et al. |
| 2009/0181290 A1 | 7/2009 | Baldwin et al. |
| 2009/0188964 A1 | 7/2009 | Orlov |
| 2009/0198272 A1 | 8/2009 | Kerver et al. |
| 2009/0204108 A1 | 8/2009 | Steffen |
| 2009/0204109 A1 | 8/2009 | Grove et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0221993 A1 | 9/2009 | Sohi et al. |
| 2009/0234273 A1 | 9/2009 | Intoccia et al. |
| 2009/0242610 A1 | 10/2009 | Shelton, IV et al. |
| 2009/0247368 A1 | 10/2009 | Chiang |
| 2009/0247901 A1 | 10/2009 | Zimmer |
| 2009/0248041 A1 | 10/2009 | Williams et al. |
| 2009/0253959 A1 | 10/2009 | Yoshie et al. |
| 2009/0255974 A1 | 10/2009 | Viola |
| 2009/0262078 A1 | 10/2009 | Pizzi |
| 2009/0270895 A1 | 10/2009 | Churchill et al. |
| 2009/0290016 A1 | 11/2009 | Suda |
| 2009/0292283 A1 | 11/2009 | Odom |
| 2009/0306639 A1 | 12/2009 | Nevo et al. |
| 2009/0308907 A1 | 12/2009 | Nalagatla et al. |
| 2010/0012703 A1 | 1/2010 | Calabrese et al. |
| 2010/0016888 A1 | 1/2010 | Calabrese et al. |
| 2010/0023024 A1 | 1/2010 | Zeiner et al. |
| 2010/0030233 A1 | 2/2010 | Whitman et al. |
| 2010/0036370 A1 | 2/2010 | Mirel et al. |
| 2010/0065604 A1 | 3/2010 | Weng |
| 2010/0069942 A1 | 3/2010 | Shelton, IV |
| 2010/0076483 A1 | 3/2010 | Imuta |
| 2010/0076489 A1 | 3/2010 | Stopek et al. |
| 2010/0081883 A1 | 4/2010 | Murray et al. |
| 2010/0094340 A1 | 4/2010 | Stopek et al. |
| 2010/0100124 A1 | 4/2010 | Calabrese et al. |
| 2010/0116519 A1 | 5/2010 | Gareis |
| 2010/0122339 A1 | 5/2010 | Boccacci |
| 2010/0133317 A1 | 6/2010 | Shelton, IV et al. |
| 2010/0145146 A1 | 6/2010 | Melder |
| 2010/0147921 A1 | 6/2010 | Olson |
| 2010/0147922 A1 | 6/2010 | Olson |
| 2010/0179022 A1 | 7/2010 | Shirokoshi |
| 2010/0180711 A1 | 7/2010 | Kilibarda et al. |

(56) References Cited

U.S. PATENT DOCUMENTS

| | | |
|---|---|---|
| 2010/0191262 A1 | 7/2010 | Harris et al. |
| 2010/0191292 A1 | 7/2010 | DeMeo et al. |
| 2010/0193566 A1 | 8/2010 | Scheib et al. |
| 2010/0204717 A1 | 8/2010 | Knodel |
| 2010/0222901 A1 | 9/2010 | Swayze et al. |
| 2010/0249497 A1 | 9/2010 | Peine et al. |
| 2010/0256675 A1 | 10/2010 | Romans |
| 2010/0258327 A1 | 10/2010 | Esenwein et al. |
| 2010/0267662 A1 | 10/2010 | Fielder et al. |
| 2010/0274160 A1 | 10/2010 | Yachi et al. |
| 2010/0292540 A1 | 11/2010 | Hess et al. |
| 2010/0298636 A1 | 11/2010 | Castro et al. |
| 2010/0312261 A1 | 12/2010 | Suzuki et al. |
| 2010/0318085 A1 | 12/2010 | Austin et al. |
| 2010/0331856 A1 | 12/2010 | Carlson et al. |
| 2011/0006101 A1 | 1/2011 | Hall et al. |
| 2011/0011916 A1 | 1/2011 | Levine |
| 2011/0016960 A1 | 1/2011 | Debrailly |
| 2011/0021871 A1 | 1/2011 | Berkelaar |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0025311 A1 | 2/2011 | Chauvin et al. |
| 2011/0034910 A1 | 2/2011 | Ross et al. |
| 2011/0036891 A1 | 2/2011 | Zemlok et al. |
| 2011/0046667 A1 | 2/2011 | Culligan et al. |
| 2011/0060363 A1 | 3/2011 | Hess et al. |
| 2011/0066156 A1 | 3/2011 | McGahan et al. |
| 2011/0082538 A1 | 4/2011 | Dahlgren et al. |
| 2011/0087276 A1 | 4/2011 | Bedi et al. |
| 2011/0087278 A1 | 4/2011 | Viola et al. |
| 2011/0088921 A1 | 4/2011 | Forgues et al. |
| 2011/0095064 A1 | 4/2011 | Taylor et al. |
| 2011/0101069 A1 | 5/2011 | Bombard et al. |
| 2011/0101794 A1 | 5/2011 | Schroeder et al. |
| 2011/0112517 A1 | 5/2011 | Peine et al. |
| 2011/0112530 A1 | 5/2011 | Keller |
| 2011/0114697 A1 | 5/2011 | Baxter, III et al. |
| 2011/0121049 A1 | 5/2011 | Malinouskas et al. |
| 2011/0125138 A1 | 5/2011 | Malinouskas et al. |
| 2011/0125176 A1 | 5/2011 | Yates et al. |
| 2011/0127945 A1 | 6/2011 | Yoneda |
| 2011/0129706 A1 | 6/2011 | Takahashi et al. |
| 2011/0144764 A1 | 6/2011 | Bagga et al. |
| 2011/0147433 A1 | 6/2011 | Shelton, IV et al. |
| 2011/0163146 A1 | 7/2011 | Ortiz et al. |
| 2011/0172495 A1 | 7/2011 | Armstrong |
| 2011/0174861 A1 | 7/2011 | Shelton, IV et al. |
| 2011/0192882 A1 | 8/2011 | Hess et al. |
| 2011/0199225 A1 | 8/2011 | Touchberry et al. |
| 2011/0218400 A1 | 9/2011 | Ma et al. |
| 2011/0218550 A1 | 9/2011 | Ma |
| 2011/0230713 A1 | 9/2011 | Kleemann et al. |
| 2011/0238044 A1 | 9/2011 | Main et al. |
| 2011/0241597 A1 | 10/2011 | Zhu et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0279268 A1 | 11/2011 | Konishi et al. |
| 2011/0290856 A1 | 12/2011 | Shelton, IV et al. |
| 2011/0293690 A1 | 12/2011 | Griffin et al. |
| 2011/0295295 A1 | 12/2011 | Shelton, IV et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0016239 A1 | 1/2012 | Barthe et al. |
| 2012/0016413 A1 | 1/2012 | Timm et al. |
| 2012/0016467 A1 | 1/2012 | Chen et al. |
| 2012/0029272 A1 | 2/2012 | Shelton, IV et al. |
| 2012/0033360 A1 | 2/2012 | Hsu |
| 2012/0059286 A1 | 3/2012 | Hastings et al. |
| 2012/0064483 A1 | 3/2012 | Lint et al. |
| 2012/0074200 A1 | 3/2012 | Schmid et al. |
| 2012/0078071 A1 | 3/2012 | Bohm et al. |
| 2012/0078139 A1 | 3/2012 | Aldridge et al. |
| 2012/0078244 A1 | 3/2012 | Worrell et al. |
| 2012/0080336 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080478 A1 | 4/2012 | Morgan et al. |
| 2012/0080498 A1 | 4/2012 | Shelton, IV et al. |
| 2012/0086276 A1 | 4/2012 | Sawyers |
| 2012/0095458 A1 | 4/2012 | Cybulski et al. |
| 2012/0109186 A1 | 5/2012 | Parrott et al. |
| 2012/0116261 A1 | 5/2012 | Mumaw et al. |
| 2012/0116265 A1 | 5/2012 | Houser et al. |
| 2012/0116266 A1 | 5/2012 | Houser et al. |
| 2012/0118595 A1 | 5/2012 | Pellenc |
| 2012/0123203 A1 | 5/2012 | Riva |
| 2012/0125792 A1 | 5/2012 | Cassivi |
| 2012/0132286 A1 | 5/2012 | Lim et al. |
| 2012/0171539 A1 | 7/2012 | Rejman et al. |
| 2012/0175398 A1 | 7/2012 | Sandborn et al. |
| 2012/0197272 A1 | 8/2012 | Oray et al. |
| 2012/0211542 A1 | 8/2012 | Racenet |
| 2012/0223121 A1 | 9/2012 | Viola et al. |
| 2012/0234895 A1 | 9/2012 | O'Connor et al. |
| 2012/0234897 A1 | 9/2012 | Shelton, IV et al. |
| 2012/0239068 A1 | 9/2012 | Morris et al. |
| 2012/0241493 A1 | 9/2012 | Baxter, III et al. |
| 2012/0248169 A1 | 10/2012 | Widenhouse et al. |
| 2012/0251861 A1 | 10/2012 | Liang et al. |
| 2012/0253328 A1 | 10/2012 | Cunningham et al. |
| 2012/0283707 A1 | 11/2012 | Giordano et al. |
| 2012/0289979 A1 | 11/2012 | Eskaros et al. |
| 2012/0292367 A1 | 11/2012 | Morgan et al. |
| 2012/0298722 A1 | 11/2012 | Hess et al. |
| 2012/0303002 A1 | 11/2012 | Chowaniec et al. |
| 2013/0006227 A1 | 1/2013 | Takashino |
| 2013/0012983 A1 | 1/2013 | Kleyman |
| 2013/0018400 A1 | 1/2013 | Milton et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0023910 A1 | 1/2013 | Solomon et al. |
| 2013/0026208 A1 | 1/2013 | Shelton, IV et al. |
| 2013/0026210 A1 | 1/2013 | Shelton, IV et al. |
| 2013/0030462 A1 | 1/2013 | Keating et al. |
| 2013/0068816 A1 | 3/2013 | Mandakolathur Vasudevan et al. |
| 2013/0087597 A1 | 4/2013 | Shelton, IV et al. |
| 2013/0090534 A1 | 4/2013 | Burns et al. |
| 2013/0096568 A1 | 4/2013 | Justis |
| 2013/0098970 A1 | 4/2013 | Racenet et al. |
| 2013/0105552 A1 | 5/2013 | Weir et al. |
| 2013/0116669 A1 | 5/2013 | Shelton, IV et al. |
| 2013/0123816 A1 | 5/2013 | Hodgkinson et al. |
| 2013/0126202 A1 | 5/2013 | Oomori et al. |
| 2013/0131476 A1 | 5/2013 | Siu et al. |
| 2013/0131651 A1 | 5/2013 | Strobl et al. |
| 2013/0136969 A1 | 5/2013 | Yasui et al. |
| 2013/0153636 A1 | 6/2013 | Shelton, IV et al. |
| 2013/0153641 A1 | 6/2013 | Shelton, IV et al. |
| 2013/0158390 A1 | 6/2013 | Tan et al. |
| 2013/0162198 A1 | 6/2013 | Yokota et al. |
| 2013/0172929 A1 | 7/2013 | Hess et al. |
| 2013/0175317 A1 | 7/2013 | Yates et al. |
| 2013/0181033 A1 | 7/2013 | Shelton, IV et al. |
| 2013/0181034 A1 | 7/2013 | Shelton, IV et al. |
| 2013/0214025 A1 | 8/2013 | Zemlok et al. |
| 2013/0214030 A1 | 8/2013 | Aronhalt et al. |
| 2013/0233906 A1 | 9/2013 | Hess et al. |
| 2013/0238021 A1 | 9/2013 | Gross et al. |
| 2013/0248578 A1 | 9/2013 | Arteaga Gonzalez |
| 2013/0253480 A1 | 9/2013 | Kimball et al. |
| 2013/0256373 A1 | 10/2013 | Schmid et al. |
| 2013/0256379 A1 | 10/2013 | Schmid et al. |
| 2013/0256380 A1 | 10/2013 | Schmid et al. |
| 2013/0270322 A1 | 10/2013 | Scheib et al. |
| 2013/0277410 A1 | 10/2013 | Fernandez et al. |
| 2013/0317753 A1 | 11/2013 | Kamen et al. |
| 2013/0324981 A1 | 12/2013 | Smith et al. |
| 2013/0324982 A1 | 12/2013 | Smith et al. |
| 2013/0327552 A1 | 12/2013 | Lovelass et al. |
| 2013/0333910 A1 | 12/2013 | Tanimoto et al. |

(56) References Cited

U.S. PATENT DOCUMENTS

| | | |
|---|---|---|
| 2013/0334280 A1 | 12/2013 | Krehel et al. |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005718 A1 | 1/2014 | Shelton, IV et al. |
| 2014/0012289 A1 | 1/2014 | Snow et al. |
| 2014/0012299 A1 | 1/2014 | Stoddard et al. |
| 2014/0014705 A1 | 1/2014 | Baxter, III |
| 2014/0018832 A1 | 1/2014 | Shelton, IV |
| 2014/0039549 A1 | 2/2014 | Belsky et al. |
| 2014/0048580 A1 | 2/2014 | Merchant et al. |
| 2014/0081176 A1 | 3/2014 | Hassan |
| 2014/0100558 A1 | 4/2014 | Schmitz et al. |
| 2014/0107640 A1 | 4/2014 | Yates et al. |
| 2014/0110456 A1 | 4/2014 | Taylor |
| 2014/0114327 A1 | 4/2014 | Boudreaux et al. |
| 2014/0115229 A1 | 4/2014 | Kothamasu et al. |
| 2014/0131418 A1 | 5/2014 | Kostrzewski |
| 2014/0151433 A1 | 6/2014 | Shelton, IV et al. |
| 2014/0158747 A1 | 6/2014 | Measamer et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175147 A1 | 6/2014 | Manoux et al. |
| 2014/0175150 A1 | 6/2014 | Shelton, IV et al. |
| 2014/0175152 A1 | 6/2014 | Hess et al. |
| 2014/0188159 A1 | 7/2014 | Steege |
| 2014/0200561 A1 | 7/2014 | Ingmanson et al. |
| 2014/0207124 A1 | 7/2014 | Aldridge et al. |
| 2014/0207125 A1 | 7/2014 | Applegate et al. |
| 2014/0224857 A1 | 8/2014 | Schmid |
| 2014/0228867 A1 | 8/2014 | Thomas et al. |
| 2014/0230595 A1 | 8/2014 | Butt et al. |
| 2014/0243865 A1 | 8/2014 | Swayze et al. |
| 2014/0246475 A1 | 9/2014 | Hall et al. |
| 2014/0248167 A1 | 9/2014 | Sugimoto et al. |
| 2014/0249557 A1 | 9/2014 | Koch, Jr. et al. |
| 2014/0249573 A1 | 9/2014 | Arav |
| 2014/0263541 A1 | 9/2014 | Leimbach et al. |
| 2014/0263552 A1 | 9/2014 | Hall et al. |
| 2014/0263554 A1 | 9/2014 | Leimbach et al. |
| 2014/0263558 A1 | 9/2014 | Hausen et al. |
| 2014/0276730 A1 | 9/2014 | Boudreaux et al. |
| 2014/0284371 A1 | 9/2014 | Morgan et al. |
| 2014/0288460 A1 | 9/2014 | Ouyang et al. |
| 2014/0291378 A1 | 10/2014 | Shelton, IV et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0303660 A1 | 10/2014 | Boyden et al. |
| 2014/0305990 A1 | 10/2014 | Shelton, IV et al. |
| 2014/0305991 A1 | 10/2014 | Parihar et al. |
| 2014/0309666 A1 | 10/2014 | Shelton, IV et al. |
| 2014/0330161 A1 | 11/2014 | Swayze et al. |
| 2014/0367445 A1 | 12/2014 | Ingmanson et al. |
| 2014/0367446 A1 | 12/2014 | Ingmanson et al. |
| 2014/0374130 A1 | 12/2014 | Nakamura et al. |
| 2014/0378950 A1 | 12/2014 | Chiu |
| 2015/0002089 A1 | 1/2015 | Rejman et al. |
| 2015/0008248 A1 | 1/2015 | Giordano et al. |
| 2015/0053737 A1 | 2/2015 | Leimbach et al. |
| 2015/0053742 A1 | 2/2015 | Shelton, IV et al. |
| 2015/0053743 A1 | 2/2015 | Yates et al. |
| 2015/0053746 A1 | 2/2015 | Shelton, IV et al. |
| 2015/0053748 A1 | 2/2015 | Yates et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0066000 A1 | 3/2015 | An et al. |
| 2015/0076207 A1 | 3/2015 | Boudreaux et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0080868 A1 | 3/2015 | Kerr |
| 2015/0083781 A1 | 3/2015 | Giordano et al. |
| 2015/0083782 A1 | 3/2015 | Scheib et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090763 A1 | 4/2015 | Murray et al. |
| 2015/0108199 A1 | 4/2015 | Shelton, IV et al. |
| 2015/0122870 A1 | 5/2015 | Zemlok et al. |
| 2015/0148830 A1 | 5/2015 | Stulen et al. |
| 2015/0150554 A1 | 6/2015 | Soltz |
| 2015/0150620 A1 | 6/2015 | Miyamoto et al. |
| 2015/0173744 A1 | 6/2015 | Shelton, IV et al. |
| 2015/0173749 A1 | 6/2015 | Shelton, IV et al. |
| 2015/0173756 A1 | 6/2015 | Baxter, III et al. |
| 2015/0173789 A1 | 6/2015 | Baxter, III et al. |
| 2015/0182220 A1 | 7/2015 | Yates et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0196347 A1 | 7/2015 | Yates et al. |
| 2015/0196348 A1 | 7/2015 | Yates et al. |
| 2015/0201932 A1 | 7/2015 | Swayze et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209031 A1 | 7/2015 | Shelton, IV et al. |
| 2015/0222212 A1 | 8/2015 | Iwata |
| 2015/0231409 A1 | 8/2015 | Racenet et al. |
| 2015/0245835 A1 | 9/2015 | Racenet et al. |
| 2015/0265276 A1 | 9/2015 | Huitema et al. |
| 2015/0265357 A1 | 9/2015 | Shelton, IV et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0280384 A1 | 10/2015 | Leimbach et al. |
| 2015/0282810 A1 | 10/2015 | Shelton, IV et al. |
| 2015/0289873 A1 | 10/2015 | Shelton, IV et al. |
| 2015/0289874 A1 | 10/2015 | Leimbach et al. |
| 2015/0297200 A1 | 10/2015 | Fitzsimmons et al. |
| 2015/0297210 A1 | 10/2015 | Widenhouse et al. |
| 2015/0297219 A1 | 10/2015 | Shelton, IV et al. |
| 2015/0297222 A1 | 10/2015 | Huitema et al. |
| 2015/0297223 A1 | 10/2015 | Huitema et al. |
| 2015/0297225 A1 | 10/2015 | Huitema et al. |
| 2015/0297228 A1 | 10/2015 | Huitema et al. |
| 2015/0297229 A1 | 10/2015 | Schellin et al. |
| 2015/0297232 A1 | 10/2015 | Huitema et al. |
| 2015/0297233 A1 | 10/2015 | Huitema et al. |
| 2015/0297234 A1 | 10/2015 | Schellin et al. |
| 2015/0297235 A1 | 10/2015 | Harris et al. |
| 2015/0297236 A1 | 10/2015 | Harris et al. |
| 2015/0303417 A1 | 10/2015 | Koeder et al. |
| 2015/0305729 A1 | 10/2015 | Fitzsimmons et al. |
| 2015/0313594 A1 | 11/2015 | Shelton, IV et al. |
| 2015/0324317 A1 | 11/2015 | Collins et al. |
| 2015/0327864 A1 | 11/2015 | Hodgkinson et al. |
| 2015/0335328 A1 | 11/2015 | Shelton, IV et al. |
| 2015/0336249 A1 | 11/2015 | Iwata et al. |
| 2015/0342607 A1 | 12/2015 | Shelton, IV et al. |
| 2015/0351758 A1 | 12/2015 | Shelton, IV et al. |
| 2015/0351762 A1 | 12/2015 | Vendely et al. |
| 2015/0352699 A1 | 12/2015 | Sakai et al. |
| 2015/0372265 A1 | 12/2015 | Morisaku et al. |
| 2015/0374360 A1 | 12/2015 | Scheib et al. |
| 2015/0374361 A1 | 12/2015 | Gettinger et al. |
| 2015/0374363 A1 | 12/2015 | Laurent, IV et al. |

(56) References Cited

U.S. PATENT DOCUMENTS

| | | |
|---|---|---|
| 2015/0374368 A1 | 12/2015 | Swayze et al. |
| 2015/0374369 A1 | 12/2015 | Yates et al. |
| 2015/0374371 A1 | 12/2015 | Richard et al. |
| 2015/0374374 A1 | 12/2015 | Shelton, IV et al. |
| 2015/0374375 A1 | 12/2015 | Shelton, IV et al. |
| 2015/0374376 A1 | 12/2015 | Shelton, IV |
| 2015/0374377 A1 | 12/2015 | Shelton, IV |
| 2015/0374378 A1 | 12/2015 | Giordano et al. |
| 2015/0374379 A1 | 12/2015 | Shelton, IV |
| 2015/0380187 A1 | 12/2015 | Zergiebel et al. |
| 2016/0000430 A1 | 1/2016 | Ming et al. |
| 2016/0000431 A1 | 1/2016 | Giordano et al. |
| 2016/0000437 A1 | 1/2016 | Giordano et al. |
| 2016/0000438 A1 | 1/2016 | Swayze et al. |
| 2016/0000442 A1 | 1/2016 | Shelton, IV |
| 2016/0000452 A1 | 1/2016 | Yates et al. |
| 2016/0000453 A1 | 1/2016 | Yates et al. |
| 2016/0000513 A1 | 1/2016 | Shelton, IV et al. |
| 2016/0007992 A1 | 1/2016 | Yates et al. |
| 2016/0015391 A1 | 1/2016 | Shelton, IV et al. |
| 2016/0023342 A1 | 1/2016 | Koenig et al. |
| 2016/0030042 A1 | 2/2016 | Heinrich et al. |
| 2016/0030103 A1 | 2/2016 | Manwaring et al. |
| 2016/0051257 A1 | 2/2016 | Shelton, IV et al. |
| 2016/0058443 A1 | 3/2016 | Yates et al. |
| 2016/0066911 A1 | 3/2016 | Baber et al. |
| 2016/0066912 A1 | 3/2016 | Baber et al. |
| 2016/0066913 A1 | 3/2016 | Swayze et al. |
| 2016/0069449 A1 | 3/2016 | Kanai et al. |
| 2016/0073909 A1 | 3/2016 | Zand et al. |
| 2016/0074040 A1 | 3/2016 | Widenhouse et al. |
| 2016/0082161 A1 | 3/2016 | Zilberman et al. |
| 2016/0089137 A1 | 3/2016 | Hess et al. |
| 2016/0089142 A1 | 3/2016 | Harris et al. |
| 2016/0089146 A1 | 3/2016 | Harris et al. |
| 2016/0089147 A1 | 3/2016 | Harris et al. |
| 2016/0089149 A1 | 3/2016 | Harris et al. |
| 2016/0089198 A1 | 3/2016 | Arya et al. |
| 2016/0095585 A1 | 4/2016 | Zergiebel et al. |
| 2016/0106431 A1 | 4/2016 | Shelton, IV et al. |
| 2016/0113653 A1 | 4/2016 | Zingman |
| 2016/0120544 A1 | 5/2016 | Shelton, IV et al. |
| 2016/0120545 A1 | 5/2016 | Shelton, IV et al. |
| 2016/0166256 A1 | 6/2016 | Baxter, III et al. |
| 2016/0166308 A1 | 6/2016 | Manwaring et al. |
| 2016/0174969 A1 | 6/2016 | Kerr et al. |
| 2016/0174971 A1 | 6/2016 | Baxter, III et al. |
| 2016/0174972 A1 | 6/2016 | Shelton, IV et al. |
| 2016/0174974 A1 | 6/2016 | Schmid et al. |
| 2016/0174984 A1 | 6/2016 | Smith et al. |
| 2016/0174985 A1 | 6/2016 | Baxter, III et al. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0183945 A1 | 6/2016 | Shelton, IV et al. |
| 2016/0192916 A1 | 7/2016 | Shelton, IV et al. |
| 2016/0192917 A1 | 7/2016 | Shelton, IV et al. |
| 2016/0192918 A1 | 7/2016 | Shelton, IV et al. |
| 2016/0192929 A1 | 7/2016 | Schmid et al. |
| 2016/0192933 A1 | 7/2016 | Shelton, IV |
| 2016/0192936 A1 | 7/2016 | Leimbach et al. |
| 2016/0192977 A1 | 7/2016 | Manwaring et al. |
| 2016/0192996 A1 | 7/2016 | Spivey et al. |
| 2016/0193673 A1 | 7/2016 | Yoshida et al. |
| 2016/0199059 A1 | 7/2016 | Shelton, IV et al. |
| 2016/0199061 A1 | 7/2016 | Shelton, IV et al. |
| 2016/0199063 A1 | 7/2016 | Mandakolathur Vasudevan et al. |
| 2016/0199064 A1 | 7/2016 | Shelton, IV et al. |
| 2016/0199089 A1 | 7/2016 | Hess et al. |
| 2016/0199956 A1 | 7/2016 | Shelton, IV et al. |
| 2016/0206310 A1 | 7/2016 | Shelton, IV |
| 2016/0206314 A1 | 7/2016 | Scheib et al. |
| 2016/0220248 A1 | 8/2016 | Timm et al. |
| 2016/0220249 A1 | 8/2016 | Shelton, IV et al. |
| 2016/0220266 A1 | 8/2016 | Shelton, IV et al. |
| 2016/0220268 A1 | 8/2016 | Shelton, IV et al. |
| 2016/0235403 A1 | 8/2016 | Shelton, IV et al. |
| 2016/0235404 A1 | 8/2016 | Shelton, IV |
| 2016/0235405 A1 | 8/2016 | Shelton, IV et al. |
| 2016/0235406 A1 | 8/2016 | Shelton, IV et al. |
| 2016/0235408 A1 | 8/2016 | Shelton, IV et al. |
| 2016/0235409 A1 | 8/2016 | Shelton, IV et al. |
| 2016/0235494 A1 | 8/2016 | Shelton, IV et al. |
| 2016/0242775 A1 | 8/2016 | Shelton, IV et al. |
| 2016/0242776 A1 | 8/2016 | Shelton, IV et al. |
| 2016/0242777 A1 | 8/2016 | Shelton, IV et al. |
| 2016/0242781 A1 | 8/2016 | Shelton, IV et al. |
| 2016/0242782 A1 | 8/2016 | Shelton, IV et al. |
| 2016/0242783 A1 | 8/2016 | Shelton, IV et al. |
| 2016/0249909 A1 | 9/2016 | Shelton, IV et al. |
| 2016/0249910 A1 | 9/2016 | Shelton, IV et al. |
| 2016/0249911 A1 | 9/2016 | Timm et al. |
| 2016/0249915 A1 | 9/2016 | Beckman et al. |
| 2016/0249916 A1 | 9/2016 | Shelton, IV et al. |
| 2016/0249917 A1 | 9/2016 | Beckman et al. |
| 2016/0249918 A1 | 9/2016 | Shelton, IV et al. |
| 2016/0249922 A1 | 9/2016 | Morgan et al. |
| 2016/0249927 A1 | 9/2016 | Beckman et al. |
| 2016/0256071 A1 | 9/2016 | Shelton, IV et al. |
| 2016/0256154 A1 | 9/2016 | Shelton, IV et al. |
| 2016/0256156 A1 | 9/2016 | Shelton, IV et al. |
| 2016/0256159 A1 | 9/2016 | Pinjala et al. |
| 2016/0256160 A1 | 9/2016 | Shelton, IV et al. |
| 2016/0256161 A1 | 9/2016 | Overmyer et al. |
| 2016/0256185 A1 | 9/2016 | Shelton, IV et al. |
| 2016/0256229 A1 | 9/2016 | Morgan et al. |
| 2016/0262745 A1 | 9/2016 | Morgan et al. |
| 2016/0262746 A1 | 9/2016 | Shelton, IV et al. |
| 2016/0270780 A1 | 9/2016 | Hall et al. |
| 2016/0278765 A1 | 9/2016 | Shelton, IV et al. |
| 2016/0278775 A1 | 9/2016 | Shelton, IV et al. |
| 2016/0287249 A1 | 10/2016 | Alexander, III et al. |
| 2016/0287250 A1 | 10/2016 | Shelton, IV et al. |
| 2016/0287251 A1 | 10/2016 | Shelton, IV et al. |
| 2016/0287253 A1 | 10/2016 | Shelton, IV et al. |
| 2016/0310143 A1 | 10/2016 | Bettuchi |
| 2016/0331375 A1 | 11/2016 | Shelton, IV et al. |
| 2016/0345976 A1 | 12/2016 | Gonzalez et al. |
| 2016/0346034 A1 | 12/2016 | Arya et al. |
| 2016/0354085 A1 | 12/2016 | Shelton, IV et al. |
| 2016/0367122 A1 | 12/2016 | Ichimura et al. |
| 2016/0367245 A1 | 12/2016 | Wise et al. |
| 2016/0367246 A1 | 12/2016 | Baxter, III et al. |
| 2016/0367247 A1 | 12/2016 | Weaner et al. |
| 2016/0367254 A1 | 12/2016 | Baxter, III et al. |
| 2016/0367255 A1 | 12/2016 | Wise et al. |
| 2016/0367256 A1 | 12/2016 | Hensel et al. |
| 2016/0374675 A1 | 12/2016 | Shelton, IV et al. |
| 2017/0000485 A1 | 1/2017 | Shelton, IV et al. |
| 2017/0007236 A1 | 1/2017 | Shelton, IV et al. |
| 2017/0007237 A1 | 1/2017 | Yates et al. |
| 2017/0007238 A1 | 1/2017 | Yates et al. |
| 2017/0007239 A1 | 1/2017 | Shelton, IV |
| 2017/0007241 A1 | 1/2017 | Shelton, IV et al. |
| 2017/0007242 A1 | 1/2017 | Shelton, IV et al. |
| 2017/0007243 A1 | 1/2017 | Shelton, IV et al. |
| 2017/0007244 A1 | 1/2017 | Shelton, IV et al. |
| 2017/0007245 A1 | 1/2017 | Shelton, IV et al. |
| 2017/0007246 A1 | 1/2017 | Shelton, IV et al. |
| 2017/0007247 A1 | 1/2017 | Shelton, IV et al. |
| 2017/0007248 A1 | 1/2017 | Shelton, IV et al. |
| 2017/0007249 A1 | 1/2017 | Shelton, IV et al. |
| 2017/0007250 A1 | 1/2017 | Shelton, IV et al. |
| 2017/0007251 A1 | 1/2017 | Yates et al. |
| 2017/0007254 A1 | 1/2017 | Jaworek et al. |
| 2017/0007255 A1 | 1/2017 | Jaworek et al. |
| 2017/0007338 A1 | 1/2017 | Swensgard et al. |
| 2017/0007340 A1 | 1/2017 | Swensgard et al. |
| 2017/0007341 A1 | 1/2017 | Swensgard et al. |
| 2017/0007347 A1 | 1/2017 | Jaworek et al. |
| 2017/0014125 A1 | 1/2017 | Shelton, IV et al. |
| 2017/0014129 A1 | 1/2017 | Shelton, IV et al. |
| 2017/0049444 A1 | 2/2017 | Schellin et al. |
| 2017/0049447 A1 | 2/2017 | Barton et al. |

(56) References Cited

U.S. PATENT DOCUMENTS

| | | |
|---|---|---|
| 2017/0049448 A1 | 2/2017 | Widenhouse et al. |
| 2017/0055986 A1 | 3/2017 | Harris et al. |
| 2017/0055989 A1 | 3/2017 | Shelton, IV et al. |
| 2017/0055996 A1 | 3/2017 | Baxter, III et al. |
| 2017/0055997 A1 | 3/2017 | Swayze et al. |
| 2017/0055998 A1 | 3/2017 | Baxter, III et al. |
| 2017/0055999 A1 | 3/2017 | Baxter, III et al. |
| 2017/0056000 A1 | 3/2017 | Nalagatla et al. |
| 2017/0056001 A1 | 3/2017 | Shelton, IV et al. |
| 2017/0056002 A1 | 3/2017 | Nalagatla et al. |
| 2017/0056004 A1 | 3/2017 | Shelton, IV et al. |
| 2017/0056005 A1 | 3/2017 | Shelton, IV et al. |
| 2017/0056006 A1 | 3/2017 | Shelton, IV et al. |
| 2017/0056007 A1 | 3/2017 | Eckert et al. |
| 2017/0079640 A1 | 3/2017 | Overmyer et al. |
| 2017/0079642 A1 | 3/2017 | Overmyer et al. |
| 2017/0079643 A1 | 3/2017 | Yates et al. |
| 2017/0079644 A1 | 3/2017 | Overmyer et al. |
| 2017/0079647 A1 | 3/2017 | Yates et al. |
| 2017/0086823 A1 | 3/2017 | Leimbach et al. |
| 2017/0086827 A1 | 3/2017 | Vendely et al. |
| 2017/0086829 A1 | 3/2017 | Vendely et al. |
| 2017/0086830 A1 | 3/2017 | Yates et al. |
| 2017/0086831 A1 | 3/2017 | Shelton, IV et al. |
| 2017/0086832 A1 | 3/2017 | Harris et al. |
| 2017/0086835 A1 | 3/2017 | Harris et al. |
| 2017/0086836 A1 | 3/2017 | Harris et al. |
| 2017/0086837 A1 | 3/2017 | Vendely et al. |
| 2017/0086838 A1 | 3/2017 | Harris et al. |
| 2017/0086839 A1 | 3/2017 | Vendely et al. |
| 2017/0086840 A1 | 3/2017 | Harris et al. |
| 2017/0086841 A1 | 3/2017 | Vendely et al. |
| 2017/0086842 A1 | 3/2017 | Shelton, IV et al. |
| 2017/0086843 A1 | 3/2017 | Vendely et al. |
| 2017/0086844 A1 | 3/2017 | Vendely et al. |
| 2017/0086845 A1 | 3/2017 | Vendely et al. |
| 2017/0086936 A1 | 3/2017 | Shelton, IV et al. |
| 2017/0119390 A1 | 5/2017 | Schellin et al. |
| 2017/0119397 A1 | 5/2017 | Harris et al. |
| 2017/0128149 A1 | 5/2017 | Heinrich et al. |
| 2017/0135695 A1 | 5/2017 | Shelton, IV et al. |
| 2017/0135697 A1 | 5/2017 | Mozdzierz et al. |
| 2017/0150983 A1 | 6/2017 | Ingmanson et al. |
| 2017/0172672 A1 | 6/2017 | Bailey et al. |
| 2017/0182211 A1 | 6/2017 | Raxworthy et al. |
| 2017/0189018 A1 | 7/2017 | Harris et al. |
| 2017/0189019 A1 | 7/2017 | Harris et al. |
| 2017/0189020 A1 | 7/2017 | Harris et al. |
| 2017/0196558 A1 | 7/2017 | Morgan et al. |
| 2017/0196560 A1 | 7/2017 | Leimbach et al. |
| 2017/0196561 A1 | 7/2017 | Shelton, IV et al. |
| 2017/0196562 A1 | 7/2017 | Shelton, IV et al. |
| 2017/0196637 A1 | 7/2017 | Shelton, IV et al. |
| 2017/0196649 A1 | 7/2017 | Yates et al. |
| 2017/0202596 A1 | 7/2017 | Shelton, IV et al. |
| 2017/0209145 A1 | 7/2017 | Swayze et al. |
| 2017/0209146 A1 | 7/2017 | Yates et al. |
| 2017/0209226 A1 | 7/2017 | Overmyer et al. |
| 2017/0215881 A1 | 8/2017 | Shelton, IV et al. |
| 2017/0224330 A1 | 8/2017 | Worthington et al. |
| 2017/0224331 A1 | 8/2017 | Worthington et al. |
| 2017/0224332 A1 | 8/2017 | Hunter et al. |
| 2017/0224333 A1 | 8/2017 | Hunter et al. |
| 2017/0224334 A1 | 8/2017 | Worthington et al. |
| 2017/0224335 A1 | 8/2017 | Weaner et al. |
| 2017/0224336 A1 | 8/2017 | Hunter et al. |
| 2017/0224339 A1 | 8/2017 | Huang et al. |
| 2017/0224342 A1 | 8/2017 | Worthington et al. |
| 2017/0224343 A1 | 8/2017 | Baxter, III et al. |
| 2017/0231623 A1 | 8/2017 | Shelton, IV et al. |
| 2017/0231626 A1 | 8/2017 | Shelton, IV et al. |
| 2017/0231627 A1 | 8/2017 | Shelton, IV et al. |
| 2017/0231628 A1 | 8/2017 | Shelton, IV et al. |
| 2017/0238928 A1 | 8/2017 | Morgan et al. |
| 2017/0238929 A1 | 8/2017 | Yates et al. |
| 2017/0245952 A1 | 8/2017 | Shelton, IV et al. |
| 2017/0245953 A1 | 8/2017 | Shelton, IV et al. |
| 2017/0249431 A1 | 8/2017 | Shelton, IV et al. |
| 2017/0258469 A1 | 9/2017 | Shelton, IV et al. |
| 2017/0265856 A1 | 9/2017 | Shelton, IV et al. |
| 2017/0281167 A1 | 10/2017 | Shelton, IV et al. |
| 2017/0281180 A1 | 10/2017 | Morgan et al. |
| 2017/0290585 A1 | 10/2017 | Shelton, IV et al. |
| 2017/0296169 A1 | 10/2017 | Yates et al. |
| 2017/0296170 A1 | 10/2017 | Shelton, IV et al. |
| 2017/0296171 A1 | 10/2017 | Shelton, IV et al. |
| 2017/0296172 A1 | 10/2017 | Harris et al. |
| 2017/0296173 A1 | 10/2017 | Shelton, IV et al. |
| 2017/0296177 A1 | 10/2017 | Harris et al. |
| 2017/0296178 A1 | 10/2017 | Miller et al. |
| 2017/0296179 A1 | 10/2017 | Shelton, IV et al. |
| 2017/0296180 A1 | 10/2017 | Harris et al. |
| 2017/0296183 A1 | 10/2017 | Shelton, IV et al. |
| 2017/0296184 A1 | 10/2017 | Harris et al. |
| 2017/0296185 A1 | 10/2017 | Swensgard et al. |
| 2017/0296189 A1 | 10/2017 | Vendely et al. |
| 2017/0296190 A1 | 10/2017 | Aronhalt et al. |
| 2017/0296191 A1 | 10/2017 | Shelton, IV et al. |
| 2017/0296213 A1 | 10/2017 | Swensgard et al. |
| 2017/0311944 A1 | 11/2017 | Morgan et al. |
| 2017/0311949 A1 | 11/2017 | Shelton, IV |
| 2017/0311950 A1 | 11/2017 | Shelton, IV et al. |
| 2017/0312040 A1 | 11/2017 | Giordano et al. |
| 2017/0312041 A1 | 11/2017 | Giordano et al. |
| 2017/0312042 A1 | 11/2017 | Giordano et al. |
| 2017/0319201 A1 | 11/2017 | Morgan et al. |
| 2017/0319207 A1 | 11/2017 | Shelton, IV et al. |
| 2017/0319209 A1 | 11/2017 | Morgan et al. |
| 2017/0319777 A1 | 11/2017 | Shelton, IV et al. |
| 2017/0333034 A1 | 11/2017 | Morgan et al. |
| 2017/0333035 A1 | 11/2017 | Morgan et al. |
| 2017/0333070 A1 | 11/2017 | Laurent et al. |
| 2017/0348043 A1 | 12/2017 | Wang et al. |
| 2017/0354415 A1 | 12/2017 | Casasanta, Jr. et al. |
| 2017/0360442 A1 | 12/2017 | Shelton, IV et al. |
| 2017/0367700 A1 | 12/2017 | Leimbach et al. |
| 2017/0367991 A1 | 12/2017 | Widenhouse et al. |
| 2018/0000483 A1 | 1/2018 | Leimbach et al. |
| 2018/0000545 A1 | 1/2018 | Giordano et al. |
| 2018/0008269 A1 | 1/2018 | Moore et al. |
| 2018/0008270 A1 | 1/2018 | Moore et al. |
| 2018/0008271 A1 | 1/2018 | Moore et al. |
| 2018/0008356 A1 | 1/2018 | Giordano et al. |
| 2018/0008357 A1 | 1/2018 | Giordano et al. |
| 2018/0028184 A1 | 2/2018 | Shelton, IV et al. |
| 2018/0028185 A1 | 2/2018 | Shelton, IV et al. |
| 2018/0042611 A1 | 2/2018 | Swayze et al. |
| 2018/0049824 A1 | 2/2018 | Harris et al. |
| 2018/0049883 A1 | 2/2018 | Moskowitz et al. |
| 2018/0055510 A1 | 3/2018 | Schmid et al. |
| 2018/0055513 A1 | 3/2018 | Shelton, IV et al. |
| 2018/0055524 A1 | 3/2018 | Shelton, IV et al. |
| 2018/0055525 A1 | 3/2018 | Shelton, IV et al. |
| 2018/0055526 A1 | 3/2018 | Shelton, IV et al. |
| 2018/0064437 A1 | 3/2018 | Yates et al. |
| 2018/0064440 A1 | 3/2018 | Shelton, IV et al. |
| 2018/0064441 A1 | 3/2018 | Shelton, IV et al. |
| 2018/0064442 A1 | 3/2018 | Shelton, IV et al. |
| 2018/0064443 A1 | 3/2018 | Shelton, IV et al. |
| 2018/0070939 A1 | 3/2018 | Giordano et al. |
| 2018/0070942 A1 | 3/2018 | Shelton, IV et al. |
| 2018/0070946 A1 | 3/2018 | Shelton, IV et al. |
| 2018/0074535 A1 | 3/2018 | Shelton, IV et al. |
| 2018/0078248 A1 | 3/2018 | Swayze et al. |
| 2018/0085116 A1 | 3/2018 | Yates et al. |
| 2018/0085117 A1 | 3/2018 | Shelton, IV et al. |
| 2018/0085123 A1 | 3/2018 | Shelton, IV et al. |
| 2018/0095487 A1 | 4/2018 | Leimbach et al. |
| 2018/0103952 A1 | 4/2018 | Aronhalt et al. |
| 2018/0103953 A1 | 4/2018 | Shelton, IV et al. |
| 2018/0103955 A1 | 4/2018 | Shelton, IV et al. |
| 2018/0110516 A1 | 4/2018 | Baxter, III et al. |
| 2018/0110518 A1 | 4/2018 | Overmyer et al. |
| 2018/0110519 A1 | 4/2018 | Lytle, IV et al. |

(56) References Cited

U.S. PATENT DOCUMENTS

| | | |
|---|---|---|
| 2018/0110520 A1 | 4/2018 | Shelton, IV et al. |
| 2018/0110521 A1 | 4/2018 | Shelton, IV et al. |
| 2018/0110522 A1 | 4/2018 | Shelton, IV et al. |
| 2018/0110523 A1 | 4/2018 | Shelton, IV |
| 2018/0110574 A1 | 4/2018 | Shelton, IV et al. |
| 2018/0110575 A1 | 4/2018 | Shelton, IV et al. |
| 2018/0116658 A1 | 5/2018 | Aronhalt, IV et al. |
| 2018/0116662 A1 | 5/2018 | Shelton, IV et al. |
| 2018/0116665 A1 | 5/2018 | Hall et al. |
| 2018/0125481 A1 | 5/2018 | Yates et al. |
| 2018/0125488 A1 | 5/2018 | Morgan et al. |
| 2018/0125489 A1 | 5/2018 | Leimbach et al. |
| 2018/0125590 A1 | 5/2018 | Giordano et al. |
| 2018/0126504 A1 | 5/2018 | Shelton, IV et al. |
| 2018/0132845 A1 | 5/2018 | Schmid et al. |
| 2018/0132850 A1 | 5/2018 | Leimbach et al. |
| 2018/0132851 A1 | 5/2018 | Hall et al. |
| 2018/0132952 A1 | 5/2018 | Spivey et al. |
| 2018/0133856 A1 | 5/2018 | Shelton, IV et al. |
| 2018/0140299 A1 | 5/2018 | Weaner et al. |
| 2018/0140368 A1 | 5/2018 | Shelton, IV et al. |
| 2018/0146960 A1 | 5/2018 | Shelton, IV et al. |
| 2018/0153542 A1 | 6/2018 | Shelton, IV et al. |
| 2018/0161034 A1 | 6/2018 | Scheib et al. |
| 2018/0168575 A1 | 6/2018 | Simms et al. |
| 2018/0168576 A1 | 6/2018 | Hunter et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168580 A1 | 6/2018 | Hunter et al. |
| 2018/0168581 A1 | 6/2018 | Hunter et al. |
| 2018/0168582 A1 | 6/2018 | Swayze et al. |
| 2018/0168583 A1 | 6/2018 | Hunter et al. |
| 2018/0168584 A1 | 6/2018 | Harris et al. |
| 2018/0168589 A1 | 6/2018 | Swayze et al. |
| 2018/0168590 A1 | 6/2018 | Overmyer et al. |
| 2018/0168591 A1 | 6/2018 | Swayze et al. |
| 2018/0168592 A1 | 6/2018 | Overmyer et al. |
| 2018/0168593 A1 | 6/2018 | Overmyer et al. |
| 2018/0168594 A1 | 6/2018 | Shelton, IV et al. |
| 2018/0168595 A1 | 6/2018 | Overmyer et al. |
| 2018/0168596 A1 | 6/2018 | Beckman et al. |
| 2018/0168597 A1 | 6/2018 | Fanelli et al. |
| 2018/0168598 A1 | 6/2018 | Shelton, IV et al. |
| 2018/0168599 A1 | 6/2018 | Bakos et al. |
| 2018/0168600 A1 | 6/2018 | Shelton, IV et al. |
| 2018/0168601 A1 | 6/2018 | Bakos et al. |
| 2018/0168602 A1 | 6/2018 | Bakos et al. |
| 2018/0168603 A1 | 6/2018 | Morgan et al. |
| 2018/0168604 A1 | 6/2018 | Shelton, IV et al. |
| 2018/0168605 A1 | 6/2018 | Baber et al. |
| 2018/0168606 A1 | 6/2018 | Shelton, IV et al. |
| 2018/0168607 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168611 A1 | 6/2018 | Shelton, IV et al. |
| 2018/0168612 A1 | 6/2018 | Shelton, IV et al. |
| 2018/0168613 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168620 A1 | 6/2018 | Huang et al. |
| 2018/0168621 A1 | 6/2018 | Shelton, IV et al. |
| 2018/0168622 A1 | 6/2018 | Shelton, IV et al. |
| 2018/0168623 A1 | 6/2018 | Simms et al. |
| 2018/0168624 A1 | 6/2018 | Shelton, IV et al. |
| 2018/0168625 A1 | 6/2018 | Posada et al. |
| 2018/0168626 A1 | 6/2018 | Shelton, IV et al. |
| 2018/0168627 A1 | 6/2018 | Weaner et al. |
| 2018/0168628 A1 | 6/2018 | Hunter et al. |
| 2018/0168629 A1 | 6/2018 | Shelton, IV et al. |
| 2018/0168630 A1 | 6/2018 | Shelton, IV et al. |
| 2018/0168631 A1 | 6/2018 | Harris et al. |
| 2018/0168632 A1 | 6/2018 | Harris et al. |
| 2018/0168633 A1 | 6/2018 | Shelton, IV et al. |
| 2018/0168634 A1 | 6/2018 | Harris et al. |
| 2018/0168635 A1 | 6/2018 | Shelton, IV et al. |
| 2018/0168636 A1 | 6/2018 | Shelton, IV et al. |
| 2018/0168637 A1 | 6/2018 | Harris et al. |
| 2018/0168638 A1 | 6/2018 | Harris et al. |
| 2018/0168639 A1 | 6/2018 | Shelton, IV et al. |
| 2018/0168640 A1 | 6/2018 | Shelton, IV et al. |
| 2018/0168641 A1 | 6/2018 | Harris et al. |
| 2018/0168642 A1 | 6/2018 | Shelton, IV et al. |
| 2018/0168644 A1 | 6/2018 | Shelton, IV et al. |
| 2018/0168645 A1 | 6/2018 | Shelton, IV et al. |
| 2018/0168646 A1 | 6/2018 | Shelton, IV et al. |
| 2018/0168649 A1 | 6/2018 | Shelton, IV et al. |
| 2018/0168651 A1 | 6/2018 | Shelton, IV et al. |
| 2018/0199940 A1 | 7/2018 | Zergiebel et al. |
| 2018/0206843 A1 | 7/2018 | Yates et al. |
| 2018/0206906 A1 | 7/2018 | Moua et al. |
| 2018/0214147 A1 | 8/2018 | Merchant et al. |
| 2018/0221046 A1 | 8/2018 | Demmy et al. |
| 2018/0221050 A1 | 8/2018 | Kostrzewski et al. |
| 2018/0228490 A1 | 8/2018 | Richard et al. |
| 2018/0250001 A1 | 9/2018 | Aronhalt et al. |
| 2018/0256184 A1 | 9/2018 | Shelton, IV et al. |
| 2018/0256185 A1 | 9/2018 | Shelton, IV et al. |
| 2018/0271520 A1 | 9/2018 | Shelton, IV et al. |
| 2018/0280020 A1 | 10/2018 | Hess et al. |
| 2018/0280021 A1 | 10/2018 | Timm et al. |
| 2018/0280022 A1 | 10/2018 | Timm et al. |
| 2018/0280023 A1 | 10/2018 | Timm et al. |

FOREIGN PATENT DOCUMENTS

| | | |
|---|---|---|
| AU | 2011218702 B2 | 6/2013 |
| AU | 2012200178 B2 | 7/2013 |
| CA | 1015829 A | 8/1977 |
| CA | 1125615 A | 6/1982 |
| CA | 2458946 A1 | 3/2003 |
| CA | 2477181 A1 | 4/2004 |
| CA | 2512960 A1 | 1/2006 |
| CA | 2514274 A1 | 1/2006 |
| CA | 2639177 A1 | 2/2009 |
| CA | 2576347 C | 8/2015 |
| CN | 86100996 A | 9/1986 |
| CN | 1163558 A | 10/1997 |
| CN | 2488482 Y | 5/2002 |
| CN | 1424891 A | 6/2003 |
| CN | 1523725 A | 8/2004 |
| CN | 1545154 A | 11/2004 |
| CN | 1634601 A | 7/2005 |
| CN | 1636525 A | 7/2005 |
| CN | 1636526 A | 7/2005 |
| CN | 2716900 Y | 8/2005 |
| CN | 2738962 Y | 11/2005 |
| CN | 1726874 A | 2/2006 |
| CN | 1726878 A | 2/2006 |
| CN | 1868411 A | 11/2006 |
| CN | 1915180 A | 2/2007 |
| CN | 2868212 Y | 2/2007 |
| CN | 1960679 A | 5/2007 |
| CN | 101011286 A | 8/2007 |
| CN | 200942099 Y | 9/2007 |
| CN | 200991269 Y | 12/2007 |
| CN | 101095621 A | 1/2008 |
| CN | 101111196 A | 1/2008 |
| CN | 201001747 Y | 1/2008 |
| CN | 101137402 A | 3/2008 |
| CN | 101143105 A | 3/2008 |
| CN | 201029899 Y | 3/2008 |
| CN | 101224122 A | 7/2008 |
| CN | 101224124 A | 7/2008 |
| CN | 101254126 A | 9/2008 |
| CN | 101507620 A | 8/2009 |
| CN | 101507622 A | 8/2009 |
| CN | 101507623 A | 8/2009 |
| CN | 101507625 A | 8/2009 |
| CN | 101507628 A | 8/2009 |
| CN | 101534724 A | 9/2009 |

(56) References Cited

FOREIGN PATENT DOCUMENTS

| | | |
|---|---|---|
| CN | 101626731 A | 1/2010 |
| CN | 101669833 A | 3/2010 |
| CN | 101675898 A | 3/2010 |
| CN | 101683280 A | 3/2010 |
| CN | 101721236 A | 6/2010 |
| CN | 101801284 A | 8/2010 |
| CN | 101828940 A | 9/2010 |
| CN | 101868203 A | 10/2010 |
| CN | 101873834 A | 10/2010 |
| CN | 101073509 B | 12/2010 |
| CN | 101912285 A | 12/2010 |
| CN | 101028205 B | 1/2011 |
| CN | 101933824 A | 1/2011 |
| CN | 101934098 A | 1/2011 |
| CN | 201719298 U | 1/2011 |
| CN | 102038531 A | 5/2011 |
| CN | 102038532 A | 5/2011 |
| CN | 101534722 B | 6/2011 |
| CN | 201879759 U | 6/2011 |
| CN | 101361666 B | 8/2011 |
| CN | 201949071 U | 8/2011 |
| CN | 101224119 B | 9/2011 |
| CN | 101336835 B | 9/2011 |
| CN | 102188270 A | 9/2011 |
| CN | 101779977 B | 12/2011 |
| CN | 101534723 B | 1/2012 |
| CN | 101310680 B | 4/2012 |
| CN | 101912284 B | 7/2012 |
| CN | 202397539 U | 8/2012 |
| CN | 202426586 U | 9/2012 |
| CN | 101317782 B | 10/2012 |
| CN | 202489990 U | 10/2012 |
| CN | 101507639 B | 11/2012 |
| CN | 101541251 A | 11/2012 |
| CN | 102835977 A | 12/2012 |
| CN | 101507633 B | 2/2013 |
| CN | 101023879 B | 3/2013 |
| CN | 101507624 B | 3/2013 |
| CN | 101327137 B | 6/2013 |
| CN | 101401736 B | 6/2013 |
| CN | 101332110 B | 7/2013 |
| CN | 101683281 B | 1/2014 |
| CN | 103648408 A | 3/2014 |
| CN | 203564285 U | 4/2014 |
| CN | 203564287 U | 4/2014 |
| CN | 203597997 U | 5/2014 |
| CN | 103829983 A | 6/2014 |
| CN | 103908313 A | 7/2014 |
| CN | 203736251 U | 7/2014 |
| CN | 102783741 B | 10/2014 |
| CN | 102973300 B | 10/2014 |
| CN | 102793571 B | 12/2014 |
| CN | 104337556 A | 2/2015 |
| CN | 102166129 B | 3/2015 |
| CN | 102469995 B | 3/2015 |
| CN | 102113902 B | 4/2015 |
| CN | 102247177 B | 2/2016 |
| CN | 103750872 B | 5/2016 |
| DE | 273689 C | 5/1914 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 3709067 A1 | 9/1988 |
| DE | 4228909 A1 | 3/1994 |
| DE | 9412228 U1 | 9/1994 |
| DE | 19509116 A1 | 9/1996 |
| DE | 19534043 A1 | 3/1997 |
| DE | 19707373 C1 | 2/1998 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 19941859 A1 | 3/2001 |
| DE | 10052679 A1 | 5/2001 |
| DE | 20112837 U1 | 10/2001 |
| DE | 20121753 U1 | 4/2003 |
| DE | 10314827 B3 | 4/2004 |
| DE | 202004012389 U1 | 9/2004 |
| DE | 10314072 A1 | 10/2004 |
| DE | 202007003114 U1 | 6/2007 |
| DE | 102010013150 A1 | 9/2011 |
| EP | 0000756 A1 | 2/1979 |
| EP | 0033633 A2 | 8/1981 |
| EP | 0122046 A1 | 10/1984 |
| EP | 0070230 B1 | 4/1985 |
| EP | 0156774 A2 | 10/1985 |
| EP | 0072754 B1 | 4/1986 |
| EP | 0033548 B1 | 5/1986 |
| EP | 0077262 B1 | 8/1986 |
| EP | 0189807 A2 | 8/1986 |
| EP | 0212278 A2 | 3/1987 |
| EP | 0129442 B1 | 11/1987 |
| EP | 0255631 A1 | 2/1988 |
| EP | 0276104 A2 | 7/1988 |
| EP | 0178940 B1 | 1/1991 |
| EP | 0178941 B1 | 1/1991 |
| EP | 0169044 B1 | 6/1991 |
| EP | 0248844 B1 | 1/1993 |
| EP | 0539762 A1 | 5/1993 |
| EP | 0541950 A1 | 5/1993 |
| EP | 0545029 A1 | 6/1993 |
| EP | 0548998 A1 | 6/1993 |
| EP | 0379721 B1 | 9/1993 |
| EP | 0277959 B1 | 10/1993 |
| EP | 0233940 B1 | 11/1993 |
| EP | 0261230 B1 | 11/1993 |
| EP | 0324636 B1 | 3/1994 |
| EP | 0591946 A1 | 4/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0623311 A2 | 11/1994 |
| EP | 0630612 A1 | 12/1994 |
| EP | 0630614 A1 | 12/1994 |
| EP | 0634144 A1 | 1/1995 |
| EP | 0639349 A2 | 2/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0387980 B1 | 10/1995 |
| EP | 0511470 B1 | 10/1995 |
| EP | 0674876 A2 | 10/1995 |
| EP | 0676173 B1 | 10/1995 |
| EP | 0679367 A2 | 11/1995 |
| EP | 0392547 B1 | 12/1995 |
| EP | 0685204 A1 | 12/1995 |
| EP | 0686374 A2 | 12/1995 |
| EP | 0364216 B1 | 1/1996 |
| EP | 0699418 A1 | 3/1996 |
| EP | 0702937 A1 | 3/1996 |
| EP | 0488768 B1 | 4/1996 |
| EP | 0705571 A1 | 4/1996 |
| EP | 0528478 B1 | 5/1996 |
| EP | 0711611 A2 | 5/1996 |
| EP | 0541987 B1 | 7/1996 |
| EP | 0667119 B1 | 7/1996 |
| EP | 0737446 A1 | 10/1996 |
| EP | 0741996 B1 | 11/1996 |
| EP | 0748646 B1 | 12/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0621009 B1 | 7/1997 |
| EP | 0625077 B1 | 7/1997 |
| EP | 0633749 B1 | 8/1997 |

(56) References Cited

FOREIGN PATENT DOCUMENTS

| | | |
|---|---|---|
| EP | 0710090 B1 | 8/1997 |
| EP | 0578425 B1 | 9/1997 |
| EP | 0623312 B1 | 9/1997 |
| EP | 0621006 B1 | 10/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0678007 B1 | 9/1998 |
| EP | 0869104 A1 | 10/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0640317 B1 | 9/1999 |
| EP | 0843906 B1 | 3/2000 |
| EP | 0552050 B1 | 5/2000 |
| EP | 0833592 B1 | 5/2000 |
| EP | 0832605 B1 | 6/2000 |
| EP | 0484677 B2 | 7/2000 |
| EP | 0830094 B1 | 9/2000 |
| EP | 1034747 A1 | 9/2000 |
| EP | 1034748 A1 | 9/2000 |
| EP | 0726632 B1 | 10/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1058177 A1 | 12/2000 |
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 0768840 B1 | 12/2001 |
| EP | 0908152 B1 | 1/2002 |
| EP | 0717959 B1 | 2/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0717967 B1 | 5/2003 |
| EP | 0869742 B1 | 5/2003 |
| EP | 0829235 B1 | 6/2003 |
| EP | 0887046 B1 | 7/2003 |
| EP | 1323384 A2 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 137478 A1 | 1/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1411626 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1453432 A2 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1496805 A2 | 1/2005 |
| EP | 1256318 B1 | 2/2005 |
| EP | 1520521 A1 | 4/2005 |
| EP | 1520522 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 0906764 B1 | 12/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621143 A2 | 2/2006 |
| EP | 1621145 A2 | 2/2006 |
| EP | 1621151 A2 | 2/2006 |
| EP | 1034746 B1 | 3/2006 |
| EP | 1201196 B1 | 3/2006 |
| EP | 1632191 A2 | 3/2006 |
| EP | 1647231 A1 | 4/2006 |
| EP | 1065981 B1 | 5/2006 |
| EP | 1082944 B1 | 5/2006 |
| EP | 1230899 B1 | 5/2006 |
| EP | 1652481 A2 | 5/2006 |
| EP | 1382303 B1 | 6/2006 |
| EP | 1253866 B1 | 7/2006 |
| EP | 1676539 A1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1723914 A1 | 11/2006 |
| EP | 1256317 B1 | 12/2006 |
| EP | 1285633 B1 | 12/2006 |
| EP | 1728473 B1 | 12/2006 |
| EP | 1736105 A1 | 12/2006 |
| EP | 1011494 B1 | 1/2007 |
| EP | 1479346 B1 | 1/2007 |
| EP | 1484024 B1 | 1/2007 |
| EP | 1749485 A1 | 2/2007 |
| EP | 1754445 A2 | 2/2007 |
| EP | 1759812 A1 | 3/2007 |
| EP | 1767157 A1 | 3/2007 |
| EP | 1767163 A1 | 3/2007 |
| EP | 1563792 B1 | 4/2007 |
| EP | 1769756 A1 | 4/2007 |
| EP | 1769758 A1 | 4/2007 |

(56) References Cited

FOREIGN PATENT DOCUMENTS

| | | | |
|---|---|---|---|
| EP | 1581128 B1 | 5/2007 |
| EP | 1780825 A1 | 5/2007 |
| EP | 1785097 A2 | 5/2007 |
| EP | 1790293 A2 | 5/2007 |
| EP | 1790294 A1 | 5/2007 |
| EP | 1563793 B1 | 6/2007 |
| EP | 1791473 A2 | 6/2007 |
| EP | 1800610 A1 | 6/2007 |
| EP | 1300117 B1 | 8/2007 |
| EP | 1813199 A1 | 8/2007 |
| EP | 1813200 A2 | 8/2007 |
| EP | 1813201 A1 | 8/2007 |
| EP | 1813202 A1 | 8/2007 |
| EP | 1813203 A2 | 8/2007 |
| EP | 1813207 A1 | 8/2007 |
| EP | 1813209 A1 | 8/2007 |
| EP | 1815950 A1 | 8/2007 |
| EP | 1330991 B1 | 9/2007 |
| EP | 1837041 A1 | 9/2007 |
| EP | 0922435 B1 | 10/2007 |
| EP | 1487359 B1 | 10/2007 |
| EP | 1599146 B1 | 10/2007 |
| EP | 1839596 A1 | 10/2007 |
| EP | 1679096 B1 | 11/2007 |
| EP | 1857057 A2 | 11/2007 |
| EP | 1402821 B1 | 12/2007 |
| EP | 1872727 A1 | 1/2008 |
| EP | 1550410 B1 | 2/2008 |
| EP | 1671593 B1 | 2/2008 |
| EP | 1897502 A1 | 3/2008 |
| EP | 1611856 B1 | 4/2008 |
| EP | 1908417 A2 | 4/2008 |
| EP | 1917929 A1 | 5/2008 |
| EP | 1330201 B1 | 6/2008 |
| EP | 1702568 B1 | 7/2008 |
| EP | 1943955 A2 | 7/2008 |
| EP | 1943957 A2 | 7/2008 |
| EP | 1943959 A1 | 7/2008 |
| EP | 1943962 A2 | 7/2008 |
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1974678 A2 | 10/2008 |
| EP | 1980213 A2 | 10/2008 |
| EP | 1980214 A2 | 10/2008 |
| EP | 1759645 B1 | 11/2008 |
| EP | 1987780 A2 | 11/2008 |
| EP | 1990014 A2 | 11/2008 |
| EP | 1992296 A1 | 11/2008 |
| EP | 1552795 B1 | 12/2008 |
| EP | 1693008 B1 | 12/2008 |
| EP | 1759640 B1 | 12/2008 |
| EP | 1997439 A2 | 12/2008 |
| EP | 2000101 A2 | 12/2008 |
| EP | 2000102 A2 | 12/2008 |
| EP | 2005894 A2 | 12/2008 |
| EP | 2005897 A2 | 12/2008 |
| EP | 2005901 A1 | 12/2008 |
| EP | 2008595 A2 | 12/2008 |
| EP | 2025293 A1 | 2/2009 |
| EP | 1736104 B1 | 3/2009 |
| EP | 1749486 B1 | 3/2009 |
| EP | 1782743 B1 | 3/2009 |
| EP | 2039302 A2 | 3/2009 |
| EP | 2039308 A2 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 2055243 A2 | 5/2009 |
| EP | 1550409 B1 | 6/2009 |
| EP | 1550413 B1 | 6/2009 |
| EP | 1719461 B1 | 6/2009 |
| EP | 1834594 B1 | 6/2009 |
| EP | 1709911 B1 | 7/2009 |
| EP | 2077093 A2 | 7/2009 |
| EP | 1745748 B1 | 8/2009 |
| EP | 2090231 A1 | 8/2009 |
| EP | 2090237 A1 | 8/2009 |
| EP | 2090241 A1 | 8/2009 |
| EP | 2090245 A1 | 8/2009 |
| EP | 2090254 A1 | 8/2009 |
| EP | 2090256 A2 | 8/2009 |
| EP | 2095777 A2 | 9/2009 |
| EP | 2098170 A2 | 9/2009 |
| EP | 2100562 A2 | 9/2009 |
| EP | 2110082 A1 | 10/2009 |
| EP | 2110083 A2 | 10/2009 |
| EP | 2110084 A2 | 10/2009 |
| EP | 2111803 A2 | 10/2009 |
| EP | 1813208 B1 | 11/2009 |
| EP | 1908426 B1 | 11/2009 |
| EP | 2116195 A1 | 11/2009 |
| EP | 2116197 A2 | 11/2009 |
| EP | 1607050 B1 | 12/2009 |
| EP | 1762190 B8 | 12/2009 |
| EP | 1815804 B1 | 12/2009 |
| EP | 1875870 B1 | 12/2009 |
| EP | 1878395 B1 | 1/2010 |
| EP | 2151204 A1 | 2/2010 |
| EP | 1813211 B1 | 3/2010 |
| EP | 2165654 A1 | 3/2010 |
| EP | 2165656 A2 | 3/2010 |
| EP | 2165660 A2 | 3/2010 |
| EP | 2165663 A2 | 3/2010 |
| EP | 2165664 A2 | 3/2010 |
| EP | 1566150 B1 | 4/2010 |
| EP | 1813206 B1 | 4/2010 |
| EP | 2184014 A2 | 5/2010 |
| EP | 1769754 B1 | 6/2010 |
| EP | 1854416 B1 | 6/2010 |
| EP | 1911408 B1 | 6/2010 |
| EP | 2198787 A1 | 6/2010 |
| EP | 2214610 A1 | 8/2010 |
| EP | 2218409 A1 | 8/2010 |
| EP | 1647286 B1 | 9/2010 |
| EP | 1825821 B1 | 9/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 2036505 B1 | 11/2010 |
| EP | 2245993 A2 | 11/2010 |
| EP | 2245994 A1 | 11/2010 |
| EP | 2253280 A1 | 11/2010 |
| EP | 1627605 B1 | 12/2010 |
| EP | 2027811 B1 | 12/2010 |
| EP | 2130498 B1 | 12/2010 |
| EP | 2258282 A2 | 12/2010 |
| EP | 2263568 A2 | 12/2010 |
| EP | 1994890 A2 | 1/2011 |
| EP | 2005900 B1 | 1/2011 |
| EP | 2277667 A1 | 1/2011 |
| EP | 2283780 A2 | 2/2011 |
| EP | 2286738 A2 | 2/2011 |
| EP | 1494595 B1 | 3/2011 |
| EP | 1690502 B1 | 3/2011 |
| EP | 1884201 B1 | 3/2011 |
| EP | 2292153 A1 | 3/2011 |
| EP | 1769755 B1 | 4/2011 |
| EP | 2090240 B1 | 4/2011 |
| EP | 2305135 A1 | 4/2011 |
| EP | 2308388 A1 | 4/2011 |
| EP | 2314254 A2 | 4/2011 |
| EP | 2316345 A1 | 5/2011 |
| EP | 2316366 A2 | 5/2011 |
| EP | 2319443 A1 | 5/2011 |
| EP | 2324776 A2 | 5/2011 |
| EP | 1813205 B1 | 6/2011 |
| EP | 2042107 B1 | 6/2011 |
| EP | 2090243 B1 | 6/2011 |
| EP | 2329773 A1 | 6/2011 |

(56) References Cited

FOREIGN PATENT DOCUMENTS

| | | |
|---|---|---|
| EP | 2090239 B1 | 7/2011 |
| EP | 2340771 A2 | 7/2011 |
| EP | 1728475 B1 | 8/2011 |
| EP | 2353545 A1 | 8/2011 |
| EP | 2361562 A1 | 8/2011 |
| EP | 2377472 A1 | 10/2011 |
| EP | 1836986 B1 | 11/2011 |
| EP | 1908414 B1 | 11/2011 |
| EP | 2153781 B1 | 11/2011 |
| EP | 2387943 A2 | 11/2011 |
| EP | 2389928 A2 | 11/2011 |
| EP | 1847225 B1 | 12/2011 |
| EP | 2397079 A1 | 12/2011 |
| EP | 2399538 A2 | 12/2011 |
| EP | 1785102 B1 | 1/2012 |
| EP | 1316290 B1 | 2/2012 |
| EP | 1962711 B1 | 2/2012 |
| EP | 2415416 A1 | 2/2012 |
| EP | 2090253 B1 | 3/2012 |
| EP | 2430986 A2 | 3/2012 |
| EP | 1347638 B1 | 5/2012 |
| EP | 1943956 B1 | 5/2012 |
| EP | 2446834 A1 | 5/2012 |
| EP | 2455007 A2 | 5/2012 |
| EP | 2457519 A1 | 5/2012 |
| EP | 2462878 A1 | 6/2012 |
| EP | 2462880 A2 | 6/2012 |
| EP | 1813204 B1 | 7/2012 |
| EP | 2189121 B1 | 7/2012 |
| EP | 2248475 B1 | 7/2012 |
| EP | 2478845 A2 | 7/2012 |
| EP | 2005895 B1 | 8/2012 |
| EP | 2090248 B1 | 8/2012 |
| EP | 2481359 A1 | 8/2012 |
| EP | 2484304 A2 | 8/2012 |
| EP | 2486860 A2 | 8/2012 |
| EP | 2486862 A2 | 8/2012 |
| EP | 2486868 A2 | 8/2012 |
| EP | 1908412 B1 | 9/2012 |
| EP | 1935351 B1 | 9/2012 |
| EP | 2497431 A1 | 9/2012 |
| EP | 1550412 B2 | 10/2012 |
| EP | 1616549 B1 | 10/2012 |
| EP | 2030579 B1 | 10/2012 |
| EP | 2090252 B1 | 10/2012 |
| EP | 2517637 A1 | 10/2012 |
| EP | 2517638 A1 | 10/2012 |
| EP | 2517642 A2 | 10/2012 |
| EP | 2517645 A2 | 10/2012 |
| EP | 2517649 A2 | 10/2012 |
| EP | 2517651 A2 | 10/2012 |
| EP | 2526877 A1 | 11/2012 |
| EP | 2526883 A1 | 11/2012 |
| EP | 1884206 B1 | 3/2013 |
| EP | 2286735 B1 | 3/2013 |
| EP | 2090238 B1 | 4/2013 |
| EP | 1806103 B1 | 5/2013 |
| EP | 2586380 A1 | 5/2013 |
| EP | 2586383 A2 | 5/2013 |
| EP | 2606812 A1 | 6/2013 |
| EP | 2606834 A2 | 6/2013 |
| EP | 1982657 B1 | 7/2013 |
| EP | 2614782 A2 | 7/2013 |
| EP | 2617369 A1 | 7/2013 |
| EP | 2620117 A1 | 7/2013 |
| EP | 2090234 B1 | 9/2013 |
| EP | 2633830 A1 | 9/2013 |
| EP | 2090244 B1 | 10/2013 |
| EP | 2644124 A1 | 10/2013 |
| EP | 2644209 A2 | 10/2013 |
| EP | 2649948 A1 | 10/2013 |
| EP | 2649949 A1 | 10/2013 |
| EP | 1997438 B1 | 11/2013 |
| EP | 2684529 A2 | 1/2014 |
| EP | 2687164 A2 | 1/2014 |
| EP | 2700367 A1 | 2/2014 |
| EP | 2713902 A1 | 4/2014 |
| EP | 1772105 B1 | 5/2014 |
| EP | 2743042 A2 | 6/2014 |
| EP | 2759267 A2 | 7/2014 |
| EP | 2764826 A1 | 8/2014 |
| EP | 2764827 A1 | 8/2014 |
| EP | 2767243 A2 | 8/2014 |
| EP | 2772206 A2 | 9/2014 |
| EP | 2772209 A1 | 9/2014 |
| EP | 2777520 A1 | 9/2014 |
| EP | 2777524 A2 | 9/2014 |
| EP | 2777528 A2 | 9/2014 |
| EP | 2777537 A1 | 9/2014 |
| EP | 2777538 A2 | 9/2014 |
| EP | 2786714 A2 | 10/2014 |
| EP | 2792313 A2 | 10/2014 |
| EP | 2803324 A2 | 11/2014 |
| EP | 2815704 A1 | 12/2014 |
| EP | 2446835 B1 | 1/2015 |
| EP | 2842500 A1 | 3/2015 |
| EP | 2845545 A1 | 3/2015 |
| EP | 1943960 B1 | 4/2015 |
| EP | 2090255 B1 | 4/2015 |
| EP | 2853220 A1 | 4/2015 |
| EP | 2923647 A2 | 9/2015 |
| EP | 2923653 A2 | 9/2015 |
| EP | 2923660 A2 | 9/2015 |
| EP | 2932913 A1 | 10/2015 |
| EP | 2944270 A1 | 11/2015 |
| EP | 1774914 B1 | 12/2015 |
| EP | 2090235 B1 | 4/2016 |
| EP | 2823773 B1 | 4/2016 |
| EP | 2131750 B1 | 5/2016 |
| EP | 2298220 B1 | 6/2016 |
| EP | 2510891 B1 | 6/2016 |
| EP | 1915957 B1 | 8/2016 |
| EP | 2296559 B1 | 8/2016 |
| EP | 2586379 B1 | 8/2016 |
| EP | 2777533 B1 | 10/2016 |
| EP | 2364651 B1 | 11/2016 |
| EP | 2747235 B1 | 11/2016 |
| EP | 2116192 B1 | 3/2017 |
| EP | 2789299 B1 | 5/2017 |
| EP | 2311386 B1 | 6/2017 |
| EP | 2839787 B1 | 6/2017 |
| EP | 2745782 B1 | 10/2017 |
| ES | 2396594 T3 | 2/2013 |
| FR | 459743 A | 11/1913 |
| FR | 999646 A | 2/1952 |
| FR | 1112936 A | 3/1956 |
| FR | 2452275 B1 | 4/1983 |
| FR | 2598905 A1 | 11/1987 |
| FR | 2689749 B1 | 7/1994 |
| FR | 2765794 A1 | 1/1999 |
| FR | 2815842 A1 | 5/2002 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2090534 B | 6/1984 |
| GB | 2272159 A | 5/1994 |
| GB | 2284242 A | 5/1995 |
| GB | 2286435 A | 8/1995 |
| GB | 2336214 A | 10/1999 |
| GB | 2425903 A | 11/2006 |
| GB | 2426391 A | 11/2006 |
| GB | 2423199 B | 5/2009 |
| GB | 2509523 A | 7/2014 |
| GR | 930100110 A | 11/1993 |
| JP | S4711908 Y1 | 5/1972 |
| JP | S5033988 U | 4/1975 |
| JP | S56112235 A | 9/1981 |
| JP | S58500053 A | 1/1983 |
| JP | S58501360 A | 8/1983 |
| JP | S59174920 A | 10/1984 |
| JP | S60100955 A | 6/1985 |

(56) References Cited

FOREIGN PATENT DOCUMENTS

| | | |
|---|---|---|
| JP | S60212152 A | 10/1985 |
| JP | S6198249 A | 5/1986 |
| JP | S61502036 A | 9/1986 |
| JP | S62170011 U | 10/1987 |
| JP | S6359764 A | 3/1988 |
| JP | S63147449 A | 6/1988 |
| JP | S63203149 A | 8/1988 |
| JP | S63270040 A | 11/1988 |
| JP | H0129503 B2 | 6/1989 |
| JP | H02279149 A | 11/1990 |
| JP | H0312126 A | 1/1991 |
| JP | H0318354 A | 1/1991 |
| JP | H0378514 U | 8/1991 |
| JP | H0385009 U | 8/1991 |
| JP | H04215747 A | 8/1992 |
| JP | H04131860 U | 12/1992 |
| JP | H0584252 A | 4/1993 |
| JP | H05123325 A | 5/1993 |
| JP | H05212039 A | 8/1993 |
| JP | H 05226945 A | 9/1993 |
| JP | H067357 A | 1/1994 |
| JP | H0630945 A | 2/1994 |
| JP | H0654857 A | 3/1994 |
| JP | H0663054 A | 3/1994 |
| JP | H0626812 U | 4/1994 |
| JP | H06121798 A | 5/1994 |
| JP | H06125913 A | 5/1994 |
| JP | H06197901 A | 7/1994 |
| JP | H06237937 A | 8/1994 |
| JP | H06327684 A | 11/1994 |
| JP | H079622 U | 2/1995 |
| JP | H0731623 A | 2/1995 |
| JP | H0747070 A | 2/1995 |
| JP | H0751273 A | 2/1995 |
| JP | H07124166 A | 5/1995 |
| JP | H07163573 A | 6/1995 |
| JP | H07163574 A | 6/1995 |
| JP | H07171163 A | 7/1995 |
| JP | H07255735 A | 10/1995 |
| JP | H07285089 A | 10/1995 |
| JP | H07299074 A | 11/1995 |
| JP | H0833641 A | 2/1996 |
| JP | H0833642 A | 2/1996 |
| JP | H08164141 A | 6/1996 |
| JP | H08173437 A | 7/1996 |
| JP | H08182684 A | 7/1996 |
| JP | H08215201 A | 8/1996 |
| JP | H08507708 A | 8/1996 |
| JP | H08229050 A | 9/1996 |
| JP | H08289895 A | 11/1996 |
| JP | H08336540 A | 12/1996 |
| JP | H08336544 A | 12/1996 |
| JP | H09501081 A | 2/1997 |
| JP | H09501577 A | 2/1997 |
| JP | H09164144 A | 6/1997 |
| JP | H09-323068 A | 12/1997 |
| JP | H10113352 A | 5/1998 |
| JP | H10118090 A | 5/1998 |
| JP | H10-200699 A | 7/1998 |
| JP | H 10296660 A | 11/1998 |
| JP | H10512465 A | 12/1998 |
| JP | H10512469 A | 12/1998 |
| JP | 2000014632 A | 1/2000 |
| JP | 2000033071 A | 2/2000 |
| JP | 2000112002 A | 4/2000 |
| JP | 3056672 B2 | 6/2000 |
| JP | 2000166932 A | 6/2000 |
| JP | 2000171730 A | 6/2000 |
| JP | 2000287987 A | 10/2000 |
| JP | 2000325303 A | 11/2000 |
| JP | 2001037763 A | 2/2001 |
| JP | 2001046384 A | 2/2001 |
| JP | 2001087272 A | 4/2001 |
| JP | 2001514541 A | 9/2001 |
| JP | 2001276091 A | 10/2001 |
| JP | 2001286477 A | 10/2001 |
| JP | 2001517473 A | 10/2001 |
| JP | 2002051974 A | 2/2002 |
| JP | 2002085415 A | 3/2002 |
| JP | 2002143078 A | 5/2002 |
| JP | 2002204801 A | 7/2002 |
| JP | 2002528161 A | 9/2002 |
| JP | 2002314298 A | 10/2002 |
| JP | 2002369820 A | 12/2002 |
| JP | 2002542186 A | 12/2002 |
| JP | 2003000603 A | 1/2003 |
| JP | 2003500153 A | 1/2003 |
| JP | 2003504104 A | 2/2003 |
| JP | 2003135473 A | 5/2003 |
| JP | 2003148903 A | 5/2003 |
| JP | 2003164066 A | 6/2003 |
| JP | 2003521301 A | 7/2003 |
| JP | 2003521304 A | 7/2003 |
| JP | 2003523251 A | 8/2003 |
| JP | 2003523254 A | 8/2003 |
| JP | 2003524431 A | 8/2003 |
| JP | 3442423 B2 | 9/2003 |
| JP | 2003300416 A | 10/2003 |
| JP | 2004147701 A | 5/2004 |
| JP | 2004162035 A | 6/2004 |
| JP | 2004229976 A | 8/2004 |
| JP | 2004524076 A | 8/2004 |
| JP | 2004531280 A | 10/2004 |
| JP | 2004532084 A | 10/2004 |
| JP | 2004532676 A | 10/2004 |
| JP | 2004-535217 A | 11/2004 |
| JP | 2004329624 A | 11/2004 |
| JP | 2004337617 A | 12/2004 |
| JP | 2004344662 A | 12/2004 |
| JP | 2004344663 A | 12/2004 |
| JP | 2005013573 A | 1/2005 |
| JP | 2005028147 A | 2/2005 |
| JP | 2005028148 A | 2/2005 |
| JP | 2005028149 A | 2/2005 |
| JP | 2005505309 A | 2/2005 |
| JP | 2005505322 A | 2/2005 |
| JP | 2005505334 A | 2/2005 |
| JP | 2005080702 A | 3/2005 |
| JP | 2005103280 A | 4/2005 |
| JP | 2005103281 A | 4/2005 |
| JP | 2005103293 A | 4/2005 |
| JP | 2005511131 A | 4/2005 |
| JP | 2005511137 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005137919 A | 6/2005 |
| JP | 2005144183 A | 6/2005 |
| JP | 2005152416 A | 6/2005 |
| JP | 2005516714 A | 6/2005 |
| JP | 2005187954 A | 7/2005 |
| JP | 2005521109 A | 7/2005 |
| JP | 2005523105 A | 8/2005 |
| JP | 2005524474 A | 8/2005 |
| JP | 2005296412 A | 10/2005 |
| JP | 2005529675 A | 10/2005 |
| JP | 2005529677 A | 10/2005 |
| JP | 2005328882 A | 12/2005 |
| JP | 2005335432 A | 12/2005 |
| JP | 2005342267 A | 12/2005 |
| JP | 2006034975 A | 2/2006 |
| JP | 2006034977 A | 2/2006 |
| JP | 2006034978 A | 2/2006 |
| JP | 2006034980 A | 2/2006 |
| JP | 2006043451 A | 2/2006 |
| JP | 2006506106 A | 2/2006 |
| JP | 2006510879 A | 3/2006 |
| JP | 3791856 B2 | 6/2006 |
| JP | 2006187649 A | 7/2006 |
| JP | 2006218228 A | 8/2006 |
| JP | 2006218297 A | 8/2006 |

(56) References Cited

FOREIGN PATENT DOCUMENTS

| | | |
|---|---|---|
| JP | 2006223872 A | 8/2006 |
| JP | 2006281405 A | 10/2006 |
| JP | 2006289064 A | 10/2006 |
| JP | 2006334412 A | 12/2006 |
| JP | 2006334417 A | 12/2006 |
| JP | 2006346445 A | 12/2006 |
| JP | 2007000634 A | 1/2007 |
| JP | 2007050253 A | 3/2007 |
| JP | 2007061628 A | 3/2007 |
| JP | 3906843 B2 | 4/2007 |
| JP | 2007083051 A | 4/2007 |
| JP | 2007098130 A | 4/2007 |
| JP | 2007105481 A | 4/2007 |
| JP | 2007117725 A | 5/2007 |
| JP | 2007130471 A | 5/2007 |
| JP | 2007130479 A | 5/2007 |
| JP | 3934161 B2 | 6/2007 |
| JP | 2007203047 A | 8/2007 |
| JP | 2007203049 A | 8/2007 |
| JP | 2007203051 A | 8/2007 |
| JP | 2007203055 A | 8/2007 |
| JP | 2007203057 A | 8/2007 |
| JP | 2007524435 A | 8/2007 |
| JP | 2007222615 A | 9/2007 |
| JP | 2007229448 A | 9/2007 |
| JP | 2007526026 A | 9/2007 |
| JP | 4001860 B2 | 10/2007 |
| JP | 2007252916 A | 10/2007 |
| JP | 2007307373 A | 11/2007 |
| JP | 2007325922 A | 12/2007 |
| JP | 2008068073 A | 3/2008 |
| JP | 2008510515 A | 4/2008 |
| JP | 2008516669 A | 5/2008 |
| JP | 2008528203 A | 7/2008 |
| JP | 2008-220032 A | 9/2008 |
| JP | 2008206967 A | 9/2008 |
| JP | 2008212637 A | 9/2008 |
| JP | 2008212638 A | 9/2008 |
| JP | 2008212640 A | 9/2008 |
| JP | 2008220956 A | 9/2008 |
| JP | 2008237881 A | 10/2008 |
| JP | 2008259860 A | 10/2008 |
| JP | 2008264535 A | 11/2008 |
| JP | 2008283459 A | 11/2008 |
| JP | 2008307393 A | 12/2008 |
| JP | 2009000531 A | 1/2009 |
| JP | 2009006137 A | 1/2009 |
| JP | 2009502351 A | 1/2009 |
| JP | 2009502352 A | 1/2009 |
| JP | 2009022742 A | 2/2009 |
| JP | 2009506799 A | 2/2009 |
| JP | 2009507526 A | 2/2009 |
| JP | 2009072595 A | 4/2009 |
| JP | 2009072599 A | 4/2009 |
| JP | 2009090113 A | 4/2009 |
| JP | 2009106752 A | 5/2009 |
| JP | 2009189821 A | 8/2009 |
| JP | 2009189823 A | 8/2009 |
| JP | 2009189836 A | 8/2009 |
| JP | 2009189837 A | 8/2009 |
| JP | 2009189838 A | 8/2009 |
| JP | 2009189846 A | 8/2009 |
| JP | 2009189847 A | 8/2009 |
| JP | 2009201998 A | 9/2009 |
| JP | 2009207260 A | 9/2009 |
| JP | 2009226028 A | 10/2009 |
| JP | 2009536082 A | 10/2009 |
| JP | 2009261944 A | 11/2009 |
| JP | 2009268908 A | 11/2009 |
| JP | 2009538684 A | 11/2009 |
| JP | 2009539420 A | 11/2009 |
| JP | 2009291604 A | 12/2009 |
| JP | 2010504808 A | 2/2010 |
| JP | 2010504809 A | 2/2010 |
| JP | 2010504813 A | 2/2010 |
| JP | 2010504846 A | 2/2010 |
| JP | 2010505524 A | 2/2010 |
| JP | 2010069307 A | 4/2010 |
| JP | 2010069310 A | 4/2010 |
| JP | 2010075694 A | 4/2010 |
| JP | 2010075695 A | 4/2010 |
| JP | 2010088876 A | 4/2010 |
| JP | 2010094514 A | 4/2010 |
| JP | 2010098844 A | 4/2010 |
| JP | 4461008 B2 | 5/2010 |
| JP | 2010-520025 A | 6/2010 |
| JP | 2010-148879 A | 7/2010 |
| JP | 2010142636 A | 7/2010 |
| JP | 4549018 B2 | 9/2010 |
| JP | 2010214166 A | 9/2010 |
| JP | 2010-240429 A | 10/2010 |
| JP | 2010240411 A | 10/2010 |
| JP | 2010246948 A | 11/2010 |
| JP | 2010-540041 A | 12/2010 |
| JP | 2010279690 A | 12/2010 |
| JP | 2010540192 A | 12/2010 |
| JP | 2011005260 A | 1/2011 |
| JP | 2011504391 A | 2/2011 |
| JP | 2011509786 A | 3/2011 |
| JP | 2011072574 A | 4/2011 |
| JP | 2011072797 A | 4/2011 |
| JP | 2011078763 A | 4/2011 |
| JP | 2011-115594 A | 6/2011 |
| JP | 2011-520564 A | 7/2011 |
| JP | 4722849 B2 | 7/2011 |
| JP | 4783373 B2 | 9/2011 |
| JP | 2011524199 A | 9/2011 |
| JP | 2011251156 A | 12/2011 |
| JP | 2012040398 A | 3/2012 |
| JP | 2012507356 A | 3/2012 |
| JP | 2012517289 A | 8/2012 |
| JP | 5140421 B2 | 2/2013 |
| JP | 5162595 B2 | 3/2013 |
| JP | 2013517891 A | 5/2013 |
| JP | 2013526342 A | 6/2013 |
| JP | 2013128791 A | 7/2013 |
| JP | 5333899 B2 | 11/2013 |
| JP | 2016-512057 A | 4/2016 |
| KR | 20100110134 A | 10/2010 |
| KR | 20110003229 A | 1/2011 |
| RU | 1814161 C | 5/1993 |
| RU | 2008830 C1 | 3/1994 |
| RU | 2052979 C1 | 1/1996 |
| RU | 2066128 C1 | 9/1996 |
| RU | 2098025 C1 | 12/1997 |
| RU | 2141279 C1 | 11/1999 |
| RU | 2144791 C1 | 1/2000 |
| RU | 2161450 C1 | 1/2001 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| RU | 61122 U1 | 2/2007 |
| RU | 2007103563 A | 8/2008 |
| SU | 189517 A | 1/1967 |
| SU | 297156 A | 5/1971 |
| SU | 328636 A | 9/1972 |
| SU | 511939 A1 | 4/1976 |
| SU | 674747 A1 | 7/1979 |
| SU | 728848 A1 | 4/1980 |
| SU | 886900 A1 | 12/1981 |
| SU | 1009439 A | 4/1983 |
| SU | 1022703 A1 | 6/1983 |
| SU | 1271497 A1 | 11/1986 |
| SU | 1333319 A2 | 8/1987 |
| SU | 1377052 A1 | 2/1988 |
| SU | 1377053 A1 | 2/1988 |
| SU | 1443874 A1 | 12/1988 |
| SU | 1509051 A1 | 9/1989 |
| SU | 1561964 A1 | 5/1990 |
| SU | 1708312 A1 | 1/1992 |

(56) References Cited

FOREIGN PATENT DOCUMENTS

| | | |
|---|---|---|
| SU | 1722476 A1 | 3/1992 |
| SU | 1752361 A1 | 8/1992 |
| SU | 1814161 A1 | 5/1993 |
| WO | WO-8202824 A1 | 9/1982 |
| WO | WO-8602254 A1 | 4/1986 |
| WO | WO-9115157 A1 | 10/1991 |
| WO | WO-9220295 A1 | 11/1992 |
| WO | WO-9221300 A1 | 12/1992 |
| WO | WO-9308755 A1 | 5/1993 |
| WO | WO-9313718 A1 | 7/1993 |
| WO | WO-9314690 A1 | 8/1993 |
| WO | WO-9315648 A1 | 8/1993 |
| WO | WO-9315850 A1 | 8/1993 |
| WO | WO-9319681 A1 | 10/1993 |
| WO | WO-9400060 A1 | 1/1994 |
| WO | WO-9411057 A1 | 5/1994 |
| WO | WO-94/14129 A1 | 6/1994 |
| WO | WO-9412108 A1 | 6/1994 |
| WO | WO-9417737 A1 | 8/1994 |
| WO | WO-9418893 A1 | 9/1994 |
| WO | WO-9420030 A1 | 9/1994 |
| WO | WO-9422378 A1 | 10/1994 |
| WO | WO-9423659 A1 | 10/1994 |
| WO | WO-9424943 A1 | 11/1994 |
| WO | WO-9424947 A1 | 11/1994 |
| WO | WO-9502369 A1 | 1/1995 |
| WO | WO-9503743 A1 | 2/1995 |
| WO | WO-9506817 A1 | 3/1995 |
| WO | WO-9509576 A1 | 4/1995 |
| WO | WO-9509577 A1 | 4/1995 |
| WO | WO-9514436 A1 | 6/1995 |
| WO | WO-9517855 A1 | 7/1995 |
| WO | WO-9518383 A1 | 7/1995 |
| WO | WO-9518572 A1 | 7/1995 |
| WO | WO-9519739 A1 | 7/1995 |
| WO | WO-9520360 A1 | 8/1995 |
| WO | WO-9523557 A1 | 9/1995 |
| WO | WO-9524865 A1 | 9/1995 |
| WO | WO-9525471 A3 | 9/1995 |
| WO | WO-9526562 A1 | 10/1995 |
| WO | WO-9529639 A1 | 11/1995 |
| WO | WO-9604858 A1 | 2/1996 |
| WO | WO-9618344 A2 | 6/1996 |
| WO | WO-9619151 A1 | 6/1996 |
| WO | WO-9619152 A1 | 6/1996 |
| WO | WO-9620652 A1 | 7/1996 |
| WO | WO-9621119 A1 | 7/1996 |
| WO | WO-9622055 A1 | 7/1996 |
| WO | WO-9623448 A1 | 8/1996 |
| WO | WO-9624301 A1 | 8/1996 |
| WO | WO-9627337 A1 | 9/1996 |
| WO | WO-9631155 A1 | 10/1996 |
| WO | WO-9635464 A1 | 11/1996 |
| WO | WO-9639085 A1 | 12/1996 |
| WO | WO-9639086 A1 | 12/1996 |
| WO | WO-9639087 A1 | 12/1996 |
| WO | WO-9639088 A1 | 12/1996 |
| WO | WO-9639089 A1 | 12/1996 |
| WO | WO-9700646 A1 | 1/1997 |
| WO | WO-9700647 A1 | 1/1997 |
| WO | WO-9701989 A1 | 1/1997 |
| WO | WO-9706582 A1 | 2/1997 |
| WO | WO-9710763 A1 | 3/1997 |
| WO | WO-9710764 A1 | 3/1997 |
| WO | WO-9711648 A2 | 4/1997 |
| WO | WO-9711649 A1 | 4/1997 |
| WO | WO-9715237 A1 | 5/1997 |
| WO | WO-9724073 A1 | 7/1997 |
| WO | WO-9724993 A1 | 7/1997 |
| WO | WO-9730644 A1 | 8/1997 |
| WO | WO-9730659 A1 | 8/1997 |
| WO | WO-9734533 A1 | 9/1997 |
| WO | WO-9737598 A1 | 10/1997 |
| WO | WO-9739688 A2 | 10/1997 |
| WO | WO-9741767 A2 | 11/1997 |
| WO | WO-9801080 A1 | 1/1998 |
| WO | WO-9817180 A1 | 4/1998 |
| WO | WO-9822154 A2 | 5/1998 |
| WO | WO-9827880 A1 | 7/1998 |
| WO | WO-9830153 A1 | 7/1998 |
| WO | WO-9847436 A1 | 10/1998 |
| WO | WO-9858589 A1 | 12/1998 |
| WO | WO-9902090 A1 | 1/1999 |
| WO | WO-9903407 A1 | 1/1999 |
| WO | WO-9903408 A1 | 1/1999 |
| WO | WO-9903409 A1 | 1/1999 |
| WO | WO-9912483 A1 | 3/1999 |
| WO | WO-9912487 A1 | 3/1999 |
| WO | WO-9912488 A1 | 3/1999 |
| WO | WO-9915086 A1 | 4/1999 |
| WO | WO-9915091 A1 | 4/1999 |
| WO | WO-9923933 A2 | 5/1999 |
| WO | WO-9923959 A1 | 5/1999 |
| WO | WO-9925261 A1 | 5/1999 |
| WO | WO-9929244 A1 | 6/1999 |
| WO | WO-9934744 A1 | 7/1999 |
| WO | WO-9945849 A1 | 9/1999 |
| WO | WO-9948430 A1 | 9/1999 |
| WO | WO-9951158 A1 | 10/1999 |
| WO | WO-0024322 A1 | 5/2000 |
| WO | WO-0024330 A1 | 5/2000 |
| WO | WO-0033755 A1 | 6/2000 |
| WO | WO-0041638 A1 | 7/2000 |
| WO | WO-0048506 A1 | 8/2000 |
| WO | WO-0053112 A2 | 9/2000 |
| WO | WO-0054653 A1 | 9/2000 |
| WO | WO-0057796 A1 | 10/2000 |
| WO | WO-0064365 A1 | 11/2000 |
| WO | WO-0072762 A1 | 12/2000 |
| WO | WO-0072765 A1 | 12/2000 |
| WO | WO-0078222 A1 | 12/2000 |
| WO | WO-0103587 A1 | 1/2001 |
| WO | WO-0105702 A1 | 1/2001 |
| WO | WO-0110482 A1 | 2/2001 |
| WO | WO-0135845 A1 | 5/2001 |
| WO | WO-0154594 A1 | 8/2001 |
| WO | WO-0158371 A1 | 8/2001 |
| WO | WO-0162158 A2 | 8/2001 |
| WO | WO-0162161 A1 | 8/2001 |
| WO | WO-0162162 A1 | 8/2001 |
| WO | WO-0162163 A1 | 8/2001 |
| WO | WO-0162164 A2 | 8/2001 |
| WO | WO-0162169 A2 | 8/2001 |
| WO | WO-0178605 A2 | 10/2001 |
| WO | WO-0180757 A2 | 11/2001 |
| WO | WO-0191646 A1 | 12/2001 |
| WO | WO-0200121 A1 | 1/2002 |
| WO | WO-0207608 A2 | 1/2002 |
| WO | WO-0207618 A1 | 1/2002 |
| WO | WO-0217799 A1 | 3/2002 |
| WO | WO-0219920 A1 | 3/2002 |
| WO | WO-0219932 A1 | 3/2002 |
| WO | WO-0226143 A1 | 4/2002 |
| WO | WO-0230297 A2 | 4/2002 |
| WO | WO-0232322 A2 | 4/2002 |
| WO | WO-0236028 A1 | 5/2002 |
| WO | WO-0243571 A2 | 6/2002 |
| WO | WO-02058568 A1 | 8/2002 |
| WO | WO-02060328 A1 | 8/2002 |
| WO | WO-02065933 A2 | 8/2002 |
| WO | WO-02067785 A2 | 9/2002 |
| WO | WO-02080781 A2 | 10/2002 |
| WO | WO-02085218 A2 | 10/2002 |
| WO | WO-02087586 A1 | 11/2002 |
| WO | WO-02098302 A1 | 12/2002 |
| WO | WO-03000138 A2 | 1/2003 |
| WO | WO-03001329 A2 | 1/2003 |
| WO | WO-03001986 A2 | 1/2003 |
| WO | WO-03013363 A1 | 2/2003 |
| WO | WO-03013372 A2 | 2/2003 |
| WO | WO-03015604 A2 | 2/2003 |
| WO | WO-03020106 A2 | 3/2003 |
| WO | WO-03020139 A2 | 3/2003 |
| WO | WO-03024339 A1 | 3/2003 |

(56) References Cited

FOREIGN PATENT DOCUMENTS

| | | |
|---|---|---|
| WO | WO-03030743 A2 | 4/2003 |
| WO | WO-03037193 A1 | 5/2003 |
| WO | WO-03055402 A1 | 7/2003 |
| WO | WO-03057048 A1 | 7/2003 |
| WO | WO-03057058 A1 | 7/2003 |
| WO | WO-03063694 A1 | 8/2003 |
| WO | WO-03077769 A1 | 9/2003 |
| WO | WO-03079911 A1 | 10/2003 |
| WO | WO-03082126 A1 | 10/2003 |
| WO | WO-03086206 A1 | 10/2003 |
| WO | WO-03088845 A2 | 10/2003 |
| WO | WO-03047436 A3 | 11/2003 |
| WO | WO-03090630 A2 | 11/2003 |
| WO | WO-03094743 A1 | 11/2003 |
| WO | WO-03094745 A1 | 11/2003 |
| WO | WO-03094746 A1 | 11/2003 |
| WO | WO-03094747 A1 | 11/2003 |
| WO | WO-03101313 A1 | 12/2003 |
| WO | WO-03105698 A2 | 12/2003 |
| WO | WO-03105702 A2 | 12/2003 |
| WO | WO-2004004578 A1 | 1/2004 |
| WO | WO-2004006980 A2 | 1/2004 |
| WO | WO-2004011037 A2 | 2/2004 |
| WO | WO-2004014238 A2 | 2/2004 |
| WO | WO-03079909 A3 | 3/2004 |
| WO | WO-2004019769 A1 | 3/2004 |
| WO | WO-2004019803 A1 | 3/2004 |
| WO | WO-2004021868 A2 | 3/2004 |
| WO | WO-2004028585 A2 | 4/2004 |
| WO | WO-2004030554 A1 | 4/2004 |
| WO | WO-2004032754 A2 | 4/2004 |
| WO | WO-2004032760 A2 | 4/2004 |
| WO | WO-2004032762 A1 | 4/2004 |
| WO | WO-2004032763 A2 | 4/2004 |
| WO | WO-2004032783 A1 | 4/2004 |
| WO | WO-2004034875 A2 | 4/2004 |
| WO | WO-2004047626 A1 | 6/2004 |
| WO | WO-2004047653 A2 | 6/2004 |
| WO | WO-2004049956 A2 | 6/2004 |
| WO | WO-2004050971 A2 | 6/2004 |
| WO | WO-2004052426 A2 | 6/2004 |
| WO | WO-2004056276 A1 | 7/2004 |
| WO | WO-2004056277 A1 | 7/2004 |
| WO | WO-2004062516 A1 | 7/2004 |
| WO | WO-2004064600 A2 | 8/2004 |
| WO | WO-2004078050 A2 | 9/2004 |
| WO | WO-2004078051 A2 | 9/2004 |
| WO | WO-2004078236 A2 | 9/2004 |
| WO | WO-2004086987 A1 | 10/2004 |
| WO | WO-2004096015 A2 | 11/2004 |
| WO | WO-2004096057 A2 | 11/2004 |
| WO | WO-2004103157 A2 | 12/2004 |
| WO | WO-2004105593 A1 | 12/2004 |
| WO | WO-2004105621 A1 | 12/2004 |
| WO | WO-2004112618 A2 | 12/2004 |
| WO | WO-2004112652 A2 | 12/2004 |
| WO | WO-2005027983 A2 | 3/2005 |
| WO | WO-2005037329 A2 | 4/2005 |
| WO | WO-2005042041 A1 | 5/2005 |
| WO | WO-2005044078 A2 | 5/2005 |
| WO | WO-2005048809 A1 | 6/2005 |
| WO | WO-2005055846 A1 | 6/2005 |
| WO | WO-2005072634 A2 | 8/2005 |
| WO | WO-2005078892 A1 | 8/2005 |
| WO | WO-2005079675 A2 | 9/2005 |
| WO | WO-2005087128 A1 | 9/2005 |
| WO | WO-2005096954 A2 | 10/2005 |
| WO | WO-2005110243 A2 | 11/2005 |
| WO | WO-2005112806 A2 | 12/2005 |
| WO | WO-2005112808 A1 | 12/2005 |
| WO | WO-2005115251 A1 | 12/2005 |
| WO | WO-2005115253 A2 | 12/2005 |
| WO | WO-2005117735 A1 | 12/2005 |
| WO | WO-2005122936 A1 | 12/2005 |
| WO | WO-2006/026520 A2 | 3/2006 |
| WO | WO-2006023486 A1 | 3/2006 |
| WO | WO-2006023578 A2 | 3/2006 |
| WO | WO-2006027014 A1 | 3/2006 |
| WO | WO-2006028314 A1 | 3/2006 |
| WO | WO-2006044490 A2 | 4/2006 |
| WO | WO-2006044581 A2 | 4/2006 |
| WO | WO-2006044810 A2 | 4/2006 |
| WO | WO-2006049852 A2 | 5/2006 |
| WO | WO-2006050360 A1 | 5/2006 |
| WO | WO-2006051252 A1 | 5/2006 |
| WO | WO-2006/057702 A2 | 6/2006 |
| WO | WO-2006059067 A1 | 6/2006 |
| WO | WO-2006/073581 A2 | 7/2006 |
| WO | WO-2006083748 A1 | 8/2006 |
| WO | WO-2006085389 A1 | 8/2006 |
| WO | WO-2006092563 A1 | 9/2006 |
| WO | WO-2006092565 A1 | 9/2006 |
| WO | WO-2006115958 A1 | 11/2006 |
| WO | WO-2006125940 A1 | 11/2006 |
| WO | WO-2006132992 A2 | 12/2006 |
| WO | WO-2007002180 A2 | 1/2007 |
| WO | WO-2007014355 A2 | 2/2007 |
| WO | WO-2007016290 A2 | 2/2007 |
| WO | WO-2007018898 A2 | 2/2007 |
| WO | WO-2007034161 A2 | 3/2007 |
| WO | WO-2007051000 A2 | 5/2007 |
| WO | WO-2007059233 A2 | 5/2007 |
| WO | WO-2007074430 A1 | 7/2007 |
| WO | WO-2007089603 A2 | 8/2007 |
| WO | WO-2007098220 A2 | 8/2007 |
| WO | WO-2007121579 A1 | 11/2007 |
| WO | WO-2007129121 A1 | 11/2007 |
| WO | WO-2007131110 A2 | 11/2007 |
| WO | WO-2007137304 A2 | 11/2007 |
| WO | WO-2007139734 A2 | 12/2007 |
| WO | WO-2007142625 A2 | 12/2007 |
| WO | WO-2007145825 A2 | 12/2007 |
| WO | WO-2007146987 A2 | 12/2007 |
| WO | WO-2007147439 A1 | 12/2007 |
| WO | WO-2008020964 A2 | 2/2008 |
| WO | WO-2008021687 A1 | 2/2008 |
| WO | WO-2008021969 A2 | 2/2008 |
| WO | WO-2008027972 A1 | 3/2008 |
| WO | WO-2008039237 A1 | 4/2008 |
| WO | WO-2008039249 A1 | 4/2008 |
| WO | WO-2008039270 A1 | 4/2008 |
| WO | WO-2008045383 A2 | 4/2008 |
| WO | WO-2008/061566 A1 | 5/2008 |
| WO | WO-2008057281 A2 | 5/2008 |
| WO | WO-2008070763 A1 | 6/2008 |
| WO | WO-2008080148 A2 | 7/2008 |
| WO | WO-2008089404 A2 | 7/2008 |
| WO | WO-2008101080 A1 | 8/2008 |
| WO | WO-2008101228 A2 | 8/2008 |
| WO | WO-2008103797 A2 | 8/2008 |
| WO | WO-2008109123 A2 | 9/2008 |
| WO | WO-2008109125 A1 | 9/2008 |
| WO | WO-2008112912 A2 | 9/2008 |
| WO | WO-2008118728 A1 | 10/2008 |
| WO | WO-2008118928 A2 | 10/2008 |
| WO | WO-2008124748 A1 | 10/2008 |
| WO | WO-2008131357 A1 | 10/2008 |
| WO | WO-2009005969 A2 | 1/2009 |
| WO | WO-2009022614 A1 | 2/2009 |
| WO | WO-2009023851 A1 | 2/2009 |
| WO | WO-2009033057 A2 | 3/2009 |
| WO | WO-2009039506 A1 | 3/2009 |
| WO | WO-2009046394 A1 | 4/2009 |
| WO | WO-2009066105 A1 | 5/2009 |
| WO | WO-2009067649 A2 | 5/2009 |
| WO | WO-2009091497 A2 | 7/2009 |
| WO | WO-2009120944 A2 | 10/2009 |
| WO | WO-2009137761 A2 | 11/2009 |
| WO | WO-2009143092 A1 | 11/2009 |
| WO | WO-2009143331 A1 | 11/2009 |
| WO | WO-2009150650 A2 | 12/2009 |
| WO | WO-2009152307 A1 | 12/2009 |
| WO | WO-2010028332 A2 | 3/2010 |
| WO | WO-2010030434 A1 | 3/2010 |

(56) References Cited

FOREIGN PATENT DOCUMENTS

| | | |
|---|---|---|
| WO | WO-2010045425 A1 | 4/2010 |
| WO | WO-2010050771 A2 | 5/2010 |
| WO | WO-2010054404 A1 | 5/2010 |
| WO | WO-2010056714 A1 | 5/2010 |
| WO | WO-2010063795 A1 | 6/2010 |
| WO | WO-2010090940 A1 | 8/2010 |
| WO | WO-2010093333 A1 | 8/2010 |
| WO | WO-2010098871 A2 | 9/2010 |
| WO | WO-2010134913 A1 | 11/2010 |
| WO | WO-2011008672 A2 | 1/2011 |
| WO | WO-2011013103 A1 | 2/2011 |
| WO | WO-2011044343 A2 | 4/2011 |
| WO | WO-2011056458 A1 | 5/2011 |
| WO | WO-2011060311 A2 | 5/2011 |
| WO | WO-2011084969 A1 | 7/2011 |
| WO | WO-2011127137 A1 | 10/2011 |
| WO | WO-2012006306 A2 | 1/2012 |
| WO | WO-2012009431 A2 | 1/2012 |
| WO | WO-2012/013577 A1 | 2/2012 |
| WO | WO-2012021671 A1 | 2/2012 |
| WO | WO-2012040438 A1 | 3/2012 |
| WO | WO-2012044551 A1 | 4/2012 |
| WO | WO-2012044554 A1 | 4/2012 |
| WO | WO-2012044597 A1 | 4/2012 |
| WO | WO-2012044606 A2 | 4/2012 |
| WO | WO-2012044820 A1 | 4/2012 |
| WO | WO-2012044844 A2 | 4/2012 |
| WO | WO-2012044853 A1 | 4/2012 |
| WO | WO-2012044854 A1 | 4/2012 |
| WO | WO-2012058213 A2 | 5/2012 |
| WO | WO-2012068156 A2 | 5/2012 |
| WO | WO-2012109760 A1 | 8/2012 |
| WO | WO-2012127462 A1 | 9/2012 |
| WO | WO-2012135705 A1 | 10/2012 |
| WO | WO-2012143913 A2 | 10/2012 |
| WO | WO-2012148667 A2 | 11/2012 |
| WO | WO-2012148668 A2 | 11/2012 |
| WO | WO-2012148703 A2 | 11/2012 |
| WO | WO-2012160163 A1 | 11/2012 |
| WO | WO-2012166503 A1 | 12/2012 |
| WO | WO-2013009252 A2 | 1/2013 |
| WO | WO-2013009699 A2 | 1/2013 |
| WO | WO-2013023114 A1 | 2/2013 |
| WO | WO-2013036409 A1 | 3/2013 |
| WO | WO-2013043707 A2 | 3/2013 |
| WO | WO-2013043717 A1 | 3/2013 |
| WO | WO-2013043721 A2 | 3/2013 |
| WO | WO-2013062978 A2 | 5/2013 |
| WO | WO-2013116869 A1 | 8/2013 |
| WO | WO-2013148762 A2 | 10/2013 |
| WO | WO-2013151888 A1 | 10/2013 |
| WO | WO-2013167427 A1 | 11/2013 |
| WO | WO-2013188130 A1 | 12/2013 |
| WO | WO-2014/008289 A2 | 1/2014 |
| WO | WO-2014004199 A1 | 1/2014 |
| WO | WO-2014004294 A2 | 1/2014 |
| WO | WO-2014/113438 A1 | 7/2014 |
| WO | WO-2014/134034 A2 | 9/2014 |
| WO | WO-2014/172213 A2 | 10/2014 |
| WO | WO-2014158882 A2 | 10/2014 |
| WO | WO-2015/032797 A1 | 3/2015 |
| WO | WO-2015/148136 A1 | 10/2015 |
| WO | WO-2015148141 A1 | 10/2015 |
| WO | WO-2015153642 A1 | 10/2015 |

OTHER PUBLICATIONS

"Indian Standard: Automotive Vehicles—Brakes and Braking Systems (IS 11852-1:2001)", Mar. 1, 2001.
Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.
Anonymous, Analog Devices Wiki, Chapter 11: The Current Mirror, Aug. 20, 2017, 22 pages. https://wiki.analog.com/university/courses/electronics/text/chapter-11?rev=1503222341.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d9395 03e5f17 [retrieved on Oct. 18, 2016].
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
B.R. Coolman, DVM, MS et al., "Comparison of Skin Staples with Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1 &SRETRY=0; [online] accessed: Sep. 22, 2008 (2 pages).
Brar et al., "Investigation of the mechanical and degradation properties of Mg-Sr and Mg-Zn-Sr alloys for use as potential biodegradable implant materials," J. Mech. Behavior of Biomed. Mater. 7 (2012) pp. 87-95.
Breedveld et al., "A New, Easily Miniaturized Sterrable Endoscope," IEEE Engineering in Medicine and Biology Magazine (Nov./Dec. 2005).
Byrne et al., "Molecular Imprinting within Hydrogels," Advanced Drug Delivery Reviews, 54 (2002) pp. 149-161.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Chen et al., "Elastomeric Biomaterials for Tissue Engineering," Progress in Polymer Science 38 (2013), pp. 584-671.
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
Covidien Brochure, "Endo GIA™ Curved Tip Reload with Tri-Staple™ Technology," (2012), 2 pages.
Covidien Brochure, "Endo GIA™ Reloads with Tri-Staple™ Technology and Endo GIA™ Ultra Universal Staplers," (2010), 2 pages.
Covidien Brochure, "Endo GIA™ Reloads with Tri-Staple™ Technology," (2010), 1 page.
Covidien Brochure, "Endo GIA™ Reloads with Tri-Staple™ Technology," (2010), 2 pages.
Covidien Brochure, "Endo GIA™ Black Reload with Tri-Staple™ Technology," (2012), 2 pages.
Covidien Brochure, "Endo GIA™ Ultra Universal Stapler," (2010), 2 pages.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
D. Tuite, Ed., "Get the Lowdown on Ultracapacitors," Nov. 15, 2007; [online] URL: http://electronicdesign.com/Articles/Print.cfm?ArticleID-17465, accessed Jan. 15, 2008 (5 pages).
Data Sheet of LM4F230H5QR, 2007.
Datasheet for Panasonic TK Relays Ultra Low Profile 2 A Polarized Relay, Copyright Matsushita Electric Works, Ltd. (Known of at least as early as Aug. 17, 2010), 5 pages.
Disclosed Anonymously, "Motor-Driven Surgical Stapler Improvements," Research Disclosure Database No. 526041, Published: Feb. 2008.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.

(56) References Cited

OTHER PUBLICATIONS

Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.

Hoffman, "Hydrogels for Biomedical Applications," Advanced Drug Delivery Reviews, 43 (2002) pp. 3-12.

Hoffman, "Hydrogels for Biomedical Applications," Advanced Drug Delivery Reviews, 54 (2002) pp. 3-12.

http://ninpgan.net/publications/51-100/89.pdf; 2004, Ning Pan, on Uniqueness of Fibrous Materials, Design & Nature II. Eds: Colins, M. and Brebbia, C. WIT Press, Boston, 493-504.

Jeong et al., "Thermosensitive Sol-Gel Reversible Hydrogels," Advanced Drug Delivery Reviews, 54 (2002) pp. 37-51.

Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.

Matsuda, "Thermodynamics of Formation of Porous Polymeric Membrane from Solutions," Polymer Journal, vol. 23, No. 5, pp. 435-444 (1991).

Miyata et al., "Biomolecule-Sensitive Hydrogels," Advanced Drug Delivery Reviews, 54 (2002) pp. 79-98.

Mouser Electronics, "LM317 3-Terminal Adjustable Regulator with Overcurrent/Overtemperature Self Protection", Sep. 30, 2016 (Sep. 30, 2016), XP055246104, Retrieved from the Internet: URL: http://www.mouser.com/ds/2/405/lm317m-440423.pdf, pp. 1-9.

Mouser Electronics, "LM317M 3-Terminal Adjustable Regulator with Overcurrent/Overtemperature Self Protection", Mar. 31, 2014 (Mar. 31, 2014), XP055246104, Retrieved from the Internet: URL: http://www.mouser.com/ds/2/405/lm317m-440423.pdf, pp. 1-8.

Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.

Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.

Peppas, "Physiologically Responsive Hydrogels," Journal of Bioactive and Compatible Polymers, vol. 6 (Jul. 1991) pp. 241-246.

Peppas, Editor "Hydrogels in Medicine and Pharmacy," vol. I, Fundamentals, CRC Press, 1986.

Pitt et al., "Attachment of Hyaluronan to Metallic Surfaces," J. Biomed. Mater. Res. 68A: pp. 95-106, 2004.

Qiu et al., "Environment-Sensitive Hydrogels for Drug Delivery," Advanced Drug Delivery Reviews, 53 (2001) pp. 321-339.

Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).

Seils et al., Covidien Summary: Clinical Study "UCONN Biodynamics: Final Report on Results," (2 pages).

Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.

Solorio et al., "Gelatin Microspheres Crosslinked with Genipin for Local Delivery of Growth Factors," J. Tissue Eng. Regen. Med. (2010), 4(7): pp. 514-523.

Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.

The Sodem Aseptic Battery Transfer Kit, Sodem Systems, 2000, 3 pages.

Van Meer et al., "A Disposable Plastic Compact Wrist for Smart Minimally Invasive Surgical Tools," LAAS/CNRS (Aug. 2005).

Yan et al, Comparison of the effects of Mg-6Zn and Ti-3AI-2.5V alloys on TGF-$\beta$/TNF-$\alpha$/VEGF/b-FGF in the healing of the intestinal track in vivo, Biomed. Mater. 9 (2014), 11 pages.

Yan et al., "Comparison of the effects of Mg-6Zn and titanium on intestinal tract in vivo," J Mater Sci: Mater Med (2013), 11 pages.

Young, "Microcellular foams via phase separation," Journal of Vacuum Science & Technology A 4(3), (May/Jun. 1986).

\* cited by examiner

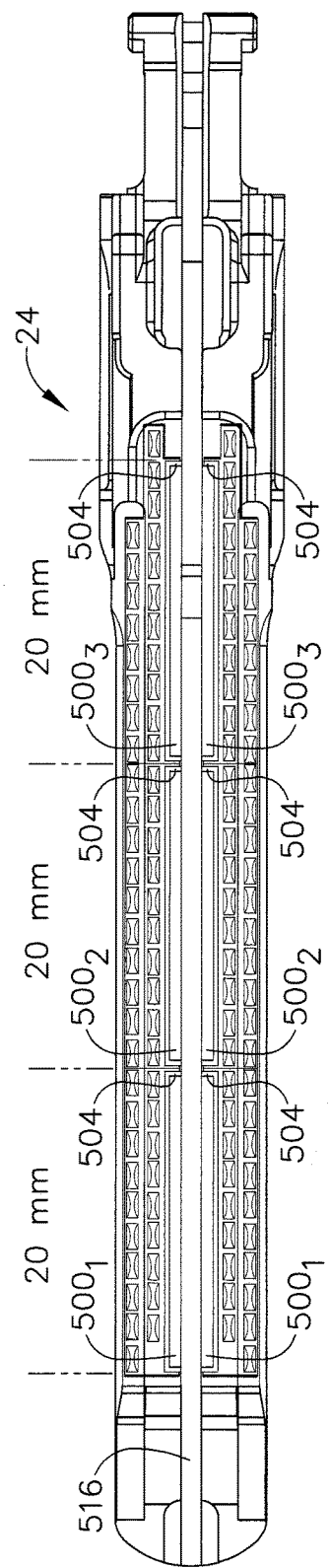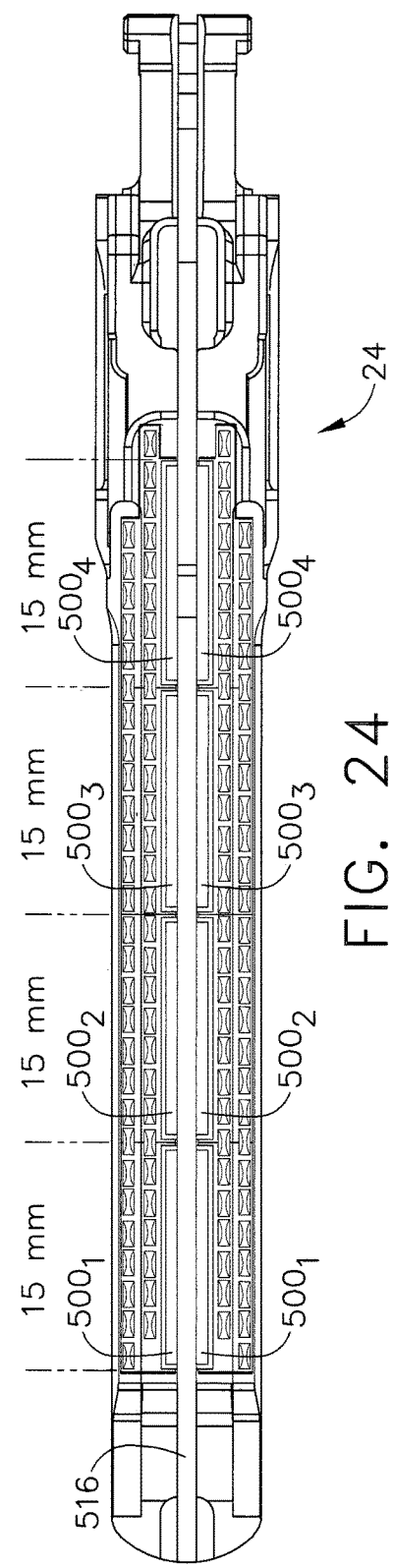

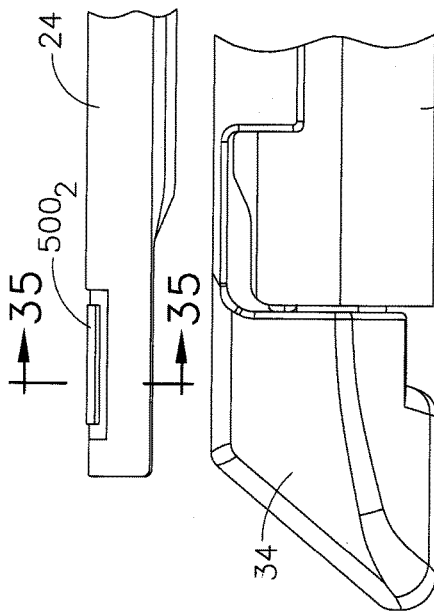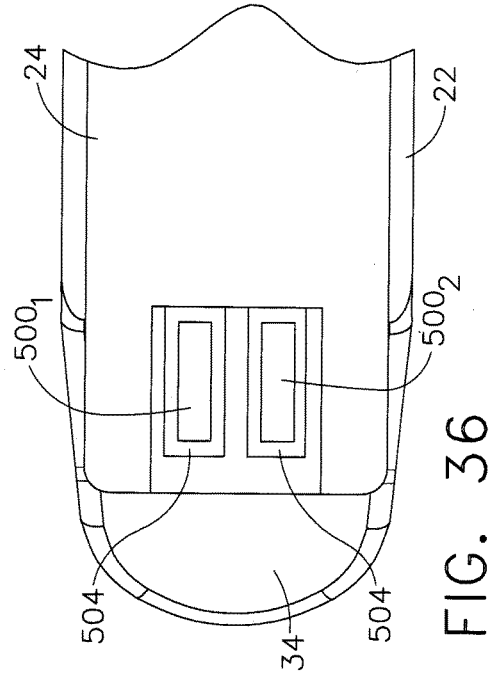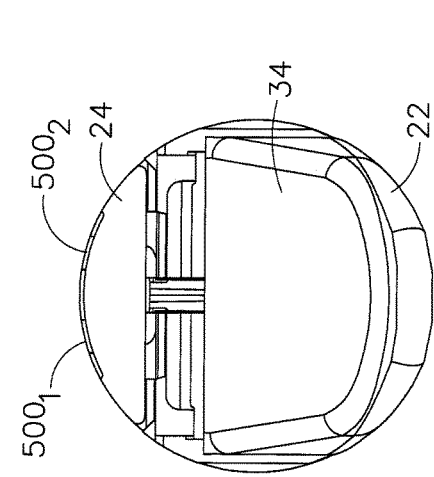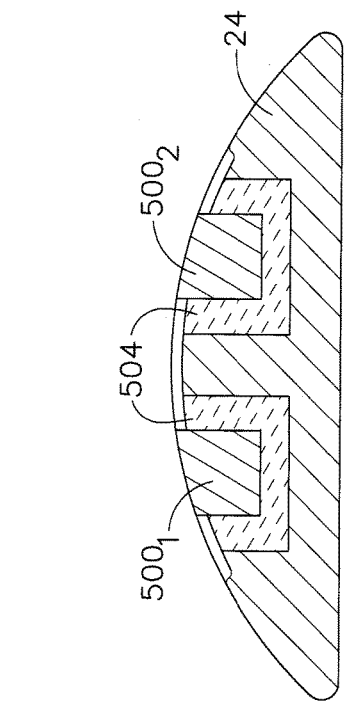
FIG. 34
FIG. 36
FIG. 33
FIG. 35

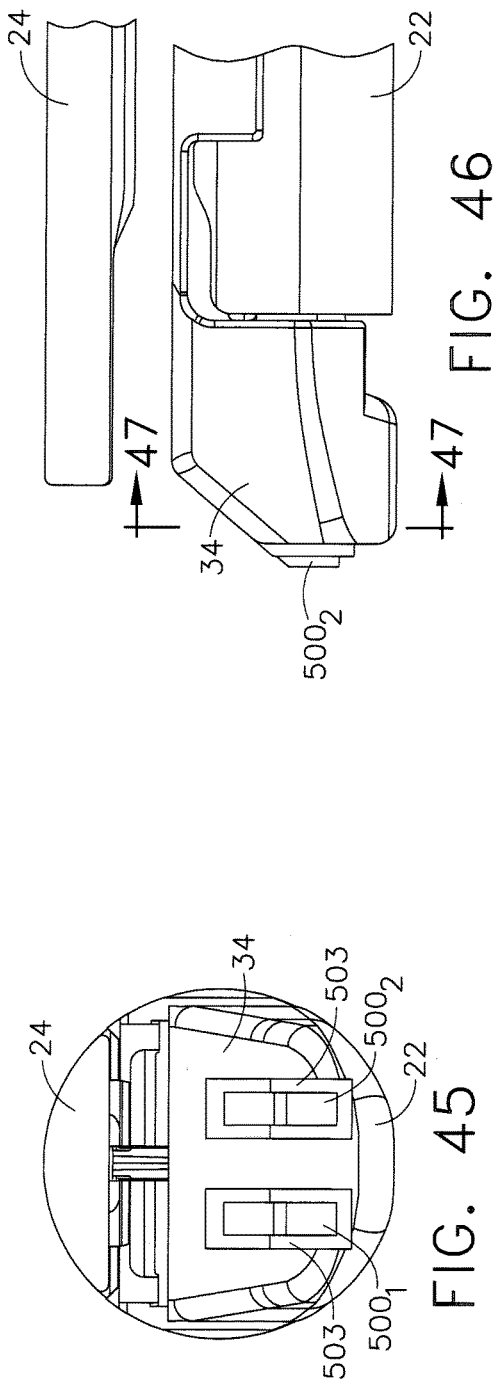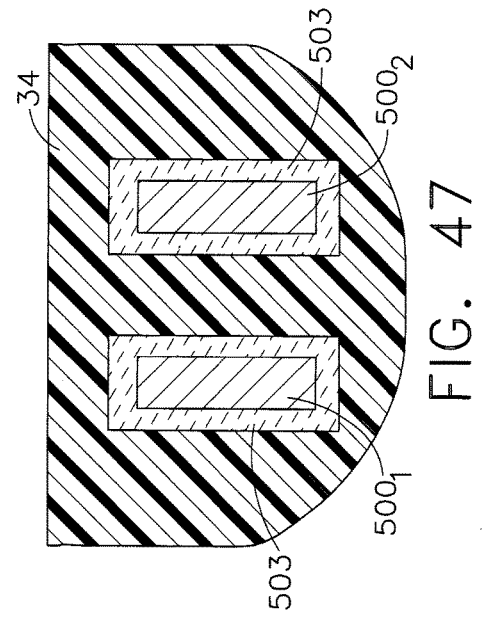

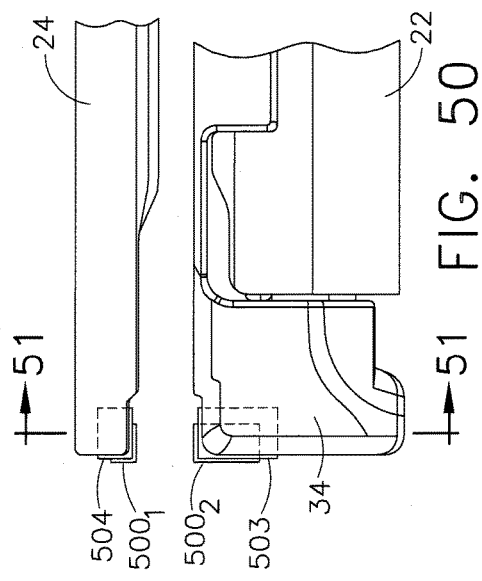
FIG. 49
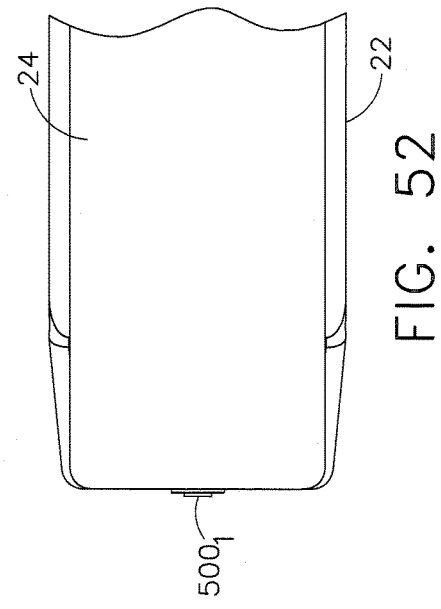
FIG. 50
FIG. 52
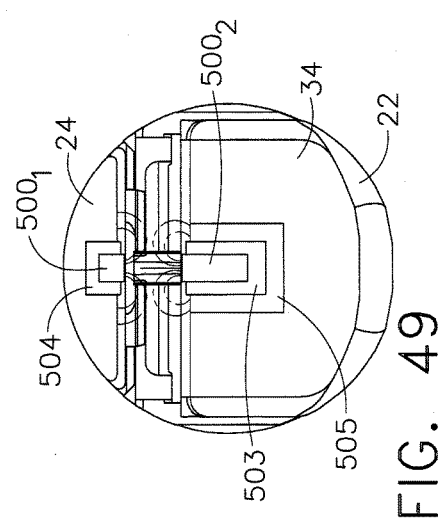
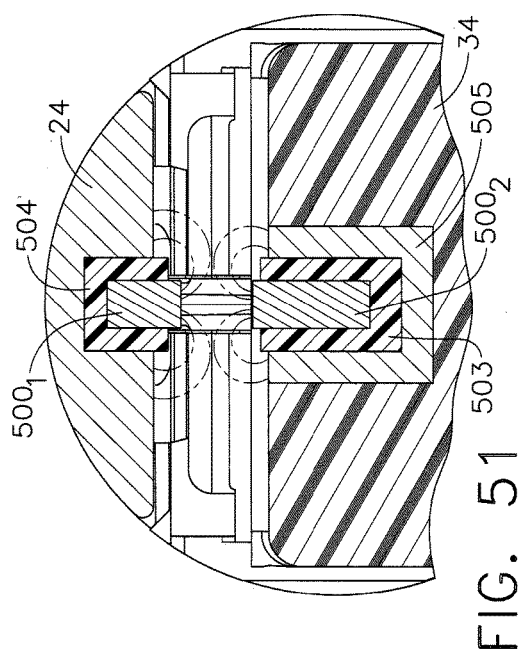
FIG. 51

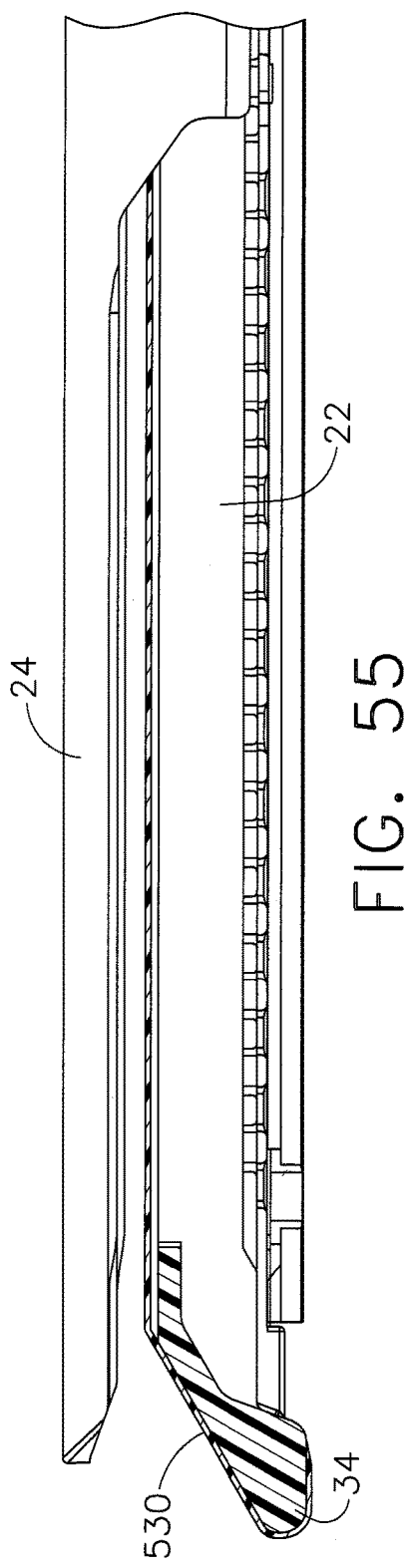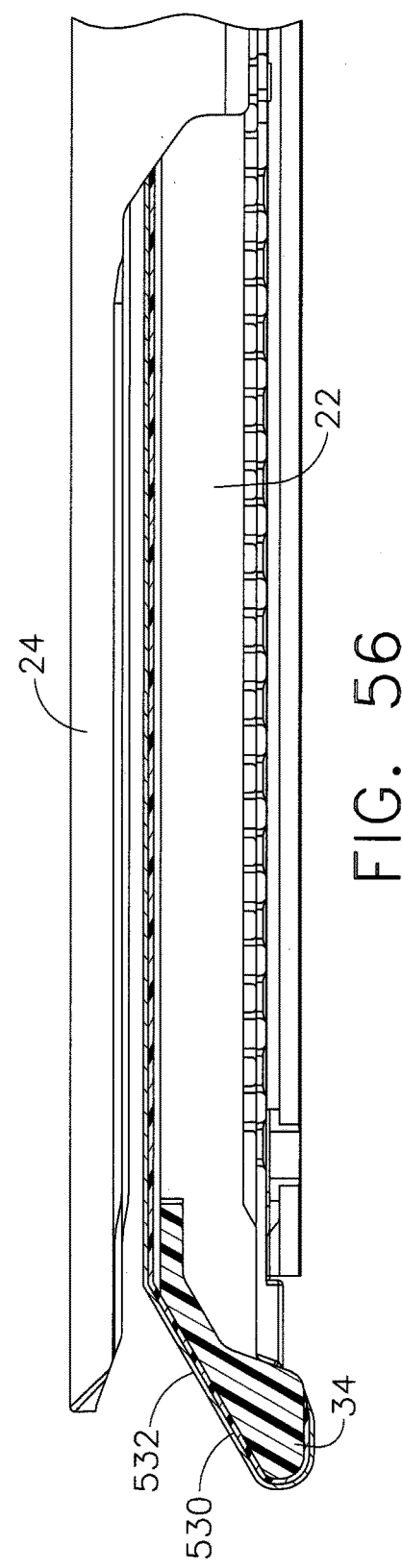

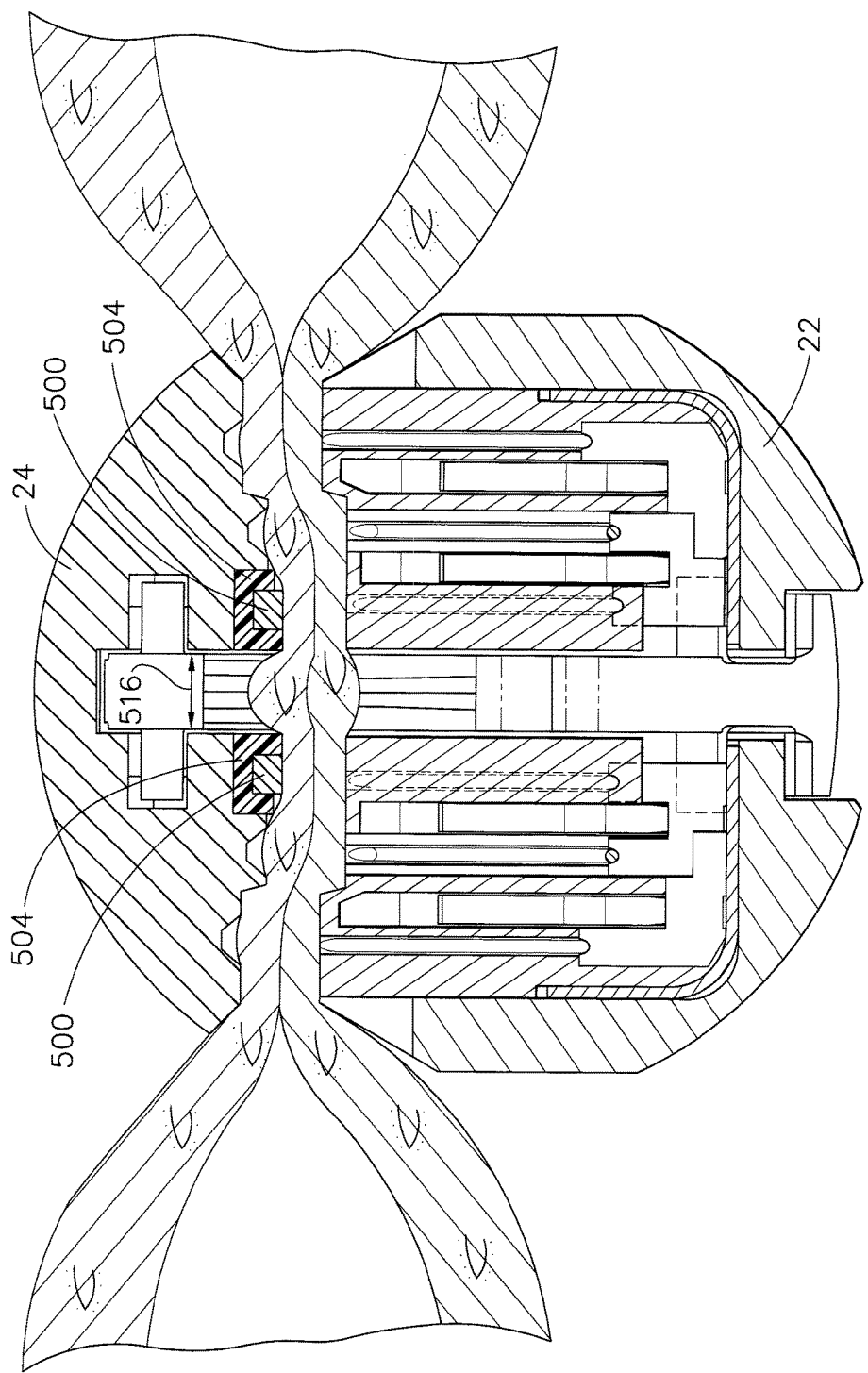

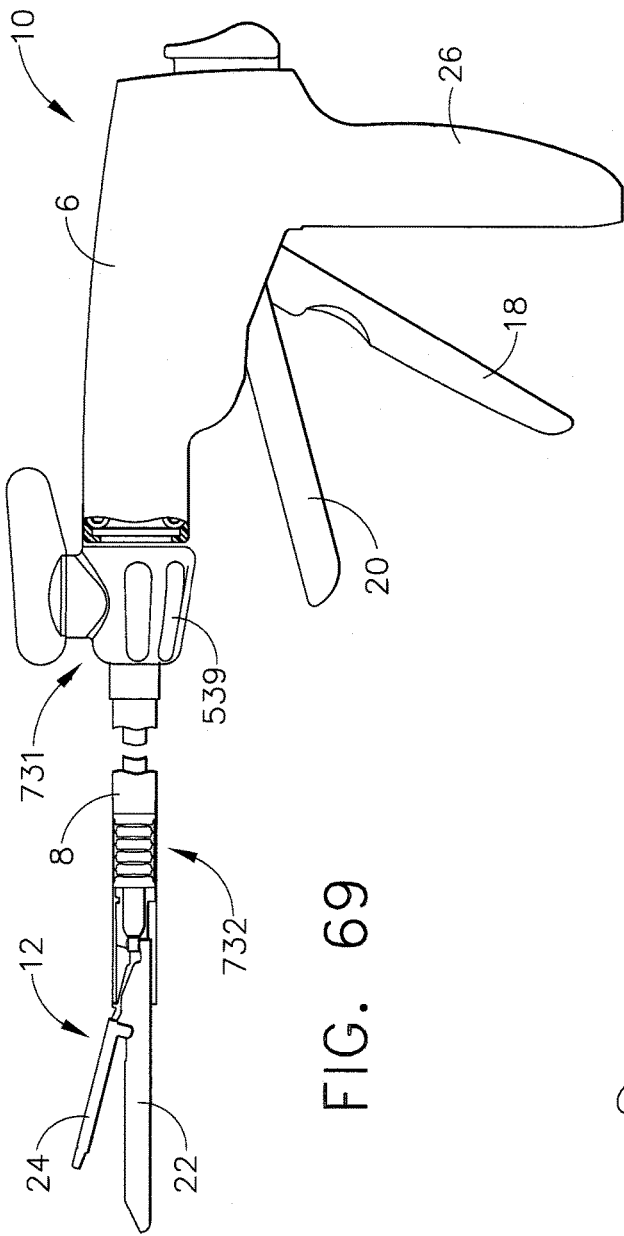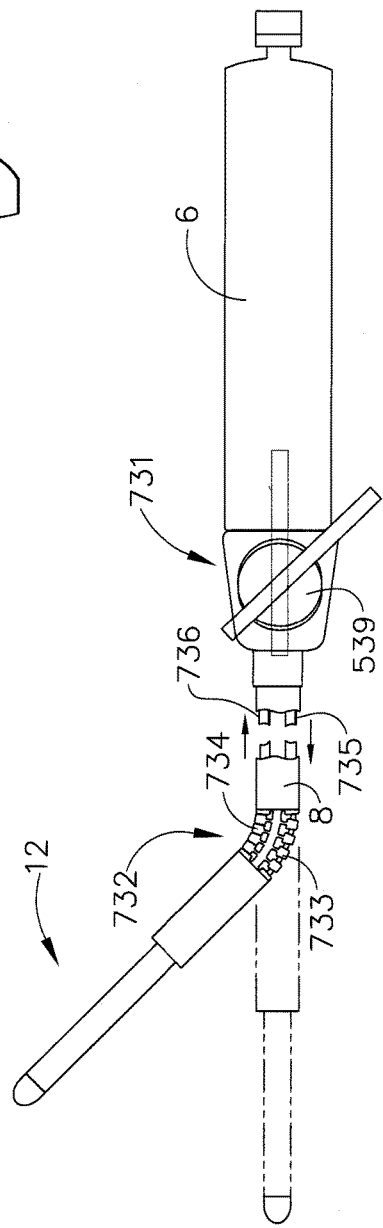

SURGICAL INSTRUMENT COMPRISING A CONTROL SYSTEM

CROSS-REFERENCE TO RELATED APPLICATIONS

The present application is a continuation application claiming priority under 35 U.S.C. § 120 to U.S. patent application Ser. No. 14/668,406, entitled SURGICAL CUTTING AND FASTENING INSTRUMENT HAVING RF ELECTRODES, filed Mar. 25, 2015, now U.S. Patent Application Publication No. 2015/0196347, which is a continuation application claiming priority under 35 U.S.C. § 120 to U.S. patent application Ser. No. 12/031,573, entitled SURGICAL CUTTING AND FASTENING INSTRUMENT HAVING RF ELECTRODES, filed Feb. 14, 2008, the entire disclosures of which are hereby incorporated by reference herein.

The present application is related to and incorporates by reference the following applications which were filed on Feb. 14, 2008:

U.S. patent application Ser. No. 12/031,542, entitled MOTORIZED SURGICAL CUTTING AND FASTENING INSTRUMENT HAVING A MAGNETIC DRIVE TRAIN TORQUE LIMITING DEVICE, now U.S. Pat. No. 8,459,525;

U.S. patent application Ser. No. 12/031,556, entitled MOTORIZED SURGICAL CUTTING AND FASTENING INSTRUMENT, now U.S. Pat. No. 8,636,736;

U.S. patent application Ser. No. 12/031,567, entitled MOTORIZED SURGICAL CUTTING AND FASTENING INSTRUMENT HAVING HANDLE BASED POWER SOURCE, now U.S. Pat. No. 8,657,174; and U.S. patent application Ser. No. 12/031,580, entitled MOTORIZED CUTTING AND FASTENING INSTRUMENT HAVING CONTROL CIRCUIT FOR OPTIMIZING BATTERY USAGE, now U.S. Pat. No. 8,622,274.

BACKGROUND

Surgical staplers have been used in the prior art to simultaneously make a longitudinal incision in tissue and apply lines of staples on opposing sides of the incision. Such instruments commonly include a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. Such instruments typically include a plurality of reciprocating wedges that, when driven distally, pass through openings in the staple cartridge and engage drivers supporting the staples to effect the firing of the staples toward the anvil.

An example of a surgical stapler suitable for endoscopic applications is described in published U.S. Patent Application Publication No. 2004/0232196, entitled SURGICAL STAPLING INSTRUMENT HAVING SEPARATE DISTINCT CLOSING AND FIRING SYSTEMS, now U.S. Pat. No. 7,000,818, the disclosure of which is herein incorporated by reference. In use, a clinician is able to close the jaw members of the stapler upon tissue to position the tissue prior to firing. Once the clinician has determined that the jaw members are properly gripping tissue, the clinician can fire the surgical stapler, thereby severing and stapling the tissue. The simultaneous severing and stapling steps avoid complications that may arise when performing such actions sequentially with different surgical tools that respectively only sever or staple.

In addition, it is also known in the prior art to include electrodes in the end effector that can be used to emit/receive RF energy to form a hemostatic line along the cut line. U.S. Pat. No. 5,403,312, entitled ELECTROSURGICAL HEMOSTATIC DEVICE (hereinafter the "'312 Patent"), which is incorporated herein by reference, discloses an electrosurgical instrument with an end effector that compresses tissue between one pole (or electrode) of a bipolar energy source on one interfacing surface, and a second pole (or electrode) on a second interfacing surface. The RF energy is applied through the compressed tissue in the end effector, which cauterizes the tissue. The end effector described in the '312 Patent also includes staples for stapling the tissue compressed in the end effector.

Motor-powered surgical cutting and fastening instruments, where the motor powers the cutting instrument, are also known in the prior art, such as described in published U.S. Patent Application Publication No. 2007/0175962, entitled MOTOR-DRIVEN SURGICAL CUTTING AND FASTENING INSTRUMENT WITH TACTILE POSITION FEEDBACK, now U.S. Pat. No. 7,422,139, which is incorporated herein by reference.

SUMMARY

In one general aspect, embodiments of the present invention are directed to surgical cutting and fastening instruments. The instruments may be endoscopic instruments, such as linear endocutters or circular cutters, or laparoscopic instruments. The instruments may be comprised of staples and/or RF electrodes for fastening tissue clamped in the end effector.

Several embodiments disclosed herein are pertinent to cordless motor-powered instruments. The instruments may be powered by a power pack comprising a DC power source, such as one or more series-connected battery cells. A cell selection switch may control how many of the battery cells are being used to power the motor at a given time to control the power available to the motor. This allows the operator of the instrument to have greater control over both the speed and the power of the motor. In another embodiment, the instrument may comprise a power regulator, including, for example, a DC-to-DC converter, that regulates the voltage supplied to the motor. Further, the voltage set point for the power regulator could be set so that the voltage delivered from the power source is less than the voltage at which the power source delivers maximum power. That way, the power source (e.g., a number of series-connected battery cells) could operate on the "left" or increasing side of the power curve, so that increases in power would be available.

In addition, according to various embodiments, the power source may comprise secondary accumulator devices, such as rechargeable batteries or supercapacitors. Such secondary accumulator devices may be charged repeatably by replaceable batteries. A charge management circuit may control the charging of the secondary accumulator devices and provide various status signals, such as an alert, when the charging of the secondary accumulator devices is complete.

In other embodiment, a power pack comprising the secondary accumulator devices may be removable from the instrument and connectable to a remote charger base. The charger base may charge the secondary accumulator devices, such as from the AC electrical mains or a battery. The charger base may also comprise a processor and memory unit. Data stored in a memory of the removable power pack may be downloaded to the charger base, from which it may be uploaded for later use and analysis, such as by the user (e.g., physician), the manufacturer or distributor of the instrument, etc. The data may comprise operating parameters, such as charge cycle information, as well as ID values for various replaceable components of the instrument, such as the staple cartridge.

In addition, the instrument may comprise a torque-limiting device to limit the torque supplied by the motor, to limit thereby actuation forces that may damage components of the instrument. According to various embodiments, the torque-limiting devices may be an electromagnetic or permanent magnet, or mechanical clutch devices connected (either directly or indirectly) to the output pole of the motor.

In another general aspect, the present invention is directed to RF instruments (i.e., surgical cutting and fastening instruments with electrodes at the end effector for applying RF energy to the tissue held by the end effector) with new types of electrode configurations. In general, the new electrode configurations include combinations of smaller active electrodes and larger return electrodes. The smaller active electrodes are used to concentrate the therapeutic energy at the tissue, while the larger return electrodes preferentially are used to complete the circuit with minimal impact on that tissue interface. The return electrodes typically have greater mass and thereby are able to stay cooler during electrosurgical application.

In addition, the end effector, according to various embodiments, may comprise a number of co-linear, segmented active electrodes. The segmented electrodes could be energized synchronously or, more preferably, in sequence. Activating the segmented electrodes in sequence provides the advantages of (1) decreased instantaneous power requirements due to a smaller targeted area of tissue coagulation and (2) allowing other segments to fire if one is shorted out.

In addition, a number of mechanisms for activating the RF electrodes and for articulating the end effector are disclosed herein.

In various embodiments, a surgical instrument comprising a first jaw, a second jaw, a staple cartridge, a firing system, an electric motor, a power source, and a control system is disclosed. The first jaw is movable relative to the second jaw to capture tissue between the first jaw and the second jaw. The staple cartridge is supported by the second jaw and comprises staples removably stored therein. The firing system is configured to drive the staples toward the first jaw. The electric motor is mechanically coupled to the firing system. The power source is electrically couplable to the electric motor. The control system is electrically connected to the power source. The control system is configured to determine a first level of power supplied by the power source and apply a second level of power to the electric motor if the first level of power exceeds a predetermined threshold. The second level of power is lower than the first level of power.

In various embodiments, a surgical instrument comprising an elongate channel, an anvil pivotably coupled to the elongate channel, a staple cartridge positioned within the elongate channel, staples removably positioned within the staple cartridge, a firing system configured to fire the staples toward the anvil, an electric motor mechanically coupled to the firing system, a power source electrically couplable to the electric motor, and a power regulator electrically coupled to the power source and the electric motor is disclosed. The setpoint of the power regulator is adjustable. The surgical instrument further comprises a control system configured to lower the setpoint of the power regulator if a level of power supplied by the power source exceeds a predetermined threshold.

In various embodiments, a surgical instrument comprising a first jaw, a second jaw pivotably connected to the first jaw, a replaceable staple cartridge removably positioned within the second jaw, staples removably positioned within the replaceable staple cartridge, a firing system configured to fire the staples toward the first jaw, an electric motor mechanically coupled to the firing system, a power source electrically couplable to the electric motor, and means for reducing a voltage applied to the electric motor if a level of power supplied by the power source exceeds a predetermined threshold is disclosed.

FIGURES

Various embodiments of the present invention are described herein by way of example in conjunction with the following figures, wherein.

Figure 57:
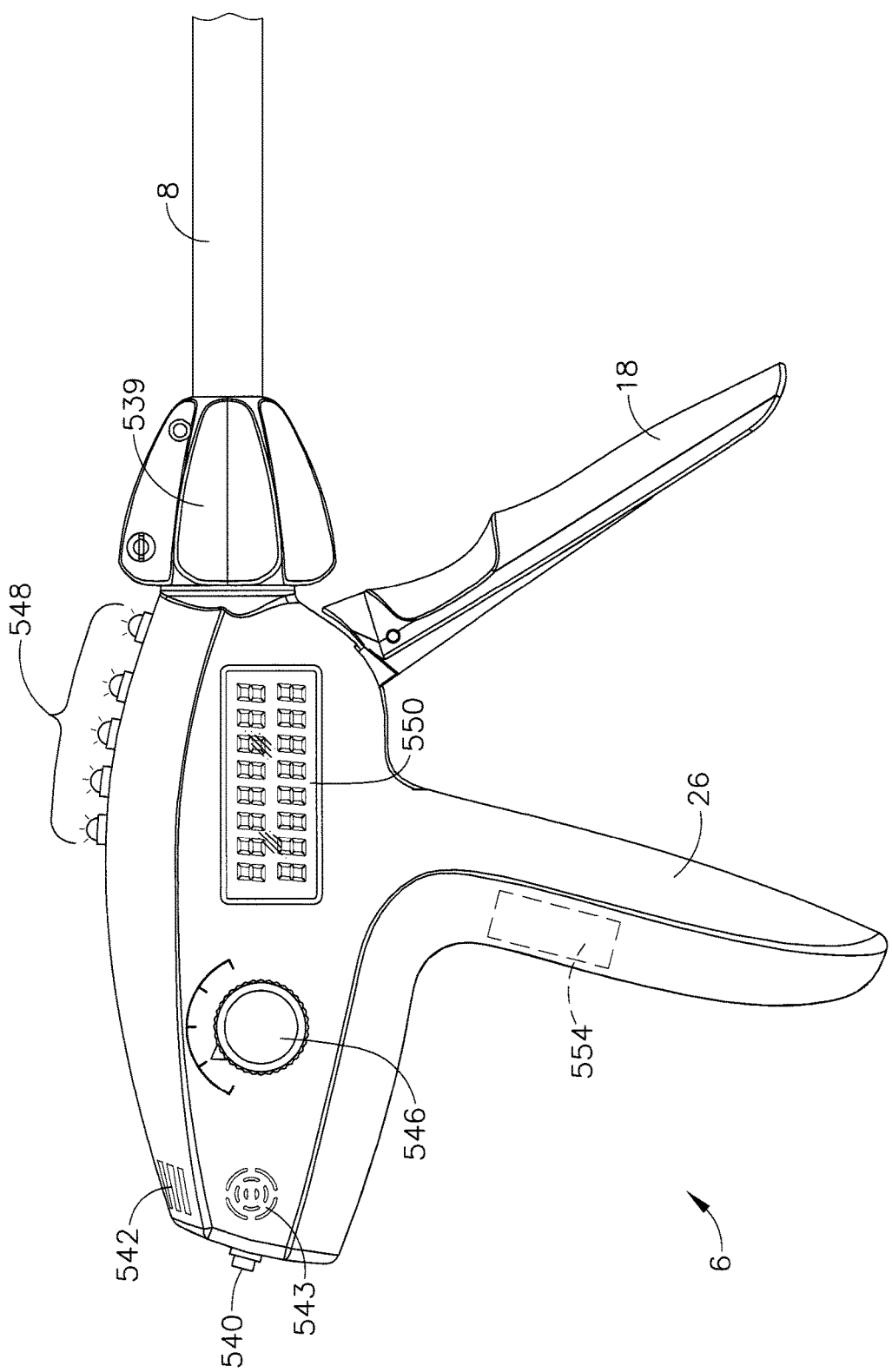
Figure 58:
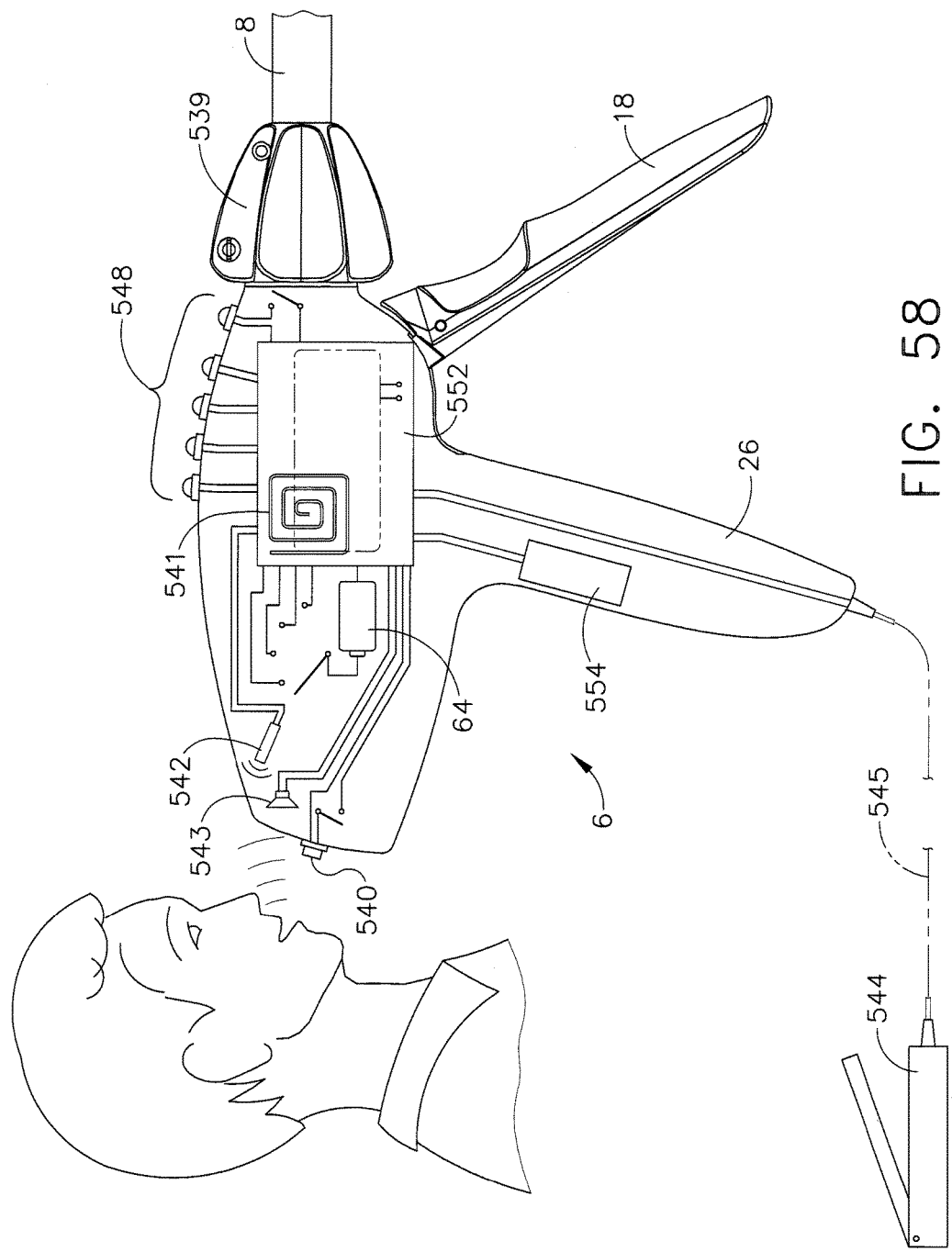
Figure 67:
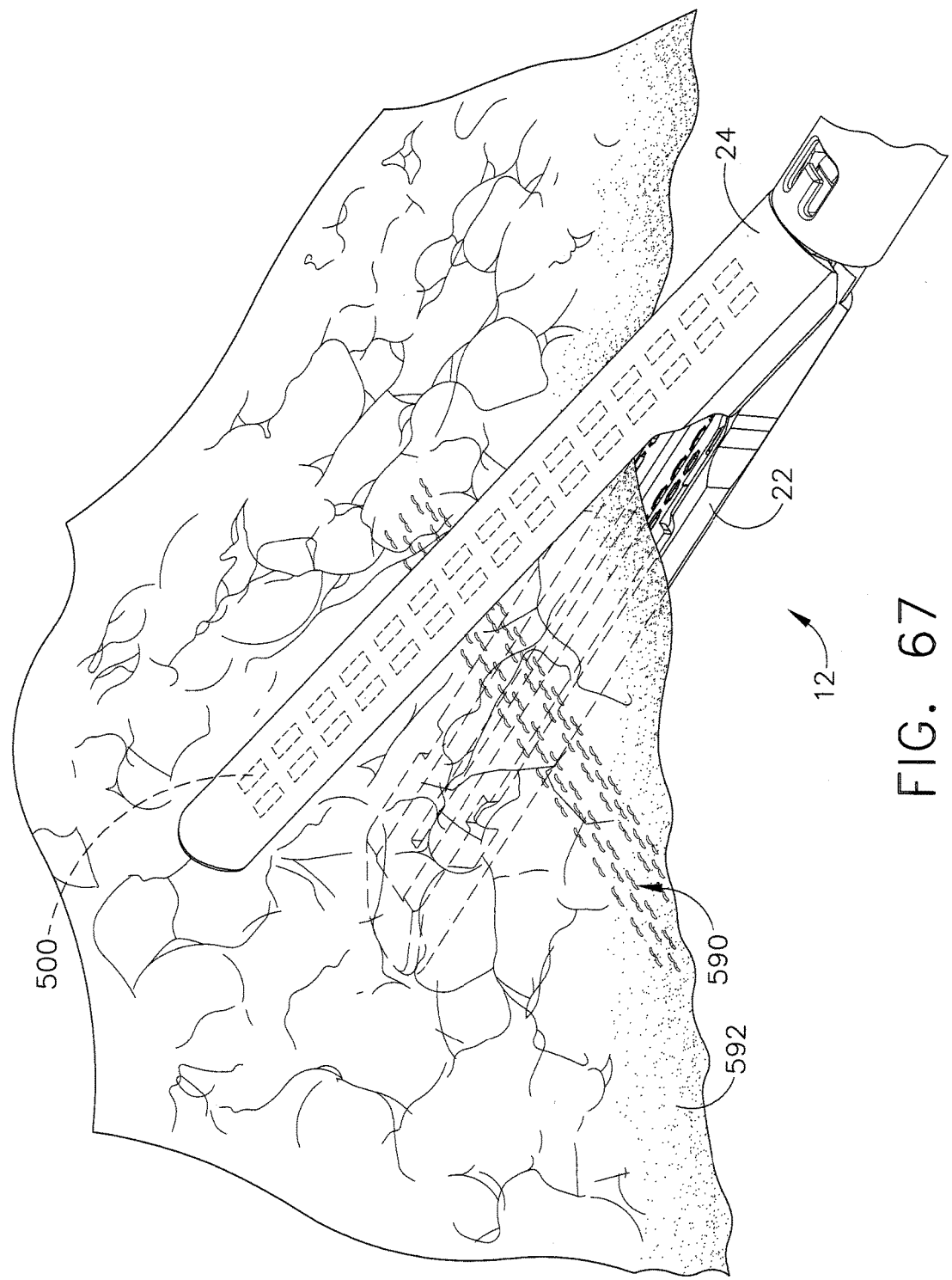

FIGS. 23-25, 27-28, and 59 are views of the lower surface of the anvil of the instrument according to various embodiments of the present invention;

FIGS. 26, 53, 54, and 68 are cross-sectional front views of the end effector according to various embodiments of the present invention;

FIGS. 29-32 show an embodiment of the end effector having RF electrodes according to various embodiments of the present invention;

FIGS. 33-36 show another embodiment of the end effector having RF electrodes according to various embodiments of the present invention;

FIGS. 37-40 show another embodiment of the end effector having RF electrodes according to various embodiments of the present invention;

FIGS. 41-44 show another embodiment of the end effector having RF electrodes according to various embodiments of the present invention;

FIGS. 45-48 show another embodiment of the end effector having RF electrodes according to various embodiments of the present invention;

FIGS. 49-52 show another embodiment of the end effector having RF electrodes according to various embodiments of the present invention;

FIGS. 55 and 56 show side views of the end effector according to various embodiments of the present invention;

FIG. 57 is a diagram of the handle of the instrument according to another embodiment of the present invention;

FIG. 58 is a cut-away view of the handle of the embodiment of FIG. 57 according to various embodiments of the present invention;

FIGS. 60-66 illustrate a multi-layer circuit board according to various embodiments of the present invention;

FIG. 67 is a diagram illustrating an end effector according to various embodiments of the present invention; and FIGS. 69 and 70 are diagram of an instrument comprising a flexible neck assembly according to various embodiments of the present invention.

DESCRIPTION

Figure 1:
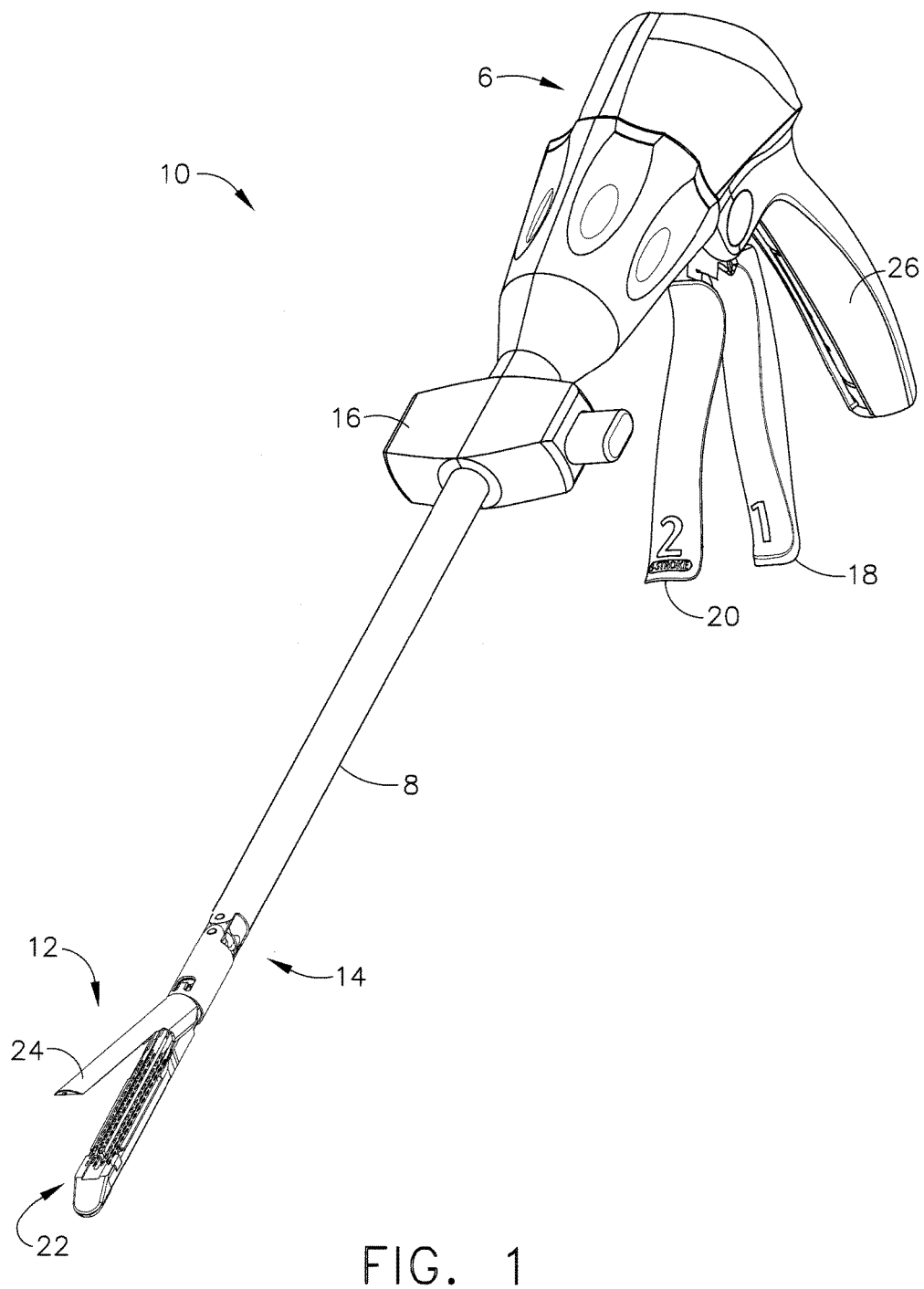
FIGS. 1 and 2 are perspective views of a surgical cutting and fastening instrument according to various embodiments of the present invention.
Figure 2:
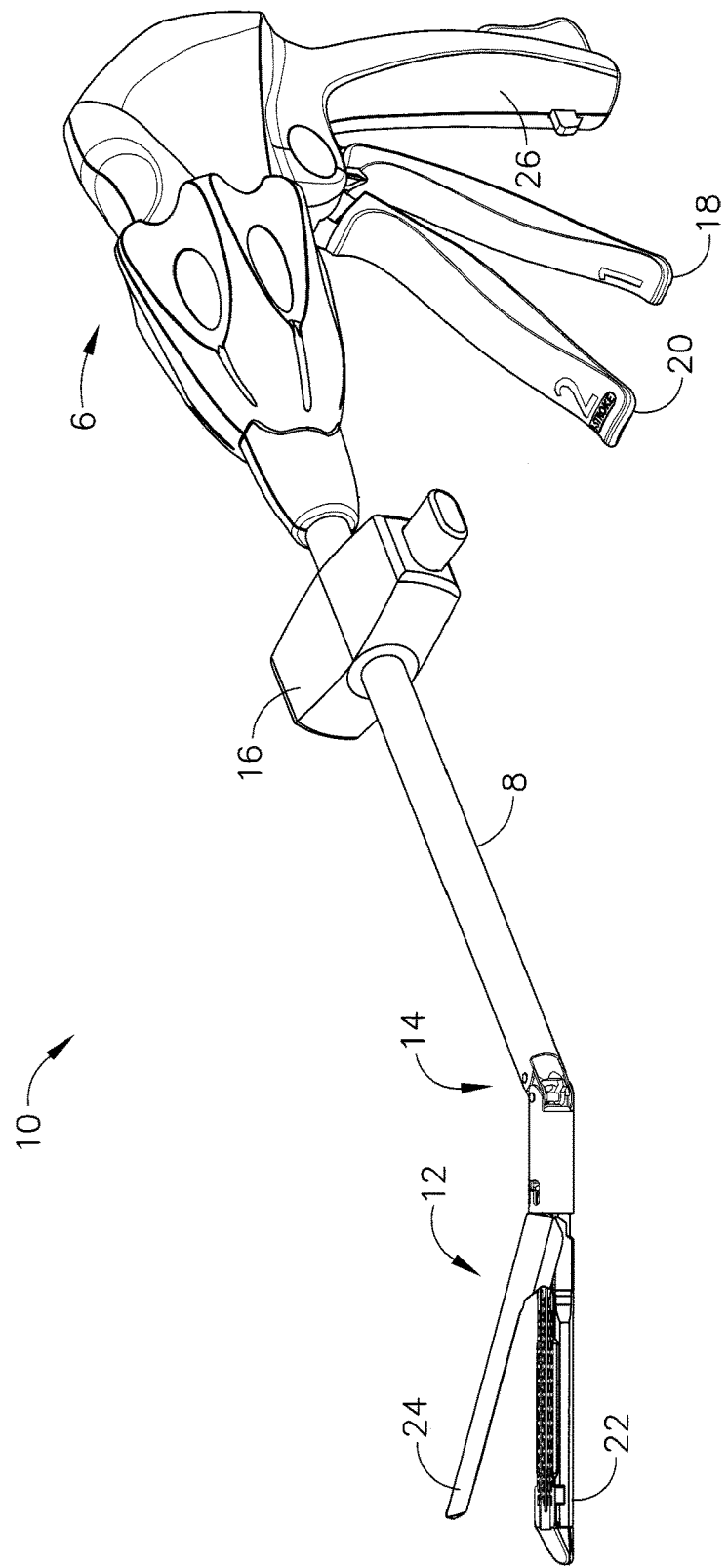

FIGS. 1 and 2 depict a surgical cutting and fastening instrument 10 according to various embodiments of the present invention. The illustrated embodiment is an endoscopic instrument and, in general, the embodiments of the instrument 10 described herein are endoscopic surgical cutting and fastening instruments. It should be noted, however, that according to other embodiments of the present invention, the instrument may be a non-endoscopic surgical cutting and fastening instrument, such as a laparoscopic instrument.

The surgical instrument 10 depicted in FIGS. 1 and 2 comprises a handle 6, a shaft 8, and an articulating end effector 12 pivotally connected to the shaft 8 at an articulation pivot 14. An articulation control 16 may be provided adjacent to the handle 6 to effect rotation of the end effector 12 about the articulation pivot 14. In the illustrated embodiment, the end effector 12 is configured to act as an endocutter for clamping, severing and stapling tissue, although, in other embodiments, different types of end effectors may be used, such as end effectors for other types of surgical devices, such as graspers, cutters, staplers, clip appliers, access devices, drug/gene therapy devices, ultrasound, RF or laser devices, etc. More details regarding RF devices may be found in the '312 Patent.

The handle 6 of the instrument 10 may include a closure trigger 18 and a firing trigger 20 for actuating the end effector 12. It will be appreciated that instruments having end effectors directed to different surgical tasks may have different numbers or types of triggers or other suitable controls for operating the end effector 12. The end effector 12 is shown separated from the handle 6 by a preferably elongate shaft 8. In one embodiment, a clinician or operator of the instrument 10 may articulate the end effector 12 relative to the shaft 8 by utilizing the articulation control 16, as described in more detail in published U.S. Patent Application Publication No. 2007/0158385, entitled SURGICAL INSTRUMENT HAVING AN ARTICULATING END EFFECTOR, now U.S. Pat. No. 7,670,334, which is incorporated herein by reference.

The end effector 12 includes in this example, among other things, a staple channel 22 and a pivotally translatable clamping member, such as an anvil 24, which are maintained at a spacing that assures effective stapling and severing of tissue clamped in the end effector 12. The handle 6 includes a pistol grip 26 towards which a closure trigger 18 is pivotally drawn by the clinician to cause clamping or closing of the anvil 24 toward the staple channel 22 of the end effector 12 to thereby clamp tissue positioned between the anvil 24 and channel 22. The firing trigger 20 is farther outboard of the closure trigger 18. Once the closure trigger 18 is locked in the closure position as further described below, the firing trigger 20 may rotate slightly toward the pistol grip 26 so that it can be reached by the operator using one hand. Then the operator may pivotally draw the firing trigger 20 toward the pistol grip 12 to cause the stapling and severing of clamped tissue in the end effector 12. In other embodiments, different types of clamping members besides the anvil 24 could be used, such as, for example, an opposing jaw, etc.

It will be appreciated that the terms "proximal" and "distal" are used herein with reference to a clinician gripping the handle 6 of an instrument 10. Thus, the end effector 12 is distal with respect to the more proximal handle 6. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

Figure 7:
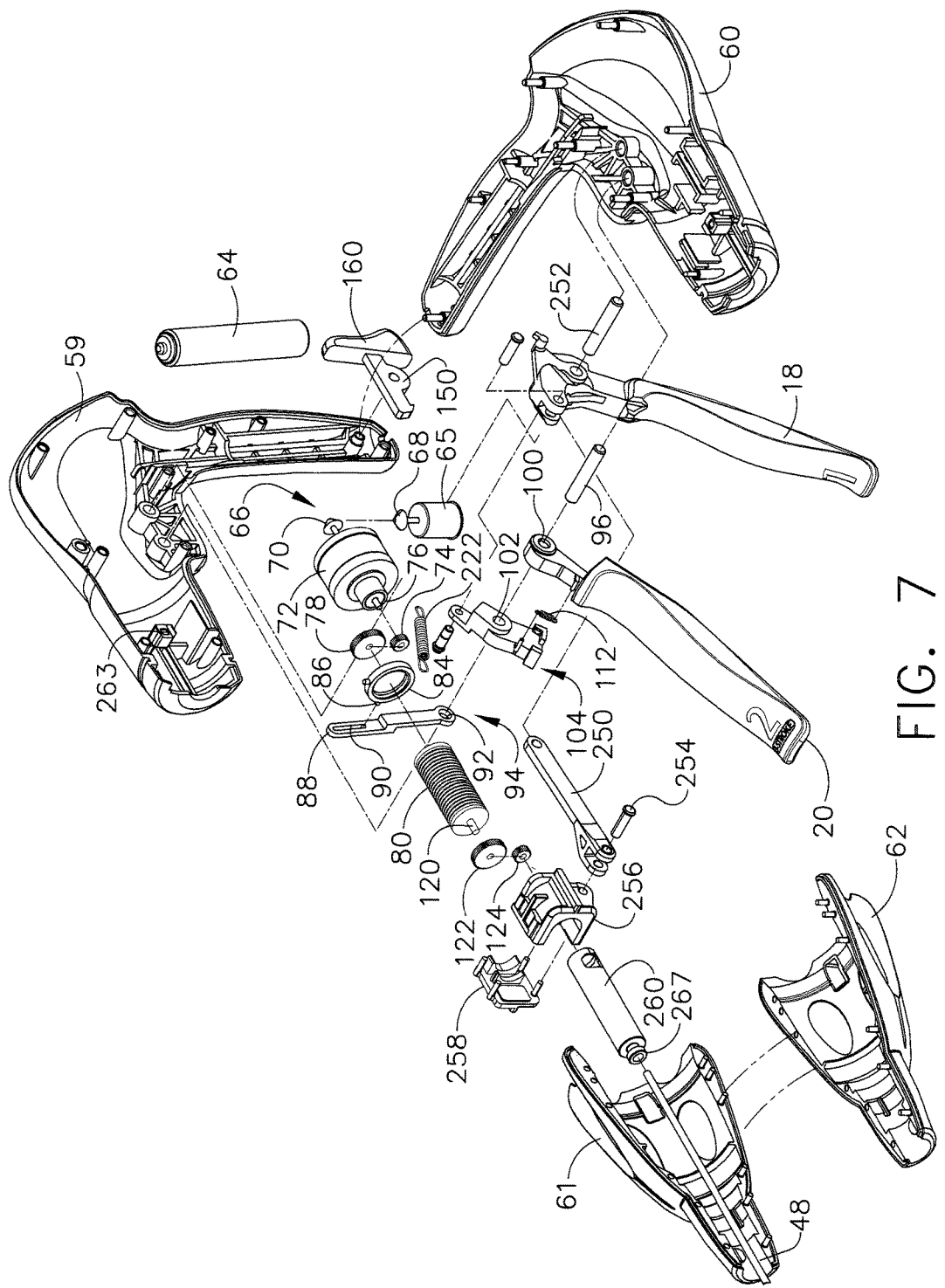
FIG. 7 is an exploded view of the handle of the instrument according to various embodiments of the present invention.

The closure trigger 18 may be actuated first. Once the clinician is satisfied with the positioning of the end effector 12, the clinician may draw back the closure trigger 18 to its fully closed, locked position proximate to the pistol grip 26. The firing trigger 20 may then be actuated. The firing trigger 20 returns to the open position (shown in FIGS. 1 and 2) when the clinician removes pressure, as described more fully below. A release button on the handle 6, when depressed may release the locked closure trigger 18. The release button may be implemented in various forms such as, for example, as a slide release button 160 shown in FIG. 7 or any of the mechanisms described in published U.S. Patent Application Publication No. 2007/0175955, which is incorporated herein by reference.

Figure 3:
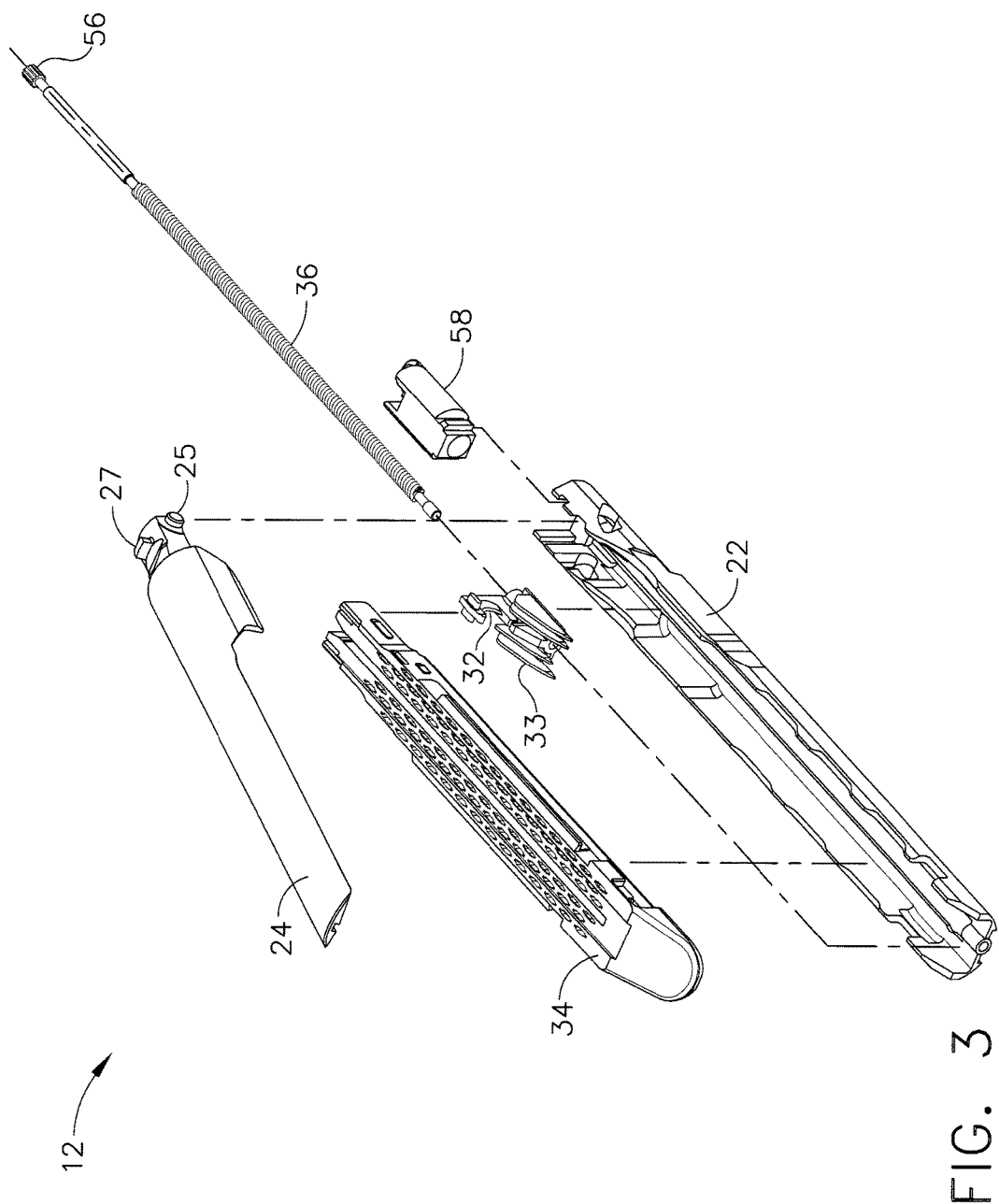
FIGS. 3-5 are exploded views of an end effector and shaft of the instrument according to various embodiments of the present invention.

FIG. 3 is an exploded view of the end effector 12 according to various embodiments. As shown in the illustrated embodiment, the end effector 12 may include, in addition to the previously mentioned channel 22 and anvil 24, a cutting instrument 32, a sled 33, a staple cartridge 34 that is removably seated in the channel 22, and a helical screw shaft 36. The cutting instrument 32 may be, for example, a knife. The anvil 24 may be pivotably opened and closed at a pivot point 25 connected to the proximate end of the channel 22. The anvil 24 may also include a tab 27 at its proximate end that is inserted into a component of the mechanical closure system (described further below) to open and close the anvil 24. When the closure trigger 18 is actuated, that is, drawn in by a user of the instrument 10, the anvil 24 may pivot about the pivot point 25 into the clamped or closed position. If clamping of the end effector 12 is satisfactory, the operator may actuate the firing trigger 20, which, as explained in more detail below, causes the knife 32 and sled 33 to travel longitudinally along the channel 22, thereby cutting tissue clamped within the end effector 12. The movement of the sled 33 along the channel 22 causes the staples of the staple cartridge 34 to be driven through the severed tissue and against the closed anvil 24, which turns the staples to fasten the severed tissue. In various embodiments, the sled 33 may be an integral component of the cartridge 34. U.S. Pat. No. 6,978,921, entitled SURGICAL STAPLING INSTRUMENT INCORPORATING AN E-BEAM FIRING MECHANISM, which is incorporated herein by reference, provides more details about such two-stroke cutting and fastening instruments. The sled 33 may be part of the cartridge 34, such that when the knife 32 retracts following the cutting operation, the sled 33 does not retract.

It should be noted that although the embodiments of the instrument 10 described herein employ an end effector 12 that staples the severed tissue, in other embodiments different techniques for fastening or sealing the severed tissue may be used. For example, end effectors that use RF energy or adhesives to fasten the severed tissue may also be used. U.S. Pat. No. 5,709,680 entitled ELECTROSURGICAL HEMOSTATIC DEVICE, and U.S. Pat. No. 5,688,270 entitled ELECTROSURGICAL HEMOSTATIC DEVICE WITH RECESSED AND/OR OFFSET ELECTRODES, which are incorporated herein by reference, disclose an endoscopic cutting instrument that uses RF energy to seal the severed tissue. Published U.S. Patent Application Publication No. 2007/0102453, now U.S. Pat. No. 7,673,783 and published U.S. Patent Application Publication No. 2007/0102452, now U.S. Pat. No. 7,607,557, which are also incorporated herein by reference, disclose endoscopic cutting instruments that use adhesives to fasten the severed tissue. Accordingly, although the description herein refers to cutting/stapling operations and the like below, it should be recognized that this is an exemplary embodiment and is not meant to be limiting. Other tissue-fastening techniques may also be used.

Figure 4:
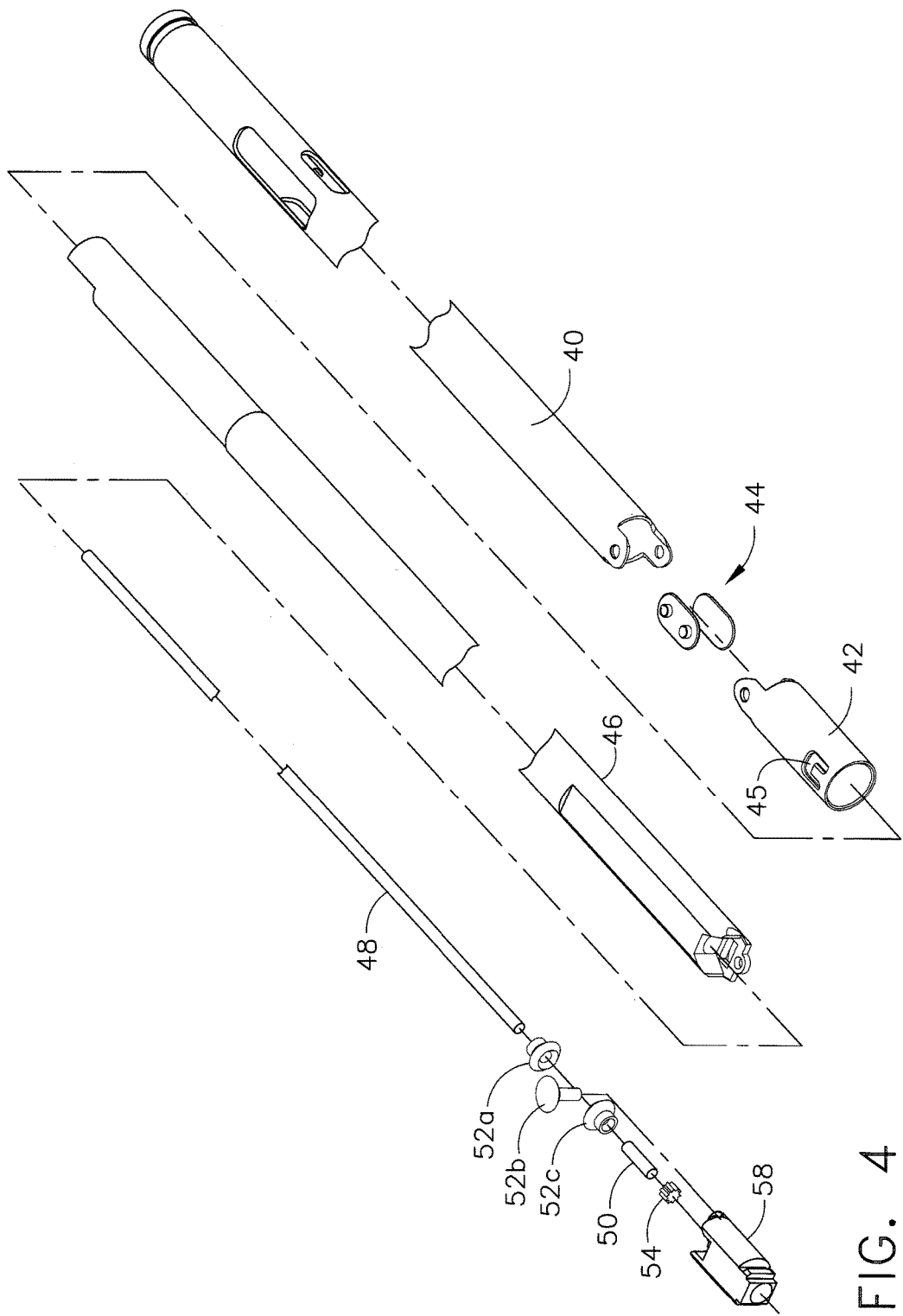
Figure 5:
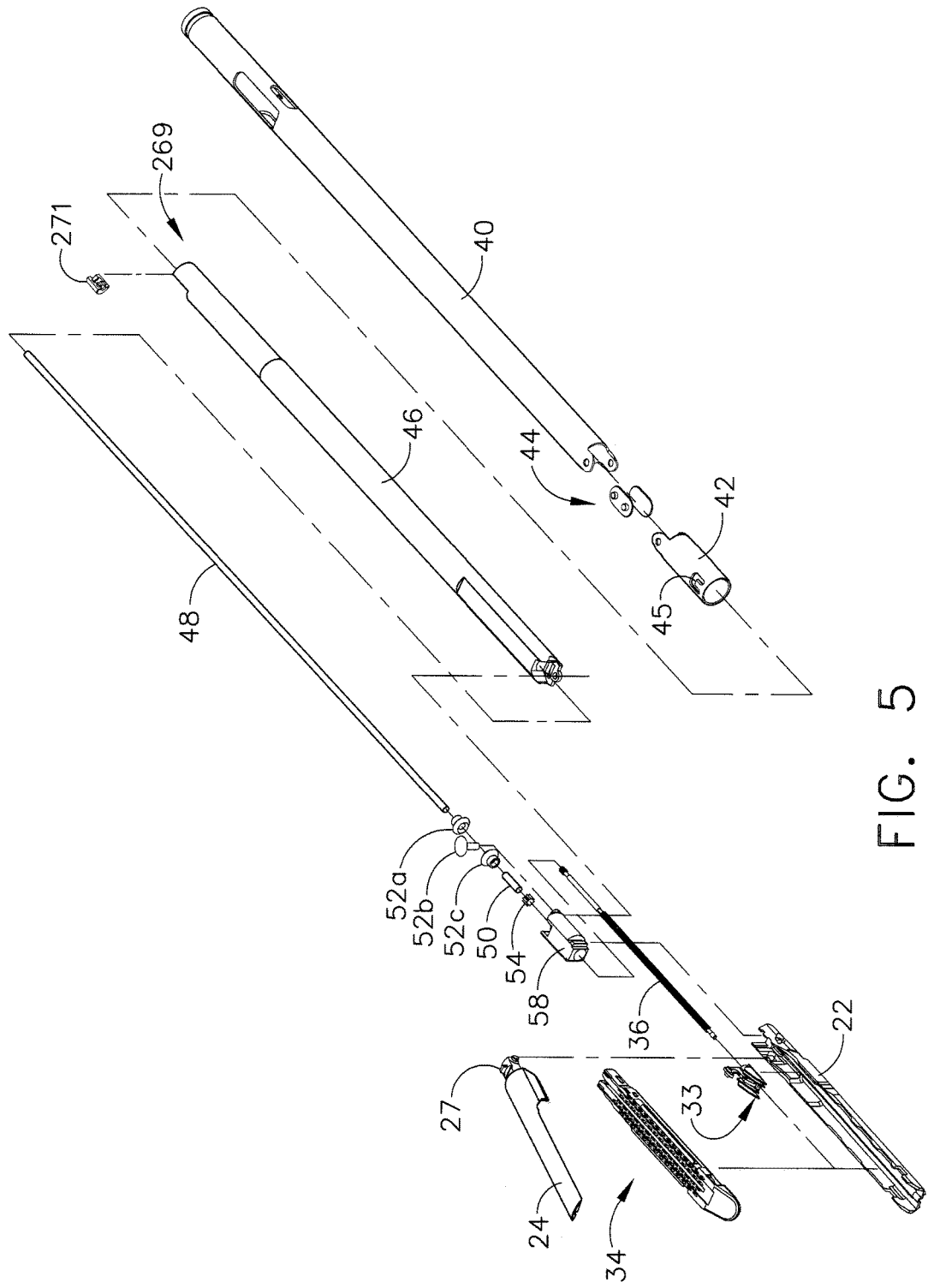
Figure 6:
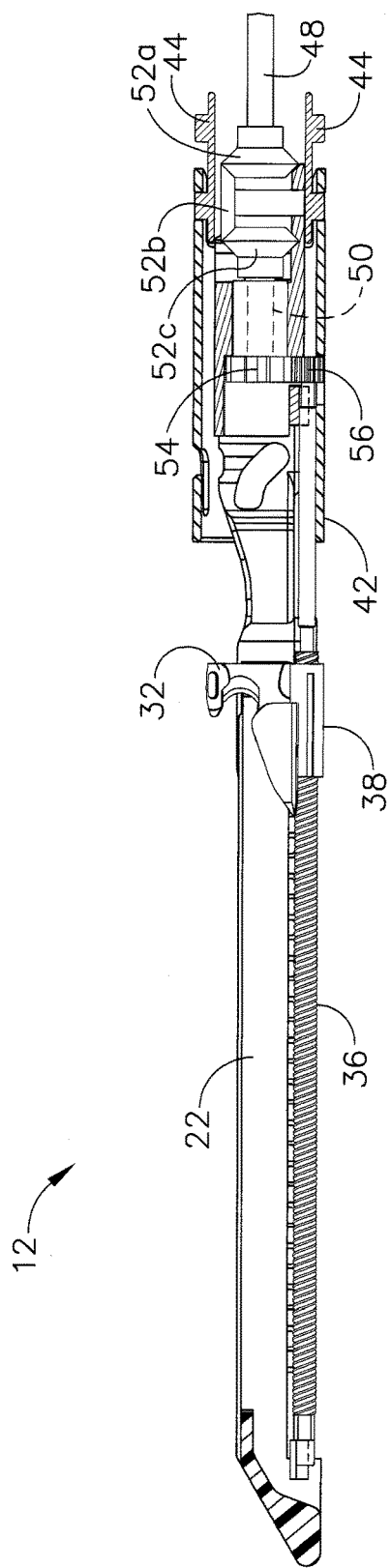
FIG. 6 is a side view of the end effector according to various embodiments of the present invention.

FIGS. 4 and 5 are exploded views and FIG. 6 is a side view of the end effector 12 and shaft 8 according to various embodiments. As shown in the illustrated embodiment, the shaft 8 may include a proximate closure tube 40 and a distal closure tube 42 pivotably linked by a pivot links 44. The distal closure tube 42 includes an opening 45 into which the tab 27 on the anvil 24 is inserted in order to open and close the anvil 24, as further described below. Disposed inside the closure tubes 40, 42 may be a proximate spine tube 46. Disposed inside the proximate spine tube 46 may be a main rotational (or proximate) drive shaft 48 that communicates with a secondary (or distal) drive shaft 50 via a bevel gear assembly 52. The secondary drive shaft 50 is connected to a drive gear 54 that engages a proximate drive gear 56 of the helical screw shaft 36. The vertical bevel gear 52b may sit and pivot in an opening 57 in the distal end of the proximate spine tube 46. A distal spine tube 58 may be used to enclose the secondary drive shaft 50 and the drive gears 54, 56. Collectively, the main drive shaft 48, the secondary drive shaft 50, and the articulation assembly (e.g., the bevel gear assembly 52a-c) are sometimes referred to herein as the "main drive shaft assembly."

A bearing 38, positioned at a distal end of the staple channel 22, receives the helical drive screw 36, allowing the helical drive screw 36 to freely rotate with respect to the channel 22. The helical screw shaft 36 may interface a threaded opening (not shown) of the knife 32 such that rotation of the shaft 36 causes the knife 32 to translate distally or proximately (depending on the direction of the rotation) through the staple channel 22. Accordingly, when the main drive shaft 48 is caused to rotate by actuation of the firing trigger 20 (as explained in more detail below), the bevel gear assembly 52a-c causes the secondary drive shaft 50 to rotate, which in turn, because of the engagement of the drive gears 54, 56, causes the helical screw shaft 36 to rotate, which causes the knife driving member 32 to travel longitudinally along the channel 22 to cut any tissue clamped within the end effector. The sled 33 may be made of, for example, plastic, and may have a sloped distal surface. As the sled 33 traverses the channel 22, the sloped forward surface may push up or drive the staples in the staple cartridge through the clamped tissue and against the anvil 24. The anvil 24 turns the staples, thereby stapling the severed tissue. When the knife 32 is retracted, the knife 32 and sled 33 may become disengaged, thereby leaving the sled 33 at the distal end of the channel 22.

FIGS. 7-10 illustrate an exemplary embodiment of a motor-driven endocutter. The illustrated embodiment provides user-feedback regarding the deployment and loading force of the cutting instrument in the end effector. In addition, the embodiment may use power provided by the user in retracting the firing trigger 20 to power the device (a so-called "power assist" mode). As shown in the illustrated embodiment, the handle 6 includes exterior lower side pieces 59, 60 and exterior upper side pieces 61, 62 that fit together to form, in general, the exterior of the handle 6. A battery 64, such as a Li ion battery, may be provided in the pistol grip portion 26 of the handle 6. The battery 64 powers a motor 65 disposed in an upper portion of the pistol grip portion 26 of the handle 6. According to various embodiments, a number of battery cells connected in series may be used to power the motor 65.

The motor 65 may be a DC brushed driving motor having a maximum rotation of approximately 25,000 RPM with no load. The motor 64 may drive a 90° bevel gear assembly 66 comprising a first bevel gear 68 and a second bevel gear 70. The bevel gear assembly 66 may drive a planetary gear assembly 72. The planetary gear assembly 72 may include a pinion gear 74 connected to a drive shaft 76. The pinion gear 74 may drive a mating ring gear 78 that drives a helical gear drum 80 via a drive shaft 82. A ring 84 may be threaded on the helical gear drum 80. Thus, when the motor 65 rotates, the ring 84 is caused to travel along the helical gear drum 80 by means of the interposed bevel gear assembly 66, planetary gear assembly 72, and ring gear 78.

The handle 6 may also include a run motor sensor 110 in communication with the firing trigger 20 to detect when the firing trigger 20 has been drawn in (or "closed") toward the pistol grip portion 26 of the handle 6 by the operator to thereby actuate the cutting/stapling operation by the end effector 12. The sensor 110 may be a proportional sensor such as, for example, a rheostat, or variable resistor. When the firing trigger 20 is drawn in, the sensor 110 detects the movement, and sends an electrical signal indicative of the voltage (or power) to be supplied to the motor 65. When the sensor 110 is a variable resistor or the like, the rotation of the motor 65 may be generally proportional to the amount of movement of the firing trigger 20. That is, if the operator only draws or closes the firing trigger 20 in a little bit, the rotation of the motor 65 is relatively low. When the firing trigger 20 is fully drawn in (or in the fully closed position), the rotation of the motor 65 is at its maximum. In other words, the harder the user pulls on the firing trigger 20, the more voltage is applied to the motor 65, causing greater rates of rotation.

The handle 6 may include a middle handle piece 104 adjacent to the upper portion of the firing trigger 20. The handle 6 also may comprise a bias spring 112 connected between posts on the middle handle piece 104 and the firing trigger 20. The bias spring 112 may bias the firing trigger 20 to its fully open position. In that way, when the operator releases the firing trigger 20, the bias spring 112 will pull the firing trigger 20 to its open position, thereby removing actuation of the sensor 110, thereby stopping rotation of the motor 65. Moreover, by virtue of the bias spring 112, any time a user closes the firing trigger 20, the user will experience resistance to the closing operation, thereby providing the user with feedback as to the amount of rotation exerted by the motor 65. Further, the operator could stop retracting the firing trigger 20 to thereby remove force from the sensor 100, to thereby stop the motor 65. As such, the user may stop the deployment of the end effector 12, thereby providing a measure of control of the cutting/fastening operation to the operator.

The distal end of the helical gear drum 80 includes a distal drive shaft 120 that drives a ring gear 122, which mates with a pinion gear 124. The pinion gear 124 is connected to the main drive shaft 48 of the main drive shaft assembly. In that way, rotation of the motor 65 causes the main drive shaft assembly to rotate, which causes actuation of the end effector 12, as described above.

The ring 84 threaded on the helical gear drum 80 may include a post 86 that is disposed within a slot 88 of a slotted arm 90. The slotted arm 90 has an opening 92 at its opposite end 94 that receives a pivot pin 96 that is connected between the handle exterior side pieces 59, 60. The pivot pin 96 is also disposed through an opening 100 in the firing trigger 20 and an opening 102 in the middle handle piece 104.

In addition, the handle 6 may include a reverse motor (or end-of-stroke sensor) 130 and a stop motor (or beginning-of-stroke) sensor 142. In various embodiments, the reverse motor sensor 130 may be a limit switch located at the distal end of the helical gear drum 80 such that the ring 84 threaded on the helical gear drum 80 contacts and trips the reverse motor sensor 130 when the ring 84 reaches the distal end of the helical gear drum 80. The reverse motor sensor 130, when activated, sends a signal to the motor 65 to reverse its rotation direction, thereby withdrawing the knife 32 of the end effector 12 following the cutting operation. The stop motor sensor 142 may be, for example, a normally-closed limit switch. In various embodiments, it may be located at the proximate end of the helical gear drum 80 so that the ring 84 trips the switch 142 when the ring 84 reaches the proximate end of the helical gear drum 80.

In operation, when an operator of the instrument 10 pulls back the firing trigger 20, the sensor 110 detects the deployment of the firing trigger 20 and sends a signal to the motor 65 to cause forward rotation of the motor 65 at, for example, a rate proportional to how hard the operator pulls back the firing trigger 20. The forward rotation of the motor 65 in turn causes the ring gear 78 at the distal end of the planetary gear assembly 72 to rotate, thereby causing the helical gear drum 80 to rotate, causing the ring 84 threaded on the helical gear drum 80 to travel distally along the helical gear drum 80. The rotation of the helical gear drum 80 also drives the main drive shaft assembly as described above, which in turn causes deployment of the knife 32 in the end effector 12. That is, the knife 32 and sled 33 are caused to traverse the channel 22 longitudinally, thereby cutting tissue clamped in the end effector 12. Also, the stapling operation of the end effector 12 is caused to happen in embodiments where a stapling-type end effector is used.

By the time the cutting/stapling operation of the end effector 12 is complete, the ring 84 on the helical gear drum 80 will have reached the distal end of the helical gear drum 80, thereby causing the reverse motor sensor 130 to be tripped, which sends a signal to the motor 65 to cause the motor 65 to reverse its rotation. This in turn causes the knife 32 to retract, and also causes the ring 84 on the helical gear drum 80 to move back to the proximate end of the helical gear drum 80.

Figure 8:
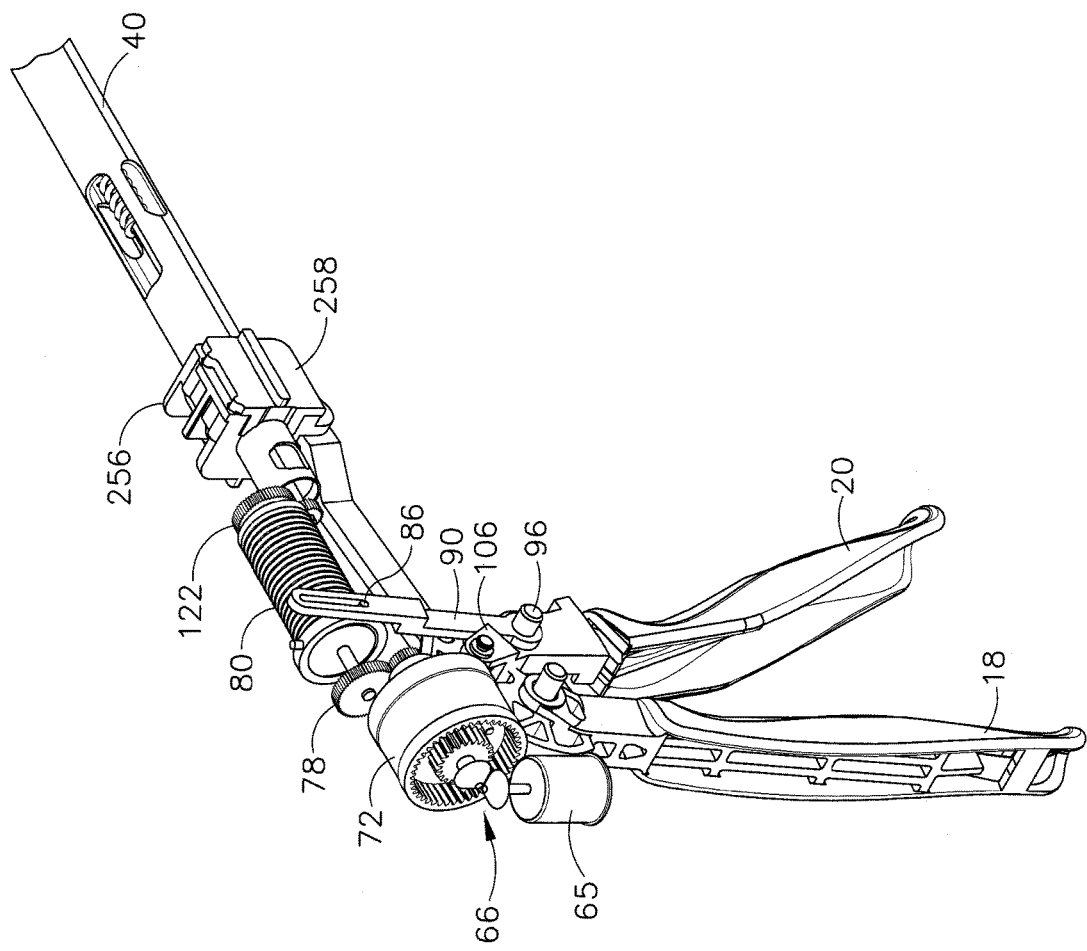
FIGS. 8 and 9 are partial perspective views of the handle according to various embodiments of the present invention.
Figure 9:
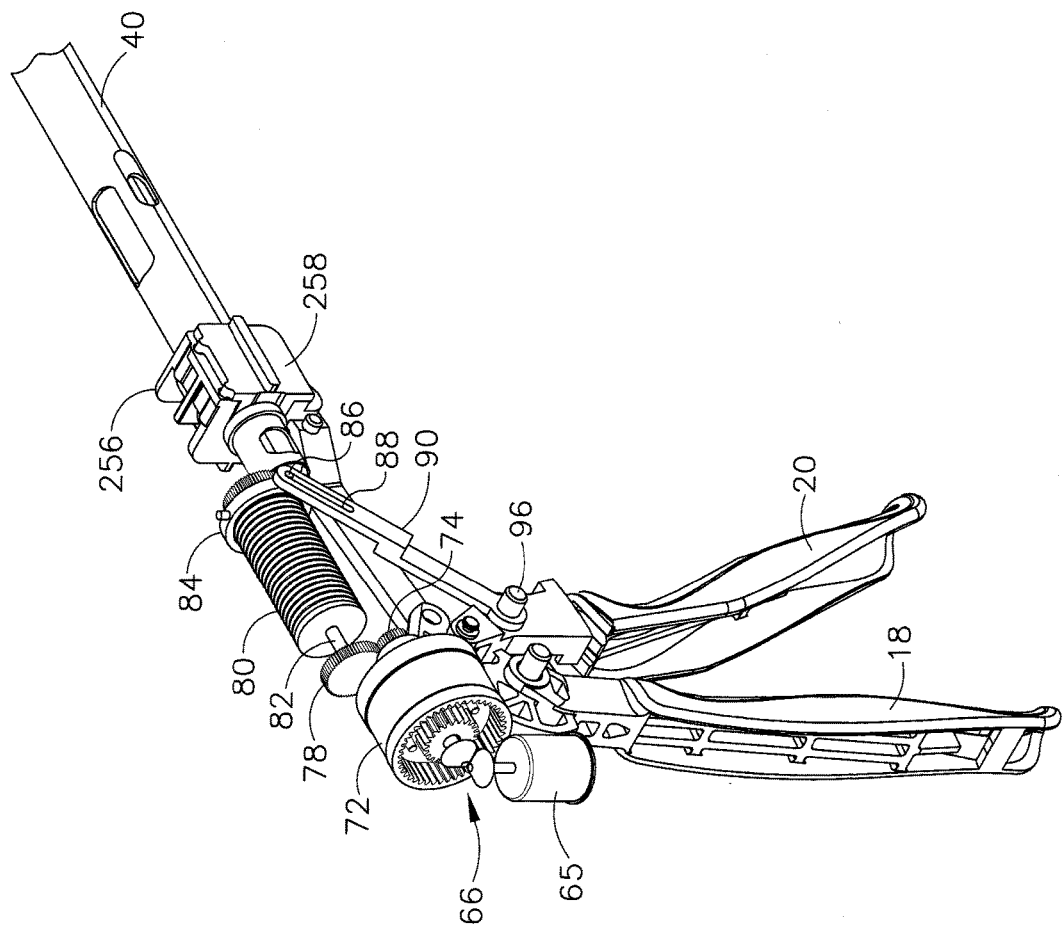
Figure 10:
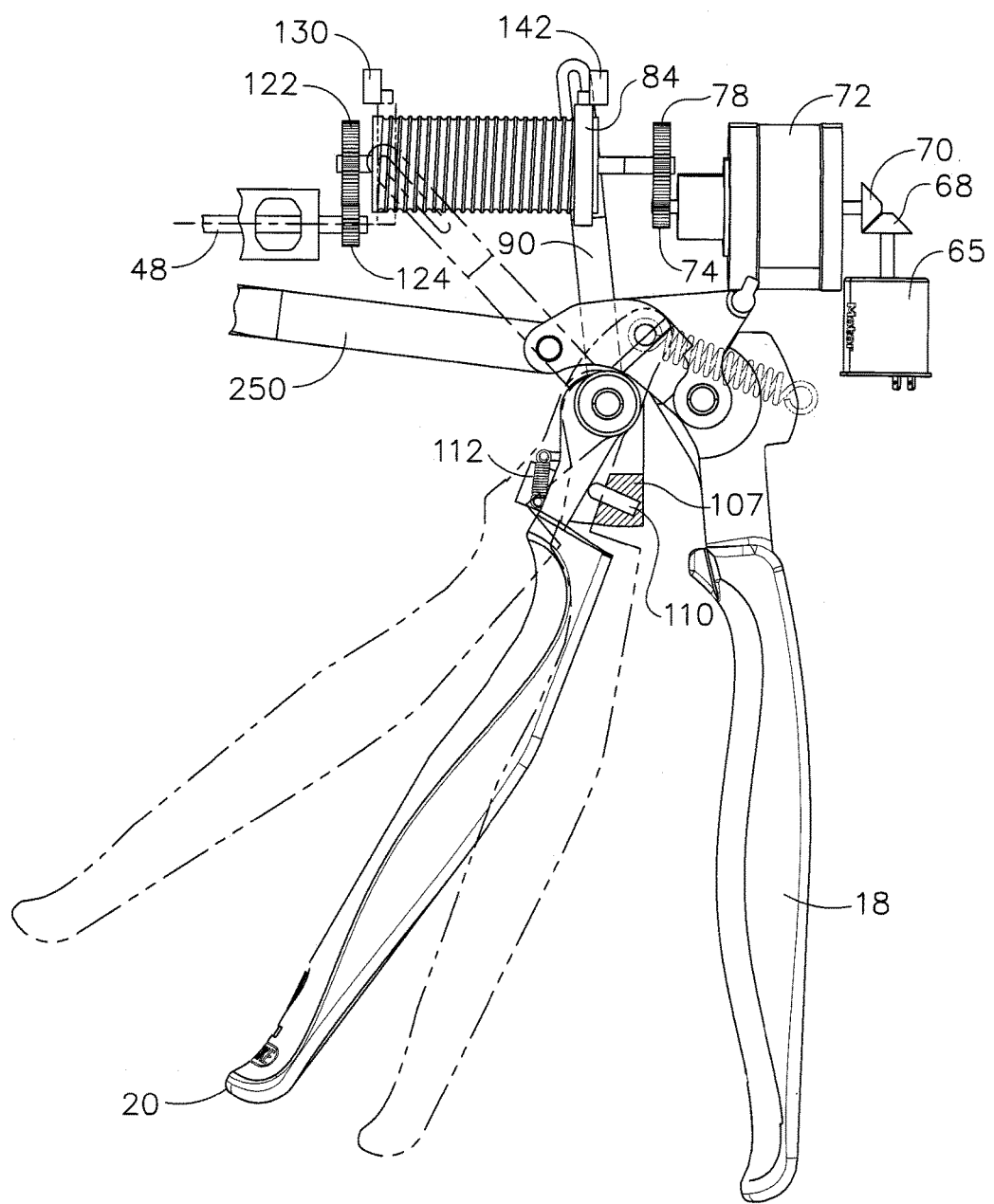
FIG. 10 is a side view of the handle according to various embodiments of the present invention.

The middle handle piece 104 includes a backside shoulder 106 that engages the slotted arm 90 as best shown in FIGS. 8 and 9. The middle handle piece 104 also has a forward motion stop 107 that engages the firing trigger 20. The movement of the slotted arm 90 is controlled, as explained above, by rotation of the motor 65. When the slotted arm 90 rotates CCW as the ring 84 travels from the proximate end of the helical gear drum 80 to the distal end, the middle handle piece 104 will be free to rotate CCW. Thus, as the user draws in the firing trigger 20, the firing trigger 20 will engage the forward motion stop 107 of the middle handle piece 104, causing the middle handle piece 104 to rotate CCW. Due to the backside shoulder 106 engaging the slotted arm 90, however, the middle handle piece 104 will only be able to rotate CCW as far as the slotted arm 90 permits. In that way, if the motor 65 should stop rotating for some reason, the slotted arm 90 will stop rotating, and the user will not be able to further draw in the firing trigger 20 because the middle handle piece 104 will not be free to rotate CCW due to the slotted arm 90.

Components of an exemplary closure system for closing (or clamping) the anvil 24 of the end effector 12 by retracting the closure trigger 18 are also shown in FIGS. 7-10. In the illustrated embodiment, the closure system includes a yoke 250 connected to the closure trigger 18 by a pin 251 that is inserted through aligned openings in both the closure trigger 18 and the yoke 250. A pivot pin 252, about which the closure trigger 18 pivots, is inserted through another opening in the closure trigger 18 which is offset from where the pin 251 is inserted through the closure trigger 18. Thus, retraction of the closure trigger 18 causes the upper part of the closure trigger 18, to which the yoke 250 is attached via the pin 251, to rotate CCW. The distal end of the yoke 250 is connected, via a pin 254, to a first closure bracket 256. The first closure bracket 256 connects to a second closure bracket 258. Collectively, the closure brackets 256, 258 define an opening in which the proximate end of the proximate closure tube 40 (see FIG. 4) is seated and held such that longitudinal movement of the closure brackets 256, 258 causes longitudinal motion by the proximate closure tube 40. The instrument 10 also includes a closure rod 260 disposed inside the proximate closure tube 40. The closure rod 260 may include a window 261 into which a post 263 on one of the handle exterior pieces, such as exterior lower side piece 59 in the illustrated embodiment, is disposed to fixedly connect the closure rod 260 to the handle 6. In that way, the proximate closure tube 40 is capable of moving longitudinally relative to the closure rod 260. The closure rod 260 may also include a distal collar 267 that fits into a cavity 269 in proximate spine tube 46 and is retained therein by a cap 271 (see FIG. 4).

In operation, when the yoke 250 rotates due to retraction of the closure trigger 18, the closure brackets 256, 258 cause the proximate closure tube 40 to move distally (i.e., away from the handle end of the instrument 10), which causes the distal closure tube 42 to move distally, which causes the anvil 24 to rotate about the pivot point 25 into the clamped or closed position. When the closure trigger 18 is unlocked from the locked position, the proximate closure tube 40 is caused to slide proximately, which causes the distal closure tube 42 to slide proximately, which, by virtue of the tab 27 being inserted in the window 45 of the distal closure tube 42, causes the anvil 24 to pivot about the pivot point 25 into the open or unclamped position. In that way, by retracting and locking the closure trigger 18, an operator may clamp tissue between the anvil 24 and channel 22, and may unclamp the tissue following the cutting/stapling operation by unlocking the closure trigger 20 from the locked position.

Figure 11:
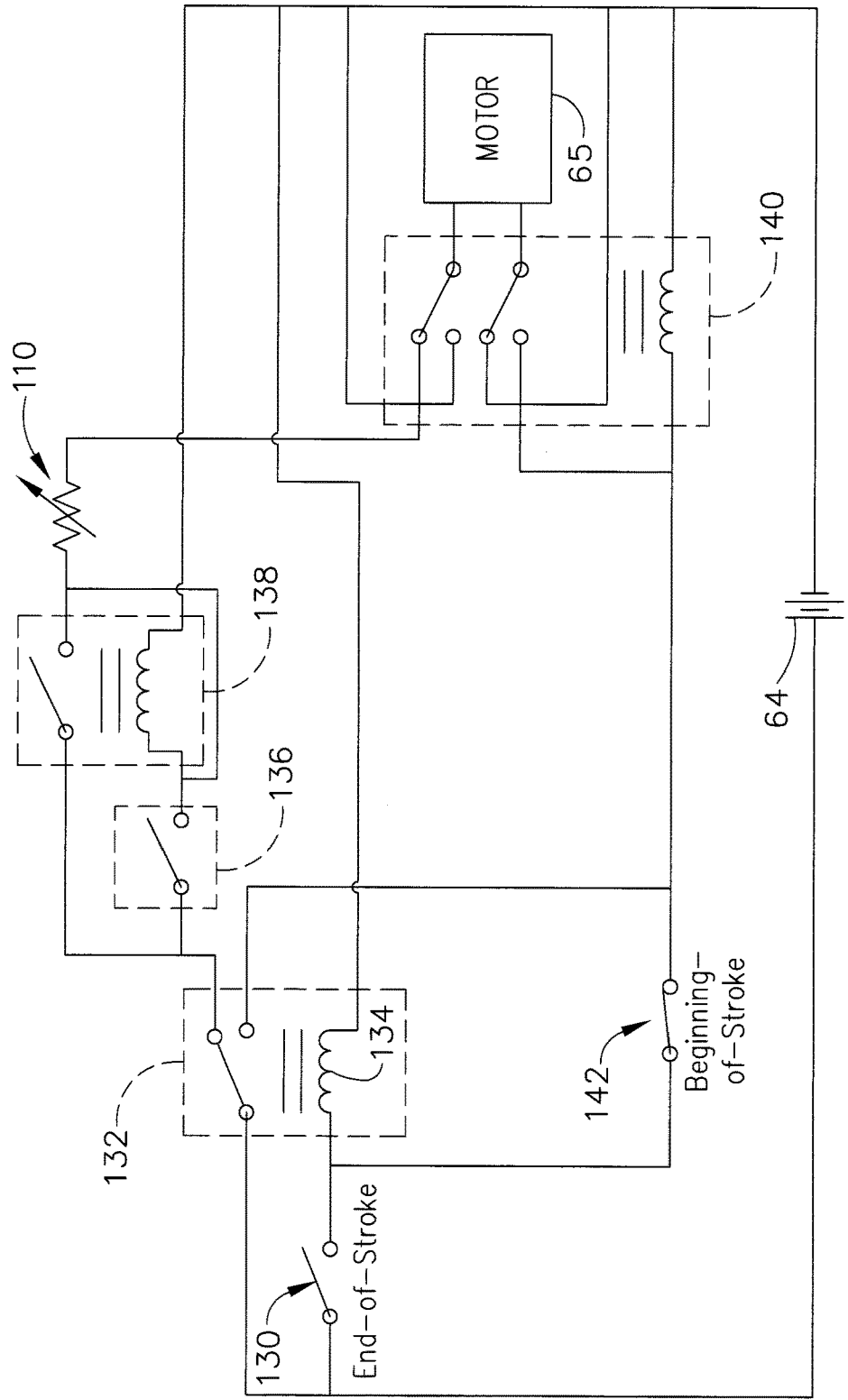
FIG. 11 is a schematic diagram of a circuit used in the instrument according to various embodiments of the present invention.

FIG. 11 is a schematic diagram of an electrical circuit of the instrument 10 according to various embodiments of the present invention. When an operator initially pulls in the firing trigger 20 after locking the closure trigger 18, the sensor 110 is activated, allowing current to flow there through. If the normally-open reverse motor sensor switch 130 is open (meaning the end of the end effector stroke has not been reached), current will flow to a single pole, double throw relay 132. Since the reverse motor sensor switch 130 is not closed, the inductor 134 of the relay 132 will not be energized, so the relay 132 will be in its non-energized state. The circuit also includes a cartridge lockout sensor 136. If the end effector 12 includes a staple cartridge 34, the sensor 136 will be in the closed state, allowing current to flow. Otherwise, if the end effector 12 does not include a staple cartridge 34, the sensor 136 will be open, thereby preventing the battery 64 from powering the motor 65.

When the staple cartridge 34 is present, the sensor 136 is closed, which energizes a single pole, single throw relay 138. When the relay 138 is energized, current flows through the relay 136, through the variable resistor sensor 110, and to the motor 65 via a double pole, double throw relay 140, thereby powering the motor 65, and allowing it to rotate in the forward direction. When the end effector 12 reaches the end of its stroke, the reverse motor sensor 130 will be activated, thereby closing the switch 130 and energizing the relay 134. This causes the relay 134 to assume its energized state (not shown in FIG. 13), which causes current to bypass the cartridge lockout sensor 136 and variable resistor 110, and instead causes current to flow to both the normally-closed double pole, double throw relay 142 and back to the motor 65, but in a manner, via the relay 140, that causes the motor 65 to reverse its rotational direction. Because the stop motor sensor switch 142 is normally closed, current will flow back to the relay 134 to keep it closed until the switch 142 opens. When the knife 32 is fully retracted, the stop motor sensor switch 142 is activated, causing the switch 142 to open, thereby removing power from the motor 65.

In other embodiments, rather than a proportional-type sensor 110, an on-off type sensor could be used. In such embodiments, the rate of rotation of the motor 65 would not be proportional to the force applied by the operator. Rather, the motor 65 would generally rotate at a constant rate. But the operator would still experience force feedback because the firing trigger 20 is geared into the gear drive train.

Additional configurations for motorized surgical instruments are disclosed in published U.S. Patent Application Publication No. 2007/0175962, entitled MOTOR-DRIVEN SURGICAL CUTTING AND FASTENING INSTRUMENT WITH TACTILE POSITION FEEDBACK, now U.S. Pat. No. 7,422,139, which is incorporated herein by reference.

Figure 12:
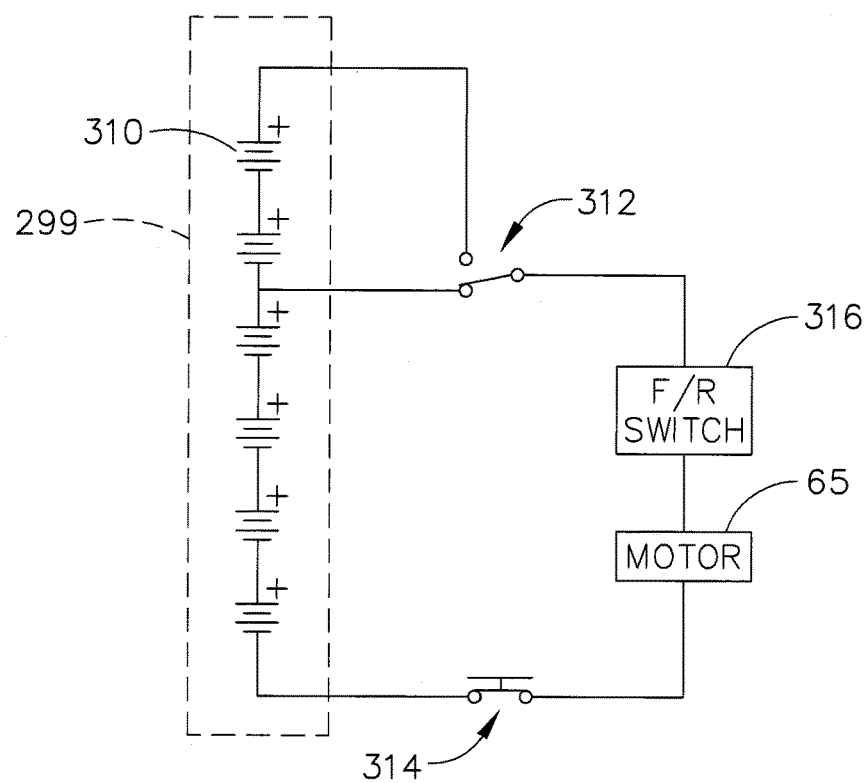
FIGS. 12-14 and 17 are schematic diagrams of circuits used to power the motor of the instrument according to various embodiments of the present invention.

In a motorized surgical instrument, such as one of the motorized endoscopic instruments described above or in a motorized circular cutter instrument, the motor may be powered by a number of battery cells connected in series. Further, it may be desirable in certain circumstances to power the motor with some fraction of the total number of battery cells. For example, as shown in FIG. 12, the motor 65 may be powered by a power pack 299 comprising six (6) battery cells 310 connected in series. The battery cells 310 may be, for example, 3-volt lithium battery cells, such as CR 123A battery cells, although in other embodiments, different types of battery cells could be used (including battery cells with different voltage levels and/or different chemistries). If six 3-volt battery cells 310 were connected in series to power the motor 65, the total voltage available to power the motor 65 would be 18 volts. The battery cells 310 may comprise rechargeable or non-rechargeable battery cells.

In such an embodiment, under the heaviest loads, the input voltage to the motor 65 may sag to about nine to ten volts. At this operating condition, the power pack 299 is delivering maximum power to the motor 65. Accordingly, as shown in FIG. 12, the circuit may include a switch 312 that selectively allows the motor 65 to be powered by either (1) all of the battery cells 310 or (2) a fraction of the battery cells 310. As shown in FIG. 12, by proper selection, the switch 312 may allow the motor 65 to be powered by all six battery cells or four of the battery cells. That way, the switch 312 could be used to power the motor 65 with either 18 volts (when using all six battery cells 310) or 12 volts (such using four of the second battery cells). In various embodiments, the design choice for the number of battery cells in the fraction that is used to power the motor 65 may be based on the voltage required by the motor 65 when operating at maximum output for the heaviest loads.

The switch 312 may be, for example, an electromechanical switch, such as a micro switch. In other embodiments, the switch 312 may be implemented with a solid-state switch, such as transistor. A second switch 314, such as a push button switch, may be used to control whether power is applied to the motor 65 at all. Also, a forward/reverse switch 316 may be used to control whether the motor 65 rotates in the forward direction or the reverse direction. The forward/reverse switch 316 may be implemented with a double pole-double throw switch, such as the relay 140 shown in FIG. 11.

In operation, the user of the instrument 10 could select the desired power level by using some sort of switch control, such as a position-dependent switch (not shown), such as a toggle switch, a mechanical lever switch, or a cam, which controls the position of the switch 312. Then the user may activate the second switch 314 to connect the selected battery cells 310 to the motor 65. In addition, the circuit shown in FIG. 12 could be used to power the motor of other types of motorized surgical instruments, such as circular cutters and/or laparoscopic instruments. More details regarding circular cutters may be found in published U.S. Patent Application Publication Nos. 2006/0047307, now U.S. Pat. No. 8,317,074, and 2007/0262116, now U.S. Pat. No. 7,500,979, which are incorporated herein by reference.

Figure 13:
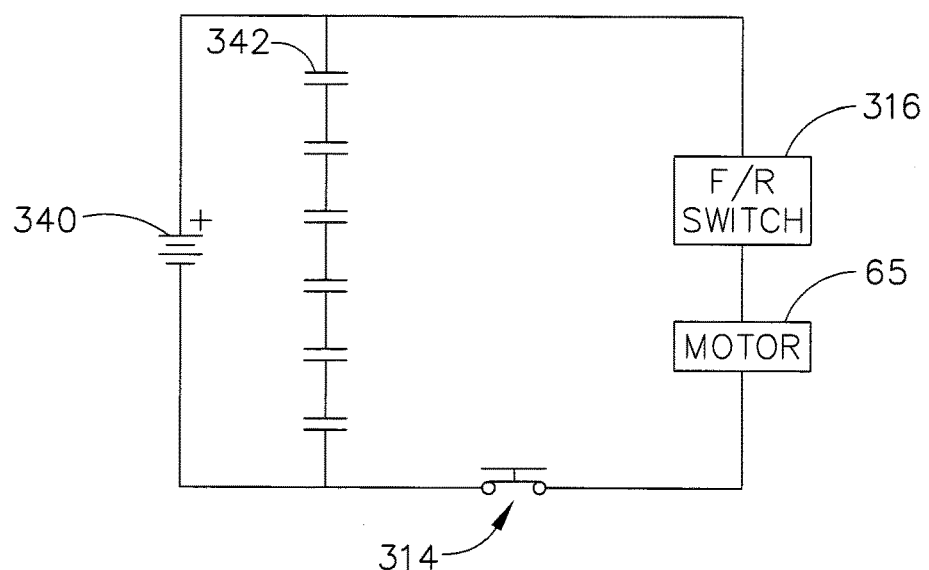

In other embodiments, as shown in FIG. 13, a primary power source 340, such as a battery cell, such as a CR2 or CR123A battery cell, may be used to charge a number of secondary accumulator devices 342. The primary power source 340 may comprise one or a number of series-connected battery cells, which are preferably replaceable in the illustrated embodiment. The secondary accumulator devices 342 may comprise, for example, rechargeable battery cells and/or supercapacitors (also known as "ultracapacitors" or "electrochemical double layer capacitors" (EDLC)). Supercapacitors are electrochemical capacitors that have an unusually high energy density when compared to common electrolytic capacitors, typically on the order of thousands of times greater than a high-capacity electrolytic capacitor.

The primary power source 340 may charge the secondary accumulator devices 342. Once sufficiently charged, the primary power source 340 may be removed and the secondary accumulator devices 342 may be used to power the motor 65 during a procedure or operation. The accumulating devices 342 may take about fifteen to thirty minutes to charge in various circumstances. Supercapacitors have the characteristic they can charge and discharge extremely rapidly in comparison to conventional batteries. In addition, whereas batteries are good for only a limited number of charge/discharge cycles, supercapacitors can often be charged/discharged repeatedly, sometimes for tens of millions of cycles. For embodiments using supercapacitors as the secondary accumulator devices 342, the supercapacitors may comprise carbon nanotubes, conductive polymers (e.g., polyacenes), or carbon aerogels.

Figure 14:
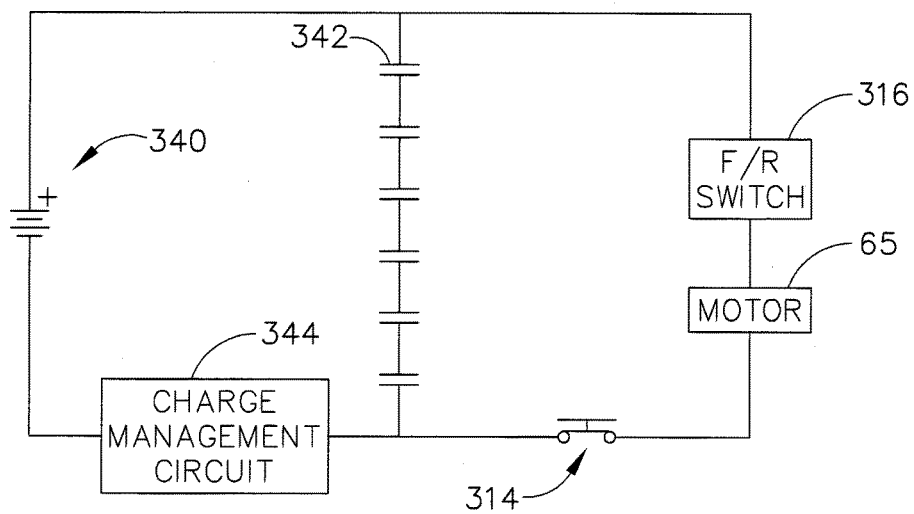

As shown in FIG. 14, a charge management circuit 344 could be employed to determine when the secondary accumulator devices 342 are sufficiently charged. The charge management circuit 344 may include an indicator, such as one or more LEDs, an LCD display, etc., that is activated to alert a user of the instrument 10 when the secondary accumulator devices 342 are sufficiently charged.

The primary power source 340, the secondary accumulator devices 342, and the charge management circuit 344 may be part of a power pack in the pistol grip portion 26 of the handle 6 of the instrument 10, or in another part of the instrument 10. The power pack may be removable from the pistol grip portion 26, in which case, when the instrument 10 is to be used for surgery, the power pack may be inserted aseptically into the pistol grip portion 26 (or other position in the instrument according to other embodiments) by, for example, a circulating nurse assisting in the surgery. After insertion of the power pack, the nurse could put the replaceable primary power source 340 in the power pack to charge up the secondary accumulator devices 342 a certain time period prior to use of the instrument 10, such as thirty minutes. When the secondary accumulator devices 342 are charged, the charge management circuit 344 may indicate that the power pack is ready for use. At this point, the replaceable primary power source 340 may be removed. During the operation, the user of the instrument 10 may then activate the motor 65, such as by activating the switch 314, whereby the secondary accumulator devices 342 power the motor 65. Thus, instead of having a number of disposable batteries to power the motor 65, one disposable battery (as the primary power source 340) could be used in such an embodiment, and the secondary accumulator devices 342 could be reusable. In alternative embodiments, however, it should be noted that the secondary accumulator devices 342 could be non-rechargeable and/or non-reusable. The secondary accumulators 342 may be used with the cell selection switch 312 described above in connection with FIG. 12.

The charge management circuit 344 may also include indicators (e.g., LEDs or LCD display) that indicate how much charge remains in the secondary accumulator devices 342. That way, the surgeon (or other user of the instrument 10) can see how much charge remains through the course of the procedure involving the instrument 10.

Figure 15:
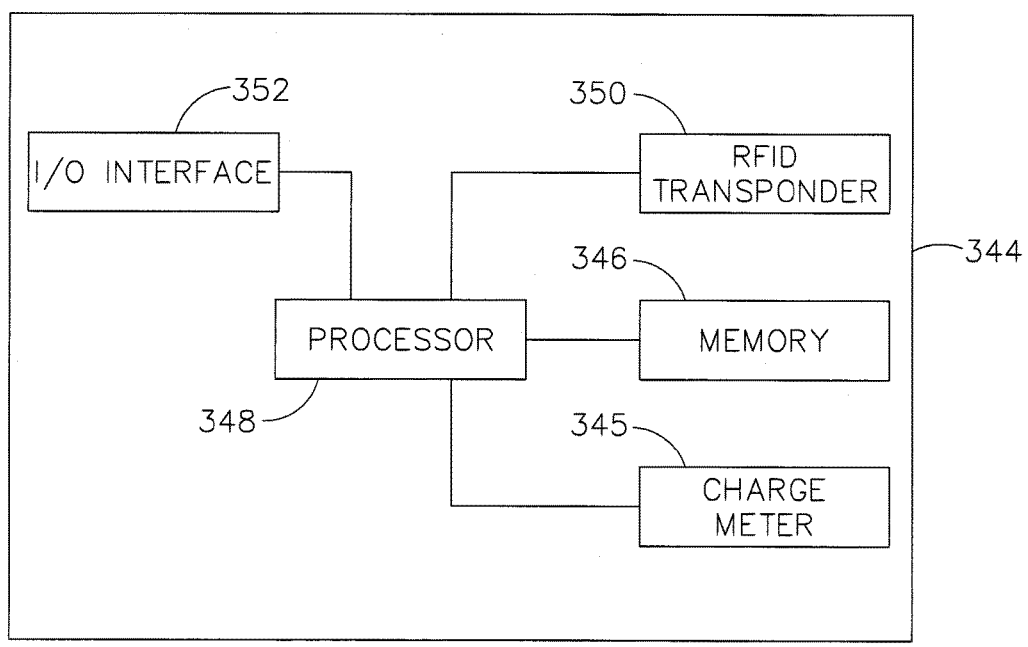
FIG. 15 is a block diagram illustrating a charge management circuit according to various embodiments of the present invention.

The charge management circuit 344, as shown in FIG. 15, may comprise a charge meter 345 for measuring the charge across the secondary accumulators 342. The charge management circuit 344 also may comprise a non-volatile memory 346, such as flash or ROM memory, and one or more processors 348. The processor(s) 348 may be connected to the memory 346 to control the memory. In addition, the processor(s) 348 may be connected to the charge meter 345 to read the readings of and otherwise control the charge meter 345. Additionally, the processor(s) 348 may control the LEDs or other output devices of the charge management circuit 344. The processor(s) 348 can store parameters of the instrument 10 in the memory 346. The parameters may include operating parameters of the instrument that are sensed by various sensors that may be installed or employed in the instrument 10, such as, for example, the number of firings, the levels of forces involved, the distance of the compression gap between the opposing jaws of the end effector 12, the amount of articulation, etc. Additionally, the parameters stored in the memory 346 may comprise ID values for various components of the instrument 10 that the charge management circuit 344 may read and store. The components having such IDs may be replaceable components, such as the staple cartridge 34. The IDs may be for example, RFIDs that the charge management circuit 344 reads via a RFID transponder 350. The RFID transponder 350 may read RFIDs from components of the instrument, such as the staple cartridge 34, that include RFID tags. The ID values may be read, stored in the memory 346, and compared by the processor 348 to a list of acceptable ID values stored in the memory 346 or another store associated with the charge management circuit, to determine, for example, if the removable/replaceable component associated with the read ID value is authentic and/or proper. According to various embodiments, if the processor 348 determines that the removable/replaceable component associated with the read ID value is not authentic, the charge management circuit 344 may prevent use of the power pack by the instrument 10, such as by opening a switch (not shown) that would prevent power from the power pack being delivered to the motor 65. According to various embodiments, various parameters that the processor 348 may evaluate to determine whether the component is authentic and/or proper include: date code; component model/type; manufacturer; regional information; and previous error codes.

The charge management circuit 344 may also comprise an i/o interface 352 for communicating with another device, such as described below. That way, the parameters stored in the memory 346 may be downloaded to another device. The i/o interface 352 may be, for example, a wired or wireless interface.

Figure 16:
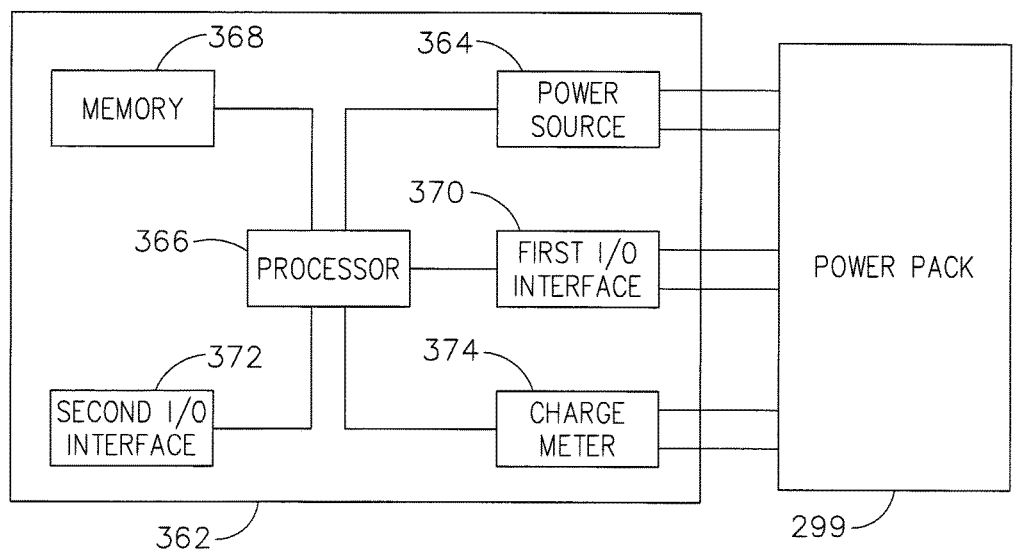
FIG. 16 is a block diagram illustrating a charger base according to various embodiments of the present invention.

As mentioned before, the power pack may comprise the secondary accumulators 342, the charge management circuit 344, and/or the f/r switch 316. According to various embodiments, as shown in FIG. 16, the power pack 299 could be connected to a charger base 362, which may, among other things, charge the secondary accumulators 342 in the power pack. The charger base 362 could be connected to the power pack 299 by connecting aseptically the charger base 362 to the power pack 299 while the power pack is installed in the instrument 10. In other embodiments where the power pack is removable, the charger base 362 could be connected to the power pack 299 by removing the power pack 299 from the instrument 10 and connecting it to the charger base 362. For such embodiments, after the charger base 362 sufficiently charges the secondary accumulators 342, the power pack 299 may be aseptically installed in the instrument 10.

As shown in FIG. 16, the charger base 362 may comprise a power source 364 for charging the secondary accumulators 342. The power source 364 of the charger base 362 may be, for example, a battery (or a number of series-connected batteries), or an AC/DC converter that converters AC power, such as from electrical power mains, to DC, or any other suitable power source for charging the secondary accumulators 342. The charger base 362 may also comprise indicator devices, such as LEDs, a LCD display, etc., to show the charge status of the secondary accumulators 342.

In addition, as shown in FIG. 16, the charger base 362 may comprise one or more processors 366, one or more memory units 368, and i/o interfaces 370, 372. Through the first i/o interface 370, the charger base 362 may communicate with the power pack 299 (via the power pack's i/o interface 352). That way, for example, data stored in the memory 346 of the power pack 299 may be downloaded to the memory 368 of the charger base 362. In that way, the processor 366 can evaluate the ID values for the removable/replaceable components, downloaded from the charge management circuit 344, to determine the authenticity and suitability of the components. The operating parameters downloaded from the charge management circuit 344 may also stored in the memory 368, and then may then be downloaded to another computer device via the second i/o interface 372 for evaluation and analysis, such as by the hospital system in which the operation involving the instrument 10 is performed, by the office of the surgeon, by the distributor of the instrument, by the manufacturer of the instrument, etc.

The charger base 362 may also comprise a charge meter 374 for measuring the charge across the secondary accumulators 342. The charge meter 374 may be in communication with the processor(s) 366, so that the processor(s) 366 can determine in real-time the suitability of the power pack 299 for use to ensure high performance.

Figure 17:
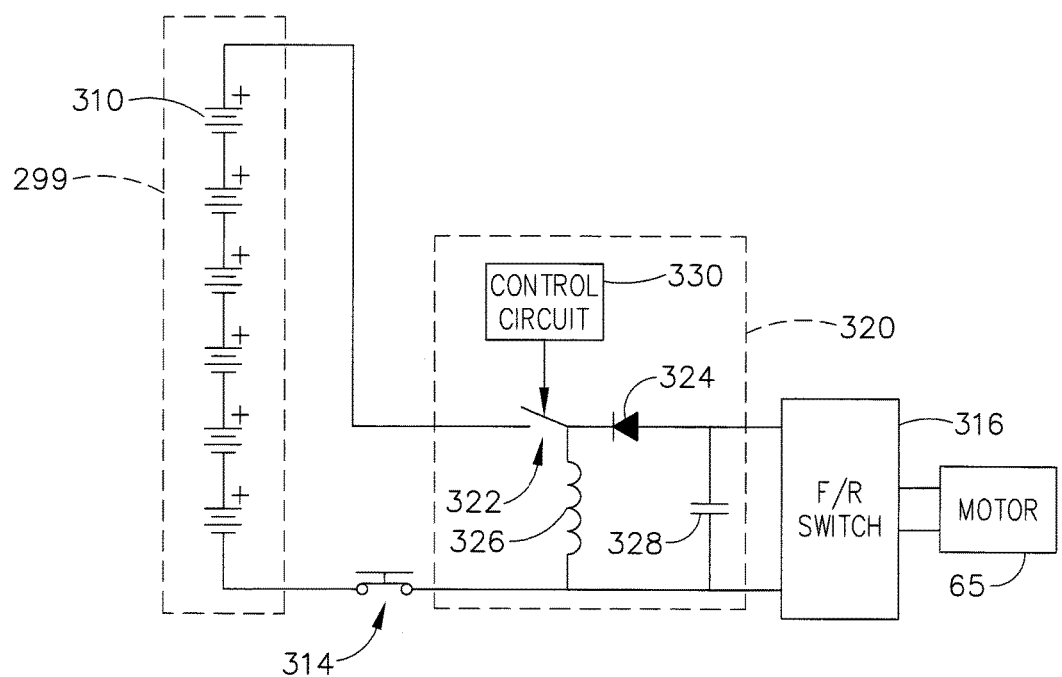

In another embodiment, as shown in FIG. 17, the battery circuit may comprise a power regulator 320 to control the power supplied by the power savers 310 to the motor 65. The power regulator 320 may also be part of the power pack 299, or it may be a separate component. As mentioned above, the motor 65 may be a brushed DC motor. The speed of brushed DC motors generally is proportional to the applied input voltage. The power regulator 320 may provide a highly regulated output voltage to the motor 65 so that the motor 65 will operate at a constant (or substantially constant) speed. According to various embodiments, the power regulator 320 may comprise a switch-mode power converter, such as a buck-boost converter, as shown in the example of FIG. 17. Such a buck-boost converter 320 may comprise a power switch 322, such as a FET, a rectifier 324, an inductor 326, and a capacitor 328. When the power switch 322 is on, the input voltage source (e.g., the power sources 310) is directly connected to the inductor 326, which stores energy in this state. In this state, the capacitor 328 supplies energy to the output load (e.g., the motor 65). When the power switch 320 is in the off state, the inductor 326 is connected to the output load (e.g., the motor 65) and the capacitor 328, so energy is transferred from the inductor 326 to the capacitor 328 and the load 65. A control circuit 330 may control the power switch 322. The control circuit 330 may employ digital and/or analog control loops. In addition, in other embodiments, the control circuit 330 may receive control information from a master controller (not shown) via a communication link, such as a serial or parallel digital data bus. The voltage set point for the output of the power regulator 320 may be set, for example, to one-half of the open circuit voltage, at which point the maximum power available from the source is available.

In other embodiments, different power converter topologies may be employed, including linear or switch-mode power converters. Other switch-mode topologies that may be employed include a flyback, forward, buck, boost, and SEPIC. The set point voltage for the power regulator 320 could be changed depending on how many of the battery cells are being used to power the motor 65. Additionally, the power regulator 320 could be used with the secondary accumulator devices 342 shown in FIG. 13. Further, the forward-reverse switch 316 could be incorporated into the power regulator 320, although it is shown separately in FIG. 17.

Figure 18:
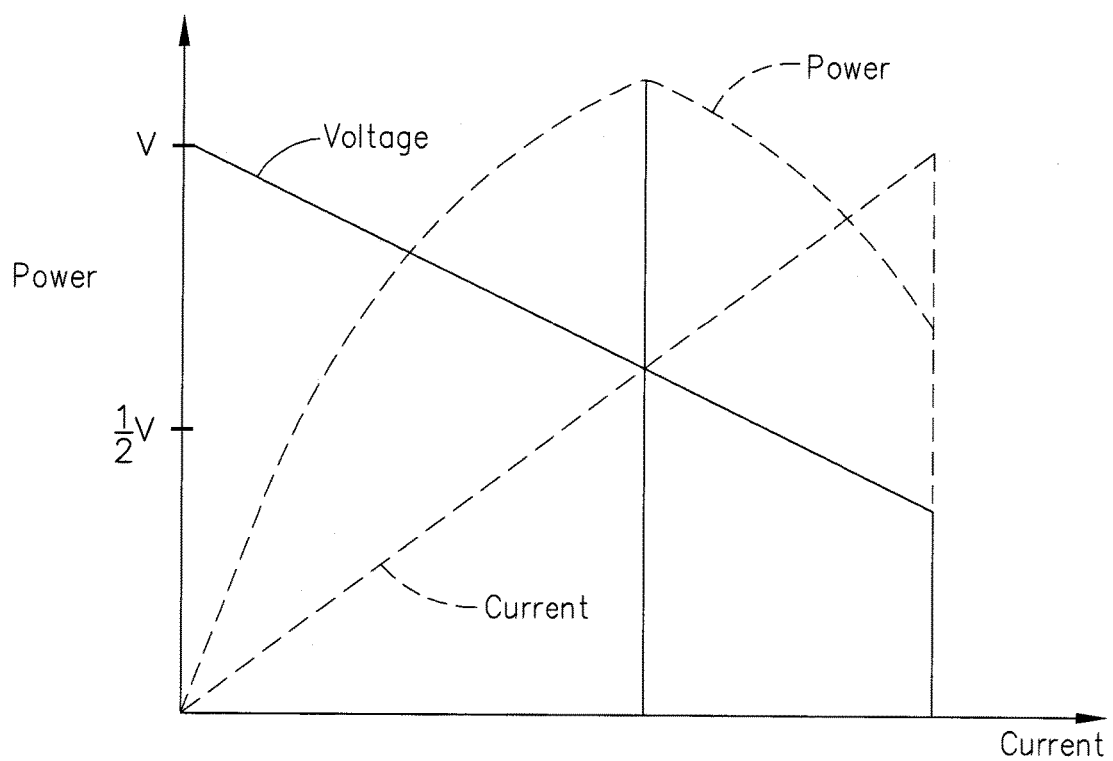
FIG. 18 illustrates a typical power curve of a battery.

Batteries can typically be modeled as an ideal voltage source and a source resistance. For an ideal model, when the source and load resistance are matched, maximum power is transferred to the load. FIG. 18 shows a typical power curve for a battery. When the battery circuit is open, the voltage across the battery is high (at its open circuit value) and the current drawn from the battery is zero. The power delivered from the battery is zero also. As more current is drawn from the battery, the voltage across the battery decreases. The power delivered by the battery is the product of the current and the voltage. The power reaches its peak around at a voltage level that is less than the open circuit voltage. As shown in FIG. 18, with most battery chemistries there is a sharp drop in the voltage/power at higher current because of the chemistry or positive temperature coefficient (PTC), or because of a battery protection device.

Particularly for embodiments using a battery (or batteries) to power the motor 65 during a procedure, the control circuit 330 can monitor the output voltage and control the set point of the regulator 320 so that the battery operates on the "left" or power-increasing side of the power curve. If the battery reaches the peak power level, the control circuit 330 can change (e.g., lower) the set point of the regulator so that less total power is being demanded from the battery. The motor 65 would then slow down. In this way, the demand from the power pack would rarely if ever exceed the peak available power so that a power-starving situation during a procedure could be avoided.

In addition, according to other embodiments, the power drawn from the battery may be optimized in such a way that the chemical reactions within the battery cells would have time to recover, to thereby optimize the current and power available from the battery. In pulsed loads, batteries typically provide more power at the beginning of the pulse that toward the end of the pulse. This is due to several factors, including: (1) the PTC may be changing its resistance during the pulse; (2) the temperature of the battery may be changing; and (3) the electrochemical reaction rate is changing due to electrolyte at the cathode being depleted and the rate of diffusion of the fresh electrolyte limits the reaction rate. According to various embodiments, the control circuit 330 may control the converter 320 so that it draws a lower current from the battery to allow the battery to recover before it is pulsed again.

According to other embodiments, the instrument 10 may comprise a clutch-type torque-limiting device. The clutch-type torque-limiting device may be located, for example, between the motor 65 and the bevel gear 68, between the bevel gear 70 and the planetary gear assembly 72, or on the output shaft of the planetary gear assembly 72. According to various embodiments, the torque-limiting device may use an electromagnetic or permanent magnetic clutch.

Figure 20:
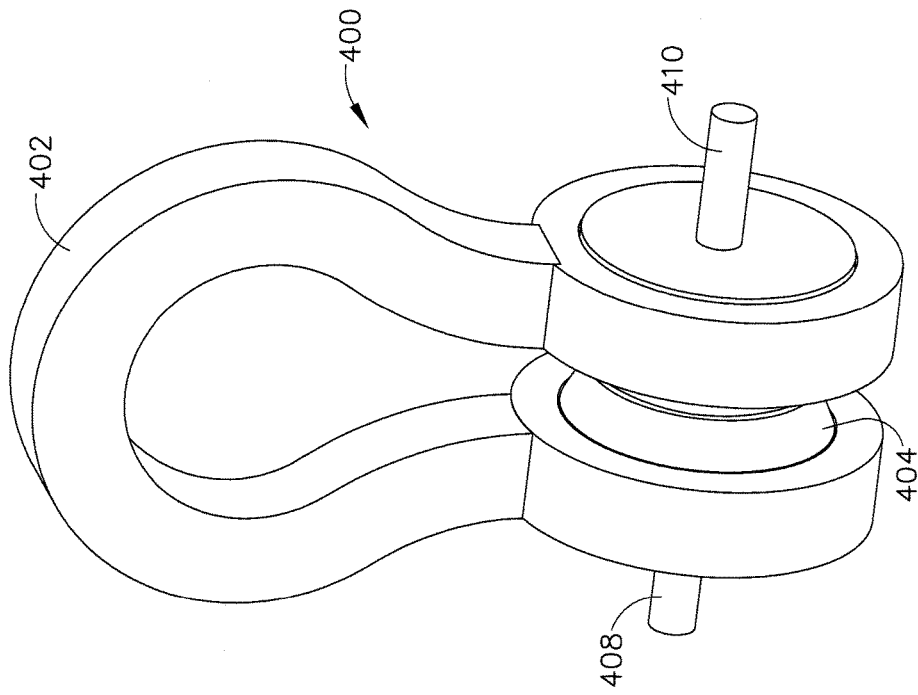
FIGS. 19-22 illustrate embodiments of an electromagnetic, clutch-type torque-limiting device according to various embodiments of the present invention.
Figure 19:
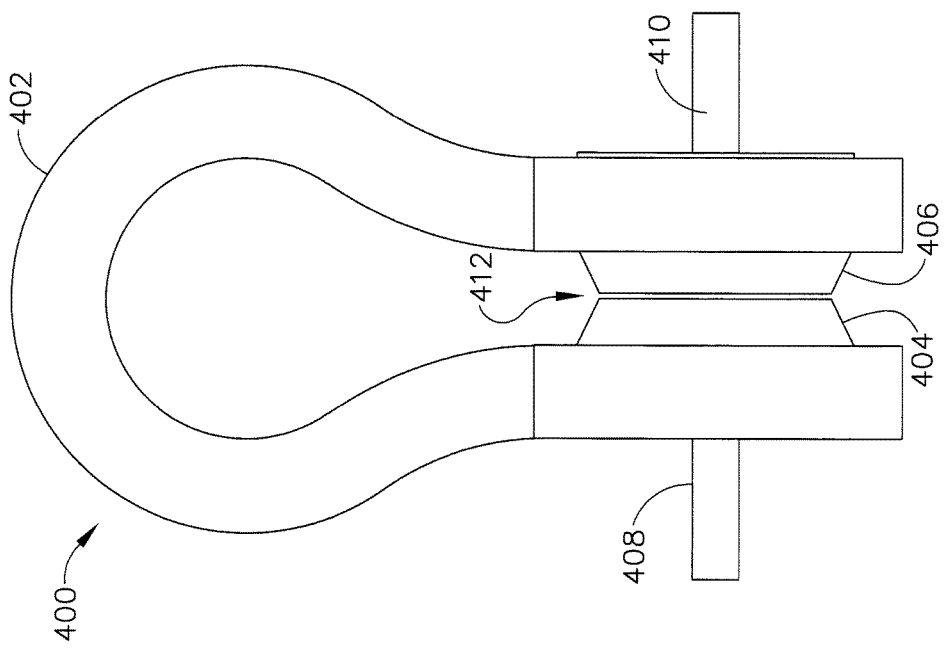
Figure 22:
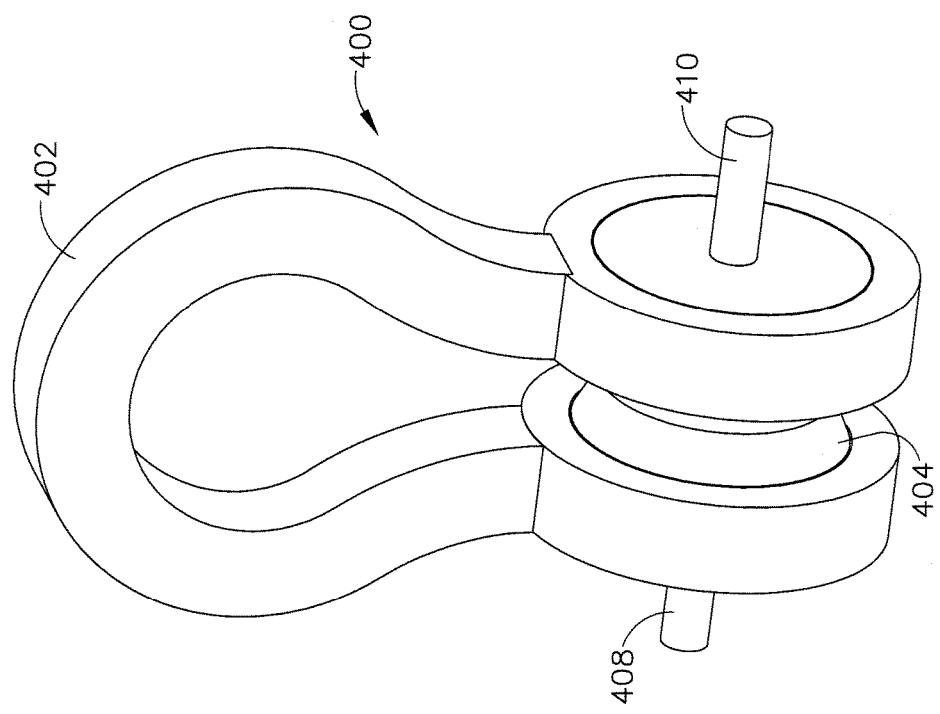
Figure 21:
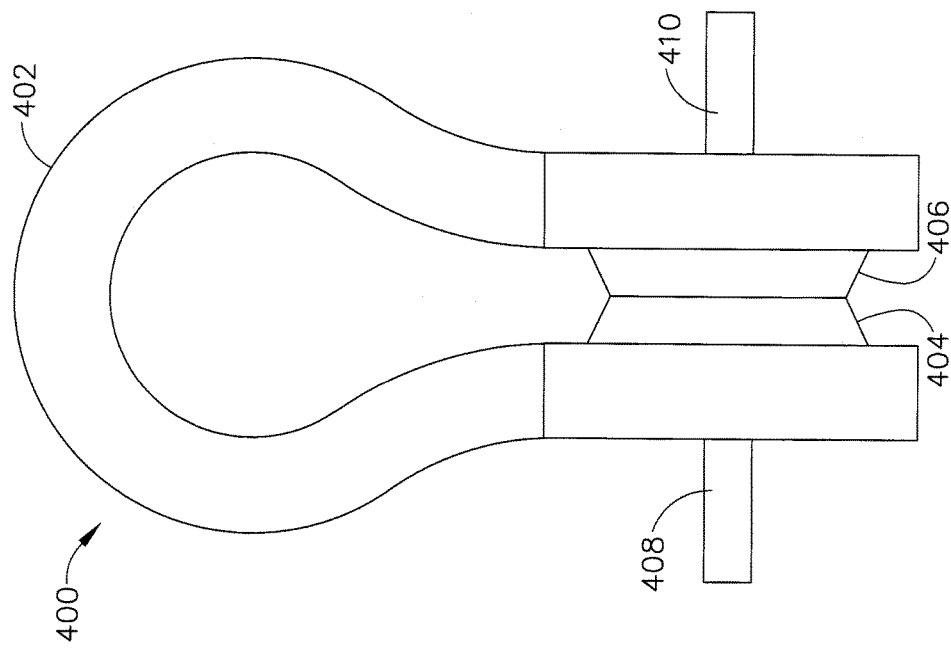

FIGS. 19 to 22 show a sample electromagnetic clutch 400 that could be used in the instrument 10 according to various embodiments. The clutch 400 may comprise a horseshoe-shaped stator 402 having magnetic disks 404, 406 at each end. The first disk 404 may be connected to an axially movable, rotatable pole piece 408, such as the output pole of the motor 65. The second magnetic disk 406 may be connected to an axially stationary, rotatable pole piece 410, such as an input pole to a gear box of the instrument 10. In the views of FIGS. 19 and 20, the first pole piece 408 is axially pulled away from the second pole piece 410 by a clearance 412 such that the magnetic disks 404, 406 are not engaged. A wire coil (not shown), which may be wrapped around the stator 402 may be used to create the electromagnetic flux needed to actuate the clutch 400. When the coil conducts an electrical current, the resulting magnetic flux may cause the two magnetic disks 404, 406 to attract, causing the first pole piece 408 to move axially toward the second pole piece 410, thereby causing the two magnetic disks 404, 406 to become engaged, as shown in FIGS. 21 and 22, such that the two pole pieces 408, 410 will rotate together until the torque exceeds the friction torque generated between the faces of magnetic disks 404 and 406.

The attractive force between the two disks 404, 406 and the corresponding torque capacity of the clutch 400 could be controlled by controlling the diameter of the disks 404, 406, the coefficient of friction between the contacting faces of magnetic disks 404 and 406, and by using magnetic materials for the disks 404, 406 that saturate at a known and controllable flux density. Therefore, even if there was an operating condition where more current was passed through the coil, the magnetic material of the disks 404, 406 would not generate a greater attractive force and subsequent limiting torque.

Utilization of such a clutch has many additional potential benefits. Being electrically controlled, the clutch 400 could be quickly deactivated by removing current from the wire to limit the amount of heat generated within the clutch 400 and within the motor 65. By disconnecting the motor from the rest of the drive train, via the clutch 400, most of the stored inertial energy in the drive train would be disconnected, limiting shock if the output were to be blocked suddenly. In addition, by being electrically controlled, some limited slipping could be designed-in to aid in reducing shocks when restarting the drive train under load. Further, because the magnetic saturation properties of one or more of the components (e.g., the magnetic disks 404, 406) within the clutch could be used to control the torque limit instead of coil current, the clutch 400 would be less sensitive to changes in system voltage. The torque limit in such embodiments would be primarily a function of the physical dimensions of the components of the clutch (e.g., the magnetic disks 404, 406) and would not require voltage regulators or other external components for proper operation.

In another embodiment, rather than using an electromagnetic clutch, the torque-limiting device may comprise a permanent magnet (not shown). The permanent magnet may be connected, for example, to the first, axially-movable, pole piece 408, and attract the axially-fixed second pole piece 410, or vice versa. In such embodiments, one of the disks 404, 406 could be made of a permanent magnet and the other one of a magnetic material like iron. In a slight variation, the stator 402 could be made in the form of a permanent magnet, causing the magnetic disks 404 and 406 to be attracted to each other. Because of the permanent magnet, the two disks 404, 406 would be engaged always. Using a permanent magnet would not provide as accurate as torque control as the electromagnetic clutch configuration described above, but it would have the advantages of: (1) not requiring controls or control logic to control the current through the coil; (2) being more compact that the electromagnetic clutch configuration; and (3) simplifying design of the instrument 10.

As mentioned previously, the end effector 12 may emit RF energy to coagulate tissue clamped in the end effector. The RF energy may be transmitted between electrodes in the end effector 12. A RF source (not shown), comprising, for example, an oscillator and an amplifier, among other components, which may supply the RF energy to the electrode, may be located in the instrument itself, such as in the handle 6 for a cordless instrument 10, or the RF source may be external to the instrument 10. The RF source may be activated as described further below.

According to various embodiments, the end effector 12 may comprise multiple sections (or segments) of electrodes. For example, as shown in the example of FIG. 23, the lower surface of the anvil 24 (i.e., the surface facing the staple cartridge 34) may comprise three co-linear RF segments. In this example, each segment has the same length (e.g., 20 mm), although in other embodiments there may be more or fewer segments, and the segments may have different lengths. In the example of FIG. 23, there are three pairs of active or "anode" terminals or electrodes 500 lined up longitudinally along each side of the channel length on the lower surface of the anvil 24. In particular, in the illustrated embodiment there is a pair of distal electrodes $500_1$, a pair of middle electrodes $500_2$, and a pair of proximate electrodes $500_3$ on each side of the knife channel 516. The metallic outer portion or channel 22 of the end effector 12 or the metallic anvil 24 may serve as the counter-electrode (or cathode) for each of the three upper active electrodes (or anodes) 500. The upper electrodes 500 may be coupled to the RF source. When energized, RF energy may propagate between the upper electrodes 500 and the counter electrode, coagulating tissue clamped between the electrodes.

The electrodes 500 may be energized simultaneously or in various orders, such as sequentially. For embodiments where the electrodes 500 are energized according to a sequence, the sequence may be automatic (controlled, for example, by a controller (not shown) in communication with the RF source) or by selection by the user. For example, the proximate electrodes $500_3$ could be energized first; then the middle electrodes $500_2$; then the distal electrodes $500_1$. That way, the operator (e.g., the operating surgeon) can selectively coagulate areas of the staple line. The electrodes in such an embodiment could be controlled by a multiplexer and/or a multiple output generator, as described further below. That way, the tissue under each electrode 500 could be treated individually according to the coagulation needs. Each electrode in the pair may be connected to the RF source so that they are energized at the same time. That is, for the distal pair of active electrodes $500_1$, each, being on opposite sides of the knife channel, may be energized by the RF source at the same time. Same for the middle pair of electrodes $500_2$ and the proximate pair of electrodes $500_3$, although, in an embodiment where the electrode pairs are energized in sequence, the distal pair is not energized at the same time as the middle and proximate pairs, and so on.

Further, various electrical parameters, such as impedance, delivered power or energy, etc., could be monitored and the output to particular electrodes 500 could be modified to produce the most desirable tissue effect. Additionally, another advantage is in the case of a metal staple or other electrically conductive object left from a previous instrument firing or surgical procedure that may cause a short of the electrodes. Such a short situation could be detected by the generator and/or multiplexer, and the energy could be modulated in a manner appropriate for the short circuit.

In addition, energizing the electrodes 500 in sequence reduces the instantaneous power required from the RF source in comparison to a design that would has one set of electrodes as long as the combined length of the three segmented electrodes 500 shown in FIG. 23. For example, for electrode configurations as shown in the '312 Patent, it has been demonstrated that it would require fifty to one-hundred watts to coagulate successfully forty-five mm lines on either side of the cut line. By using smaller active electrodes (e.g., the upper electrodes 500) that have less surface area than the larger return electrodes (e.g., the metallic anvil 24), the smaller active electrodes 500 can concentrate the therapeutic energy at the tissue while the larger, return electrode is used to complete the circuit with minimal impact on the tissue interface. In addition, the return electrode preferably has greater mass and thereby is able to stay cooler during electrosurgical application.

The electrodes 500 may be surrounded by an electrically insulating material 504, which may comprise a ceramic material.

FIG. 24 shows another embodiment having segmented RF electrodes. In the embodiment shown in FIG. 24, there are four co-linear segmented electrodes $500_{1-4}$ of equal length (15 mm in this example). Like the embodiment of FIG. 23, the electrodes 500 of FIG. 24 could be energized simultaneously or sequentially.

Figure 25:
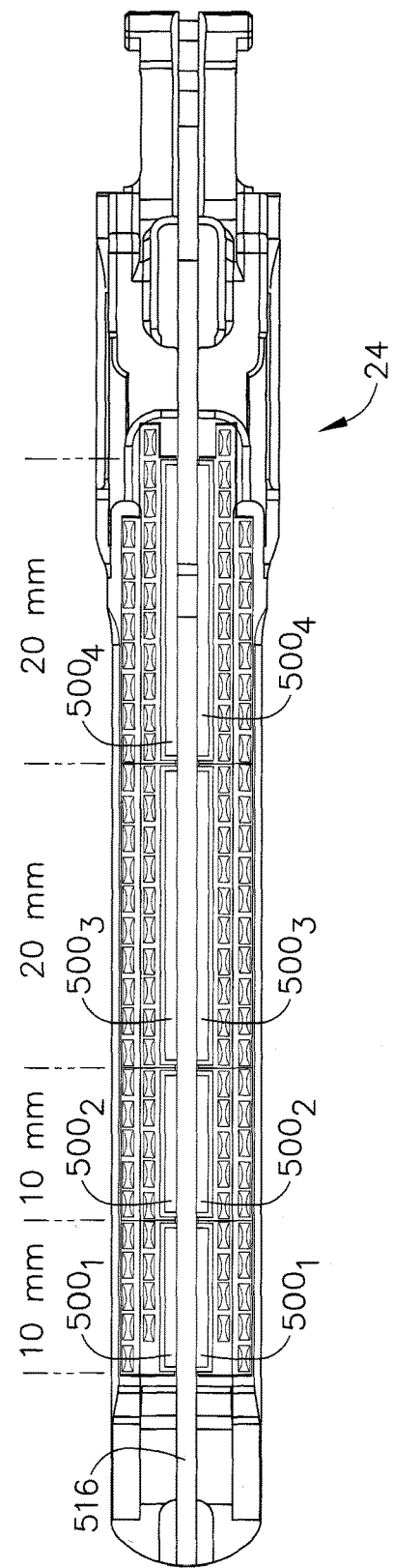

FIG. 25 shows yet another embodiment, in which the segmented electrodes have different lengths. In the illustrated embodiment, there are four co-linear segmented electrodes, but the most distal electrodes $500_1$, $500_2$ are 10 mm in length, and the two proximate electrodes $500_3$, $500_4$ are 20 mm in length. Having short distal electrodes may provide the advantage of concentrating the therapeutic energy, as mentioned above.

Figure 59:
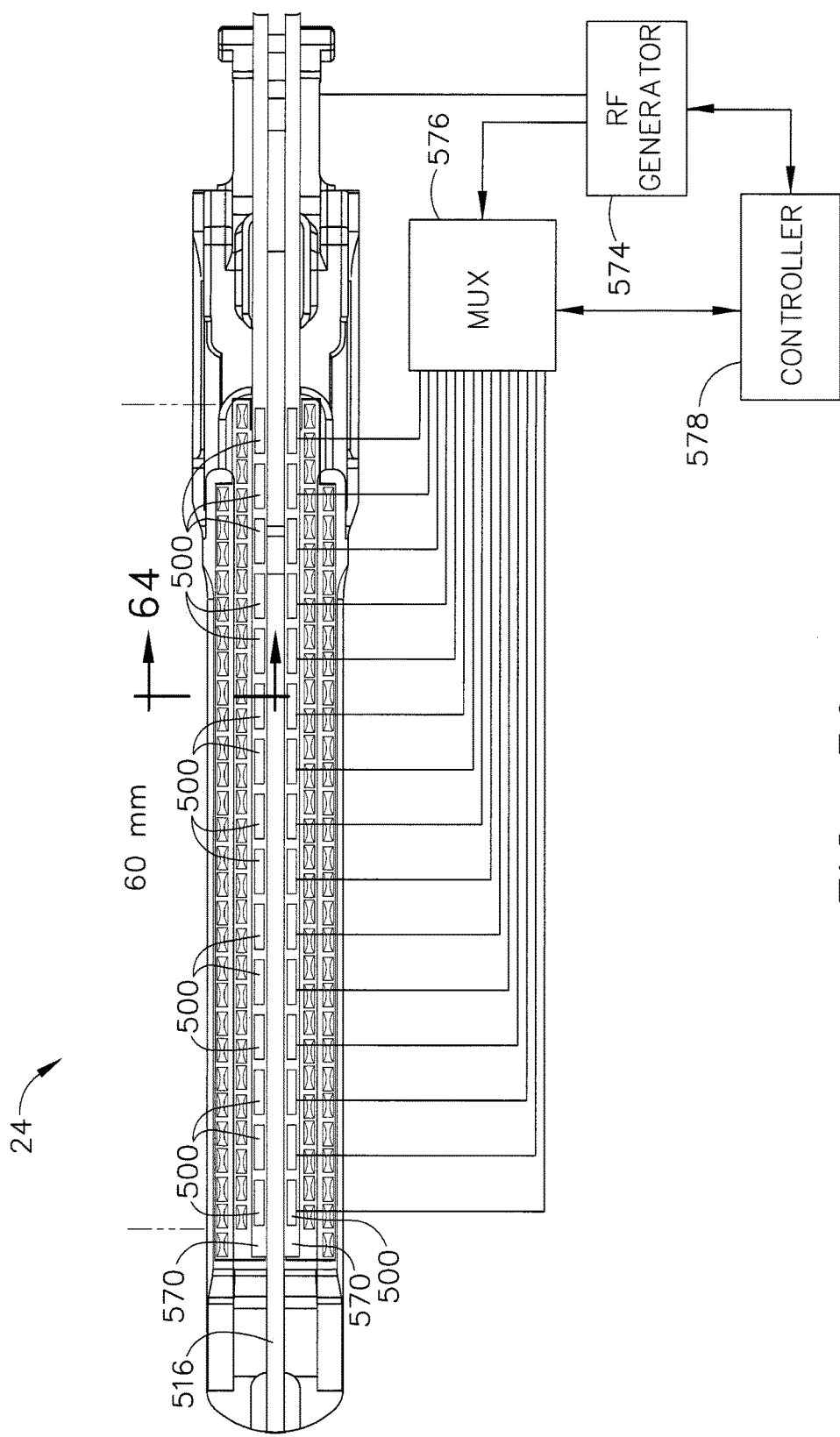

FIG. 59 shows an embodiment having fifteen pairs of segmented RF electrodes 500 on a circuit board 570, or other type of suitable substrate, on the lower surface of the anvil 24 (i.e., the surface facing the channel 22). The various electrode pairs are energized by the RF source (or generator) 574. The multiplexer 576 may distribute the RF energy to the various electrode pairs as desired under the control of a controller 578. According to various embodiments, the RF source 574, the multiplexer 576, and the controller 578 may be located in the handle 6 of the instrument.

Figure 60:
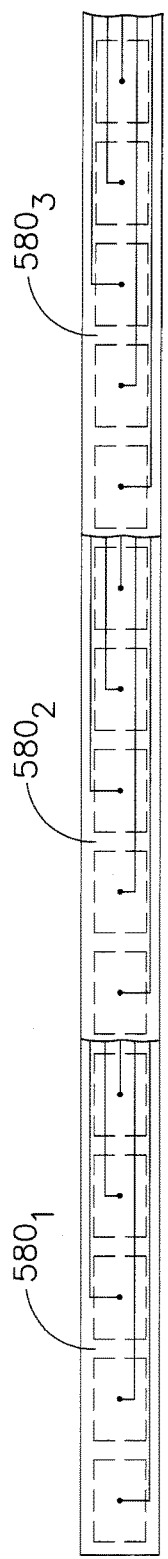
Figure 61:
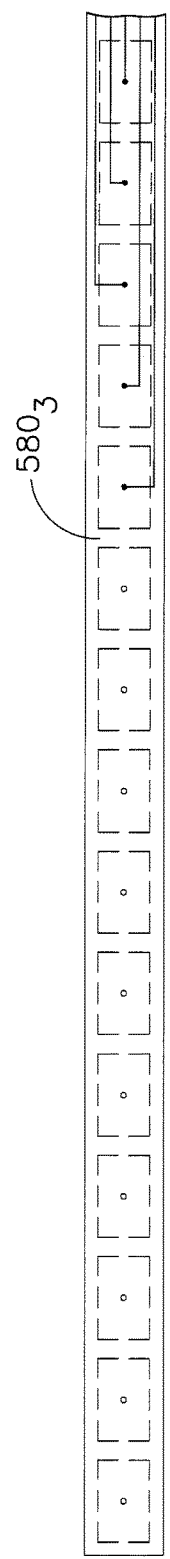
Figure 62:
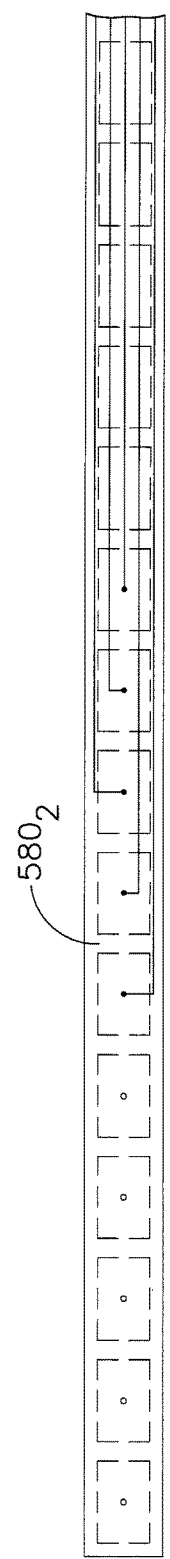
Figure 63:
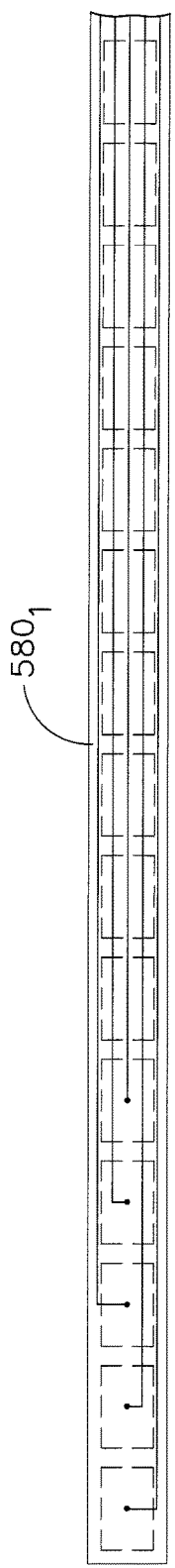

In such an embodiment, the circuit board 570 may comprise multiple layers that provide electrical connections between the multiplexer 576 and the various electrode pairs. For example, as shown in FIGS. 60 to 63, the circuit board may comprise three layers $580_{1-3}$, each layer 580 providing connections to five of the electrode pairs. For example, the upper most layer $580_3$ may provide connections to the most proximate five electrode pairs, as shown in FIGS. 60 and 61; the middle layer $580_2$ may provide connections to the middle five electrode pairs, as shown in FIGS. 60 and 62; and the lowest layer $580_1$ may provide connections to the most distal five electrode pairs, as shown in FIGS. 60 and 63.

Figure 64:
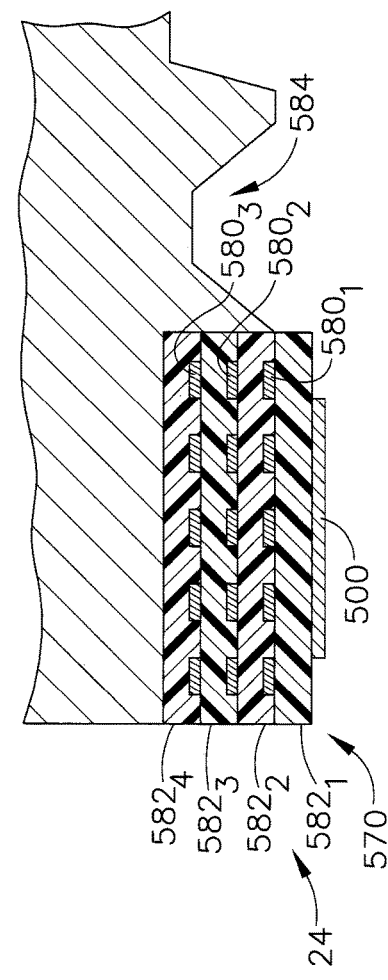
Figure 65:
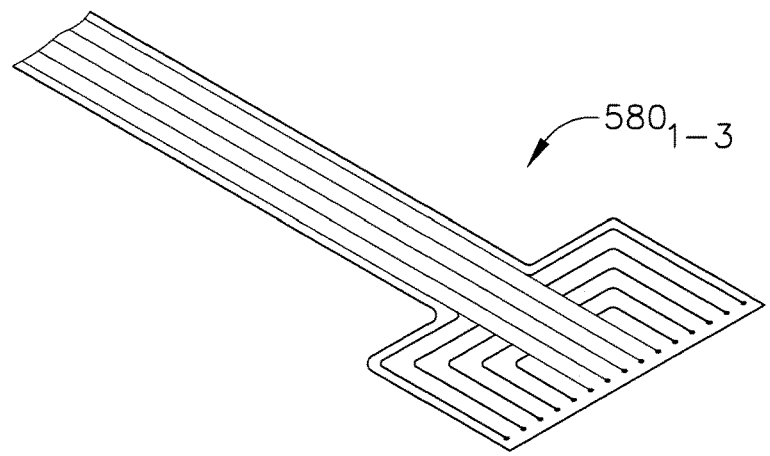
Figure 66:
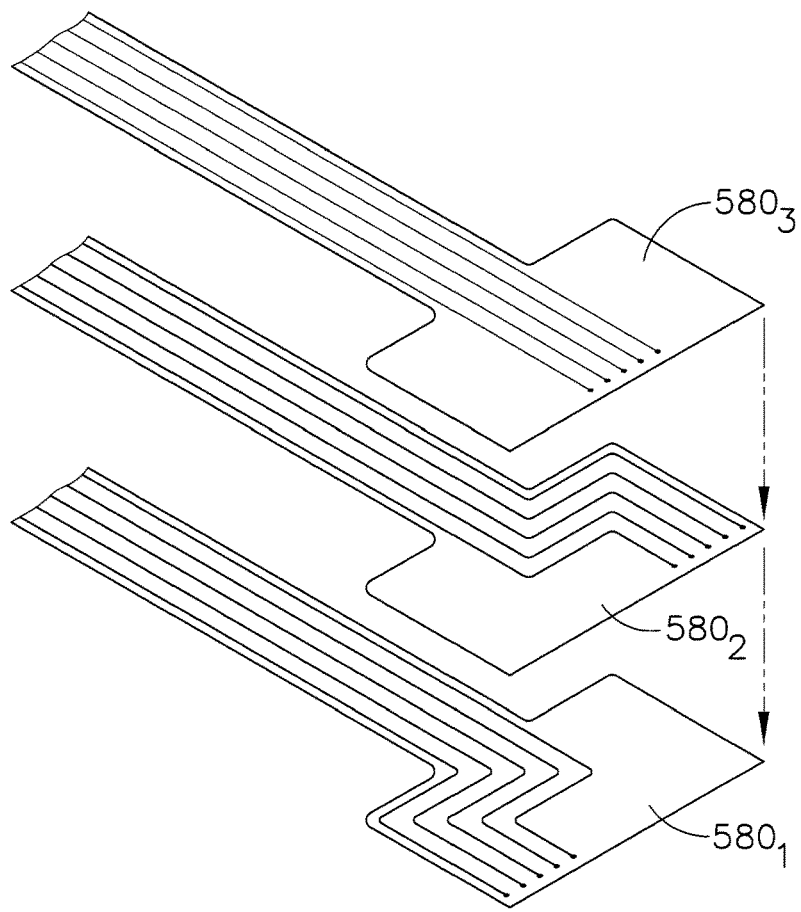

FIG. 64 shows a cross-sectional end view of the anvil 24 according to such an embodiment. The circuit board 570, adjacent to the staple pockets 584, comprises three conducting layers $580_{1-3}$, having insulating layers $582_{1-4}$ therebetween. FIGS. 65 and 66 show how the various layers $580_{1-3}$ may be stacked to connect back to the multiplexer 576 in the handle.

An advantage of having so many RF electrodes in the end effector 12, as shown in FIG. 67, is that, in the case of a metal staple line 590 or other electrically conductive object left in the tissue 592 from a previous instrument firing or surgical procedure that may cause a short of the electrodes, such a short situation could be detected by the generator and multiplexer, and the energy could be modulated in a manner appropriate for the short circuit.

Figure 27:
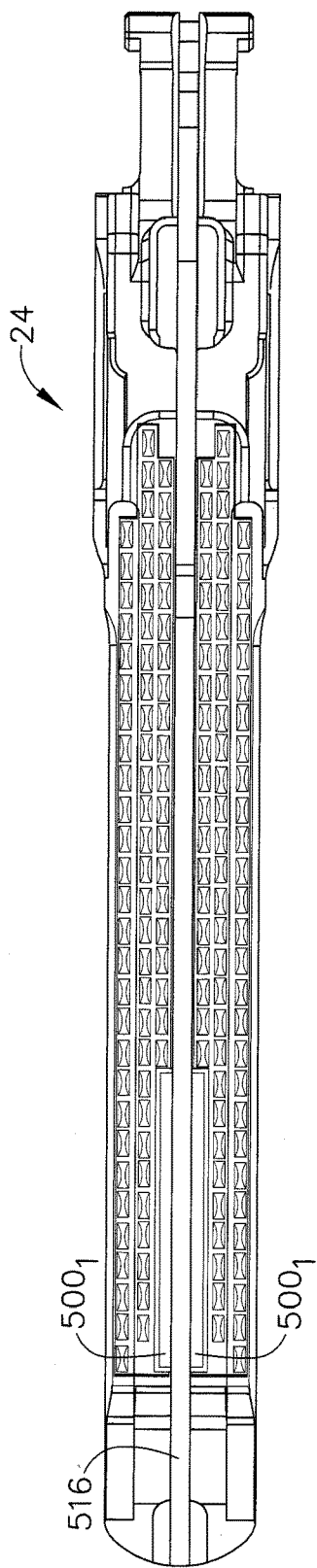

FIG. 27 shows another end effector 12 with RF electrodes. In this embodiment, the end effector 12 only comprises distal electrodes $500_1$, with the metallic anvil 24 serving as the return electrode. The distal electrodes $500_1$ do not span the entire length of the anvil 24, but only a fraction of the length. In the illustrated embodiment, distal electrodes $500_1$ are only approximately 20 mm in length along a 60 mm anvil, so that the distal electrodes $500_1$ only cover approximately the most distal ⅓ of the anvil length. In other embodiments, the distal electrodes $500_1$ could cover the most distal ¹⁄₁₀ to ½ of the anvil length. Such embodiments could be used for spot coagulation, as described in U.S. Pat. No. 5,599,350, which is incorporated herein by reference.

Figure 28:
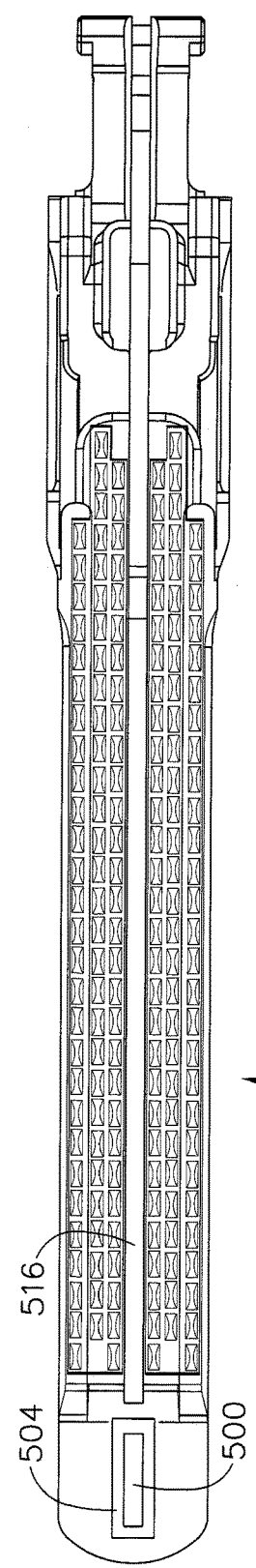

FIG. 28 shows yet another embodiment of the end effector 12 with RF electrodes. In this embodiment, an active electrode 500 is positioned at the distal tip of the anvil 24, insulated by the anvil 24 by an electrically non-conductive insulator 504, which may be made of ceramic material. Such an embodiment may be used for spot coagulation.

Figure 29:
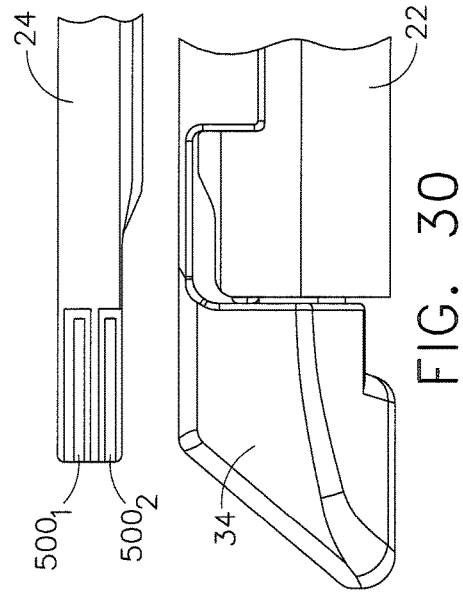
Figure 30:
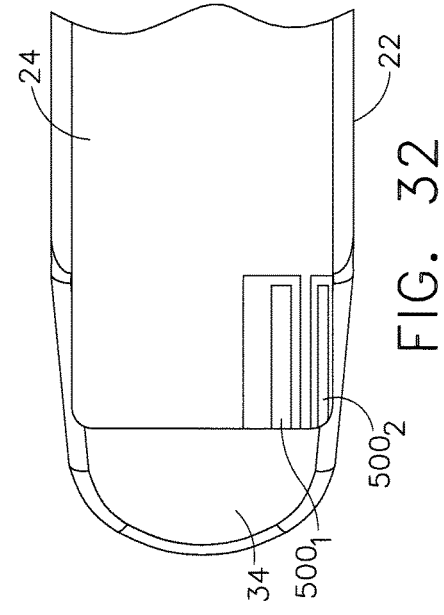
Figure 31:
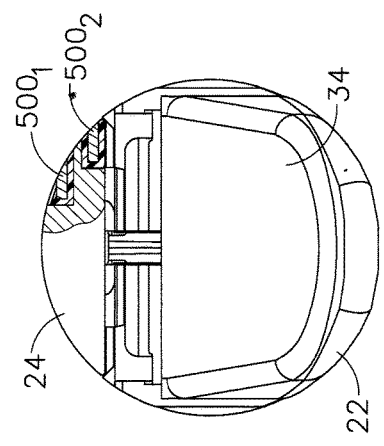
Figure 32:
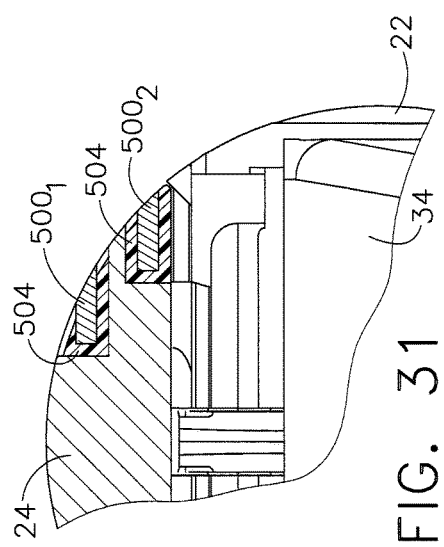
Figure 37:
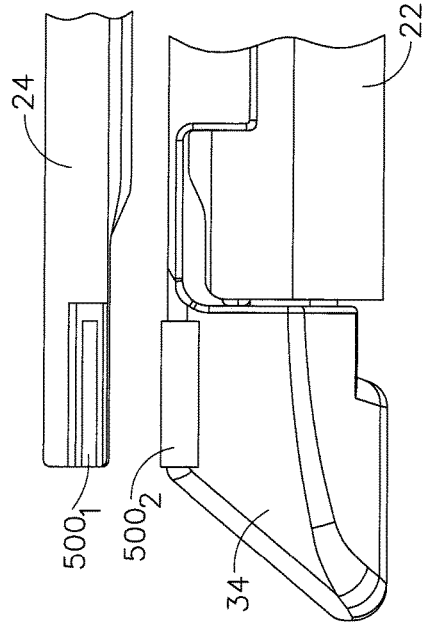
Figure 38:
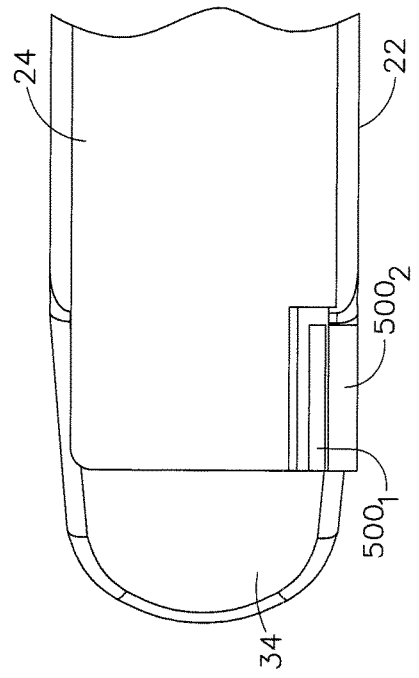
Figure 39:
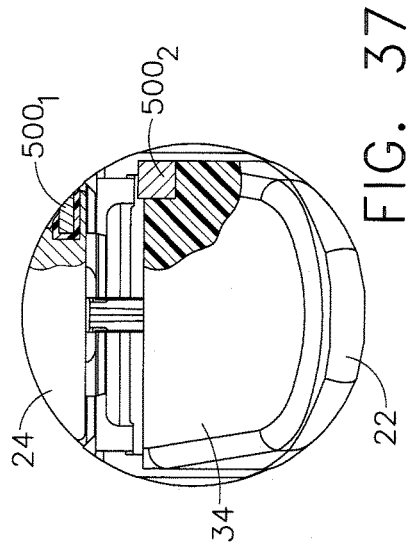
Figure 40:
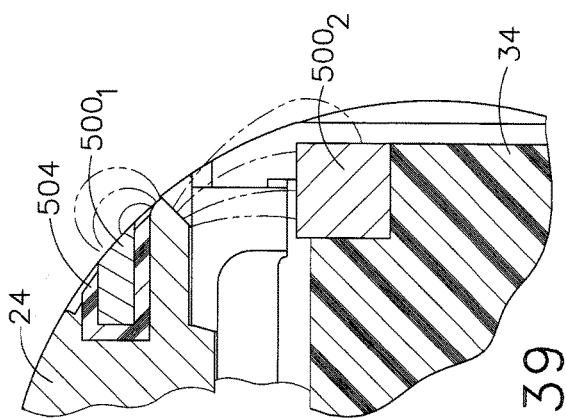
Figure 41:
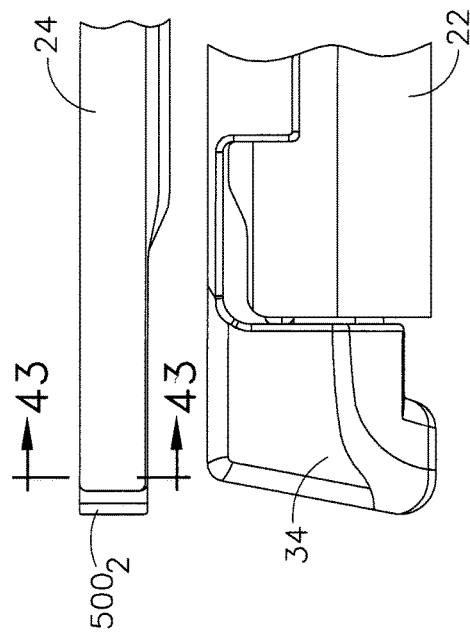
Figure 42:
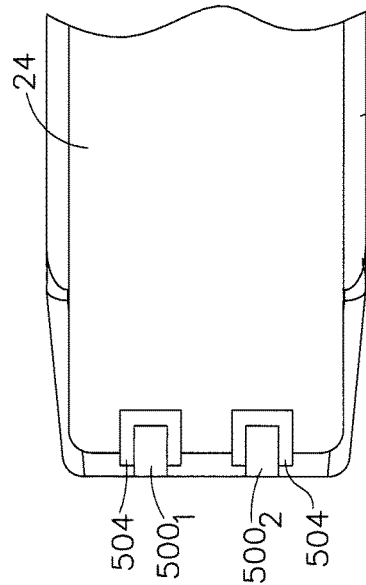
Figure 43:
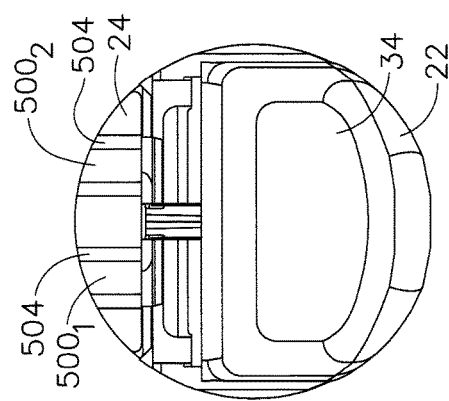
Figure 44:
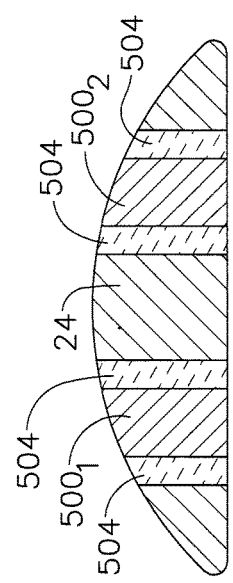

FIGS. 29 to 32 illustrate other embodiments of the end effector 12 that may be useful for spot coagulation. In these embodiments, the anvil 24 comprises a pair of electrodes $500_1$, $500_2$ at the distal end of the anvil 24 and along a lateral side of the anvil 24. FIG. 29 is front-end view of the anvil 24 according to such an embodiment, FIG. 30 is a side view, FIG. 31 is an enlarged fragmentary front-end view, and FIG. 32 is a top view. In such an embodiment, the metallic anvil 24 may act as the return electrode. The active electrodes $500_1$, $500_2$ may be insulated from the anvil 24 by electrically non-conductive insulators 504, which may comprise ceramic material.

FIGS. 33 to 36 show an embodiment where the anvil 24 comprises two distal electrodes $500_1$, $500_2$ located at the top, center of the anvil 24. Again, the metallic anvil 24 may act as the return electrode, and the active electrodes $500_1$, $500_2$ may be insulated from the anvil 24 by electrically non-conductive insulators 504.

FIGS. 37 to 40 show an embodiment where one active electrode $500_1$ (e.g., the active electrode) is positioned on the anvil 24, and another active electrode $500_2$ is positioned on the lower jaw 22, and preferably on the cartridge 34. The metallic anvil 24 may serve as the return electrode. The anvil electrode $500_1$ is insulated from the anvil 24 by an insulator 504. The electrode $500_2$, being positioned in the cartridge 34, which is preferably made from a non-conductive material such as plastic, is insulated from the metallic channel 22 by the cartridge 34.

FIGS. 41 to 44 show an embodiment where the anvil 24 has two active electrodes $500_1$, $500_2$ at the very most distal end of the anvil 24 that extend completely from the upper surface of the anvil 24 to the lower surface. Again, the metallic anvil 24 may act as the return electrode, and the active electrodes $500_1$, $500_2$ may be insulated from the anvil 24 by electrically non-conductive insulators 504.

FIGS. 45 to 48 show an embodiment where the cartridge 34 has two active electrodes $500_1$, $500_2$ at the very most distal end of the staple cartridge 34. In such an embodiment, the metallic anvil 24 or the metallic channel 22 may act as the return electrode. In this illustrated embodiment, the electrodes $500_1$, $500_2$ are connected to insulator inserts 503, but in other embodiments, the insulator inserts 503 could be omitted and the plastic cartridge 34 may serve as the insulator for the electrodes $500_1$, $500_2$.

FIGS. 49 to 52 show an embodiment having one active electrode $500_1$ at the very most distal end of the anvil 24 and another active electrode $500_2$ at the very most distal end of the cartridge 34. Again, in such an embodiment, the metallic anvil 24 or the metallic channel 22 may act as the return electrode. In this illustrated embodiment, the electrode $500_2$ is connected to insulator inserts 503, 505, but in other embodiments, the insulator inserts 503, 505 could be omitted and the plastic cartridge 34 may serve as the insulator for the electrode $500_2$.

FIG. 57 is a side view and FIG. 58 is a cross-sectional side of the handle 6 according to other embodiments of the present invention. The illustrated embodiment only includes one trigger, the closure trigger 18. Activation of the knife, staple drivers, and/or RF electrodes in this embodiment may be achieved through means other than a separate firing trigger. For example, as shown in FIG. 57, actuation of the knife, staple drivers, and/or RF electrodes may be activated by a push-button switch 540 or other type of switch that is in a position that is convenient for the operator. In FIG. 57, the switch 540 is shown at the most proximate portion of the handle 6. In another embodiment, the switch may be positioned near the distal end of the handle 6 so that pulling of the nozzle 539 activates the switch to cause actuation of the instrument. In such an embodiment, a switch (not shown) may be placed under or near the nozzle 539 so that movement of the nozzles toggles the switch.

Alternatively, actuation of the knife, staple drivers, and/or RF electrodes may be activated by voice or other sound commands detected by a microphone 542. In other embodiments, the handle 6 may comprise a RF or sonic transceiver 541, which may receive and/or transmit RF or sonic signals to activate the instrument. Also, as shown in FIG. 58, a foot pedal or switch 544 could be used to active the instrument 10. The foot pedal 544 may be connected to the handle 6 by a cord 545. Also, the handle 6 may comprise a dial control 546 or some other suitable control device for controlling actuation of the segmented RF electrodes (see, for example, FIGS. 23 and 24). Using such a control device 546, the operator may serially activate the various pairs of RF electrodes 500 in the end effector 12.

The instrument 10 shown in FIGS. 57 and 58 also includes many feedback systems for the user. As mentioned above, the instrument 10 may comprise the speaker 543 for audibleizing commands or instructions to the operator. In addition, the handle 6 may comprise visual indicators 548, such as LEDs or other light sources that provide visual feedback regarding actuation of the various segmented RF electrodes. For example, each of the visual indicators 548 could correspond to one of the segmented RF electrode pairs. The corresponding visual indicator 548 may be activated when the segmented RF electrode pair is activated. In addition, the handle 6 may comprise an alphanumeric display 550, which may be an LED or LCD display, for example. The display 550 may be connected to a circuit board 552 inside the handle 6. The handle 6 may also comprise a vibrator 554 in the pistol grip portion 26 that may provide vibrational feedback to the operator. For example, the vibrator 554 could vibrate each time that one of the segmented pairs of the RF electrodes in the end effector 12 is activated.

Figure 26:
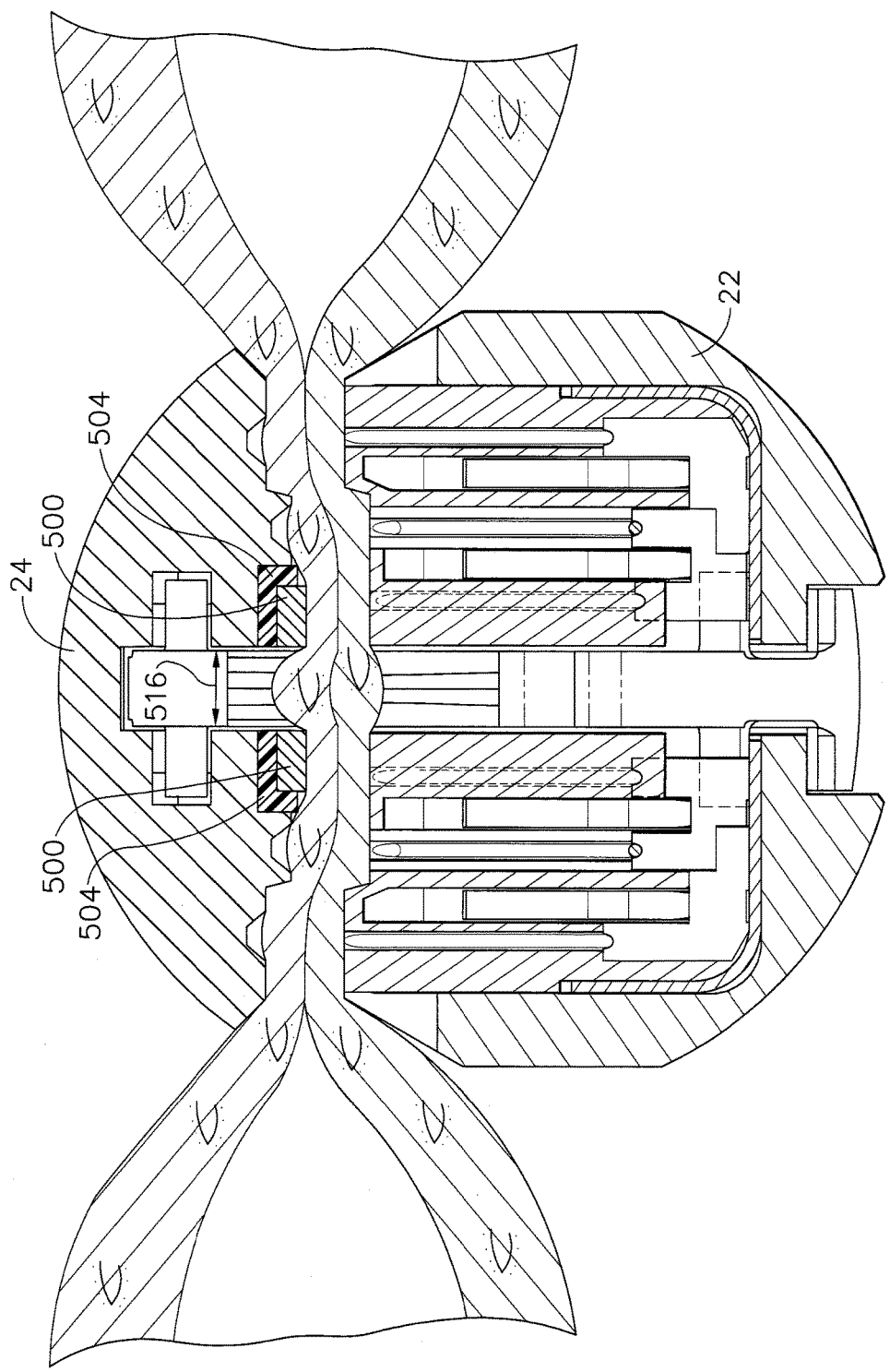

FIG. 26 is a cross-sectional view of the end effector 12 according to various embodiments where the electrodes are on the upper jaw (or anvil) 24. In the illustrated embodiment, the active electrodes 500 are positioned adjacent the knife slot 516. The metal anvil 24 may serve as the return electrode. Insulators 504, which may be made of ceramic, insulate the electrodes 500 from the metallic anvil 24. The embodiment of FIG. 68 is similar to that of FIG. 26, except that electrodes 500 are made smaller, such that a portion of the insulators 504 can extend between the respective electrodes 500 and the edges of the knife channel 516.

Figure 53:
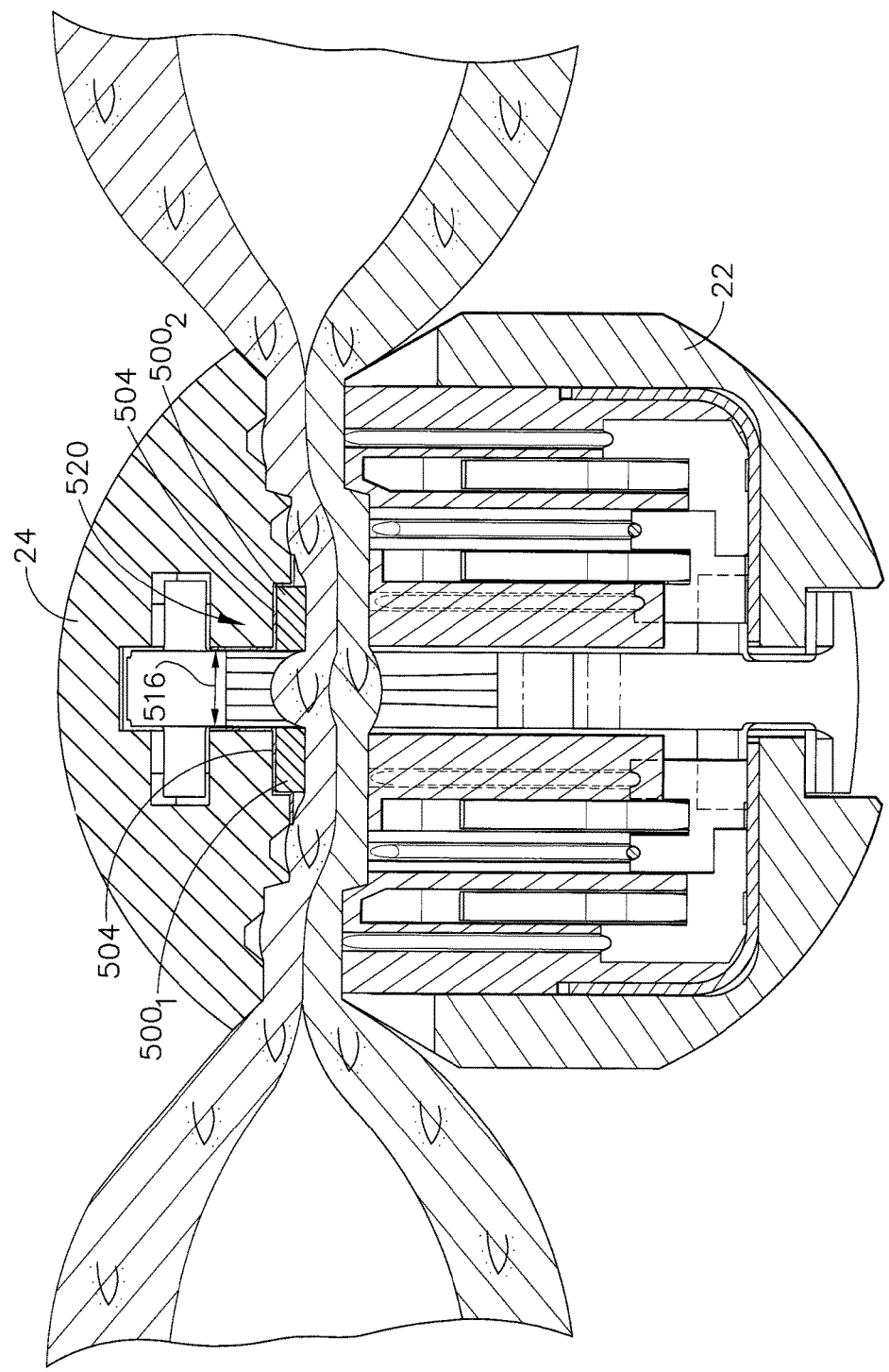

FIG. 53 is a cross-sectional end view of the end effector 12 according to another embodiment. In this embodiment, like the embodiment of FIG. 26, the active electrodes $500_1$, $500_2$ are on the anvil 24 on opposite sides of the knife channel. The electrodes $500_1$, $500_2$ are insulated from the metallic anvil by insulators 504, which again preferably comprise ceramic material. In this embodiment, however, the insulators 504 are made very thin (compare with FIG. 26). Making the insulators 504 very thin provides the potential advantage that the anvil 24 may include a relatively large metal section 520 above the electrodes 500, thereby potentially supporting a slimmer anvil profile for a given anvil stiffness, or a stiffer profile for a given anvil cross-sectional dimension. The insulators 504 may be cast in or sputter coated onto the anvil 24.

Figure 54:
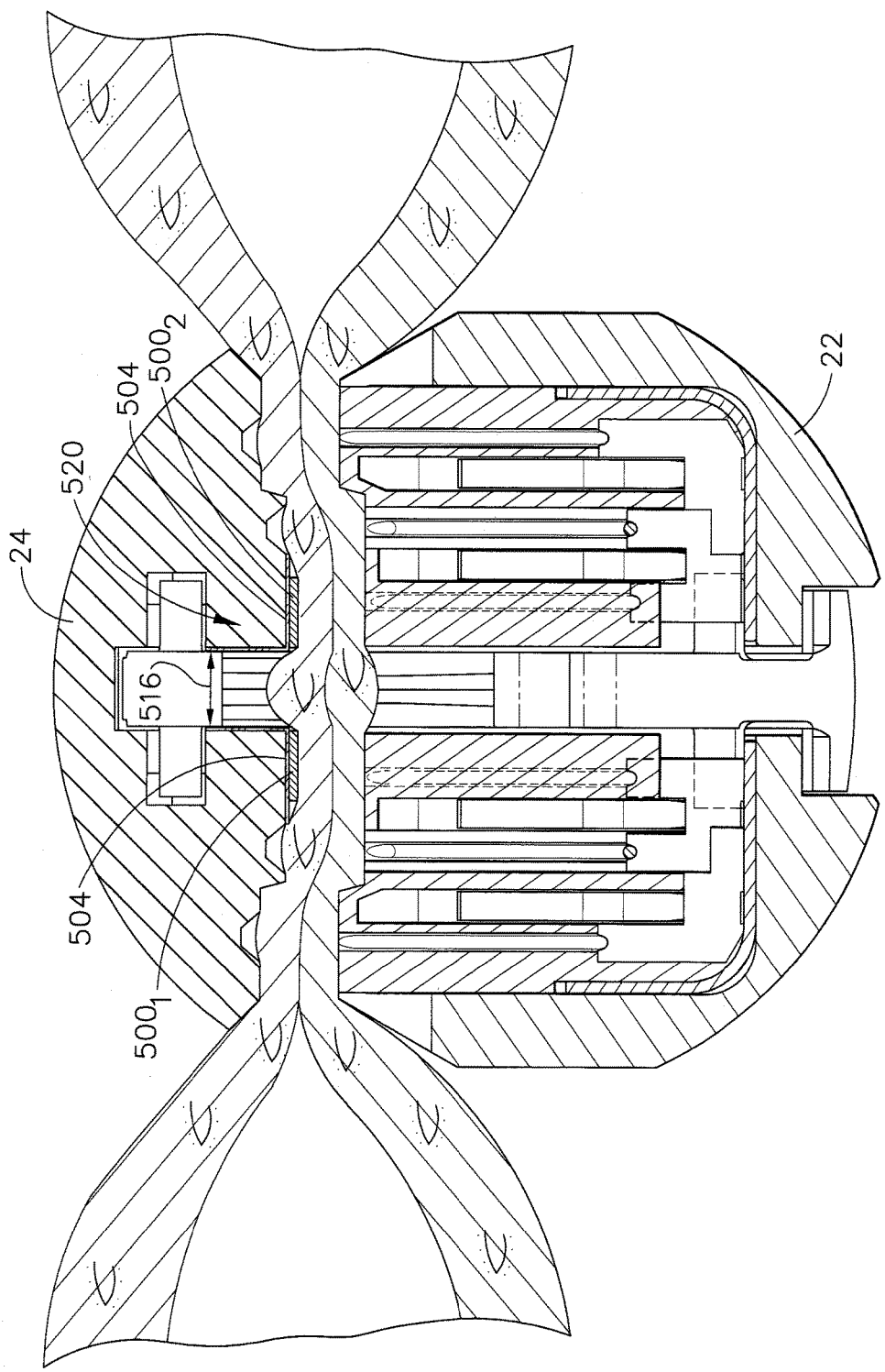

FIG. 54 illustrates another embodiment. In this embodiment, the active electrodes $500_1$, $500_2$ are sputter coated or bonded to the insulators 504, which may also be sputter coated or bonded to the anvil 24. Like the embodiment of FIG. 53, this design allows for more anvil material above the electrodes. In such an embodiment, the electrodes $500_1$, $500_2$ may comprise silver, which is a good conductor of electricity and has antimicrobial properties.

FIG. 55 shows a side view of the end effector according to another embodiment. In this embodiment, a thin film of electrically insulating material 530 is deposited on the face of the cartridge 34. The insulating film 530 preferably comprises a heat- and arc-resistant material, such as ceramic. This would tend to increase the resistance of the cartridge 34 to arc-tracking and shorting, permitting more firings between changes of the cartridge 34. In addition, if the cartridge 34 was a poor electrical conductor, it would support quicker heating of tissue and reduce the overall energy requirements. The active electrodes (not shown in FIG. 55) may be in the anvil 24, as described in embodiments above.

FIG. 56 shows an embodiment that is similar to that shown in FIG. 55, except that in FIG. 56, a thin layer 532 of slightly electrically conductive material is deposited on top of the insulating film 530. The conductivity of the thin, slightly conductive layer 532 may be lower than the conductive of the tissue clamped in the end effector 12 for treatment. As such, the thin, slightly conductive layer 532 would provide a reduced-conductivity path to provide additional heating of the clamped tissue. This would tend to reduce the time required to heat the tissue and achieve coagulation.

As described above, the instrument 10 may comprise an articulation pivot 14 for articulating the end effector 12. A clinician or operator of the instrument 10 may articulate the end effector 12 relative to the shaft 8 by utilizing the articulation control 16, as described in more detail in published U.S. Patent Application Publication No. 2007/0158385, entitled SURGICAL INSTRUMENT HAVING AN ARTICULATING END EFFECTOR, now U.S. Pat. No. 7,670,334, which is incorporated herein by reference. In other embodiments, rather than a control device that is integrated with the instrument 10, the end effector 12 may be articulated by a separate instrument, such as gripper, that is inserted into the patient so that its operative portion is near the end effector 12 so that it can articulate the end effector 12 as desired. The separate instrument may be inserted through a different opening as the end effector 12, or through the same opening. Also, different operators can operate the separate instruments, or one person can operate both instruments, to articulate the end effector 12. In another passive articulation scenario, the end effector 12 may be articulated by carefully pushing it against other parts of the patient to achieve the desired articulation.

In another embodiment, the end effector 12 may be connected to the handle by a flexible cable. In such an embodiment, the end effector 12 could be positioned as desired and held in position by use of another instrument, e.g., a separate gripper instrument. In addition, in other embodiments, the end effector 12 could be positioned by a separate instrument and clamped by a second separate instrument. In addition, the end effector 12 could be made sufficiently small, such as 8 to 9 mm wide by 10 to 11 mm tall, so that a pull-to-close mechanism could be used to clamp the end effector from the handle 6. The pull-to-close mechanism could be adapted from that described in U.S. Pat. No. 5,562,701, entitled CABLE-ACTUATED JAW ASSEMBLY FOR SURGICAL INSTRUMENTS, which is incorporated herein by reference. The cable 600 could be disposed in or along a flexible endoscope for use, for example, in upper or lower gastro-intestinal tract procedures.

In yet another embodiment, as shown in FIGS. 69 and 70, the instrument 10 may comprise a flexible neck assembly 732 enabling articulation of the end effector 12. When an articulation transmission assembly 731 coupled to the shaft 8 is rotated, it may cause remote articulation of the flexible neck assembly 732. The flexible neck assembly 732 may comprise first and second flexible neck portions 733, 734, which receive first and second flexible band assemblies 735, 736. Upon rotation of the articulation transmission assembly 731, one of the first and second flexible transmission band assemblies 735, 736 is moved forwardly and the other band assembly is moved rearwardly. In response to the reciprocating movement of the band assemblies within the first and second flexible neck portions 733, 734 of the flexible neck assembly 732, the flexible neck assembly 732 bends to provide articulation. A further description of the flexible neck is described in U.S. Pat. No. 5,704,534, which is incorporated herein by reference.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments of the invention described herein will be processed before surgery. First, a new or used instrument is obtained and if necessary cleaned. The instrument can then be sterilized. In one sterilization technique, the instrument is placed in a closed and sealed container, such as a thermoformed plastic shell covered with a sheet of TYVEK (commercially available from E. I. du Pont de Nemours and Company). The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam and other methods.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. The various embodiments of the present invention represent vast improvements over prior staple methods that require the use of different sizes of staples in a single cartridge to achieve staples that have differing formed (final) heights.

Accordingly, the present invention has been discussed in terms of endoscopic procedures and apparatus. However, use herein of terms such as "endoscopic" should not be construed to limit the present invention to a surgical stapling and severing instrument for use only in conjunction with an endoscopic tube (i.e., trocar). On the contrary, it is believed that the present invention may find use in any procedure where access is limited, including but not limited to laparoscopic procedures, as well as open procedures. Moreover, the unique and novel aspects of the various staple cartridge embodiments of the present invention may find utility when used in connection with other forms of stapling apparatuses without departing from the spirit and scope of the present invention.

What is claimed is:

1. A surgical instrument, comprising:
   a first jaw;
   a second jaw, wherein the first jaw is movable relative to the second jaw to capture tissue between the first jaw and the second jaw;
   a staple cartridge supported by the second jaw, wherein the staple cartridge comprises staples removably stored therein;
   a firing system configured to drive the staples toward the first jaw;
   an electric motor mechanically coupled to the firing system;
   a power source electrically couplable to the electric motor; and
   a control system electrically connected to the power source, wherein the control system is configured to:
      determine a first level of power supplied by the power source; and
      apply a second level of power to the electric motor if the first level of power exceeds a predetermined threshold, wherein the second level of power is lower than the first level of power.

2. The surgical instrument of claim 1, wherein the first jaw comprises an anvil.

3. The surgical instrument of claim 1, wherein the staple cartridge is removably seated in the second jaw.

4. The surgical instrument of claim 1, wherein the power source comprises a rechargeable power source.

5. The surgical instrument of claim 1, wherein the power source comprises a replaceable power source.

6. The surgical instrument of claim 1, wherein the power source comprises a plurality of battery cells.

7. The surgical instrument of claim 1, wherein the control system comprises a power regulator electrically connected to the power source and the electric motor.

8. The surgical instrument of claim 7, wherein the power regulator is configured to control a voltage applied to the electric motor.

9. The surgical instrument of claim 1, wherein the control system is further configured to measure:
   a power source voltage; and
   a current drawn from the power source.

10. A surgical instrument, comprising:
an elongate channel;
an anvil pivotably coupled to the elongate channel;
a staple cartridge positioned within the elongate channel;
staples removably positioned within the staple cartridge;
a firing system configured to fire the staples toward the anvil;
an electric motor mechanically coupled to the firing system;
a power source electrically couplable to the electric motor;
a power regulator electrically coupled to the power source and the electric motor, wherein a setpoint of the power regulator is adjustable; and
a control system configured to lower the setpoint of the power regulator if a level of power supplied by the power source exceeds a predetermined threshold.

11. The surgical instrument of claim 10, wherein the staple cartridge is a replaceable staple cartridge.

12. The surgical instrument of claim 10, wherein the power source comprises a rechargeable power source.

13. The surgical instrument of claim 10, wherein the power source comprises a replaceable power source.

14. The surgical instrument of claim 10, wherein the power source comprises a plurality of battery cells.

15. The surgical instrument of claim 10, wherein the control system is further configured to measure:
a power source voltage; and
a current drawn from the power source.

16. A surgical instrument, comprising:
a first jaw;
a second jaw pivotably connected to the first jaw;
a replaceable staple cartridge removably positioned within the second jaw;
staples removably positioned within the replaceable staple cartridge;
a firing system configured to fire the staples toward the first jaw;
an electric motor mechanically coupled to the firing system;
a power source electrically couplable to the electric motor; and
means for reducing a voltage applied to the electric motor if a level of power supplied by the power source exceeds a predetermined threshold.

* * * * *